(12) United States Patent
Scott et al.

(10) Patent No.: US 12,279,867 B2
(45) Date of Patent: Apr. 22, 2025

(54) SYSTEMS, DEVICES, AND METHODS RELATED TO THE INDIVIDUALIZED CALIBRATION AND/OR MANUFACTURING OF MEDICAL DEVICES

(71) Applicant: ABBOTT DIABETES CARE INC., Alameda, CA (US)

(72) Inventors: Steven Scott, Pleasanton, CA (US); Christopher J. Bennell, Carterton (GB); Claire Bhogal, Witney (GB); Katie A. Cranfield, Reading (GB); Marc B. Taub, Mountain View, CA (US); Bree M. Winter, Witney (GB); Owen D. Reynolds, Cricklade (GB); Jean-Pierre Babka, San Rafael, CA (US); Dharmendra S. Patel, Stanton Harcourt (GB); Christopher A. Thomas, Cheltenham (GB); Udo Hoss, San Ramon, CA (US); Mark S. Yahnke, Alameda, CA (US); Tahir S. Khan, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 18/233,935

(22) Filed: Aug. 15, 2023

(65) Prior Publication Data
US 2023/0389838 A1 Dec. 7, 2023

Related U.S. Application Data

(63) Continuation of application No. 17/950,538, filed on Sep. 22, 2022, which is a continuation of application
(Continued)

(51) Int. Cl.
*A61B 5/1495* (2006.01)
*A61B 5/00* (2006.01)
(Continued)

(52) U.S. Cl.
CPC ........ *A61B 5/1495* (2013.01); *A61B 5/14503* (2013.01); *A61B 5/14532* (2013.01);
(Continued)

(58) Field of Classification Search
None
See application file for complete search history.

(56) References Cited

U.S. PATENT DOCUMENTS 2,892,990 A 6/1959 Werndl
4,561,443 A 12/1985 Hogrefe et al.
(Continued)

FOREIGN PATENT DOCUMENTS

CA 2 605 530 11/2006
EP 0 838 230 4/1998
(Continued)

OTHER PUBLICATIONS

U.S. Appl. No. 60/587,787, filed Jul. 13, 2004, Brister, et al.
(Continued)

*Primary Examiner* — Lore R Jarrett
(74) *Attorney, Agent, or Firm* — Baker Botts L.L.P.

(57) ABSTRACT

Systems, devices, kits, and methods are provided herein in the form of example embodiments that relate to calibration of medical devices. The medical devices can be sensors adapted to sense a biochemical attribute. The embodiments can be used to determine calibration information specific to an individual medical device. The embodiments can determine the calibration information by reference to one or more parameters obtained during manufacturing of the medical device. The embodiments can also determine the calibration
(Continued)

information by reference to in vitro testing of the medical devices. The embodiments also apply to systems incorporating those medical devices in their use in the field. Also described are embodiments of modifications to surfaces of sensor substrates, such as through applied radiation and/or the creation of a well, to aid in the placement and/or sizing of a sensor element on the substrate.

29 Claims, 47 Drawing Sheets

Related U.S. Application Data

No. 17/891,588, filed on Aug. 19, 2022, which is a continuation of application No. 17/543,633, filed on Dec. 6, 2021, which is a continuation of application No. 17/306,833, filed on May 3, 2021, now Pat. No. 11,191,463, which is a continuation of application No. 15/999,212, filed on Aug. 17, 2018, now Pat. No. 10,993,646.

(60) Provisional application No. 62/547,635, filed on Aug. 18, 2017.

(51) Int. Cl.
 *A61B 5/145* (2006.01)
 *A61M 1/16* (2006.01)

(52) U.S. Cl.
 CPC ........ *A61B 5/14546* (2013.01); *A61B 5/0002* (2013.01); *A61B 2560/0223* (2013.01); *A61B 2562/12* (2013.01); *A61M 1/1603* (2014.02)

(56) References Cited

U.S. PATENT DOCUMENTS

| | | |
|---|---|---|
| 4,639,062 A | 1/1987 | Taniguchi et al. |
| 4,650,547 A | 3/1987 | Gough |
| 4,703,756 A | 11/1987 | Gough et al. |
| 4,750,496 A | 6/1988 | Reinhart et al. |
| 5,034,112 A | 7/1991 | Murase et al. |
| 5,089,112 A | 2/1992 | Skotheim et al. |
| 5,145,381 A | 9/1992 | Volz |
| 5,165,407 A | 11/1992 | Wilson et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,320,715 A | 6/1994 | Berg |
| 5,322,063 A | 6/1994 | Allen et al. |
| 5,352,351 A | 10/1994 | White et al. |
| 5,390,671 A | 2/1995 | Lord et al. |
| 5,391,250 A | 2/1995 | Cheney, II et al. |
| 5,411,647 A | 5/1995 | Johnson et al. |
| 5,482,473 A | 1/1996 | Lord et al. |
| 5,497,772 A | 3/1996 | Schulman et al. |
| 5,559,828 A | 9/1996 | Armstrong et al. |
| 5,569,186 A | 10/1996 | Lord et al. |
| 5,584,813 A | 12/1996 | Livingston et al. |
| 5,591,137 A | 1/1997 | Stevens |
| 5,593,852 A | 1/1997 | Heller et al. |
| 5,690,119 A | 11/1997 | Rytky et al. |
| 5,695,623 A | 12/1997 | Michel et al. |
| 5,700,360 A | 12/1997 | Chan et al. |
| 5,786,439 A | 7/1998 | Van Antwerp et al. |
| 5,791,344 A | 8/1998 | Schulman et al. |
| 5,849,174 A | 12/1998 | Sanghera et al. |
| 5,863,400 A | 1/1999 | Drummond et al. |
| 6,001,067 A | 12/1999 | Shults et al. |
| 6,096,268 A | 8/2000 | Inbar |
| 6,103,033 A | 8/2000 | Say et al. |
| 6,134,461 A | 10/2000 | Say et al. |
| 6,159,181 A | 12/2000 | Crossman et al. |
| 6,168,957 B1 | 1/2001 | Matzinger et al. |
| 6,175,752 B1 | 1/2001 | Say et al. |
| 6,180,221 B1 | 1/2001 | Crotzer et al. |
| 6,203,354 B1 | 3/2001 | Kuwahara et al. |
| 6,212,417 B1 | 4/2001 | Ikeda et al. |
| 6,232,609 B1 | 5/2001 | Snyder et al. |
| 6,237,394 B1 | 5/2001 | Harris et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,340,588 B1 | 1/2002 | Nova et al. |
| 6,360,888 B1 | 3/2002 | McIvor et al. |
| 6,366,794 B1 | 4/2002 | Moussy et al. |
| 6,368,141 B1 | 4/2002 | VanAntwerp et al. |
| 6,377,894 B1 | 4/2002 | Deweese et al. |
| 6,400,974 B1 | 6/2002 | Lesho |
| 6,424,847 B1 | 7/2002 | Mastrototaro et al. |
| 6,475,372 B1 | 11/2002 | Ohara et al. |
| 6,475,750 B1 | 11/2002 | Han et al. |
| 6,522,903 B1 | 2/2003 | Berman et al. |
| 6,558,321 B1 | 5/2003 | Burd et al. |
| 6,560,471 B1 | 5/2003 | Heller et al. |
| 6,565,509 B1 | 5/2003 | Say et al. |
| 6,587,704 B1 | 7/2003 | Fine et al. |
| 6,616,819 B1 | 9/2003 | Liamos et al. |
| 6,618,934 B1 | 9/2003 | Feldman et al. |
| 6,650,471 B2 | 11/2003 | Doi |
| 6,673,022 B1 | 1/2004 | Bobo et al. |
| 6,676,600 B1 | 1/2004 | Conero et al. |
| 6,689,056 B1 | 2/2004 | Kilcoyne et al. |
| 6,695,860 B1 | 2/2004 | Ward et al. |
| 6,736,957 B1 | 5/2004 | Forrow et al. |
| 6,741,877 B1 | 5/2004 | Shults et al. |
| 6,746,582 B2 | 6/2004 | Heller et al. |
| 6,809,653 B1 | 10/2004 | Mann et al. |
| 6,835,553 B2 | 12/2004 | Han et al. |
| 6,850,859 B1 | 2/2005 | Schuh |
| 6,895,263 B2 | 5/2005 | Shin et al. |
| 6,931,327 B2 | 8/2005 | Goode, Jr. et al. |
| 6,990,366 B2 | 1/2006 | Say et al. |
| 7,220,387 B2 | 5/2007 | Flaherty et al. |
| 7,299,082 B2 | 11/2007 | Feldman et al. |
| 7,323,142 B2 | 1/2008 | Pendo et al. |
| 7,344,500 B2 | 3/2008 | Talbot et al. |
| 7,418,285 B2 | 8/2008 | Ghesquiere et al. |
| 7,491,303 B2 | 2/2009 | Sakata et al. |
| 7,501,053 B2 | 3/2009 | Karinka et al. |
| 7,525,315 B2 | 4/2009 | Fredette et al. |
| 7,545,272 B2 | 6/2009 | Goodnow et al. |
| 7,725,148 B2 | 5/2010 | Shah et al. |
| 7,749,740 B2 | 7/2010 | Eiteman et al. |
| 7,754,093 B2 | 7/2010 | Forrow et al. |
| 7,811,231 B2 | 10/2010 | Jin et al. |
| 7,866,026 B1 | 1/2011 | Wang et al. |
| 8,083,928 B2 | 12/2011 | Feldman et al. |
| 8,115,635 B2 | 2/2012 | Goodnow et al. |
| 8,236,166 B2 | 8/2012 | Karinka et al. |
| 8,260,556 B2 | 9/2012 | Likuski et al. |
| 8,268,143 B2 | 9/2012 | Liu et al. |
| 8,280,474 B2 | 10/2012 | Liu et al. |
| 8,297,128 B2 | 10/2012 | Delbos et al. |
| 8,396,670 B2 | 3/2013 | St-Pierre |
| 8,497,777 B2 | 7/2013 | Harper |
| 8,583,205 B2 | 11/2013 | Budiman et al. |
| 8,771,183 B2 | 7/2014 | Sloan |
| 8,828,330 B2 | 9/2014 | Galasso et al. |
| 9,211,065 B2 | 12/2015 | Marsh et al. |
| 9,241,631 B2 | 1/2016 | Valdes et al. |
| 9,504,471 B2 | 11/2016 | Vaitekunas et al. |
| 9,538,943 B1 | 1/2017 | Cross et al. |
| 9,782,112 B2 | 10/2017 | Moein et al. |
| 9,788,766 B2 | 10/2017 | Simpson et al. |
| 9,801,577 B2 | 10/2017 | Budiman et al. |
| 9,808,574 B2 | 11/2017 | Yodfat et al. |
| 10,709,364 B2 | 7/2020 | Kamath et al. |
| 10,820,842 B2 | 11/2020 | Harper |
| 10,827,954 B2 | 11/2020 | Hoss et al. |
| 10,874,338 B2 | 12/2020 | Stafford |

(56) References Cited

U.S. PATENT DOCUMENTS

| | | |
|---|---|---|
| 10,881,341 B1 | 1/2021 | Curry et al. |
| 10,945,647 B2 | 3/2021 | Mazza et al. |
| 10,945,649 B2 | 3/2021 | Lee et al. |
| 10,952,653 B2 | 3/2021 | Harper |
| 10,959,654 B2 | 3/2021 | Curry et al. |
| 10,966,644 B2 | 4/2021 | Stafford |
| 10,973,443 B2 | 4/2021 | Funderburk et al. |
| 10,980,461 B2 | 4/2021 | Simpson et al. |
| 11,000,213 B2 | 5/2021 | Kamath et al. |
| 11,000,216 B2 | 5/2021 | Curry et al. |
| 11,013,440 B2 | 5/2021 | Lee et al. |
| 11,020,031 B1 | 6/2021 | Simpson et al. |
| 11,064,917 B2 | 7/2021 | Simpson et al. |
| 11,141,084 B2 | 10/2021 | Funderburk et al. |
| 2002/0010390 A1 | 1/2002 | Guice et al. |
| 2002/0043651 A1 | 4/2002 | Darrow et al. |
| 2002/0161288 A1 | 10/2002 | Shin et al. |
| 2002/0169369 A1 | 11/2002 | Ward et al. |
| 2002/0177764 A1 | 11/2002 | Sohrab |
| 2003/0003524 A1 | 1/2003 | Taniike et al. |
| 2003/0042137 A1 | 3/2003 | Mao et al. |
| 2003/0065536 A1 | 4/2003 | Hansen et al. |
| 2003/0076082 A1 | 4/2003 | Morgan et al. |
| 2003/0097082 A1 | 5/2003 | Purdy et al. |
| 2003/0100040 A1 | 5/2003 | Bonnecaze et al. |
| 2003/0114836 A1 | 6/2003 | Estes et al. |
| 2003/0144581 A1 | 7/2003 | Conn et al. |
| 2003/0153900 A1 | 8/2003 | Aceti et al. |
| 2003/0225361 A1 | 12/2003 | Sabra |
| 2004/0018486 A1 | 1/2004 | Dunn et al. |
| 2004/0022438 A1 | 2/2004 | Hibbard |
| 2004/0061232 A1 | 4/2004 | Shah et al. |
| 2004/0087876 A1 | 5/2004 | Eskuri |
| 2004/0106858 A1 | 6/2004 | Say et al. |
| 2004/0106860 A1 | 6/2004 | Say et al. |
| 2004/0117204 A1 | 6/2004 | Mazar et al. |
| 2004/0118704 A1 | 6/2004 | Wang et al. |
| 2004/0122353 A1 | 6/2004 | Shahmirian et al. |
| 2004/0127777 A1 | 7/2004 | Ruchti et al. |
| 2004/0133164 A1 | 7/2004 | Funderburk et al. |
| 2004/0244151 A1 | 12/2004 | Sakata et al. |
| 2005/0004439 A1 | 1/2005 | Shin et al. |
| 2005/0027180 A1 | 2/2005 | Goode, Jr. et al. |
| 2005/0027181 A1 | 2/2005 | Goode, Jr. et al. |
| 2005/0027463 A1 | 2/2005 | Goode, Jr. et al. |
| 2005/0038332 A1 | 2/2005 | Saidara et al. |
| 2005/0043598 A1 | 2/2005 | Goode, Jr. et al. |
| 2005/0059871 A1 | 3/2005 | Gough et al. |
| 2005/0069892 A1 | 3/2005 | Iyengar et al. |
| 2005/0143636 A1 | 6/2005 | Zhang et al. |
| 2005/0151976 A1 | 7/2005 | Toma |
| 2005/0176136 A1 | 8/2005 | Burd et al. |
| 2005/0192557 A1 | 9/2005 | Brauker et al. |
| 2005/0215871 A1 | 9/2005 | Feldman et al. |
| 2005/0239154 A1 | 10/2005 | Feldman et al. |
| 2005/0240245 A1 | 10/2005 | Bange et al. |
| 2005/0242479 A1 | 11/2005 | Petisce et al. |
| 2005/0245799 A1 | 11/2005 | Brauker et al. |
| 2005/0261563 A1 | 11/2005 | Zhou et al. |
| 2006/0016700 A1 | 1/2006 | Brister et al. |
| 2006/0019327 A1 | 1/2006 | Brister et al. |
| 2006/0020187 A1 | 1/2006 | Brister et al. |
| 2006/0020188 A1 | 1/2006 | Kamath et al. |
| 2006/0020192 A1 | 1/2006 | Brister et al. |
| 2006/0025663 A1 | 2/2006 | Talbot et al. |
| 2006/0036143 A1 | 2/2006 | Brister et al. |
| 2006/0091006 A1 | 5/2006 | Wang et al. |
| 2006/0094944 A1 | 5/2006 | Chuang |
| 2006/0094945 A1 | 5/2006 | Barman et al. |
| 2006/0142651 A1 | 6/2006 | Brister et al. |
| 2006/0193375 A1 | 8/2006 | Lee |
| 2006/0222566 A1 | 10/2006 | Brauker et al. |
| 2006/0257996 A1 | 11/2006 | Simpson et al. |
| 2006/0258929 A1 | 11/2006 | Goode, Jr. et al. |
| 2006/0258959 A1 | 11/2006 | Sode |
| 2006/0276771 A1 | 12/2006 | Galley et al. |
| 2006/0281985 A1 | 12/2006 | Ward et al. |
| 2006/0293576 A1 | 12/2006 | Van Antwerp et al. |
| 2007/0038044 A1 | 2/2007 | Dobbles et al. |
| 2007/0237678 A1 | 10/2007 | Roesicke et al. |
| 2007/0249922 A1 | 10/2007 | Peyser et al. |
| 2007/0299617 A1 | 12/2007 | Willis |
| 2008/0066305 A1 | 3/2008 | Wang et al. |
| 2008/0161666 A1 | 7/2008 | Feldman et al. |
| 2008/0172205 A1 | 7/2008 | Breton et al. |
| 2008/0234561 A1 | 9/2008 | Roesicke et al. |
| 2008/0267823 A1 | 10/2008 | Wang et al. |
| 2008/0278333 A1 | 11/2008 | Fennell et al. |
| 2008/0287761 A1 | 11/2008 | Hayter et al. |
| 2008/0312842 A1 | 12/2008 | Hayter et al. |
| 2009/0006034 A1* | 1/2009 | Hayter .................. G16H 40/67 702/182 |
| 2009/0076360 A1 | 3/2009 | Brister et al. |
| 2009/0102678 A1 | 4/2009 | Mazza et al. |
| 2009/0108992 A1 | 4/2009 | Shafer |
| 2009/0143659 A1 | 6/2009 | Li et al. |
| 2009/0163789 A1 | 6/2009 | Say et al. |
| 2009/0178459 A1 | 7/2009 | Li et al. |
| 2009/0240120 A1 | 9/2009 | Mensinger et al. |
| 2009/0247857 A1 | 10/2009 | Harper et al. |
| 2010/0057042 A1 | 3/2010 | Hayter |
| 2010/0094111 A1 | 4/2010 | Heller et al. |
| 2010/0094112 A1 | 4/2010 | Heller et al. |
| 2010/0094610 A1 | 4/2010 | Matsuura |
| 2010/0145377 A1 | 6/2010 | Lai et al. |
| 2010/0198142 A1 | 8/2010 | Sloan et al. |
| 2010/0200538 A1 | 8/2010 | Petisce et al. |
| 2010/0230285 A1 | 9/2010 | Hoss et al. |
| 2010/0274515 A1 | 10/2010 | Hoss et al. |
| 2011/0120865 A1 | 5/2011 | Bommakanti et al. |
| 2011/0124994 A1 | 5/2011 | Bommakanti et al. |
| 2011/0177780 A1 | 7/2011 | Sato et al. |
| 2011/0178717 A1 | 7/2011 | Goodnow et al. |
| 2011/0213225 A1 | 9/2011 | Bernstein et al. |
| 2012/0150005 A1 | 6/2012 | Hoss et al. |
| 2012/0262298 A1 | 10/2012 | Bohm et al. |
| 2012/0265037 A1 | 10/2012 | Bohm et al. |
| 2012/0323098 A1 | 12/2012 | Moein et al. |
| 2014/0017709 A1 | 1/2014 | Lowe et al. |
| 2014/0060145 A1 | 3/2014 | Hoss et al. |
| 2014/0121480 A1 | 5/2014 | Budiman et al. |
| 2014/0200917 A1 | 7/2014 | Galasso et al. |
| 2014/0266776 A1 | 9/2014 | Miller et al. |
| 2014/0266785 A1 | 9/2014 | Miller et al. |
| 2014/0273858 A1 | 9/2014 | Panther et al. |
| 2014/0278189 A1 | 9/2014 | Vanslyke et al. |
| 2014/0313052 A1 | 10/2014 | Yarger et al. |
| 2015/0005601 A1 | 1/2015 | Hoss et al. |
| 2015/0038818 A1 | 2/2015 | Cole |
| 2015/0118658 A1 | 4/2015 | Mayou et al. |
| 2015/0205947 A1 | 7/2015 | Berman et al. |
| 2016/0007890 A1 | 1/2016 | Kovatchev et al. |
| 2017/0071512 A1 | 3/2017 | Garcia et al. |
| 2017/0074757 A1* | 3/2017 | Garcia ............... A61B 5/14532 |
| 2017/0112531 A1 | 4/2017 | Schoonmaker et al. |
| 2017/0135618 A1 | 5/2017 | Brister et al. |
| 2017/0181681 A1 | 6/2017 | Boock et al. |
| 2017/0184527 A1 | 6/2017 | Nogueira et al. |
| 2017/0188906 A1 | 7/2017 | Ma et al. |
| 2017/0188907 A1 | 7/2017 | Ma et al. |
| 2017/0188908 A1 | 7/2017 | Hoss et al. |
| 2017/0196491 A1 | 7/2017 | Brister et al. |
| 2018/0350468 A1 | 12/2018 | Friedman et al. |
| 2019/0274598 A1 | 9/2019 | Scott et al. |

FOREIGN PATENT DOCUMENTS

| | | |
|---|---|---|
| EP | 1 391 728 | 2/2004 |
| EP | 1 413 245 | 4/2004 |
| EP | 1 413 879 | 1/2012 |
| EP | 2 407 094 | 1/2012 |
| EP | 1 075 209 | 10/2014 |
| EP | 3 575 796 | 12/2019 |
| EP | 3 797 682 | 3/2021 |

(56) References Cited

FOREIGN PATENT DOCUMENTS

| EP | 3831282 | 3/2022 |
|---|---|---|
| GB | 2067764 | 7/1981 |
| WO | WO 98/16975 | 4/1998 |
| WO | WO 98/56293 | 12/1998 |
| WO | WO 99/56613 | 11/1999 |
| WO | WO 99/58190 | 11/1999 |
| WO | WO 00/49941 | 8/2000 |
| WO | WO 01/17425 | 3/2001 |
| WO | WO 01/52727 | 7/2001 |
| WO | WO 02/15778 | 2/2002 |
| WO | WO 02/058537 | 8/2002 |
| WO | WO 2003/005891 | 1/2003 |
| WO | WO 2003/009207 | 1/2003 |
| WO | WO 03/012422 | 2/2003 |
| WO | WO 03/032411 | 4/2003 |
| WO | WO 03/056319 | 7/2003 |
| WO | WO 03/094714 | 11/2003 |
| WO | WO 2004/088275 | 10/2004 |
| WO | WO 2005/011489 | 2/2005 |
| WO | WO 2005/018450 | 3/2005 |
| WO | WO 2005/026689 | 3/2005 |
| WO | WO 2005/041766 | 5/2005 |
| WO | WO 2005/065542 | 7/2005 |
| WO | WO 2005/070287 | 8/2005 |
| WO | WO 2005/089103 | 9/2005 |
| WO | WO 2006/026741 | 3/2006 |
| WO | WO 2006/040083 | 4/2006 |
| WO | WO 2006/064397 | 6/2006 |
| WO | WO 2006/079114 | 7/2006 |
| WO | WO 2006/094513 | 9/2006 |
| WO | WO 2006/099151 | 9/2006 |
| WO | WO 2007/097754 | 8/2007 |
| WO | WO 2008/021913 | 2/2008 |
| WO | WO 2008/042918 | 4/2008 |
| WO | WO 2008/063626 | 5/2008 |
| WO | WO 2008/138006 | 11/2008 |
| WO | WO 2008/143943 | 11/2008 |
| WO | WO 2009/146391 | 12/2009 |
| WO | WO 2010/099507 | 9/2010 |
| WO | WO 2011/011643 | 1/2011 |
| WO | WO 2012/142502 | 10/2012 |
| WO | WO 2014/105631 | 7/2014 |
| WO | WO 2014/158327 | 10/2014 |
| WO | WO 2014/179343 | 11/2014 |
| WO | WO 2017/044654 | 3/2017 |
| WO | WO 2017/116503 | 7/2017 |
| WO | WO 2017/117416 | 7/2017 |
| WO | WO 2017/172781 | 10/2017 |

OTHER PUBLICATIONS

U.S. Appl. No. 60/606,334, filed Aug. 31, 2004, Griffith, et al.
U.S. Appl. No. 60/614,683, filed Sep. 30, 2004, Brister, et al.
U.S. Appl. No. 60/687,199, filed Jun. 2, 2005, Ward, et al.
U.S. Appl. No. 61/155,889, filed Feb. 26, 2009, Hoss, et al.
U.S. Appl. No. 61/227,967, filed Jul. 23, 2009, Hoss, et al.
U.S. Appl. No. 15/999,212 (U.S. Pat. No. 10,993,646), filed Aug. 17, 2018 (May 4, 2021).
U.S. Appl. No. 17/306,833 (U.S. Pat. No. 11,191,463), filed May 3, 2021 (Nov. 17, 2021).
U.S. Appl. No. 17/543,633 (US 2022/0087576), filed Dec. 6, 2021 (Mar. 24, 2022).
U.S. Appl. No. 17/891,588 (US 2022/0386903), filed Aug. 19, 2022 (Dec. 8, 2022).
U.S. Appl. No. 17/950,538 (US 2023/0028587), filed Sep. 22, 2022 (Jan. 26, 2023).
U.S. Appl. No. 17/950,538, Sep. 7, 2023 Request for Continued Examination (RCE).
U.S. Appl. No. 17/950,538, Jul. 3, 2023 Notice of Allowance.
U.S. Appl. No. 17/950,538, Jun. 5, 2023 Response to Non-Final Office Action.
U.S. Appl. No. 17/950,538, Apr. 27, 2023 Non-Final Office Action.
U.S. Appl. No. 17/950,538, Mar. 31, 2023 Amendment and Request for Continued Examination (RCE).
U.S. Appl. No. 17/950,538, Mar. 13, 2023 Advisory Action.
U.S. Appl. No. 17/950,538, Feb. 24, 2023 Response After Final Action.
U.S. Appl. No. 17/950,538, Feb. 13, 2023 Final Office Action.
U.S. Appl. No. 17/950,538, Jan. 23, 2023 Response to Non-Final Office Action.
U.S. Appl. No. 17/950,538, Dec. 21, 2022 Non-Final Office Action.
U.S. Appl. No. 17/891,588, Sep. 12, 2023 Request for Continued Examination (RCE).
U.S. Appl. No. 17/891,588, Sep. 5, 2023 Notice of Allowance.
U.S. Appl. No. 17/891,588, Nov. 25, 2022 Non-Final Office Action.
U.S. Appl. No. 17/891,588, Aug. 21, 2023 Response to Non-Final Office Action.
U.S. Appl. No. 17/891,588, Jun. 8, 2023 Non-Final Office Action.
U.S. Appl. No. 17/891,588, May 16, 2023 Amendment and Request for Continued Examination (RCE).
U.S. Appl. No. 17/891,588, Mar. 16, 2023 Final Office Action.
U.S. Appl. No. 17/891,588, Feb. 27, 2023 Response to Non-Final Office Action.
U.S. Appl. No. 17/543,633, Dec. 4, 2022 Requestion for Continued Examination (RCE).
U.S. Appl. No. 17/543,633, Oct. 13, 2022 Notice of Allowance.
U.S. Appl. No. 17/543,633, Sep. 7, 2022 Requestion for Continued Examination (RCE).
U.S. Appl. No. 17/543,633, Aug. 18, 2022 Advisory Action.
U.S. Appl. No. 17/543,633, Aug. 8, 2022 Response to Final Office Action.
U.S. Appl. No. 17/543,633, Jun. 7, 2022 Final Office Action.
U.S. Appl. No. 17/543,633, May 9, 2022 Response to Non-Final Office Action.
U.S. Appl. No. 17/543,633, Feb. 16, 2022 Non-Final Office Action.
U.S. Appl. No. 17/306,833, Nov. 10, 2021, Corrected Notice of Allowance.
U.S. Appl. No. 17/306,833, Nov. 2, 2021 Issue Fee Payment.
U.S. Appl. No. 17/306,833, Oct. 28, 2021 Notice of Allowance.
U.S. Appl. No. 17/306,833, Oct. 15, 2021 Response to Non-Final Office Action.
U.S. Appl. No. 17/306,833, Jul. 15, 2021 Non-Final Office Action.
U.S. Appl. No. 15/999,212, Mar. 18, 2021 Issue Fee Payment.
U.S. Appl. No. 15/999,212, Mar. 17, 2021 Notice of Allowance.
U.S. Appl. No. 15/999,212, Mar. 8, 2021 Response after Final Action.
U.S. Appl. No. 15/999,212, Jan. 6, 2021 Final Office Action.
U.S. Appl. No. 15/999,212, Dec. 3, 2020 Response to Non-Final Office Action.
U.S. Appl. No. 15/999,212, Sep. 3, 2020 Non-Final Office Action.
"FDA authorizes first fully interoperable continuous glucose monitoring system, streamlines review pathway for similar devices," FDA News Release, https://www.fda.gov/news-events/press-announcements/fda-authorizes-first-fully-interopeable-continuous-glucose-monitoring-system-streamlines-reviews, 3 pages, Mar. 27, 2018.
"Abbott Receives CE Mark for Freestyle® Libre, A Revolutionary Glucose Monitoring System for People with Diabetes," 8 pages (2023).
"Abbott's Continuous Blood Glucose Monitor Approval Soon" retrieved from https://www.diabetesincontrol.com/abbotts-continuous-blood-glucose-monitor-approval-soon/, Oct. 3, 2006, 3 pages.
"Application-specific integrated circuit" retrieved from "https://en.wikipedia.org/w/index.php?title=Application-specific_integrated_circuit&oldid=212118523" on Sep. 15, 2021, 7 pages.
"Children with Diabetes, Report from Diabetes Technology Meeting" retrieved from https://archive.childrenwithdiabetes.com/d_0j_129.htm on Jan. 21, 2022, 3 pages.
"Cyclic redundacy check" retrieved from "https://en.wikipedia.org/w/index.php?title=Cyclic_redundancy_check&oldid=215595857" on Sep. 20, 2021, 9 pages.
"Definition of analyte" retrieved from "https://www.merriam-webster.com/dictionary/analyte" on Nov. 15, 2022, 5 pages.

(56) References Cited

OTHER PUBLICATIONS

"Frequency-shift keying" retrieved from "https://en.wikipedia.org/w/index.php?title=Frequency-shift_keying&oldid=205244993" on Oct. 7, 2021, 3 pages.
"IEEE 802.11a-1999" retrieved from "http://en.wikipedia.org/wiki/IEEE_802.11a-1999" on Aug. 28, 2017, pp. 1-3.
"In Vivo Glucose Sensing", Chemical Analysis, A Series of Monographs on Analytical Chemistry and its Applications, vol. 174, 466 pages (2010).
"Leading the Way for You and Your Patients with Continuous Glucose Monitoring" Brochure, Dexcom Inc., 12 pages (2010).
"Line code" retrieved from https://en.wikipedia.org/w/index.php?title=Line_code&oldid=214176050 on Sep. 15, 2021, 4 pages.
"Manchester code" retrieved from "https://en.wikipedia.org/w/index.php?title=Manchester_code&oldid=215372891" on Oct. 7, 2021, 4 pages.
"Orthogonal frequency-division multiplexing" retrieved from "http://en.wikipedia.org/wiki/Orthogonal_frequency-division_multiplexing" on Aug. 28, 2017, pp. 1-11.
"TheraSense Files Premarket Approval Application for Freestyle Navigator(TM) Cont" retrieved from https:www.diabetesincontrol.com/therasense-files-premarket-approval-application-for-freestyle-navigatortm-cont/, Dec. 13, 2003, 3 pages.
"Therasense Navigates Continuous Glucose Monitor PMA, Prepares for Flash", The Gray Sheet, 29(37):18 (2003).
"U.S. Food & Drug Administration, Premarket Approval (PMA) for Freestyle Navigator Continuous Glucose Monitor" retrieved from https:www.accessdata.fda.gov/scripts/cdrh/cfdocs/cfpma/pma.cfm?id=P050020 on Jan. 23, 2022, 6 pages.
"Within Definition & Meaning" retrieved from "https://www.dictionary.com/browse/within" on Sep. 9, 2022, 5 pages.
Abel, et al., "Biosensors for in vivo glucose measurement: can we cross the experimental stage", Biosensors and Bioelectronics, 17:1059-1070 (2002).
Acciaroli et al., "Reduction of Blood Glucose Measurements to Calibrate Subcutaneous Glucose Sensors: A Bayesian Multiday Framework", IEEE Transactions on Biomedical Engineering, vol. 65, No. 3, Mar. 2018, pp. 587-595.
Atanasov, et al., "Implantation of a refillable glucose monitoring-telemetry device", Biosensors & Bioelectronics, 12(7):669-680 (1997).
ATTD Program, 4 pages (2009).
Bard, et al., Electrochemical Methods, Fundamentals and Applications, pp. 174-175 (1980).
Bindra, "Development of potentially implantable glucose sensors", The University of Arizona, 227 pages (1990).
Bluetooth Specification, Encryption and Authentication Overview, vol. 6, Version 4.0, 1 page (2010).
Boise, Interview with Dexcom CEO, Dexcom CEO Kevin Sayer Explains G6, 9 pages (2018).
Bruckel et al., "In Vivo Measurement of Subcutaneous Glucose Concentrations with an Enzymatic Glucose Sensor and a Wick Method," Klin Wochenschr, 67:491-495 (1989).
Cambridge Dictionary of American English, Cambridge University Press, 3 pages (2000)—Recess.
Chen et al., "Current and Emerging Technology for Continuous Glucose Monitoring", Sensors, 2017, vol. 17, pp. 182-200.
Chen, et al., "A novel fault-tolerant sensor system for sensor drift compensation", Sensors and Actuators, A 147:623-632 (2008).
Chen, et al., "Defining the Period of Recovery of the Glucose Concentration after Its Local Perturbation by the Implantation of a Miniature Sensor", Clin Chem Lab Med, 40(8):786-789 (2002).
Chen, et al., "Glucose microbiosensor based on alumina sol gel matrix/eletropolymerized composite membrane", Biosensors and Bioelectronics, 17:1005-1013 (2002).
Chen, et al., "In Situ Assembled Mass-Transport Controlling Micromembranes and Their Application in Implanted Amperometric Glucose Sensors", Analytical Chemistry, 72(16):3757-3763 (2000).
Chen, et al., "In vivo Glucose Monitoring with Miniature "Wired" Glucose Oxidase Electrodes", Analytical Sciences, 17:1297-1300 (2001).
Choleau, et al., "Calibration of a subcutaneous amperometric glucose sensor Part 1. Effect of measurement uncertainties on the determination of sensor sensitivity and background current", Biosensors and Bioelectronics, 17:641-646 (2002).
Choleau, et al., "Calibration of a subcutaneous amperometric glucose sensor implanted for 7 days in diabetic patients Part 2. Superiority of the one-point calibration method", Biosensors and Bioelectronics, 17:647-654 (2002).
Chung, "In vitro Evaluation of the Continuous Monitoring Glucose Sensors with Perfluorinated Tetrafluoroethylene Coatings", Bull. Korean Chem. Soc., 24(4):514-516 (2003).
COHRlastic Silicone Rubber Products, Saint-Gobain Performance Plastics, 7 pages (2002).
Couch, II, Leon W., "Complex Envelope Representations for Modulated Signals", The Mobile Communications Handbook, Second Edition, 39 pages (1999).
Csöregi, et al., "Design, Characterization, and One-Point in Vivo Calibration of a Subcutaneously Implanted Glucose Electrode", Anal. Chem., 66(19):3131-3138 (1994).
De Block, et al., "Minimally-Invasive and Non-Invasive Continuous Glucose Monitoring Systems: Indications, Advantages, Limitations and Clinical Aspects", Current Diabetes Reviews, 4:159-168 (2008).
Declaration of John Mastrototaro, Ph.D. (2022).
Determination of Regulatory Review Period for Purposes of Patent Extension; SEVENFACT, Department of Health and Human Services, Food and Drug Administration, Notice, Federal Register, 86(211):60827-60829 (2021).
Dexcom (DXCM) Company Profile, 2017 /Q4 Earnings call transcript, 12 pages (2017).
DexCom (DXCM) Q1 2018 Results—Earnings Call Transcript, 4 pages (2018).
Dexcom G6 Continuous Glucose Monitoring System User Guide, 7 pages (2020).
Dexcomg6, Continuous Glucose Monitoring System, User Guide, 22 pages (2020).
Dexcomg6, Start Here, Set up, Dexcom G6 Continuous Glucose Monitoring (CGM) System (G6), 8 pages (2019).
DexcomG6, Using Your G6, 7 pages (Mar. 2020).
Diabetes Close Up, Conferences #2, Diabetes Technology—DAWN Summit, https://www.closeconcerns.com/, pp. 1-8, (2003).
Dowla, "The Basics of Radio Frequency Identification (RFID) Technology", Handbook of RF & Wireless Technologies, Chapter 14, 44 pages (2004).
Drawing Sheets for U.S. Pat. No. 10,973,443 issued Apr. 13, 2021, 2 pages.
Elastosil RT 602, RTV-2 Silicone Encapsulant, Version 3.00, Wacker Silicones, 2 pages (2004).
Elastosil RTV-1 Silicone Rubber, Wacker Silicone, 16 pages (2001).
Email communication from Sophie Hood, Jan. 24, 2023, 6 pages.
Evans et al., "Clinical temperature acquisition using proximity telemetry", J. Biomed. Eng., 13:83-86 (1991).
Examiner's Report dated May 26, 2022 in corresponding Canadian Patent Application No. 3,065,746.
Excerpts from Expert Report of Catharine M. Lawton—Ex. 36, Spruce Point Capital Management, Does Dexcom Really Have a Future if it Can't Match Abbott's Scale? 2 pages, Mar. 21, 2019.
Exhibit 3, GE Silicones—Master Grade, General Electric Company, 2 pages (2003).
Exhibit 4, Elastosil LR 3162 A, B, Version 3.00, Wacker Silicones, 3 pages (2004).
Extended European Search Report dated Apr. 28, 2023 corresponding to European Patent Application No. EP 23 16 3721.
FDA Premarket Approval (PMA), Freestyle Navigator Continuous Glucose Monitor, 6 pages (2005).
Feldman, et al., "A Continuous Glucose Sensor Based on Wired Enzyme™ Technology—Results from a 3-Day Trial in Patients with Type 1 Diabetes", Diabetes Technology & Therapeutics, 5(5):769-779 (2003).
Figures for U.S. Pat. No. 10,973,443 issued Apr. 13, 2021, 2 pages.

(56) References Cited

OTHER PUBLICATIONS

Finkenzeller, "RFID Handbook: Fundamentals and Applications in Contactless Smart Cards and Identification", Second Edition, 114 pages (2003).
Fischer, "Fundamentals of Glucose Sensors", Diabetic Medicine, 8:309-321 (1991).
FreeStyle Navigator Continuous Glucose Monitoring System, Pre Market Approval Letter from the FDA, Mar. 12, 2008, 7 pages.
FreeStyle Navigator Continuous Glucose Monitoring System, Summary of Safety and Effectiveness Data in support of Pre-Market Approval (PMA) No. P050020, Abbott Diabetes Care, 27 pages (2008).
FreeStyle Navigator Continuous Glucose Monitoring System, User Guide, Abbott Diabetes Care Inc., 195 pages (2008).
FreeStyle Navigator Continuous Glucose Monitoring System, User's Guide, Abbott Diabetes Care Inc., 38 pages, (2008).
Freudenthal, et al., "Suitability of NFC for Medical Device Communication and Power Delivery", IEEE Dallas Engineering in Medicine and Biology Workshop, 4 pages (2007).
Frost, et al., "Implantable chemical sensors for real-time clinical monitoring: progress and challenges", Current Opinion in Chemical Biology, 6:633-641 (2002).
Fujipoly New High Performance Silver ZEBRA° Connector, Fujipoly Data Sheet No. FPDS 01-34 / Version 2, 7 pages (2002).
Funderburk et al., Joint Declaration, U.S. Appl. No. 15/963,828, 11 pages (2020).
Gandrud et al., "Functionality of the MiniMed Continuous Glucose Monitoring System (CGMS) in Young Childen with Type 1 Diabetes," Abstracts of the 64th Scientific Sessions of the American Diabetes Association, vol. 50, Supplement 2 (2004).
Gerritsen, et al., "Performance of subcutaneously implanted glucose sensors for continuous monitoring", The Netherlands Journal of Medicine, 54:167-179 (1999).
Guardian® REAL-Time, Continuous Glucose Monitoring System, User Guide, Medtronic MiniMed, Inc., 181 pages (2006).
Guardian® REAL-Time, Continuous Glucose Monitoring System, User Guide, Medtronic MiniMed, Inc., 184 pages (2006).
Guardian® RT, Continuous Glucose Monitoring System, REF MMT-7900, User Guide, Medtronic MiniMed, 128 pages (2005).
Hall, Interview with Kevin Sayer, President and CEO of Dexcom About The New Dexcom G6, College Diabetes Network, 6 pages (2021).
Heinemann et al., "Benefits and Limitations of MARD as a Performance Parameter for Continuous Glucose Monitoring in the Interstitial Space," Journal of Diabetes Science and Technology, vol. 14 (1) 135-150 (2020).
Heise, et al., "Hypoglycemia Warning Signal and Glucose Sensors: Requirements and Concepts", Diabetes Technology & Therapeutics, 5(4):563-571 (2003).
Heller, "Implanted Electrochemical Glucose Sensors for the Management of Diabetes", Annu. Rev. Biomed. Eng., 01:153-175 (1999).
Heller, "Integrated Medical Feedback Systems for Drug Delivery", AIChE Journal, 51(4):1054-1066 (2005).
Heller, et al., "Electrochemical Glucose Sensors and Their Applications in Diabetes Management", Chemical Reviews, 108(7):2482-2505 (2008).
Heller, et al., "Electrochemistry in Diabetes Management", Accounts of Chemical Research, 43(7):963-973 (2010).
HIPAA Security Series, "Security Standards: Technical Safeguards", Centers for Medicare and Medicaid Services (CMS), 2(4):1-17 (2005).
Hoss et al., "Continuous Glucose Monitoring in Subcutaneous Tissue Using Factory-Calibrated Sensors: A Pilot Study," Diabetes Technology & Therapeutics, vol. 12, No. 8, DOI: 10.1089/dia.2010.0051, 591-597 (2010).
Hoss et al., "Continuous glucose monitoring in the tissue: Do we really need to calibrate in-vivo?," Diabetes Technology & Therapeutics, vol. 11, No. 2, (2009).
Hoss et al., "Factory-Calibrated Continuous Glucose Sensors: The Science Behind the Technology," Diabetes Technology & Therapeutics, 2017, vol. 19, Supplement 2, pp. S44-S50.
Hoss et al., "Feasibility of Factory Calibration for Subcutaneous Glucose Sensors in Subjects with Diabetes," Journal of Diabetes Science and Technology, 2014, vol. 8, No. 1, pp. 89-94.
IEEE 100 The Authoritative Dictionary of IEEE Standards Terms, 7th Ed., 3 pages (2020).
Jansen, et al., "Proximity Beacons and Mobile Device Authentication: An Overview and Implementation", National Institute of Standards and Technology, NISTIR 7200, pp. 1-31 (2005).
Jiménez, et al., "Glucose sensor based on an amperometric microelectrode with a photopolymerizable enzyme membrane", Sensors and Actuators B, 26-27:421-424 (1995).
Johnson, et al., "In Vivo evaluation of an electroenzymatic glucose sensor implanted in subcutaneous tissue", Biosensors & Bioelectronics, 7:709-714 (1992).
Johnson, et al., "Reduction of Electrooxidizable Interferent Effects: Optimization of the Applied Potential for Amperometric Glucose Sensors", Electroanalysis, 6:321-326 (1994).
Kalivas, et al., "Compensation for Drift and Interferences in Multicomponent Analysis", Laboratory for Chemometrics, Department of Chemistry, University of Washington, 38 pages (1982).
Kerner, et al., "The function of a hydrogen peroxide-detecting electroenzymatic glucose electrode is markedly impaired in human sub-cutaneous tissue and plasma", Biosensors & Bioelectronics, 8:473-482 (1993).
Koschinsky, et al., "Sensors for glucose monitoring: technical and clinical aspects", Diabetes/Metabolism Research and Reviews, 17:113-123 (2001).
Koschwanez, et al., "In vitro, in vivo and post explantation testing of glucose-detecting biosensors: Current methods and recommendations", Biomaterials, 28:3687-3703 (2007).
Koudelka, et al., "In-vivo Behaviour of Hypodermically Implanted Microfabricated Glucose Sensors", Biosensors & Bioelectronics, 6:31-36 (1991).
Kovatchev, et al., "Evaluating the Accuracy of Continuous Glucose-Monitoring Sensors", Diabetes Care, 27(8):1922-1928 (2004).
Labiod et al., Wi-Fi™, Bluetooth™, ZigBee™ and WiMax™, "Appendix A: Structure of IEEE 802.11 Packets at Various Physical Layers", pp. 281-316 (2007).
Lee, "RFID Coil Design", Microchip Technology Inc., DS00678B, pp. 1-19 (1998).
Liang, et al., "An implantable bi-directional wireless transmission system for transcutaneous biological signal recording", Physiological Measurement, 26:83-97 (2005).
Lodwig, et al., "Continuous Glucose Monitoring with Glucose Sensors: Calibration and Assessment Criteria", Diabetes Technology & Therapeutics, 5(4):573-587 (2003).
Mastrototaro et al., An electroenzymatic glucose sensor fabricated on a flexible substrate, Sensors and Actuators B, 5:139-144 (1991).
McGarraugh, "The Chemistry of Commercial Continuous Glucose Monitors," Diabetes Technology & Therapeutics, 2009, vol. 11, Supplement 1, pp. S17-S24.
Merriam-Webster's Collegiate Dictionary, 10th Ed., 4 pages (1999)—Housing and recess.
Merriam-Webster's Collegiate Dictionary, 10th Ed., 4 pages (1999)—Release and retain.
Moatti-Sirat, et al., "Evaluating in vitro and in vivo the interference of ascorbate and acetaminophen on glucose detection by a needle-type glucose sensor", Biosensors and Bioelectronics, 7(5):345-352 (1992).
Moussy, et al. "Performance of Subcutaneously Implanted Needle-Type Glucose Sensors Employing a Novel Trilayer Coating", Anal. Chem., 65:2072-2077 (1993).
Near Field Communication (NFC) Technology and Measurements, White Paper, Rohde & Schwarz, 18 pages (2011).
Near Field Communication Interface and Protocol (NFCIP-1), ECMA International, Standard ECMA-340, 2nd Edition (2004).
Nishida, et al., "Development of a ferrocene-mediated needle-type glucose sensor covered with newly designed biocompatible mem-

(56) References Cited

OTHER PUBLICATIONS brane, 2-methacryloyloxyethyl phosphorylcholine-co-n-butyl methacrylate", Medical Progress through Technology, 21:91-103 (1995).
Non-Final Office Action for U.S. Appl. No. 14/884,622 dated Jun. 13, 2018, 7 pages.
Non-Final Office Action for U.S. Appl. No. 17/030,030 dated Dec. 17, 2020, 7 pages.
Notice of Allowance for U.S. Appl. No. 15/963,828 dated Mar. 3, 2021, 32 pages.
Omnipod image, Exhibit 182, 2 pages, Sep. 22, 2022.
Original Premarket Approval Application, FreeStyle Navigator Continuous Glucose Monitoring System, Section VII: Manufacturing Section Steven Label Sensor Sheet Validation Plan, vol. 28 of 31, TheraSense, Inc., 61 pages (2005).
Pickup, et al., "In vivo glucose sensing for diabetes management: progress towards non-invasive monitoring", BMJ, 319, pp. 1-4 (1999).
Pickup, et al., "Responses and calibration of amperometric glucose sensors implanted in the subcutaneous tissue of man", Acta Diabetol, 30:143-148 (1993).
Poitout, et al., "Calibration in dogs of a subcutaneous miniaturized glucose sensor using a glucose meter for blood glucose determination", Biosensors & Bioelectronics 7:587-592 (1992).
Premarket Approval Application Amendment, FreeStyle Navigator Continuous Glucose Monitoring System, vol. 2 of 39, Section III, Device Description, Abbott Diabetes Care, Inc., 89 pages (2006).
U.S. Appl. No. 60/614,683, 447 pages (2004).
Radio Frequency Identification RFID, AIM Inc., White Paper, Document Version 1.2, 17 pages (2001).
Rebrin, et al., "Subcutaneous glucose predicts plasma glucose independent of insulin: implications for continuous monitoring", American Journal of Physiology—Endocrinology and Metabolism, 277(3):E561-E571 (1999).
Reiterer et al., "Significance and Reliability of MARD for the Accuracy of CGM Systems," Journal of Diabetes Science and Technology, vol. 11 (1) 59-67 (2017).
Related European Patent Application No. 18769490.6, Examination Report mailed May 3, 2022.
Related European Patent Application No. 18769490.6, Examination Report mailed Oct. 7, 2022.
Response to Non-Final Office Action for U.S. Appl. No. 15/963,828, filed Dec. 8, 2020, 17 pages.
Response to Restriction Requirement for U.S. Appl. No. 14/884,622, filed Apr. 5, 2018, 15 pages.
Rhodes, et al., "Prediction of Pocket-Portable and Implantable Glucose Enzyme Electrode Performance from Combined Species Permeability and Digital Simulation Analysis", Analytical Chemistry, 66(9):1520-1529 (1994).
Rodriguez, et al., "Flexible Communication and Control Protocol for Injectable Neuromuscular Interfaces", IEEE Transactions on Biomedical Circuits and Systems, 1(1):19-27 (2007).
S&P Global Market Intelligence "DexCom, Inc. NasdaqGS:DXCM, Company Conference Presentation," 17 pages (2021).
S&P Global Market Intelligence "DexCom, Inc. NasdaqGS:DXCM, Company Conference Presentation," 10 pages (2020).
S&P Global Market Intelligence "DexCom, Inc. NasdaqGS:DXCM, Company Conference Presentation," 11 pages (2019).
Sakakida, et al., "Ferrocene-mediated needle-type glucose sensor covered with newly designed biocompatible membrane", Sensors and Actuators B, 13-14:319-322 (1993).
Salonidis, et al., "Proximity Awareness and Ad Hoc Network Establishment in Bluetooth", Institute for Systems Research Technical Reports, 26 pages (2001).
Sayer, CGMS Changing Diabetes Management: Kevin Sayer, DIC Interview Transcript, Featuring Steve Freed, 11 pages (2019).
Schmidtke, et al., "Accuracy of the One-Point in Vivo Calibration of "Wired" Glucose Oxidase Electrodes Implanted in Jugular Veins of Rats in Periods of Rapid Rise and Decline of the Glucose Concentration", Anal. Chem., 70:2149-2155 (1998).

SILASTIC 94-595, Product Information Liquid Silicone Rubber, Dow Corning, 4 pages (2002).
Sonix, Dexcom CEO—Prime Position in Our Market—Mad Money—CNBC.mp4, 4 pages (2023).
Sorrells, "Passive RFID Basics", Microchip Technology Inc., DS00680B, pp. 1-5 (1998).
Specification of the Bluetooth System, Bluetooth, Specification vol. 1, Version 1.1 (2001).
Specification of the Bluetooth System, Experience More, Specification vol. 0, Covered Core Package Version: 4.0, 89 pages (2010).
Tegnestedt et al., "Levels and sources of sound in the intensive care unit—an observational study of three room types," Acta Anaesthesiol Scand (2013).
The CGM Resource Center References/Bibliography, 14 pages (2011).
The Chambers Dictionary, Chambers Harrap Publishers Ltd (1998/1999), 4 pages (2000).
The MiniMed Paradigm® REAL-Time Insulin Pump and Continuous Glucose Monitoring System, Insulin Pump User Guide, Paradigm® 522 and 722 Insulin Pumps, Medtronic MiniMed, Inc., 25 pages (2008).
The New Oxford American Dictionary, Oxford University Press, 3 pages (2001)—Retract.
The New PENGUIN English Dictionary, Penguin Books, 4 pages (2000)—Recess.
Thévenot, et al., "Electrochemical Biosensors: Recommended Definitions and Classification (Technical Report)", Pure Appl. Chem. 71(12):2333-2348 (1999).
Tierney, et al., "Effect of Acetaminophen on the Accuracy of Glucose Measurements Obtained with the GlucoWatch Biographer", Diabetes Technology & Therapeutics, 2(2):199-207 (2000).
Turner, et al., Biosensors: Fundamentals and Applications, Oxford University Press, New York, 786 pages (1987).
U.S. Food & Drug Administration, "Deciding When to Submit a 510(k) for a Change to an Existing Device, Guidance for Industry and Food and Drug Administration Staff," 78 pages (2017).
U.S. Food & Drug Administration, "Deciding When to Submit a 510(k) for a Change to an Existing Device, Guidance for Industry and Food and Drug Administration Staff," 32 pages (2017).
U.S. Appl. No. 12/842,013 Office Action mailed Aug. 26, 2015.
U.S. Appl. No. 12/842,013 Office Action mailed Mar. 23, 2016.
U.S. Appl. No. 12/842,013 Office Action mailed Nov. 6, 2014.
U.S. Pat. No. 10,827,954 issued Nov. 10, 2020, 7 pages.
U.S. Pat. No. 10,973,443 issued Apr. 13, 2021, 22 pages.
United States Securities and Exchange Commission, Form 10-K, DexCom, Inc., 59 pages (2005).
United States Securities and Exchange Commission, Form S-1, DexCom, Inc. 309 pages (2005).
Velho, et al., "Strategies for Calibrating a Subcutaneous Glucose Sensor", Biomed. Biochim. Acta, vol. 48, pp. 957-964 (1989).
Walt, et al., "The chemistry of enzyme and protein immobilization with glutaraldehyde", Trends in Analytical Chemistry, 13(10):425-430 (1994).
Wang, et al., "Bluetooth: Opening a blue sky for healthcare", Mobile Information Systems, 2:151-167 (2006).
Ward et al., "A Wire-Based Dual-Analyte Sensor for Glucose and Lactate: In Vitro and In Vivo Evaluation," Diabetes Technology & Therapeutics, 389-401 (2004).
Ward, et al., "A new amperometric glucose microsensor: in vitro and short-term in vivo evaluation", Biosensors & Bioelectronics, 17:181-189 (2002).
Ward, et al., "Rise in background current over time in a subcutaneous glucose sensor in the rabbit: relevance to calibration and accuracy", Biosensors & Bioelectronics, 15:53-61 (2000).
Watkin, "An Introduction to Flash Glucose Monitoring," 16 pages (2013).
Webster's New College Dictionary, 2 pages (2001)—Alcove.
Webster's Third New International Dictionary, 5 pages (1993)—Retract.
Wilson, et al., "Biosensors for real-time in vivo measurements", Biosensors and Bioelectronics, 20:2388-2403 (2005).
Wilson, et al., "Introduction to the Glucose Sensing Problem" In Vivo Glucose Sensing, Chapter 1, pp. 1-27 (2010).

(56) References Cited

OTHER PUBLICATIONS

Wisniewski, et al., "Analyte flux through chronically implanted subcutaneous polyamide membranes differs in humans and rats", Am J Physiol Endocrinol Metab, 282:E1316-E1323 (2002).
WO PCT/IB2018/056223 Invitation to Pay Additional Fees Jan. 10, 2019.
WO PCT/IB2018/056223 Isr and Written Opinion May 20, 2019.
Yang, et al., "Glucose Biosensors Based on Oxygen Electrode with Sandwich-Type Membranes", Annals of Biomedical Engineering, 23:833-839 (1995).
Yang, et al., "Glucose Biosensors with Enzyme Entrapped in Polymer Coating", Biomedical Instrumentation & Technology, 29(2):125-133 (1995).
Z-Carbon LCD Connector, Z-Axis Connector Company, 2 pages (2004).
Zhang, "Investigations of potentially implantable glucose sensors", University of Kansas, 24 pages (1991).
Armour, et al., "Application of Chronic Intravascular Blood Glucose Sensor in Dogs", Diabetes, 39:1519-1526 (1990).
Chen, "The Development and Application of Glucose Electrodes Based on "Wired" Glucose Oxidase", Dissertation—The University of Texas at Austin, 168 pages (2001).
Knobbe et al., Symposium Paper, "The Extended Kalman Filter for Continuous Glucose Monitoring," Diabetes Technology & Therapeutics, 7, 1, 15-27 (2005).
Microchip, microID® 13.56 MHz RFID System Design Guide, Microchip Technology Inc., 214 pages (2004).
Schmidt, "Design and Development of a Wearable Glucose Sensor, In vitro and in vivo studies", 60 pages (1991).
Atanasov, P., et al., "Implantation of a refillable glucose monitoring-telemetry device", Biosensors & Bioelectronics 1997, vol. 12, No. 7, pp. 669-680.
Dock, E. et al., "Multivariate data analysis of dynamic amperometric biosensor responses from binary analyte mixtures—applications of sensitivity correction algorithms", Talanta, 65, 2005 pp. 298-305.
Schmidt, F.J., et al., "Calibration of a wearable glucose sensor", The International Journal of Artificial Organs, 1992, vol. 15, No. 1, pp. 055-061.
Abbott Press Release—"Abbott Receives CE Mark for FreeStyle® Libre, A Revolutionary Glucose Monitoring System for People with Diabetes" retrieved from https://abbott.mediaroom.com/2014-09-03-Abbott-Receives-CE-Mark-for-FreeStyle-Libre-a-Revolutionary~Glucose-Monitoring-System-for-People-with-Diabetes/, Sep. 3, 2014, 3 pages.
Abbott Press Release—"Abbott Receives FDA Approval for the FreeStyle Libre Pro™ System, A Revolutionary Diabetes Sensing Technology for Healthcare Professionals to Use with their Patients" retrieved from https://abbott.mediaroom.com/2016-09-28-Abbott-Receives-FDA-Approval-for-the-FreeStyle-Libre-Pro-System-a-Revolutionary-Diabetes-Sensing-Technology-for-Healthcare-Professionals-to-use-with-their-Patients/, Sep. 28, 2016, 5 pages.
Abbott Press Release—"Abbott's FreeStyle® Libre 14 Day Flash Glucose Monitoring System Now Approved in U.S." retrieved from https://abbott.mediaroom.com/2018-07-27-Abbotts-FreeStyle-R-Libre-14-Day-Flash-Glucose-Monitoring-System-Now-Approved-in-U-S/, Jul. 27, 2018, 3 pages.
Alcock, et al., "Continuous Analyte Monitoring to Aid Clinical Practice", IEEE Engineering in Medicine and Biology, vol. 13, No. 3, pp. 319-325 (1994).
ANZHSN, National Horizon Scanning Unit Horizon Scanning Report, "GlucoWatch® G2 Biographer for the non-invasive monitoring of glucose levels", 46 pages, May 2004.
Baltensperger, "Vials, Caps, Septa & Various Products in Comparison", CTC Analytics AG, Switzerland, 3 pages, Apr. 9, 2020.
Beardsall, et al., "The continuous glucose monitoring sensor in neonatal intensive care", Arch Dis Child Fetal Neonatal, 90:F307-F310 (2005).
Black, et al., Handbook of Biomaterial Properties, Springer Science+Business Media, Dordrecht, 5 pages (1998).

Cather, CGM Frustrations Survey dated Jun. 2020, 37 pages in *Abbott Diabetes Care Inc., et al. v. Dexcom, Inc.*, Case No. 1:21-cv-00977-KAJ (District of Delaware).
Clinical Trials, Competitor and Ecosystem Players dated Jun. 25, 2020, 29 pages in *Abbott Diabetes Care Inc., et al. v. Dexcom, Inc.*, Case No. 1:21-cv-00977-KAJ (District of Delaware).
Declaration of Dr. Anthony Edward Cass in Support of Petition for Inter Partes Review of U.S. Pat. No. 11,020,031 in *Abbott Diabetes Care Inc. v. Dexcom, Inc.*, Case No. IPR2024-00890, In the United States Patent and Trademark Office, Before the Patent Trial and Appeal Board, May 10, 2024, 138 pages.
Declaration of Dr. Anthony Edward Cass in Support of Petition for Inter Partes Review of U.S. Pat. No. 10,709,364 in *Abbott Diabetes Care Inc. v. Dexcom, Inc.*, Case No. IPR2024-00841, In the United States Patent and Trademark Office, Before the Patent Trial and Appeal Board, Apr. 26, 2024, 101 pages.
Declaration of Karl R. Leinsing, MSME, PE, in Support of Abbott's Motion for Summary Judgment dated May 19, 2023, 81 pages in *Abbott Diabetes Care Inc., et al. v. Dexcom, Inc.*, Case No. 1:21-cv-00977-KAJ (District of Delaware).
Declaration of Sylvia D. Hall-Ellis, Ph.D. in Inter Partes Review of U.S. Pat. No. 10,709,364 in *Abbott Diabetes Care Inc. v. Dexcom, Inc.*, Case No. IPR2024-00841, In the United States Patent and Trademark Office, Before the Patent Trial and Appeal Board, Apr. 25, 2024, 203 pages.
Declaration of Sylvia D. Hall-Ellis, Ph.D. in Inter Partes Review of U.S. Pat. No. 11,020,031 in *Abbott Diabetes Care Inc. v. Dexcom, Inc.*, Case No. IPR2024-00890, In the United States Patent and Trademark Office, Before the Patent Trial and Appeal Board, May 3, 2024, 232 pages.
Dock, et al., "Multivariate data analysis of dynamic amperometric biosensor responses from binary analyte mixtures—application of sensitivity correction algorithms", Talanta, 65:298-305 (2005).
Effectiveness and Safety Study of the DexCom™ G4 Continuous Glucose Monitoring System, DexCom, Inc., U.S. National Library of Medicine, ClinicalTrials.gov Identifier: NCT01111370, 4 pages (2017).
E-mail Communication from Christopher M. Dougherty regarding Bi Monthly Global Commercial Insights Meeting dated Dec. 17, 2019, 69 pages in *Abbott Diabetes Care Inc., et al. v. Dexcom, Inc.*, Case No. 1:21-cv-00977-KAJ (District of Delaware).
Encyclopedia of Polymer Science and Engineering, Second Edition, vol. 15, Scattering to Structural Foams, John Wiley & Sons, Inc., 132 pages (1989).
Design U.S. Appl. No. 29/101,218, filed Feb. 25, 1999, 11 pages.
U.S. Pat. No. 10,709,364 issued Jul. 14, 2020, 875 pages.
U.S. Pat. No. 11,020,031 issued Jun. 1, 2021, 1058 pages.
Fraser, "An Introduction to in vivo Biosensing: Progress and Problems", Biosensors in the Body: Continuous In Vivo Monitoring, pp. 1-56 (1997).
FreeStyle Libre 2 HCP Pulse, Mar. 2021 Report, dated Mar. 1, 2021, 14 pages in *Abbott Diabetes Care Inc., et al. v. Dexcom, Inc.*, Case No. 1:21-cv-00977-KAJ (District of Delaware).
Godek, et al., Chapter 2, "The Macrophage in Wound Healing Surrounding Implanted Devices", In Vivo Glucose Sensing, 36 pages (2010).
Gross, et al., "Performance Evaluation of the MiniMed® Continuous Glucose Monitoring System During Patient Home Use", Diabetes Technology & Therapeutics, vol. 2, No. 1, 8 pages (2000).
Hager, "Why Double Electrocoat and Powder Coat?", MerCruiser, 5 pages (1999).
Hamilton Company, Selecting the Right Syringe, retrieved from https://web.archive.org/web/20030625132534/http://www.hamiltoncompany.com/product/syringe/Syringe%20Selection.html, 4 pages (2003).
Henning, Chapter 5, "Commercially Available Continuous Glucose Monitoring Systems", In Vivo Glucose Sensing, 50 pages (2010).
Koudelka-Hep, "Electrochemical Sensors for in vivo Glucose Sensing", Biosensors in the Body: Continuous In Vivo Monitoring, 12 pages (1997).
Kreith, et al., The CRC Handbook of Mechanical Engineering, 3 pages (1998).

(56) References Cited

OTHER PUBLICATIONS

Lesperance, et al., "Calibration of the Continuous Glucose Monitoring System for Transient Glucose Monitoring", Diabetes Technology & Therapeutics, vol. 9, No. 2, pp. 183-190 (2007).
MD&DI, Silicone Rubber for Medical Device Applications, retrieved from https://www.mddionline.com/orthopedic/silicone-rubber-for-medical-device-applications, 8 pages (Nov. 1, 1999).
Petition for Inter Partes Review of U.S. Pat. No. 11,020,031 in *Abbott Diabetes Care Inc. v. Dexcom, Inc.,* Case No. IPR2024-00890, In the United States Patent and Trademark Office, Before the Patent Trial and Appeal Board, May 10, 2024, 86 pages.
Princy, et al., "Studies on Conductive Silicone Rubber Compounds", Journal of Applied Polymer Science, vol. 69, pp. 1043-1050 (1998).
Project Status Update, Glucose Sensor Applicator Dexcom (project #2554), Design Concepts, Inc., 6 pages (2014).
Scheduling Order dated Sep. 19, 2023, 14 pages in *Abbott Diabetes Care Inc., et al. v. Dexcom, Inc.,* Case No. 1:23-cv-00239-KAJ (District of Delaware).
Schlosser, et al., "Biocompatibility of Active Implantable Devices", Biosensors in the Body: Continuous in vivo Monitoring, 34 pages (1997).
Seagrove Partners, International Diabetes Device, 2022 Blue Book dated 2022, 143 pages in *Abbott Diabetes Care Inc., et al. v. Dexcom, Inc.,* Case No. 1:21-cv-00977-KAJ (District of Delaware).
Silastic® MDX4-4210 BioMedical Grade Elastomer, Dow Corning Corp, 4 pages (2005).
The Wayback Machine—The Apple Rubber Seal Design Guide, Apple Rubber Products, Inc., 182 pages (2003).
Wampler, et al., Chapter 6, "Carbon Black", Rubber Compounding, Chemistry and Applications, pp. 239-284 (2004).
Wikipedia, The Free Encyclopedia, "Gender of connectors and fasteners", retrieved from https://en.wikipedia.org/w/index.php?title=Gender_of_connectors_and_fasteners&oldid=1225173660, 6 pages (May 22, 2024).
Wilson, et al., Chapter 1, "Introduction to the Glucose Sensing Problem," In Vivo Glucose Sensing, 32 pages (2010).
Wisniewski, et al., "Characterization of implantable biosensor membrane biofouling", Fresenius J Anal Chem, 366:611-621 (2000).
Z-Carbon Connector Data Sheet, retrieved from http://www.zaxisconnector.com/SS_zc.shtml, Z-Axis Connector Company, 2 pages (2004).
Z-Silver Connector Data Sheet, retrieved from http://www.zaxisconnector.com/SS_zs.shtml, Z-Axis Connector Company, 2 pages (2004).
Description of the LINEST function in Excel 2003, https;//web.archive.org/web/20041119192208/http:/support.microsoft.com/kb/828533 2004, 16 pages.
Crawshaw, J., et al., "A Concise Course In A-Level Statistics—with Worked Examples", $2^{nd}$ Edition, 1990, pp. 559-628.
File History for U.S. Pat. No. 10,709,364, Issued Jul. 14, 2020.
Hanson, K. et al., "Comparison of Point Accuracy Between Two Widely Used Continuous Glucose Monitoring Systems", Journal of Diabetes Science and Technology, 2024, pp. 1-10.
Padgette et al., "Guide to Bluetooth Security, Recommendations of the National Institute of Standards and Technology," National Institute of Standards and Technology, U.S. Department of Commerce, Special Publication 800-121 Revision 1, 48 pages, May 2007.
Specification Bluetooth System Experience More, 134 pages, Jun. 2010.
Specification Bluetooth System Wireless connections, 92 pages, Nov. 2003.
TI-82 Graphing Calculator Guidebook, Texas Instruments, 1993, 278 pages.
Custodio, et al., "A Review on Architectures and Communications Technologies for Wearable Health-Monitoring Systems", Sensors, 2012, pp. 13907-13946.
Dorland's Illustrated Medical $31^{st}$ Edition Dictionary, definition of "fluid, intersitial", (2007), 3 pages.
Extract from the privacy notice for Libreview, 2024, 7 pages.
Forlenza, G.P., et al., "Factory-Calibrated Continuous Glucose Monitoring: How and Why It Works, and the Dangers of Reuse Beyond Approved Duration of Wear", Diabetes Technology & Therapeutics, vol. 21, No. 4, (2019) 13 pages.
LibreLinkUp User Guide, 2023, 28 pages.
Mosa, et al., "A systematic Revie of Healthcare Applications for Smartphones", BMC Medical Informatics & Decision Making, 2012, pp. 1-31.
Seidel-Jacobs, E., et al., "Epidemiologie des Diabetes in Deutschland", German Health Report Diabetes 2023, 24 pages with translation.
Stephens Inc., Research Bulletin, "DexCom, Inc., A True Game Changer: The G6 Eliminates Fingersticks", (2018) 5 pages.
The American Heritage® Medical Dictionary, definition of "cathether" and "interstitial fluid", (2007), 4 pages.
Vaddiraju, S., et al., "Technologies for Continuous Glucose Monitoring: Current Problems and Future Promises", Journal of Diabetes Science and Technology, vol. 4, Issue 6, (2010) 23 pages.

\* cited by examiner

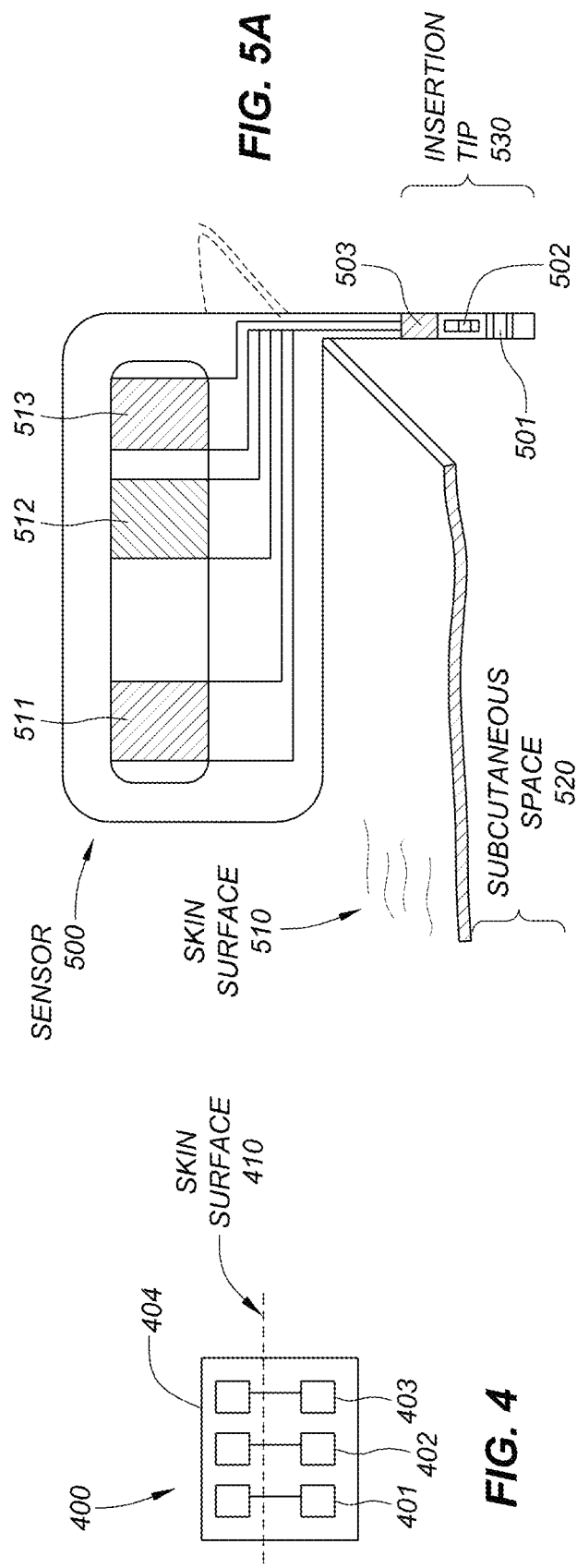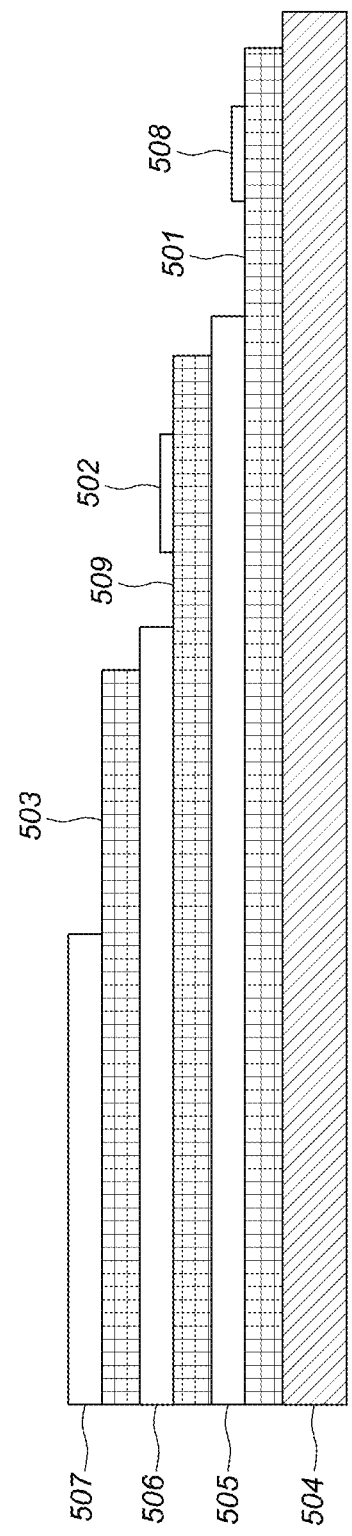

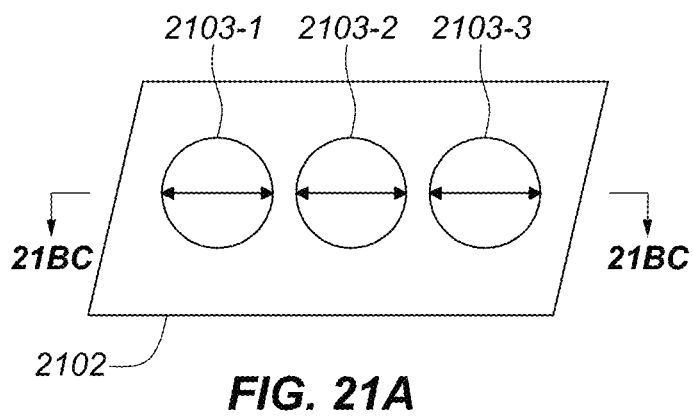
FIG. 21A
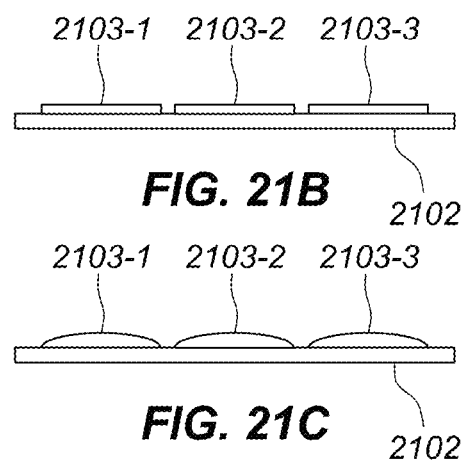
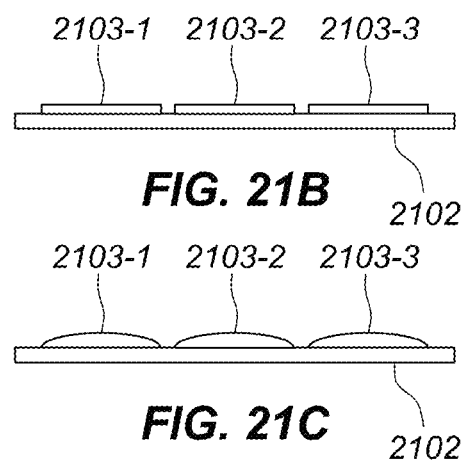
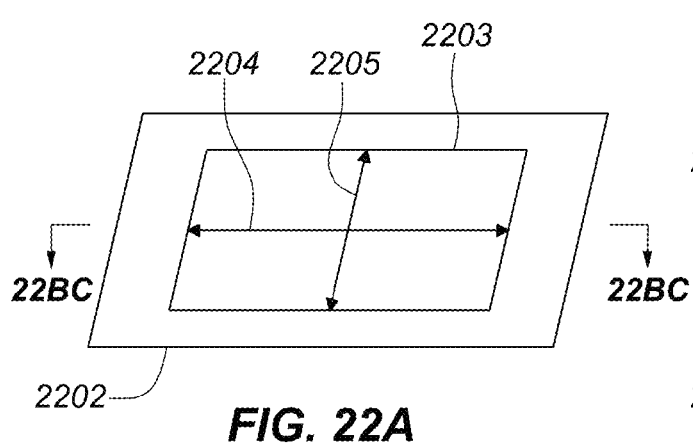
FIG. 22A
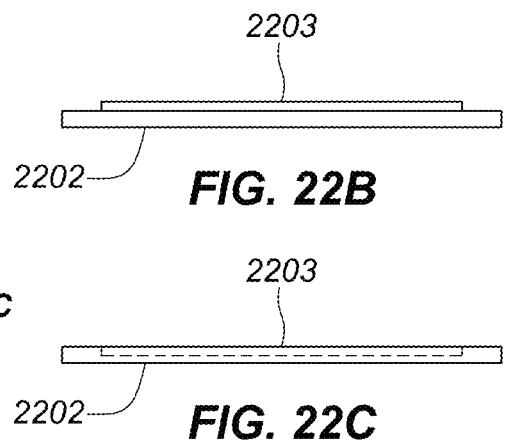
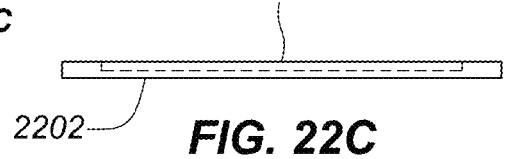
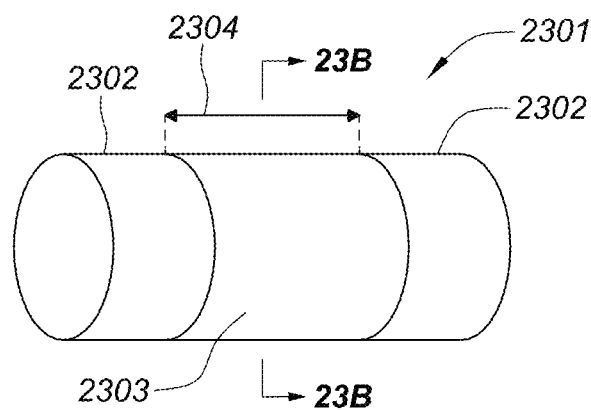
FIG. 23A
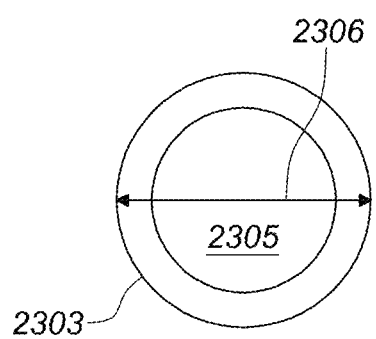
FIG. 23B

2700

```
An in vitro sensing characteristic of a respective medical device in
the distribution subset is determined using at least a
representation of the individualized manufacturing parameter      — 2702
for the respective medical device and a representation of the in
vitro sensing characteristic of the baseline subset
```
↓
```
Individualized calibration information is determined for the
respective medical device that corresponds to the representation   — 2705
of the in vitro sensing characteristic of the
respective medical device
```

```
An in vitro sensing characteristic of a respective medical device in
the distribution subset is determined using at least a
representation of the individualized manufacturing parameter      — 2712
for the respective medical device and a representation of the in
vitro sensing characteristic of the baseline subset
```
↓
```
A representation of an in vivo sensing characteristic of the
respective medical device is determined using a representation of  — 2714
the in vitro sensing characteristic of the respective medical device
```
↓
```
Individualized calibration information is determined for the
respective medical device that corresponds to the representation   — 2715
of the in vitro sensing characteristic of the
respective medical device
```

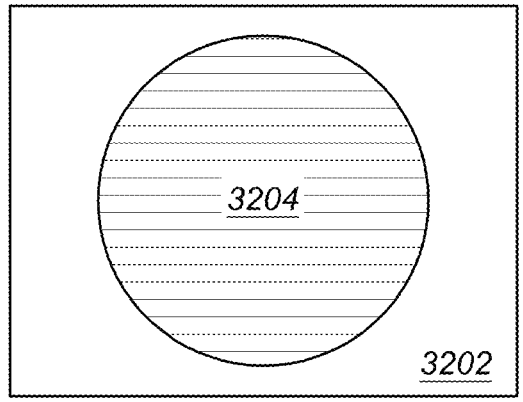
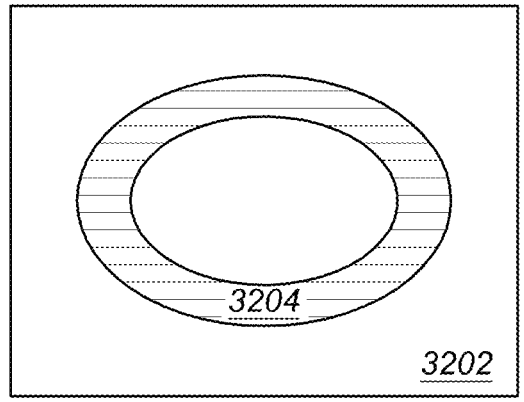
FIG. 35A                FIG. 35B
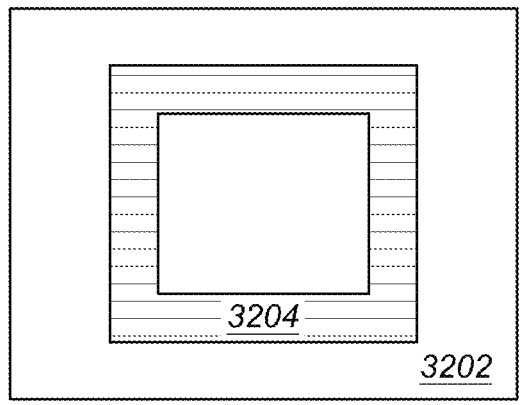
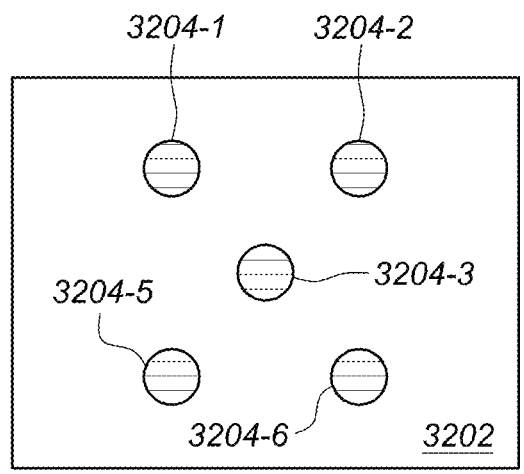
FIG. 35C                FIG. 35D

*3600*

```
┌─────────────────────────────────────────────────────────────┐
│ An area of a surface of a sensor substrate can be modified  │──3602
│ with radiated energy to create a modified area              │
└─────────────────────────────────────────────────────────────┘
                              │
                              ▼
┌─────────────────────────────────────────────────────────────┐
│ A liquid can be applied to the surafce of the substrate such│
│ that the liquid comes to rest in a taget area on the surface,│──3604
│ where the target area is determined at least in part by the │
│ location of the modified area                               │
└─────────────────────────────────────────────────────────────┘
```

```
┌─────────────────────────────────────────────────────────────┐
│ A size of the modified area can be entered into the         │──3612
│ laser marking system                                        │
└─────────────────────────────────────────────────────────────┘
                              │
                              ▼
┌─────────────────────────────────────────────────────────────┐
│ The laser marking system can focus on a substrate of a sensor│──3614
└─────────────────────────────────────────────────────────────┘
                              │
                              ▼
┌─────────────────────────────────────────────────────────────┐
│ The laser marking system can radiate energy to create a     │──3616
│ modified area on the substrate                              │
└─────────────────────────────────────────────────────────────┘
                              │
                              ▼
┌─────────────────────────────────────────────────────────────┐
│ If two or more modified areas are to be created on a single │
│ substrate, then either the substrate or the laser can be    │──3618
│ moved and step 3616 (and optionally step 3614) can be       │
│ repeated to create the next modified area                   │
└─────────────────────────────────────────────────────────────┘
                              │
                              ▼
┌─────────────────────────────────────────────────────────────┐
│ The substrate can be transferred to a electrochemical       │
│ dispersion system, and the electrochemical agent can be     │──3620
│ deposited such that the liquid comes to rest in a target    │
│ area defined by each modified area                          │
└─────────────────────────────────────────────────────────────┘
```

FIG. 36B

SYSTEMS, DEVICES, AND METHODS RELATED TO THE INDIVIDUALIZED CALIBRATION AND/OR MANUFACTURING OF MEDICAL DEVICES

CROSS-REFERENCE TO RELATED APPLICATIONS

This application is a continuation of U.S. patent application Ser. No. 17/950,538, filed Sep. 22, 2022, which is a continuation of U.S. patent application Ser. No. 17/891,588, filed Aug. 19, 2022, which is a continuation of U.S. patent application Ser. No. 17/543,633, filed Dec. 6, 2021, which is a continuation of U.S. patent application Ser. No. 17/306,833, filed May 3, 2021, now U.S. Pat. No. 11,191,463, which is a continuation of U.S. patent application Ser. No. 15/999,212, filed Aug. 17, 2018, now U.S. Pat. No. 10,993,646, which claims the benefit of and priority to U.S. Provisional Patent Application Ser. No. 62/547,635, filed Aug. 18, 2017, all of which are incorporated by reference herein in their entireties and for all purposes.

FIELD

The subject matter described herein relates generally to systems, devices, and methods for determining or utilizing calibration information specific to individual medical devices such as physiological sensors, and/or the manufacturing of physiological sensors.

BACKGROUND

A vast and growing market exists for monitoring the health and condition of humans and other living animals. Information that describes the physical or physiological condition of the human can be used in countless ways to assist and improve quality of life and diagnose and treat undesirable human conditions.

A common device used to collect such information is a physiological sensor such as a biochemical sensor, or a device capable of sensing a chemical attribute of a biological entity. Biochemical sensors come in many forms and can be used to sense attributes in fluids, tissues, or gases forming part of or produced by a biological entity, such as a human being. These biochemical sensors can be used on or within the body itself, or they can be used on biological substances that have already been removed from the body.

The performance of a biochemical sensor can be characterized in a number of ways, and a characteristic of particular importance can be the accuracy of a biochemical sensor, or the degree to which the biochemical sensor correctly measures the concentration or content of the chemical being measured. The precision of the biochemical sensor, or the degree to which the measured value is exact or refined, can also be important.

Although biochemical sensors often have a complex and well-studied design, they can still be subject to a degree of performance variation. This can be caused by a number of factors, including variations in the manufacturing process and variations in the constituent materials used to fabricate the sensors. These variations can cause sensors of the same design and manufacturing process to have measurable differences in their performance. For these and other reasons, needs exist to improve the performance of manufactured biochemical sensors.

SUMMARY

A number of example embodiments are provided herein that can be used to improve the performance of medical devices such as biochemical sensors, as well as the devices and systems utilizing these sensors. These example embodiments relate to improved techniques for assessing and predicting the performance of biochemical sensors when put to use by patients, healthcare professionals (HCPs), or other users. Many of these example embodiments pertain to the determination of calibration information based on parameters measured, recorded, or otherwise obtained during the manufacturing process. These parameters can be individualized, or specific to a discrete sensor, and the calibration information determined therefrom can likewise be individualized, or specific to that discrete sensor.

In many example embodiments, the calibration information is determined by also taking reference to actual tests of the sensing capability or characteristics of certain sensors. The data resulting from those tests can be used with the one or more parameters obtained during the manufacturing process to determine, estimate, extrapolate, or otherwise predict the performance of the sensor once distributed to the user. The tests, e.g., in vitro tests, used to assess sensing characteristics are often destructive, contaminatory, or otherwise of a nature that render the tested sensor unsuitable for distribution to the user. In a number of embodiments, the tests are performed on one or more sensors and the results obtained therefrom are used with the manufacturing parameter of a different, untested sensor to predict the performance of that untested sensor. In this way, the performance of a particular sensor can be predicted without subjecting the sensor to an in vitro test.

The information that represents the predicted performance of the sensor can be embodied as calibration information, and this calibration information can be made available to any device that seeks to use the sensing signal or data produced by the biochemical sensor to determine the end result of the measurement, e.g., the concentration or content of the substance being sensed. While applicable to smaller scales, the embodiments described herein are particularly useful when applied to high-volume manufacturing processes. For example, the embodiments described herein can be applied to groups or batches of sensors that are manufactured together. For example, in certain embodiments a subset of one or more sensors from that group or batch are subjected to in vitro testing, and the resulting test data is used with one or more manufacturing parameters obtained from a different subset of sensors of the same group or batch to predict the performance of that different subset of sensors when distributed to users. Other example embodiments are also described that incorporate one or more of the aspects described here, as well as other example embodiments that differ from that described here.

Also provided herein are a number of example embodiments of systems, devices, and methods for modifying a surface of a sensor substrate to aid in placement and/or sizing of a sensor element. In some of these embodiments, an area of a surface of a sensor substrate can be modified with electromagnetic radiation to create a modified area. The modified area can have a surface characteristic that is changed such that the mobility of a liquid applied to the substrate surface is either increased or decreased by the modified area. Application of a liquid to the surface of the sensor substrate can be performed such that the liquid comes to rest in a target area on the surface, where the target area is determined at least in part by the location of the modified area. The electromagnetic radiation can take various forms, such as laser radiation. In these and other embodiments, the surface modification can be the creation of a well in which a sensing element can be placed. The well can be created in various ways, such as by application of a mechanical force. Example embodiments of sensors manufactured with modified areas and/or wells are within the scope of this disclosure, as are devices, systems, and kits incorporating the same.

Other systems, devices, methods, features, and advantages of the subject matter described herein will be or will become apparent to one with skill in the art upon examination of the following figures and detailed description. It is intended that all such additional systems, methods, features, and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 4 as a schematic diagram depicting an example embodiment of an analyte sensor.

FIG. 5A is a perspective view depicting an example embodiment of an analyte sensor penetrating through the skin.

FIG. 5B is a cross sectional view depicting a portion of the analyte sensor of FIG. 5A.

FIG. 21A is a top down view depicting an example embodiment of a portion of an analyte sensor.

FIGS. 21B-21C are cross-sectional views depicting example embodiments of a portion of an analyte sensor as viewed along line 21BC-21BC of FIG. 21A.

FIG. 22A is a top down view depicting an example embodiment of a portion of an analyte sensor.

FIGS. 22B-22C are cross-sectional views depicting example embodiments of a portion of an analyte sensor as viewed along line 22BC-22BC of FIG. 22A.

FIG. 23A is a perspective view depicting an example embodiment of a portion of an analyte sensor.

FIG. 23B is a cross-sectional view depicting an example embodiment of a portion of an analyte sensor taken along line 23B-23B of FIG. 23A.

FIGS. 27A-27F are flow diagrams depicting example embodiments of methods of determining individualized calibration information.

FIGS. 35A-35D are schematic views depicting example embodiments of modified areas on sensor substrates.

FIGS. 36A-36B are flow diagrams depicting example embodiments of methods of manufacturing one or more sensing elements.

DETAILED DESCRIPTION

Figure 1:
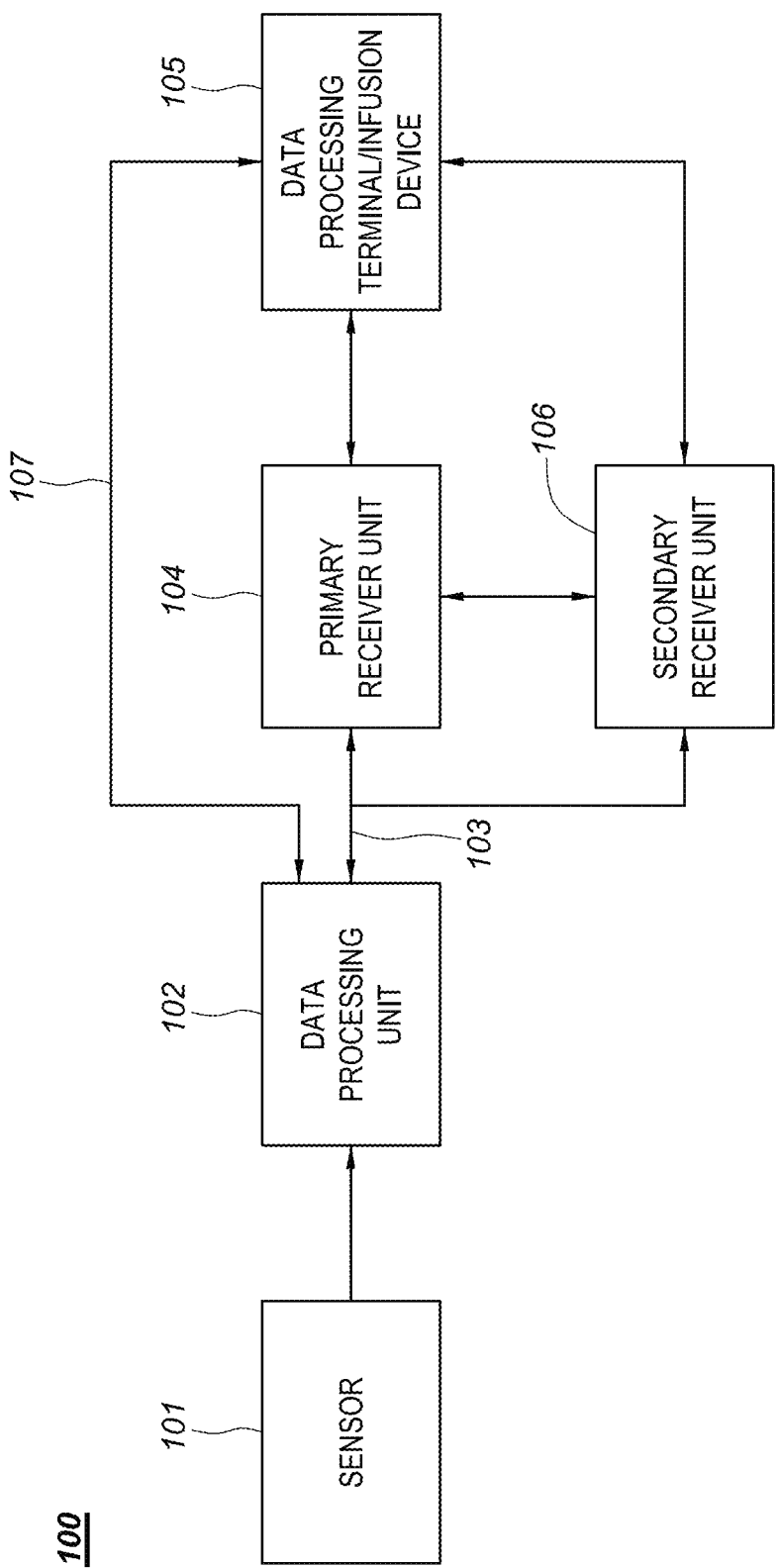
FIG. 1 is a block diagram depicting an example embodiment of an in vivo analyte monitoring system.

The present subject matter is described in detail with reference to example embodiments. These example embodiments are set forth for illustrative purposes to aid those of ordinary skill in the art in understanding and appreciating the full scope of the present subject matter. These example embodiments do not constitute an exhaustive recitation of all manners in which the present subject matter can be implemented, as such an exhaustive recitation is both burdensome and unnecessary in light of the example embodiments explicitly set forth. As such, the present subject matter is of a breadth that extends beyond those particular embodiments explicitly set forth herein.

The subject matter described herein generally relates to advancements in techniques for calibrating medical devices capable of sensing one or more biochemical attributes, as well as systems and devices for performing these calibration techniques. In many embodiments, the techniques permit the determination of individualized calibration information that varies between and is particular to individual medical devices, as opposed to a single calibration value that is determined for groups of medical devices as a whole. There are many classes of medical devices that sense biochemical attributes, and thus there are many applications with which this subject matter can be utilized. Several of these classes of medical devices will be described herein, but these are merely examples and do not constitute an exhaustive recitation of all classes of medical devices with which the present subject matter finds utility.

Medical devices capable of sensing or monitoring chemical levels in bodily fluids can often be classified as part of either in vivo systems or in vitro systems. In vivo systems include one or more medical devices that sense one or more biochemical attributes of bodily fluid that is within the human body, often by partially or wholly implanting the medical device (e.g., a sensor) within the human body. A common example is an in vivo analyte sensor useful in monitoring analyte levels in the human body. These analyte sensors can be designed to detect glucose or other analytes that are particularly relevant in monitoring a diabetic condition.

In vitro systems include one or more medical devices that sense one or more biochemical attributes of bodily fluid, such as blood, plasma, urine, etc., that has been removed from the human body, or other substances such as a homogenized biopsy sample. In vitro systems can also be referred to as ex vivo systems. A common example is an in vitro analyte sensor such as a test strip. In vitro test strips can also be designed to detect and measure glucose or other analytes that are particularly relevant for monitoring a diabetic condition.

Systems and devices incorporating or utilizing data from either in vivo or in vitro medical devices are broadly referred to herein as biochemical monitoring systems and biochemical monitoring devices, respectively. Systems and devices incorporating or utilizing data from medical devices that are designed to sense the level of an analyte (e.g., glucose) are referred to herein as analyte monitoring systems and analyte monitoring devices, respectively.

Example embodiments relating to these calibration techniques will be presented by reference to their application to in vivo medical devices and in vitro medical devices. The majority of the embodiments are described with respect to in vivo medical devices, particularly, in vivo analyte sensors. This is merely to facilitate the presentation of the features and aspects of these example embodiments, and is not intended to limit these calibration techniques to use with only in vivo analyte sensors. Indeed, as noted already, the present subject matter is broadly applicable to other types of medical devices, a number of embodiments of which will also be explicitly described.

Certain example embodiments relating to these calibration techniques permit the determination of individualized calibration information specific to an individual sensor and, if desired, the subsequent use of that individualized calibration information to calibrate an output of the individual sensor. In many embodiments, the individualized calibration information is specific to each individual medical device within a common manufacturing group or lot and can vary between each individual medical device with the common group. These embodiments are in contrast to approaches where a single calibration value is determined for a group or lot of medical devices as a whole such that every medical device in the common manufacturing group has the same calibration value.

In some example embodiments, a sensing characteristic of a first subset (e.g., a sample or baseline subset) of medical devices is determined. For analyte sensors, this sensing characteristic can be, e.g., a sensitivity of the sensor to the analyte. The sensing characteristic can be determined with in vitro (or in vivo use) testing of the first subset of medical devices. Examples of such testing will be described in more detail herein. One or more individualized manufacturing parameter can be measured from each medical device in a different second subset of medical devices (e.g., a distribution subset intended for distribution from the manufacturer to third party users). In some example embodiments, the baseline and distribution subsets are taken from the same production lot. The measurement of the individualized manufacturing parameter can be performed by, e.g., the manufacturer during or after the manufacturing process. The individualized manufacturing parameter can directly or indirectly correlate to the sensing characteristic of the medical device, and numerous examples of such individualized manufacturing parameters are described herein.

Individualized calibration information can then be independently determined for each medical device within the distribution subset of medical devices using at least the individualized manufacturing parameter of each device within the distribution subset and the sensing characteristic of the baseline subset. This can result in calibration information that is specific to each medical device in the distribution subset and that can vary between the medical devices from variation of the individualized manufacturing parameter. In some embodiments, two or more individualized manufacturing parameters are used to determine the calibration information. In some embodiments, one or more qualitative manufacturing parameters are used, either alone or in conjunction with a quantitative individualized manufacturing parameter.

As will be discussed in further detail herein, studies have confirmed that embodiments of the present subject matter result in tangible improvements in the accuracy of biochemical sensing measurements made by the medical devices. This represents an improvement in the operation of the calibrated medical devices themselves, which in turn results in an improvement in the operation of the monitoring systems and/or monitoring devices incorporating these medical devices, as well as an improvement in the operation of the computing devices that process or otherwise utilize the improved accuracy data produced by the calibrated medical devices. Improvements through lessening variations between medical devices were also confirmed, as were improvements to the manufacturing yield of the medical devices.

Before describing the embodiments relating to individualized calibration techniques in detail, it is first desirable to describe example embodiments of in vivo analyte monitoring systems and in vitro analyte monitoring systems, as well as examples of their operations, all of which can be used with embodiments of these calibration techniques.

Example Embodiments of In Vivo Analyte Monitoring Systems

There are various types of analyte monitoring systems used with in vivo sensors. "Continuous Analyte Monitoring" systems (e.g., "Continuous Glucose Monitoring" systems), for example, are in vivo systems that can transmit data from a sensor control device to a reader device repeatedly or continuously without prompting, e.g., automatically according to a schedule. "Flash Analyte Monitoring" systems (e.g., "Flash Glucose Monitoring" systems or simply "Flash" systems), as another example, are in vivo systems that can transfer data from a sensor control device in response to a scan or request for data by a reader device, such as with a Near Field Communication (NFC) or Radio Frequency Identification (RFID) protocol.

An in vivo analyte sensor can be partially or wholly implanted within the human body such that it makes contact with the bodily fluid in the user and senses the analyte levels therein. The in vivo sensor can be part of a sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, a "sensor data communication" device or unit, or a transmitter device or unit, to name a few. The term "on body" or "on-body" refers to any device that resides directly on the body or in close proximity to the body, such as a wearable device (e.g., glasses, armband, wristband or bracelet, neckband, or necklace, etc.).

In vivo monitoring systems can also include one or more reader devices that receive sensed analyte data from the sensor control device. These reader devices can process, retransmit, and/or display the sensed analyte data, in any number of forms. These devices, and variations thereof, can be referred to as "handheld reader devices," "reader devices" (or simply, "readers"), "display devices," "handheld electronics" (or handhelds), "portable data processing" devices or units, "data receivers," "receiver" devices or units (or simply receivers), "relay" devices or units, "remote" devices or units, "companion" devices or units, "human interface" devices or units, to name a few. Computing devices such as personal computers can be used as a reader device.

In vivo analyte monitoring systems can be used with in vitro medical devices as well. For example, a reader device can incorporate or be coupled with a port for receiving an in vitro test strip carrying a bodily fluid of the user, which can be analyzed to determine the user's analyte level.

In Vivo Sensors

In vivo sensors can be formed on a substrate, e.g., a substantially planar substrate, or a non-planar rounded or cylindrical substrate. In many embodiments, the sensor comprises at least one electrically conductive structure, e.g., an electrode. Sensor embodiments can be single electrode embodiments (e.g., having no more than one electrode), or multiple electrode embodiments (e.g., having exactly two, exactly three, or more electrodes). Embodiments of the sensor will often include a working electrode, and can also include at least one counter electrode (or counter/reference electrode), and/or at least one reference electrode (or at reference/counter electrode). Electrodes can be arranged as discrete regions electrically isolated by insulative regions, and can be electrically connected to circuitry for receiving (and optionally conditioning and/or processing) the electrical signals produced by the electrodes. Electrodes can have planar (e.g., relatively flat) surfaces or non-planar (e.g., relatively curved or rounded, such as semi-hemispherical, cylindrical, or irregular surfaces and combinations thereof). Electrodes can be arranged in layers or concentrically or otherwise.

Accordingly, embodiments include analyte monitoring devices and systems that include an analyte sensor at least a portion of which is positionable beneath the skin surface of the user for the in vivo detection of an analyte, including glucose, lactate, and the like, in a body fluid. Embodiments include wholly implantable analyte sensors and analyte sensors in which only a portion of the sensor is positioned under the skin and a portion of the sensor resides above the skin, e.g., for contact to a sensor control device (which may include a transmitter), a receiver/display unit, transceiver, processor, etc. The sensor may be, for example, positionable through an exterior skin surface of a user for the continuous or periodic monitoring (periodic according to a regular interval, an irregular interval, a schedule, frequent repeats, etc.) of a level of an analyte in the user's bodily fluid (e.g., interstitial fluid, subcutaneous fluid, dermal fluid, blood, or other bodily fluid of interest). For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the user's bloodstream. Analyte sensors may be insertable into a vein, artery, or other portion of the body containing fluid. Embodiments of the analyte sensors may be configured for monitoring the level of the analyte over a time period which may range from seconds, minutes, hours, days, weeks, to months, or longer.

In certain embodiments, the analyte sensors, such as glucose sensors, are capable of in vivo detection of an analyte for one hour or more, e.g., a few hours or more, e.g., a few days or more, e.g., three or more days, e.g., five days or more, e.g., seven days or more, e.g., several weeks or more, or one month or more. Future analyte levels may be predicted based on information obtained, e.g., the current analyte level at time to, the rate of change of the analyte, etc. Predictive alarms may notify the user of predicted analyte levels that may be of concern in advance of the user's analyte level reaching the future predicted analyte level. This provides the user an opportunity to take corrective action.

In an electrochemical embodiment, the sensor is placed, transcutaneously, for example, into a subcutaneous site such that subcutaneous fluid of the site comes into contact with the sensor. In other in vivo embodiments, placement of at least a portion of the sensor may be in a blood vessel. The sensor operates to electrolyze an analyte of interest in the subcutaneous fluid or blood such that a current is generated between the working electrode and the counter electrode. A value for the current associated with the working electrode is determined. If multiple working electrodes are used, current values from each of the working electrodes may be determined. A microprocessor may be used to collect these periodically determined current values or to further process these values.

If an analyte concentration is successfully determined, it may be displayed, stored, transmitted, and/or otherwise processed to provide useful information. By way of example, raw signal or analyte concentrations may be used as a basis for determining a rate of change in analyte concentration, which should not change at a rate greater than a predetermined threshold amount. If the rate of change of analyte concentration exceeds the predefined threshold, an indication maybe displayed or otherwise transmitted to indicate this fact. In certain embodiments, an alarm is activated to alert a user if the rate of change of analyte concentration exceeds the predefined threshold.

As demonstrated herein, the present embodiments are useful in connection with a device that is used to measure or monitor an analyte (e.g., glucose), such as any such device described herein. The embodiments described herein can be used to monitor and/or process information regarding any number of one or more different analytes. Analytes that may be monitored include, but are not limited to, acetyl choline, amylase, bilirubin, carbon dioxide, cholesterol, chorionic gonadotropin, glycosylated hemoglobin (HbAlc), creatine kinase (e.g., CK-MB), creatine, creatinine, DNA, fructosamine, glucose, glucose derivatives, glutamine, growth hormones, hormones, ketones, ketone bodies, lactate, oxygen, peroxide, prostate-specific antigen, proteins, prothrombin, RNA, thyroid stimulating hormone, troponin, and any combination thereof. The concentration of drugs, such as, for example, antibiotics (e.g., gentamicin, vancomycin, and the like), digitoxin, digoxin, drugs of abuse, theophylline, and warfarin, may be monitored in addition to or instead of analytes. In embodiments that monitor more than one analyte, the analytes may be monitored at the same or different times. These methods may also be used in connection with a device that is used to measure or monitor another analyte (e.g., ketones, ketone bodies, HbAlc, and the like), including oxygen, carbon dioxide, proteins, drugs, or another moiety of interest, for example, or any combination thereof, found in bodily fluid, including subcutaneous fluid, dermal fluid, interstitial fluid, or other bodily fluid of interest, for example, or any combination thereof. In general, the device is in good contact, such as thorough and substantially continuous contact, with the bodily fluid.

According to embodiments of the present disclosure, the measurement sensor is one suited for electrochemical measurement of analyte concentration, for example glucose concentration, in a bodily fluid. In these embodiments, the measurement sensor includes at least a working electrode and a counter electrode. Other embodiments may further include a reference electrode. The working electrode is typically associated with a glucose-responsive enzyme. A mediator may also be included. In certain embodiments, hydrogen peroxide, which may be characterized as a mediator, is produced by a reaction of the sensor and may be used to infer the concentration of glucose. In some embodiments, a mediator is added to the sensor by a manufacturer, e.g., is included with the sensor prior to use. The redox mediator may be disposed relative to the working electrode and is capable of transferring electrons between a compound and a working electrode, either directly or indirectly. The redox mediator may be, for example, immobilized on the working electrode, e.g., entrapped on a surface or chemically bound to a surface.

Embodiments of the subject disclosure include in vivo analyte monitoring devices, systems, kits, and processes of analyte monitoring and making analyte monitoring devices, systems, and kits. Included are on-body (e.g., at least a portion of a device, system or a component thereof is maintained on the body of or in close proximity to a user to monitor an analyte), physiological monitoring devices configured for real time measurement/monitoring of desired analyte level such as a glucose level over one or more predetermined time periods such as one or more predetermined monitoring time periods. Embodiments include transcutaneously positioned analyte sensors that are electrically coupled with electronics provided in a housing that is designed to be attached to the body of a user, for example, to a skin surface of a user, during the usage life of the analyte sensors or predetermined monitoring time periods. For example, on body electronics assembly include electronics that are operatively coupled to an analyte sensor and provided in a housing for placement on the body of a user.

Such device and system with analyte sensors provide continuous or periodic analyte level monitoring that is executed automatically, or semi-automatically by control logic or routines programmed or programmable in the monitoring devices or systems. As used herein, continuous, automatic, and/or periodic monitoring refer to the in vivo monitoring or detection of analyte levels with transcutaneously positioned analyte sensors.

In certain embodiments, the results of the in vivo monitored analyte level are automatically communicated from an electronics unit to another device or component of the system. That is, when the results are available, the results are automatically transmitted to a display device (or other user interaction device) of the system, for example, according to a fixed or dynamic data communication schedule executed by the system. In other embodiments, the results of the in vivo monitored analyte level are not automatically communicated, transferred, or output to one or more device or component of the system. In such embodiments, the results are provided only in response to a query to the system. That is, the results are communicated to a component or a device of the system only in response to the query or request for such results. In certain embodiments, the results of the in vivo monitoring may be logged or stored in a memory of the system and only communicated or transferred to another device or component of the system after the one or more predetermined monitoring time periods.

Embodiments include software and/or hardware to transform any one of the devices, components, or systems into any one of the other devices, components, or systems, where such transformation may be user-configurable after manufacture. Transformation modules that include hardware and/or software to accomplish such transformation may be mateable to a given system to transform it.

Embodiments include electronics coupled to analyte sensors that provide functionalities to operate the analyte sensors for monitoring analyte levels over a predetermined monitoring time period such as for example, about 30 days (or more in certain embodiments), about 14 days, about 10, about 5 days, about 1 day, less than about 1 day. In certain embodiments, the usage life of each analyte sensor may be the same as or different from the predetermined monitoring time periods. Components of the electronics to provide the functionalities to operate the analyte sensors in certain embodiments include control logic or microprocessors coupled to a power supply such as a battery to drive the in vivo analyte sensors to perform electrochemical reactions to generate resulting signals that correspond to the monitored analyte levels.

Electronics may also include other components such as one or more data storage units or memory (volatile and/or non-volatile), communication component(s) to communicate information corresponding to the in vivo monitored analyte level to a display device automatically when the information is available, or selectively in response to a request for the monitored analyte level information. Data communication between display devices and the electronics coupled to the sensor in certain embodiments are implemented serially (e.g., data transfer between them are not performed at the same time), or in parallel. For example, the display device in certain embodiments is configured to transmit a signal or data packet to the electronics coupled to the sensor, and upon receipt of the transmitted signal or data packet, the electronics coupled to the sensor communicates back to the display device. In certain embodiments, a display device may be configured to provide RF power and data/signals continually, and detecting or receiving one or more return data packet or signal from electronics coupled to the sensor when it is within a predetermined RF power range from the display device. In certain embodiments, the display device and the electronics coupled to the sensor may be configured to transmit one or more data packets at the same time.

Embodiments also include electronics programmed to store or log in the one or more data storage units or a memory data associated with the monitored analyte level over the sensor usage life or during a monitoring time period. During the monitoring time period, information corresponding to the monitored analyte level may be stored but not displayed or output during the sensor usage life, and the stored data may be later retrieved from memory at the end of the sensor usage life or after the expiration of the predetermined monitoring time period, e.g., for clinical analysis, therapy management, etc.

In certain embodiments, the predetermined monitoring time period is the same as the sensor usage life time period such that when an analyte sensor usage life expires (thus no longer used for in vivo analyte level monitoring), the predetermined monitoring time period ends. In certain embodiments, the predetermined monitoring time period may include multiple sensor usage life time periods such that when an analyte sensor usage life expires, the predetermined monitoring time period has not ended, and the expired analyte sensor is replaced with another analyte sensor during the same predetermined monitoring time period. The predetermined monitoring time period in certain embodiments includes the replacement of multiple analyte sensors for use.

Analyte level trend information in certain embodiments is generated or constructed based on stored analyte level information spanning a time period (e.g., corresponding to a temperature time period, or other) and communicated to the display device. The trend information in certain embodiments is output graphically and/or audibly and/or tactilely, and/or numerically and/or otherwise presented on a user interface of the display device to provide indication of the analyte level variation during this time period.

Embodiments include wirelessly communicating analyte level information from an on body electronics device to a second device such as a display device. Examples of communication protocols between on body electronics and the display device may include radio frequency identification (RFID) protocols or RF communication protocols. Example RFID protocols include but are not limited to Near Field Communication (NFC) protocols that include short communication ranges (e.g., about 12 inches or less, or about 6 inches or less, or about 3 inches or less, or about 2 inches or less), high frequency wireless communication protocols, far field communication protocols (e.g., using ultra high frequency (UHF) communication systems) for providing signals or data from on body electronics to display devices.

Communication protocols in certain embodiments use 433 MHz frequency, 13.56 MHz frequency, 2.45 GHz frequency, or other suitable frequencies for wireless communication between the on body electronics that includes electronics coupled to an analyte sensor, and one or more display devices and/or other devices such as a personal computer. While certain data transmission frequencies and/or data communication ranges are described above, within the scope of the present disclosure, other data suitable data transmission frequencies and/or data communication ranges can be used between the various devices in the analyte monitoring system.

Embodiments include data management systems including, for example, a data network and/or personal computer and/or a server terminal and/or one or more remote computers that are configured to receive collected or stored data from the display device for presenting analyte information and/or further processing in conjunction with the physiological monitoring for health management. For example, a display device may include one or more communication ports (hard wired or wireless) for connection to a data network or a computer terminal to transfer collected or stored analyte related data to another device and/or location. Analyte related data in certain embodiments are directly communicated from the electronics coupled to the analyte sensor to a personal computer, server terminal, and/or remote computers over the data network.

In certain embodiments, analyte information is only provided or evident to a user (provided at a user interface device) when desired by the user even though an in vivo analyte sensor automatically and/or continuously monitors the analyte level in vivo, e.g., the sensor automatically monitors analyte such as glucose on a pre-defined time interval over its usage life. For example, an analyte sensor may be positioned in vivo and coupled to on body electronics for a given sensing period, e.g., about 14 days, about 21 days, or about 30 days or more. In certain embodiments, the sensor-derived analyte information is automatically communicated from the sensor electronics assembly to a remote monitor device or display device for output to a user throughout the 14 day period according to a schedule programmed at the on body electronics (e.g., about every 1 minute or about every 5 minutes or about every 10 minutes, or the like). In certain embodiments, sensor-derived analyte information is only communicated from the sensor electronics assembly to a remote monitor device or display device at user-determined times, e.g., whenever a user decides to check analyte information. At such times, a communications system is activated and sensor-derived information is then sent from the on body electronics to the remote device or display device. For example, using RFID communication, in one embodiment, the user positions the display device in close proximity to the on body electronics coupled to the analyte sensor and receives the real time (and/or historical) analyte level information from the on body electronics (herein after referred to as "on demand" reading).

In still other embodiments, the information may be communicated from a first device to a second device automatically and/or continuously when the analyte information is available, and the second device stores or logs the received information without presenting or outputting the information to the user. In such embodiments, the information is received by the second device from the first device when the information becomes available (e.g., when the sensor detects the analyte level according to a time schedule). However, the received information is initially stored in the second device and only output to a user interface or an output component of the second device (e.g., display) upon detection of a request for the information on the second device.

Accordingly, in certain embodiments once a sensor electronics assembly is placed on the body so that at least a portion of the in vivo sensor is in contact with bodily fluid and the sensor is electrically coupled to the electronics unit, sensor derived analyte information may be communicated from the on body electronics to a display device on-demand by powering on the display device (or it may be continually powered), and executing a software algorithm stored in and accessed from a memory of the display device, to generate one or more request commands, control signal or data packet to send to the on body electronics. The software algorithm executed under, for example, the control of the microprocessor or application specific integrated circuit (ASIC) of the display device may include routines to detect the position of the on body electronics relative to the display device to initiate the transmission of the generated request command, control signal and/or data packet.

Display devices may also include programming stored in memory for execution by one or more microprocessors and/or ASICs to generate and transmit the one or more request command, control signal or data packet to send to the on body electronics in response to a user activation of an input mechanism on the display device such as depressing a button on the display device, triggering a soft button associated with the data communication function, and so on. The input mechanism may be alternatively or additionally provided on or in the on body electronics which may be configured for user activation. In certain embodiments, voice commands or audible signals may be used to prompt or instruct the microprocessor or ASIC to execute the software routine(s) stored in the memory to generate and transmit the one or more request command, control signal or data packet to the on body device. In the embodiments that are voice activated or responsive to voice commands or audible signals, on body electronics and/or display device includes a microphone, a speaker, and processing routines stored in the respective memories of the on body electronics and/or the display device to process the voice commands and/or audible signals. In certain embodiments, positioning the on body device and the display device within a predetermined distance (e.g., close proximity) relative to each other initiates one or more software routines stored in the memory of the display device to generate and transmit a request command, control signal or data packet.

Different types and/or forms and/or amounts of information may be sent for each on demand reading, including but not limited to one or more of current analyte level information (e.g., real time or the most recently obtained analyte level information temporally corresponding to the time the reading is initiated), rate of change of an analyte over a predetermined time period, rate of the rate of change of an analyte (acceleration in the rate of change), historical analyte information corresponding to analyte information obtained prior to a given reading and stored in memory of the assembly. Some or all of real time, historical, rate of change, rate of rate of change (such as acceleration or deceleration) information may be sent to a display device for a given reading. In certain embodiments, the type and/or form and/or amount of information sent to a display device may be preprogrammed and/or unchangeable (e.g., preset at manufacturing), or may not be preprogrammed and/or unchangeable so that it may be selectable and/or changeable in the field one or more times (e.g., by activating a switch of the system, etc.).

Accordingly, in certain embodiments, for each on demand reading, a display device will output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of on body electronics (e.g., in the form of a graphical trace). Additionally, the on skin or sensor temperature reading or measurement associated with each on demand reading may be communicated from the on body electronics to the display device. The temperature reading or measurement, however, may not be output or displayed on the display device, but rather, used in conjunction with a software routine executed by the display device to correct or compensate the analyte measurement output to the user on the display device.

As described, embodiments include in vivo analyte sensors and on body electronics that together provide body wearable sensor electronics assemblies. In certain embodiments, in vivo analyte sensors are fully integrated with on body electronics (fixedly connected during manufacture), while in other embodiments they are separate but connectable post manufacture (e.g., before, during or after sensor insertion into a body). On body electronics may include an in vivo glucose sensor, electronics, battery, and antenna encased (except for the sensor portion that is for in vivo positioning) in a waterproof housing that includes or is attachable to an adhesive pad. In certain embodiments, the housing withstands immersion in about one meter of water for up to at least 30 minutes. In certain embodiments, the housing withstands continuous underwater contact, e.g., for longer than about 30 minutes, and continues to function properly according to its intended use, e.g., without water damage to the housing electronics where the housing is suitable for water submersion.

Embodiments include sensor insertion devices, which also may be referred to herein as sensor delivery units, or the like. Insertion devices may retain on body electronics assemblies completely in an interior compartment, e.g., an insertion device may be "pre-loaded" with on body electronics assemblies during the manufacturing process (e.g., on body electronics may be packaged in a sterile interior compartment of an insertion device). In such embodiments, insertion devices may form sensor assembly packages (including sterile packages) for pre-use or new on body electronics assemblies, and insertion devices configured to apply on body electronics assemblies to recipient bodies.

Embodiments include portable handheld display devices, as separate devices and spaced apart from an on body electronics assembly, that collect information from the assemblies and provide sensor derived analyte readings to users. Such devices can be referred to in a number of ways that have already been set forth. Certain embodiments may include an integrated in vitro analyte meter. In certain embodiments, display devices include one or more wired or wireless communications ports such as USB, serial, parallel, or the like, configured to establish communication between a display device and another unit (e.g., on body electronics, power unit to recharge a battery, a PC, etc.). For example, a display device communication port may enable charging a display device battery with a respective charging cable and/or data exchange between a display device and its compatible informatics software.

Compatible informatics software in certain embodiments include, for example, but not limited to stand alone or network connection enabled data management software program, resident or running on a display device, personal computer, a server terminal, for example, to perform data analysis, charting, data storage, data archiving and data communication as well as data synchronization. Informatics software in certain embodiments may also include software for executing field upgradable functions to upgrade firmware of a display device and/or on body electronics unit to upgrade the resident software on the display device and/or the on body electronics unit, e.g., with versions of firmware that include additional features and/or include software bugs or errors fixed, etc.

Embodiments include programming embedded on a computer readable medium, e.g., computer-based application software (may also be referred to herein as informatics software or programming or the like) that processes analyte information obtained from the system and/or user self-reported data. Application software may be installed on a host computer such as a mobile telephone, PC, an Internet-enabled human interface device such as an Internet-enabled phone, personal digital assistant, or the like, by a display device or an on body electronics unit. Informatics programming may transform data acquired and stored on a display device or on body unit for use by a user.

As described in detail below, embodiments include devices, systems, kits and/or methods to monitor one or more physiological parameters such as, for example, but not limited to, analyte levels, temperature levels, heart rate, user activity level, over a predetermined monitoring time period. Also provided are methods of manufacturing. Predetermined monitoring time periods may be less than about 1 hour, or may include about 1 hour or more, e.g., about a few hours or more, e.g., about a few days of more, e.g., about 3 or more days, e.g., about 5 days or more, e.g., about 7 days or more, e.g., about 10 days or more, e.g., about 14 days or more, e.g., about several weeks, e.g., about 1 month or more. In certain embodiments, after the expiration of the predetermined monitoring time period, one or more features of the system may be automatically deactivated or disabled at the on body electronics assembly and/or display device.

For example, a predetermined monitoring time period may begin with positioning the sensor in vivo and in contact with a bodily fluid such as interstitial fluid, and/or with the initiation (or powering on to full operational mode) of the on body electronics. Initialization of on body electronics may be implemented with a command generated and transmitted by a display device in response to the activation of a switch and/or by placing the display device within a predetermined distance (e.g., close proximity) to the on body electronics, or by user manual activation of a switch on the on body electronics unit, e.g., depressing a button, or such activation may be caused by the insertion device, e.g., as described in U.S. Patent Publication No. 2011/0213225A1, the disclosure of which is incorporated by reference in its entirety.

When initialized in response to a received command from a display device, the on body electronics retrieves and executes from its memory software routine to fully power on the components of the on body electronics, effectively placing the on body electronics in full operational mode in response to receiving the activation command from the display device. For example, prior to the receipt of the command from the display device, a portion of the components in the on body electronics may be powered by its internal power supply such as a battery while another portion of the components in the on body electronics may be in powered down or low power including no power, inactive mode, or all components may be in an inactive mode, powered down mode. Upon receipt of the command, the remaining portion (or all) of the components of the on body electronics is switched to active, fully operational mode.

Embodiments of on body electronics may include one or more printed circuit boards with electronics including control logic implemented in ASIC, microprocessors, memory, and the like, and transcutaneously positionable analyte sensors forming a single assembly. On body electronics may be configured to provide one or more signals or data packets associated with a monitored analyte level upon detection of a display device of the analyte monitoring system within a predetermined proximity for a period of time (for example, about 2 minutes, e.g., 1 minute or less, e.g., about 30 seconds or less, e.g., about 10 seconds or less, e.g., about 5 seconds or less, e.g., about 2 seconds or less) and/or until a confirmation, such as an audible and/or visual and/or tactile (e.g., vibratory) notification, is output on the display device indicating successful acquisition of the analyte related signal from the on body electronics. A distinguishing notification may also be output for unsuccessful acquisition in certain embodiments.

In certain embodiments, the monitored analyte level may be correlated and/or converted to glucose levels in blood or other bodily fluids. Such conversion may be accomplished by the on body electronics, but in other embodiments, will be accomplished with display device electronics.

Referring now to FIG. 1, the analyte monitoring system 100 includes an analyte sensor 101, a data processing unit 102 connectable to the sensor 101, and a primary receiver unit or display device 104. In some instances, the primary display device 104 is configured to communicate with the data processing unit 102 via a communication link 103. In certain embodiments, the primary display device 104 may be further configured to transmit data to a data processing terminal 105 to evaluate or otherwise process or format data received by the primary display device 104. The data processing terminal 105 may be configured to receive data directly from the data processing unit 102 via a communication link 107, which may optionally be configured for bi-directional communication. Further, the data processing unit 102 may include electronics and a transmitter or a transceiver to transmit and/or receive data to and/or from the primary display device 104 and/or the data processing terminal 105 and/or optionally a secondary receiver unit or display device 106.

Also shown in FIG. 1 is an optional secondary display device 106 which is operatively coupled to the communication link 103 and configured to receive data transmitted from the data processing unit 102. The secondary display device 106 may be configured to communicate with the primary display device 104, as well as the data processing terminal 105. In certain embodiments, the secondary display device 106 may be configured for bi-directional wireless communication with each of the primary display device 104 and the data processing terminal 105. As discussed in further detail below, in some instances, the secondary display device 106 may be a de-featured receiver as compared to the primary display device 104, for instance, the secondary display device 106 may include a limited or minimal number of functions and features as compared with the primary display device 104. As such, the secondary display device 106 may include a smaller (in one or more, including all, dimensions), compact housing or embodied in a device including a wrist watch, arm band, PDA, mp3 player, cell phone, etc., for example. Alternatively, the secondary display device 106 may be configured with the same or substantially similar functions and features as the primary display device 104. The secondary display device 106 may include a docking portion configured to mate with a docking cradle unit for placement by, e.g., the bedside for night time monitoring, and/or a bi-directional communication device. A docking cradle may recharge a power supply.

Only one analyte sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a user for analyte monitoring at the same or different times. In certain embodiments, analyte information obtained by a first sensor positioned in a user may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit 102 may include a fixation element, such as an adhesive or the like, to secure it to the user's body. A mount (not shown) attachable to the user and mateable with the data processing unit 102 may be used. For example, a mount may include an adhesive surface. The data processing unit 102 performs data processing functions, where such functions may include, but are not limited to, filtering and encoding of data signals, each of which corresponds to a sampled analyte level of the user, for transmission to the primary display device 104 via the communication link 103. In some embodiments, the sensor 101 or the data processing unit 102 or a combined sensor/data processing unit may be wholly implantable under the skin surface of the user.

In certain embodiments, the primary display device 104 may include an analog interface section including an RF receiver and an antenna that is configured to communicate with the data processing unit 102 via the communication link 103, and a data processing section for processing the received data from the data processing unit 102 including data decoding, error detection and correction, data clock generation, data bit recovery, etc., or any combination thereof.

In operation, the primary display device 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels monitored by the sensor 101.

Referring again to FIG. 1, the data processing terminal 105 may include a personal computer, a portable computer including a laptop or a handheld device (e.g., a personal digital assistant (PDA), a telephone including a cellular phone (e.g., a multimedia and Internet-enabled mobile phone including an iPhone®, a Blackberry®, an Android phone, or similar phone), an mp3 player (e.g., an iPOD™, etc.), a pager, and the like), and/or a drug delivery device (e.g., an infusion device), each of which may be configured for data communication with the display devices via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include a drug delivery device (e.g., an infusion device) such as an insulin infusion pump or the like, which may be configured to administer a drug (e.g., insulin) to the user, and which may be configured to communicate with the primary display device 104 for receiving, among others, the measured analyte level. Alternatively, the primary display device 104 may be configured to integrate an infusion device therein so that the primary display device 104 is configured to administer an appropriate drug (e.g., insulin) to users, for example, for administering and modifying basal profiles, as well as for determining appropriate boluses for administration based on, among others, the detected analyte levels received from the data processing unit 102. An infusion device may be an external device or an internal device, such as a device wholly implantable in a user.

In certain embodiments, the data processing terminal 105, which may include an infusion device, e.g., an insulin pump, may be configured to receive the analyte signals from the data processing unit 102, and thus, incorporate the functions of the primary display device 104 including data processing for managing the user's insulin therapy and analyte monitoring. In certain embodiments, the communication link 103, as well as one or more of the other communication interfaces shown in FIG. 1, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

Figure 2:
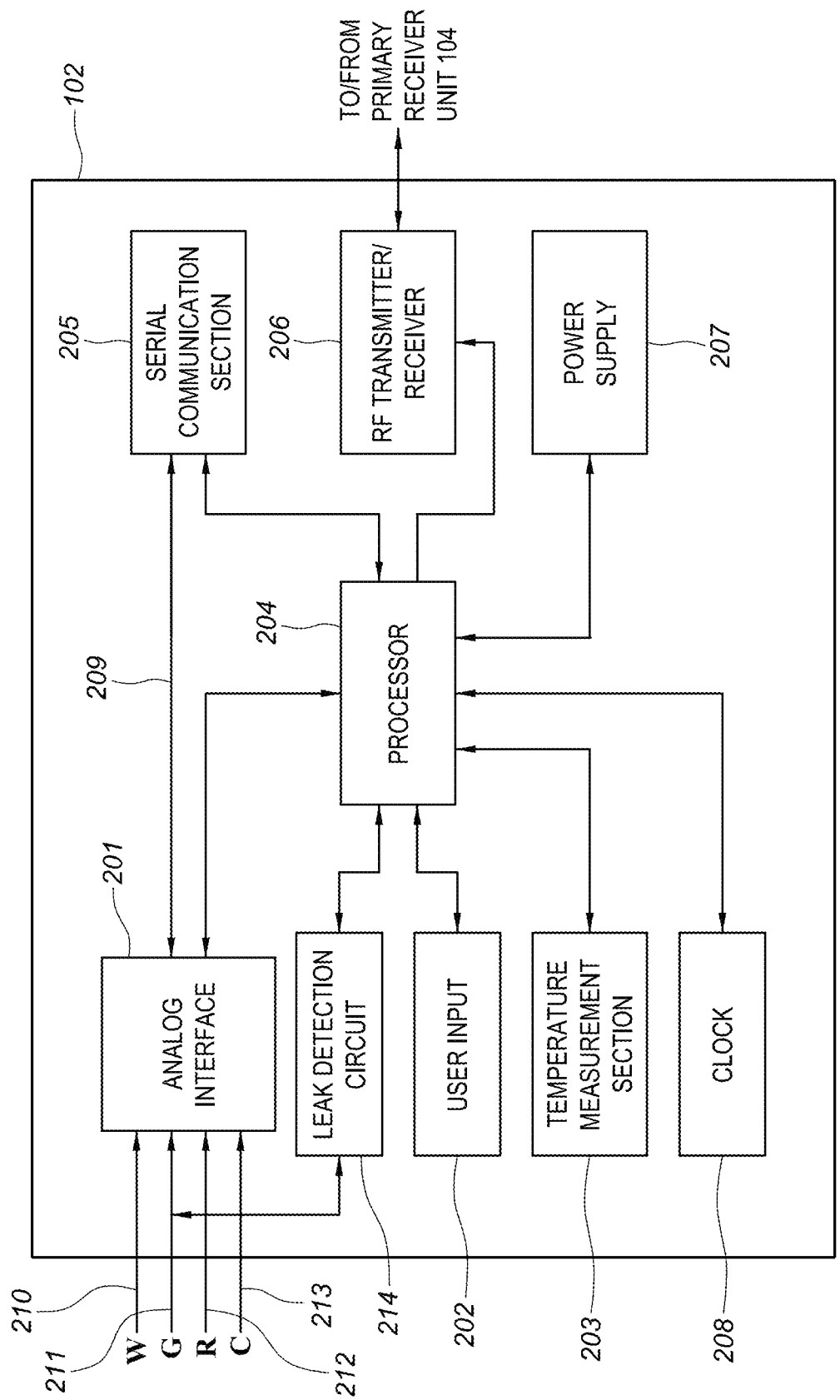
FIG. 2 is a block diagram depicting an example embodiment of a data processing unit.

FIG. 2 is a block diagram depicting an embodiment of a data processing unit 102 of the analyte monitoring system shown in FIG. 1. User input and/or interface components may be included or a data processing unit may be free of user input and/or interface components. In certain embodiments, one or more application-specific integrated circuits (ASIC) (e.g., having processing circuitry and non-transitory memory for storing software instructions for execution by the processing circuitry) may be used to implement one or more functions or routines associated with the operations of the data processing unit (and/or display device) using for example one or more state machines and buffers.

As can be seen in the embodiment of FIG. 2, the analyte sensor 101 (FIG. 1) includes four contacts, three of which are electrodes: a working electrode (W) 210, a reference electrode (R) 212, and a counter electrode (C) 213, each operatively coupled to the analog interface 201 of the data processing unit 102. This embodiment also shows an optional guard contact (G) 211. Fewer or greater electrodes may be employed. For example, the counter and reference electrode functions may be served by a single counter/reference electrode. In some cases, there may be more than one working electrode and/or reference electrode and/or counter electrode, etc.

Figure 3:
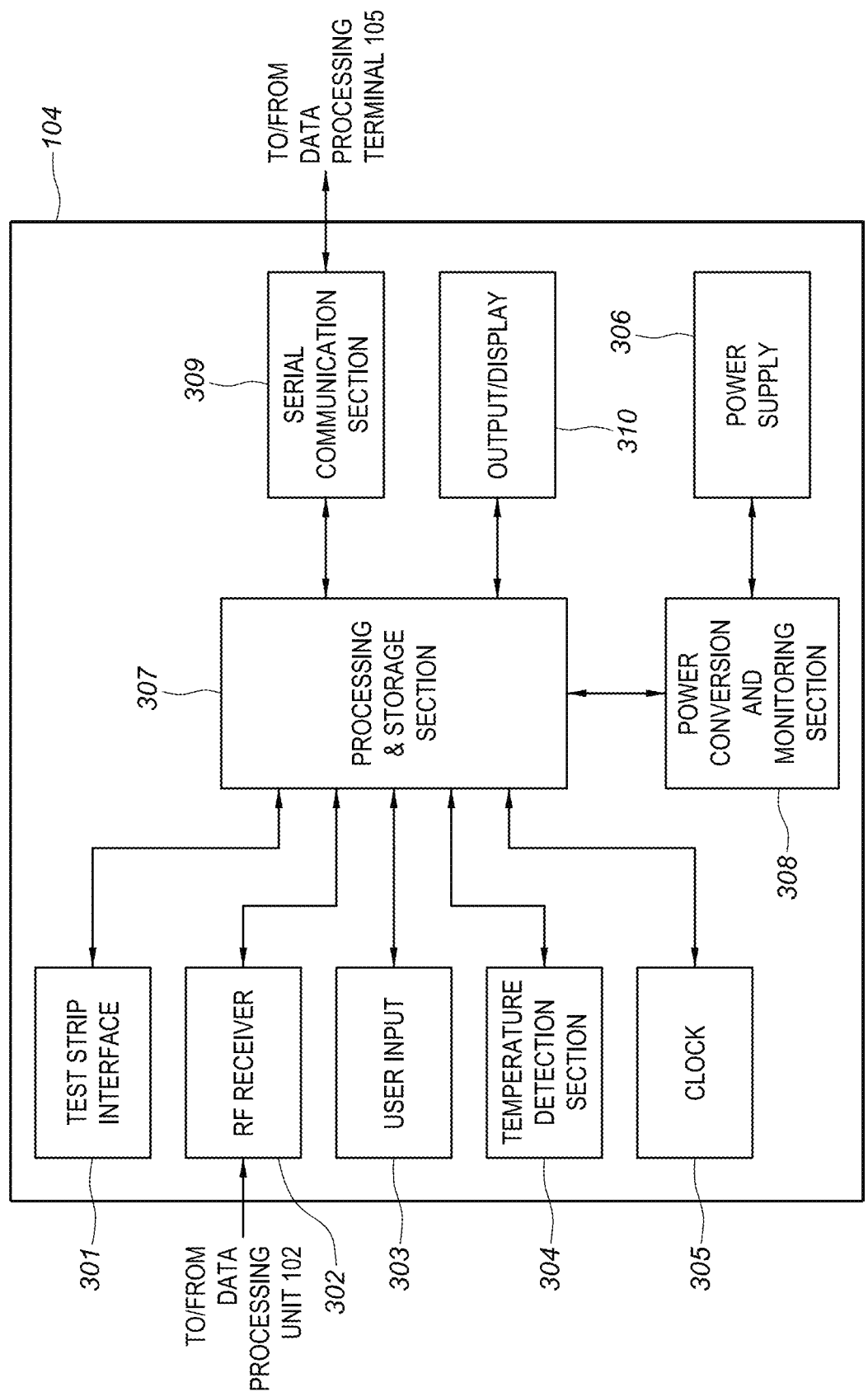
FIG. 3 is a block diagram depicting an example embodiment of a display device.

FIG. 3 is a block diagram of an embodiment of a receiver/monitor unit such as the primary display device 104 of the analyte monitoring system shown in FIG. 1. The primary display device 104 includes one or more of: a test strip interface 301, an RF receiver 302, a user input 303, an optional temperature detection section 304, and a clock 305, each of which is operatively coupled to a processing and storage section 307 (that can include processing circuitry and non-transitory memory storing software instructions for execution by the processing circuitry). The primary display device 104 also includes a power supply 306 operatively coupled to a power conversion and monitoring section 308. Further, the power conversion and monitoring section 308 is also coupled to the processing and storage section 307. Moreover, also shown are a receiver serial communication section 309, and an output 310, each operatively coupled to the processing and storage section 307. The primary display device 104 may include user input and/or interface components or may be free of user input and/or interface components.

In certain embodiments, the test strip interface 301 includes an analyte testing portion (e.g., a glucose level testing portion) to receive a blood (or other body fluid sample) analyte test or information related thereto. For example, the test strip interface 301 may include a test strip port to receive a test strip (e.g., a glucose test strip). The device may determine the analyte level of the test strip, and optionally display (or otherwise notice) the analyte level on the output 310 of the primary display device 104. Any suitable test strip may be employed, e.g., test strips that only require a very small amount (e.g., 3 microliters or less, e.g., 1 microliter or less, e.g., 0.5 microliters or less, e.g., 0.1 microliters or less), of applied sample to the strip in order to obtain accurate glucose information. Glucose information obtained by an in vitro glucose testing device may be used for a variety of purposes, computations, etc. For example, the information may be used to calibrate sensor 101 (FIG. 1), confirm results of sensor 101 to increase the confidence thereof (e.g., in instances in which information obtained by sensor 101 is employed in therapy related decisions), etc.

In further embodiments, the data processing unit 102 and/or the primary display device 104 and/or the secondary display device 106, and/or the data processing terminal/infusion device 105 may be configured to receive the analyte value wirelessly over a communication link from, for example, a blood glucose meter. In further embodiments, a user manipulating or using the analyte monitoring system 100 may manually input the analyte value using, for example, a user interface (for example, a keyboard, keypad, voice commands, and the like) incorporated in one or more of the data processing unit 102, the primary display device 104, secondary display device 106, or the data processing terminal/infusion device 105.

FIG. 4 schematically shows an embodiment of an analyte sensor 400 in accordance with the embodiments of the present disclosure. This sensor embodiment includes electrodes 401, 402 and 403 on a base 404. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include, but are not limited to, any one or more of aluminum, carbon (including graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The analyte sensor 400 may be wholly implantable in a user or may be configured so that only a portion is positioned within (internal) a user and another portion outside (external) a user. For example, the sensor 400 may include a first portion positionable above a surface of the skin 410, and a second portion positioned below the surface of the skin. In such embodiments, the external portion may include contacts (connected to respective electrodes of the second portion by traces) to connect to another device also external to the user such as a sensor control device. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

FIG. 5A shows a perspective view of an embodiment of an analyte sensor 500 having a first portion (which in this embodiment may be characterized as a major portion) positionable above a surface of the skin 510, and a second portion (which in this embodiment may be characterized as a minor portion) that includes an insertion tip 530 positionable below the surface of the skin, e.g., penetrating through the skin and into, e.g., the subcutaneous space 520, in contact with the user's biofluid, such as interstitial fluid. Contact portions of a working electrode 511, a reference electrode 512, and a counter electrode 513 are positioned on the first portion of the sensor 500 situated above the skin surface 510. A working electrode 501, a reference electrode 502, and a counter electrode 503 are shown at the second portion of the sensor 500 and particularly at the insertion tip 530. Traces may be provided from the electrodes at the tip 530 to the contacts, as shown in FIG. 5A. It is to be understood that greater or fewer electrodes may be provided on a sensor. For example, a sensor may include more than one working electrode and/or the counter and reference electrodes may be a single counter/reference electrode, etc.

FIG. 5B shows a cross sectional view of a portion of the sensor 500 of FIG. 5A. The electrodes 501, 509/502 and 503, of the sensor 500 as well as the substrate and the dielectric layers are provided in a layered configuration or construction. For example, as shown in FIG. in one embodiment, the sensor 500 (such as the analyte sensor 101 of FIG. 1), includes a substrate layer 504, and a first conducting layer 501 such as carbon, gold, etc., disposed on at least a portion of the substrate layer 504, and which may provide the working electrode. Also shown disposed on at least a portion of the first conducting layer 501 is a sensing region 508.

A first insulation layer 505, such as a first dielectric layer in certain embodiments, is disposed or layered on at least a portion of the first conducting layer 501, and further, a second conducting layer 509 may be disposed or stacked on top of at least a portion of the first insulation layer (or dielectric layer) 505. As shown in FIG. 5B, the second conducting layer 509 in conjunction with a second conducting material 502, such as a layer of silver/silver chloride (Ag/AgCl), may provide the reference electrode.

A second insulation layer 506, such as a second dielectric layer in certain embodiments, may be disposed or layered on at least a portion of the second conducting layer 509. Further, a third conducting layer 503 may be disposed on at least a portion of the second insulation layer 506 and may provide the counter electrode 503. Finally, a third insulation layer 507 may be disposed or layered on at least a portion of the third conducting layer 503. In this manner, the sensor 500 may be layered such that at least a portion of each of the conducting layers is separated by a respective insulation layer (for example, a dielectric layer). The embodiments of FIGS. 5A and 5B show the layers having different lengths. In certain instances, some or all of the layers may have the same or different lengths and/or widths.

In certain embodiments, some or all of the electrodes 501, 502, 503 may be provided on the same side of the substrate 504 in the layered construction as described above, or alternatively, may be provided in a co-planar manner such that two or more electrodes may be positioned on the same plane (e.g., side-by side (e.g., parallel) or angled relative to each other) on the substrate 504. For example, co-planar electrodes may include a suitable spacing therebetween and/or include a dielectric material or insulation material disposed between the conducting layers/electrodes.

Furthermore, in certain embodiments, one or more of the electrodes 501, 502, 503 may be disposed on opposing sides of the substrate 504. In such embodiments, contact pads may be on the same or different sides of the substrate. For example, an electrode may be on a first side and its respective contact may be on a second side, e.g., a trace connecting the electrode and the contact may traverse through the substrate.

Figure 6:
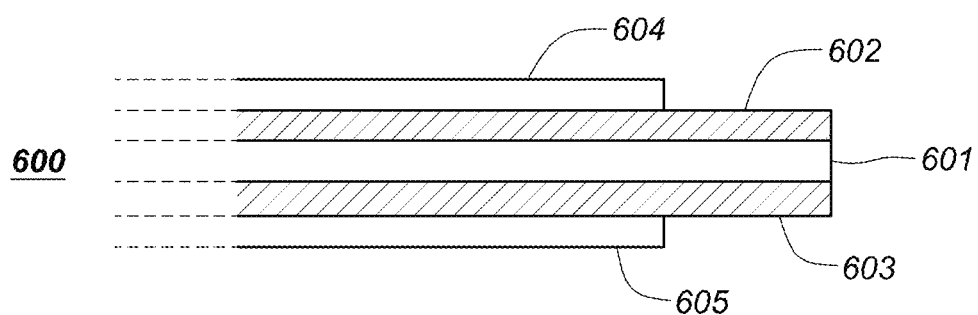
FIGS. 6-9 are cross-sectional views depicting example embodiments of analyte sensors.

Embodiments of a double-sided, stacked sensor configuration which may be utilized in connection with the present disclosure are described below with reference to FIGS. 6-8. FIG. 6 shows a cross-sectional view of a distal portion of a double-sided analyte sensor 600. Analyte sensor 600 includes an at least generally planar insulative base substrate 601, e.g., an at least generally planar dielectric base substrate, having a first conductive layer 602 which substantially covers the entirety of a first surface area, e.g., the top surface area, of insulative substrate 601, e.g., the conductive layer substantially extends the entire length of the substrate to the distal edge and across the entire width of the substrate from side edge to side edge. A second conductive layer 603 substantially covers the entirety of a second surface, e.g., the bottom side, of insulative base substrate 601. However, one or both of the conductive layers may terminate proximally of the distal edge and/or may have a width which is less than that of insulative substrate 601 where the width ends a selected distance from the side edges of the substrate, which distance may be equidistant or vary from each of the side edges.

One of the first or second conductive layers, e.g., first conductive layer 602, may be configured to include the sensor's working electrode. The opposing conductive layer, here, second conductive layer 603, may be configured to include a reference and/or counter electrode. Where conductive layer 603 serves as either a reference or counter electrode, but not both, a third electrode may optionally be provided either on a surface area of the proximal portion of the sensor (not shown), on a separate substrate, or as an additional conductive layer positioned either above or below conductive layer 602 or 603 and separated from those layers by an insulative layer or layers. For example, in some embodiments, where analyte sensor 600 is configured to be partially implanted, conductive layer 603 may be configured to include a reference electrode, and a third electrode (not shown) and present only on a non-implanted proximal portion of the sensor may be configured to include the sensor's counter electrode.

A first insulative layer 604 covers at least a portion of conductive layer 602 and a second insulative layer 605 covers at least a portion of conductive layer 603. In one embodiment, at least one of first insulative layer 604 and second insulative layer 605 does not extend to the distal end of analyte sensor 600 leaving an exposed region of the conductive layer or layers.

Figure 7:
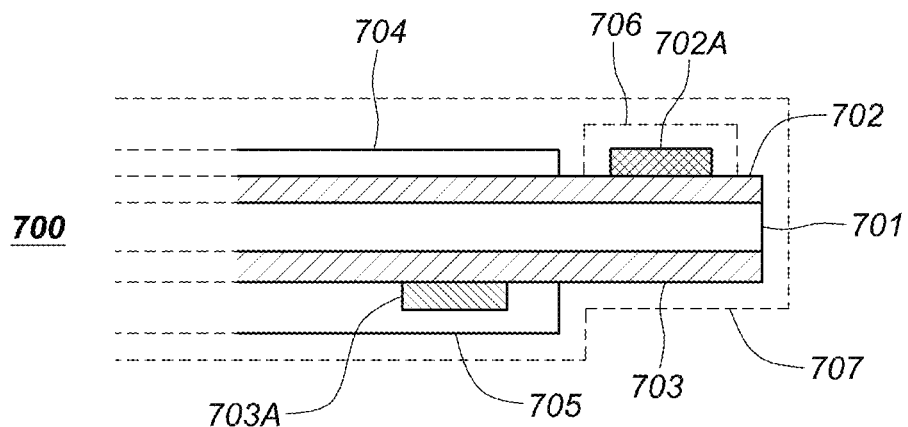

FIG. 7 shows a cross-sectional view of a distal portion of a double-sided analyte sensor 700 including an at least generally planar insulative base substrate 701, e.g., an at least generally planar dielectric base substrate, having a first conductive layer 702 which substantially covers the entirety of a first surface area, e.g., the top surface area, of insulative substrate 701, e.g., the conductive layer substantially extends the entire length of the substrate to the distal edge and across the entire width of the substrate from side edge to side edge. A second conductive layer 703 substantially covers the entirety of a second surface, e.g., the bottom side, of insulative base substrate 701. However, one or both of the conductive layers may terminate proximally of the distal edge and/or may have a width which is less than that of insulative substrate 701 where the width ends a selected distance from the side edges of the substrate, which distance may be equidistant or vary from each of the side edges.

In the embodiment of FIG. 7, conductive layer 702 is configured to include a working electrode which includes a sensing region 702A disposed on at least a portion of the first conductive layer 702 as shown and as discussed in greater detail below. While a single sensing region 702A is shown, it should be noted that in other embodiments a plurality of spatially separated sensing elements may be utilized.

In the embodiment of FIG. 7, conductive layer 703 is configured to include a reference electrode which includes a secondary layer of conductive material 703A, e.g., Ag/AgCl, disposed over a distal portion of conductive layer 703.

A first insulative layer 704 covers a portion of conductive layer 702 and a second insulative layer 705 covers a portion of conductive layer 703. First insulative layer 704 does not extend to the distal end of analyte sensor 700 leaving an exposed region of the conductive layer where the sensing region 702A is positioned. The insulative layer 705 on the bottom/reference electrode side of the sensor, may extend any suitable length of the sensor's distal section, e.g., it may extend the entire length of both of the primary and secondary conductive layers or portions thereof. For example, as illustrated in FIG. 7, bottom insulative layer 705 extends over the entire bottom surface area of secondary conductive material 703A but terminates proximally of the distal end of the length of the conductive layer 703. It is noted that at least the ends of the secondary conductive material 703A which extend along the side edges of the substrate 701 are not covered by insulative layer 705 and, as such, are exposed to the environment when in operative use.

Figure 8:
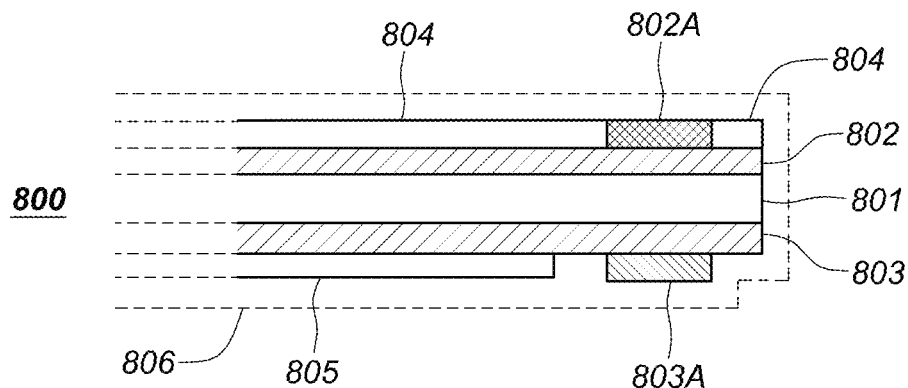

In an alternative embodiment, as shown in FIG. 8, analyte sensor 800 has an insulative layer 804 on the working electrode side of an insulative base substrate 801, which may be provided prior to sensing region 802A whereby the insulative layer 804 has at least two portions spaced apart from each other on conductive layer 802. The sensing region 802A is then provided in the spacing between the two portions. More than two spaced apart portions may be provided, e.g., where a plurality of sensing components or layers is desired. Bottom insulative layer 805 has a length which terminates proximally of secondary conductive layer 803A on bottom primary conductive layer 803. Additional conducting and dielectric layers may be provided on either or both sides of the sensors, as described above.

While FIGS. 6-8 depict or are discussed herein as capable of providing the working and reference electrodes in a particular layered configuration, it should be noted that the relative positioning of these layers may be modified. For example, a counter electrode layer may be provided on one side of an insulative base substrate while working and reference electrode layers are provided in a stacked configuration on the opposite side of the insulative base substrate. In addition, a different number of electrodes may be provided than depicted in FIGS. 6-8 by adjusting the number of conductive and insulative layers. For example, a 3 or four electrode sensor may be provided.

One or more membranes, which may function as one or more of an analyte flux modulating layer and/or an interferent-eliminating layer and/or biocompatible layer, discussed in greater detail below, may be included with, on or about the sensor, e.g., as one or more of the outermost layer(s). Those of ordinary skill in the art will readily recognize that the membrane can take many forms. The membrane can include just one component, or multiple components. The membrane can have a globular shape, such as if encompassing a terminal region of the sensor (e.g., the lateral sides and terminal tip). The membrane can have a generally planar structure, and can be characterized as a layer. Planar membranes can be smooth or can have minor surface (topological) variations. The membrane can also be configured as other non-planar structures. For example, the membrane can have a cylindrical shape or a partially cylindrical shape, a hemispherical shape or other partially spherical shape, an irregular shape, or other rounded or curved shape.

In certain embodiments, as illustrated in FIG. 7, a first membrane layer 706 may be provided solely over the sensing region 702A on the working electrode 702 to modulate the rate of diffusion or flux of the analyte to the sensing region. For embodiments in which a membrane layer is provided over a single component/material, it may be suitable to do so with the same striping configuration and method as used for the other materials/components. Here, the membrane material 706 preferably has a width greater than that of sensing component 702A. As it acts to limit the flux of the analyte to the sensor's active area, and thus contributes to the sensitivity of the sensor, controlling the thickness of membrane 706 is important. Providing membrane 706 in the form of a stripe/band facilitates control of its thickness. A second membrane layer 707, which coats the remaining surface area of the sensor tail, may also be provided to serve as a biocompatible conformal coating and provide smooth edges over the entirety of the sensor. In other sensor embodiments, as illustrated in FIG. 8, a single, homogenous membrane 806 may be coated over the entire sensor surface area, or at least over both sides of the distal tail portion. It is noted that to coat the distal and side edges of the sensor, the membrane material may have to be applied subsequent to singulation of the sensor precursors. In some embodiments, the analyte sensor is dip-coated following singulation to apply one or more membranes. Alternatively, the analyte sensor could be slot-die coated wherein each side of the analyte sensor is coated separately.

Figure 9:
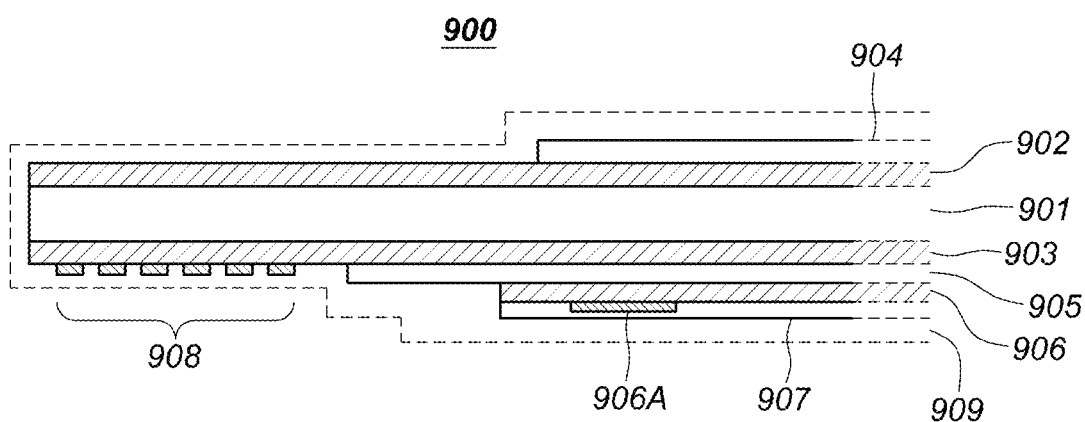

FIG. 9 shows a cross-sectional view of a distal portion of an example double-sided analyte sensor 900 according to one embodiment of the present disclosure, wherein the double-sided analyte sensor includes an at least generally planar insulative base substrate 901, e.g., an at least generally planar dielectric base substrate, having a first conductive layer 902. A second conductive layer 903 is positioned on a first side, e.g., the bottom side, of insulative base substrate 901. While depicted as extending to the distal edge of the sensor, one or both of the conductive layers may terminate proximally of the distal edge and/or may have a width which is less than that of insulative substrate 901 where the width ends a selected distance from the side edges of the substrate, which distance may be equidistant or vary from each of the side edges. See, for example, the analyte sensor assembly 900, discussed in more detail below, wherein first and second conductive layers are provided which define electrodes, including, e.g., electrode traces, which have widths which are less than that of the insulative base substrate.

In the embodiment of FIG. 9, conductive layer 903 is configured to include a working electrode which includes a sensing region 908 disposed on at least a portion of the conductive layer 903, which sensing region is discussed in greater detail below. It should be noted that a plurality of spatially separated sensing components or layers may be utilized in forming the working electrode, e.g., one or more sensing "dots" or areas may be provided on the conductive layer 903, as shown herein, or a single sensing component may be used (not shown).

In the embodiment of FIG. 9, conductive layer 906 is configured to include a reference electrode which includes a secondary layer of conductive material 906A, e.g., Ag/AgCl, disposed on a distal portion of conductive layer 906. Like conductive layers 902 and 903, conductive layer 906 may terminate proximally of the distal edge and/or may have a width which is less than that of insulative substrate 901 where the width ends a selected distance from the side edges of the substrate, which distance may be equidistant or vary from each of the side edges, as discussed in greater detail below in reference to FIGS. 10A-10C.

In the embodiment shown in FIG. 9, conductive layer 902 is configured to include a counter electrode. A first insulative layer 904 covers a portion of conductive layer 902 and a second insulative layer 905 covers a portion of conductive layer 903. First insulative layer 904 does not extend to the distal end of analyte sensor 900 leaving an exposed region of the conductive layer 902 which acts as the counter electrode. An insulative layer 905 covers a portion of conductive layer 903 leaving an exposed region of the conductive layer 903 where the sensing region 908 is positioned. As discussed above, multiple spatially separated sensing components or layers may be provided (as shown) in some embodiments, while in other embodiments a single sensing region may be provided. The insulative layer 907 on a first side, e.g., the bottom side of the sensor (in the view provided by FIG. 9), may extend any suitable length of the sensor's distal section, e.g., it may extend the entire length of both of conductive layers 906 and 906A or portions thereof. For example, as illustrated in FIG. 9, bottom insulative layer 907 extends over the entire bottom surface area of secondary conductive material 906A and terminates distally of the distal end of the length of the conductive layer 906. It is noted that at least the ends of the secondary conductive material 906A which extend along the side edges of the substrate 901 are not covered by insulative layer 907 and, as such, are exposed to the environment when in operative use.

As illustrated in FIG. 9, a homogenous membrane 909 may be coated over the entire sensor surface area, or at least over both sides of the distal tail portion. It is noted that to coat the distal and side edges of the sensor, the membrane material may have to be applied subsequent to singulation of the sensor precursors. In some embodiments, the analyte sensor is dip-coated following singulation to apply one or more membranes (or to apply one membrane in various stages). Alternatively, the analyte sensor could be slot-die coated wherein each side of the analyte sensor is coated separately. Membrane 909 is shown in FIG. 9 as having a squared shape matching the underlying surface variations, but can have a more globular or amorphous shape as well.

When manufacturing layered sensors, it may be desirable to utilize relatively thin insulative layers to reduce total sensor width. For example, with reference to FIG. 9, insulative layers 904, 905 and 907 may be relatively thin relative to insulative substrate layer 901. For example, insulative layers 904, 905 and 907 may have a thickness in the range of 20-25 µm while substrate layer 901 has a thickness in the range of 0.1 to 0.15 mm. However, during singulation of the sensors where such singulation is accomplished by cutting through two or more conductive layers which are separated by such thin insulative layers, shorting between the two conductive layers may occur.

One method of addressing this potential issue is to provide one of the conductive layers, e.g., electrodes layers, at least in part as a relatively narrow electrode, including, e.g., a relatively narrow conductive trace, such that during the singulation process the sensor is cut on either side of the narrow electrode such that one electrode is cut without cutting through the narrow electrode.

Figure 10A:
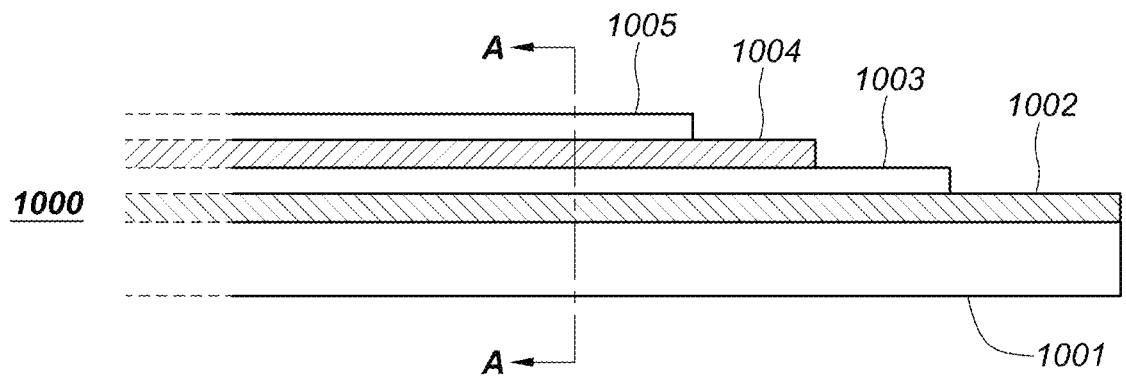
FIG. 10A is a cross-sectional view depicting an example embodiment of an analyte sensor.
Figure 10B:
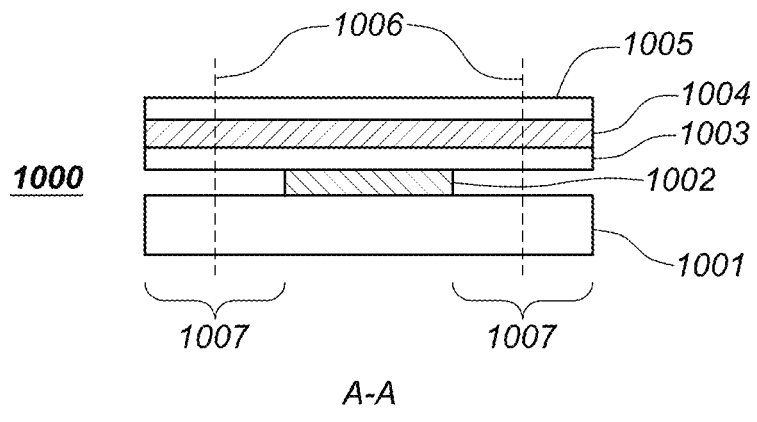
FIGS. 10B-10C are cross-sectional views depicting example embodiments of analyte sensors as viewed from line A-A of FIG. 10A.
Figure 10C:
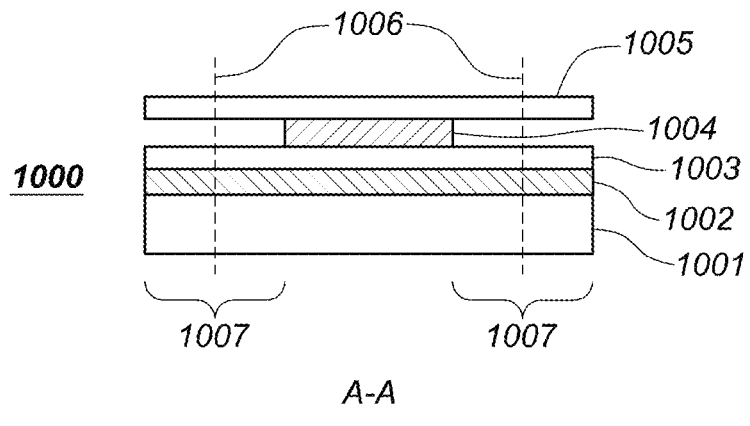

For example, with reference to FIGS. 10A-10C, a sensor 1000 is depicted which includes insulative layers 1003 and 1005. Insulative layers 1003 and 1005 may be thin relative to generally planar insulative base substrate layer 1001, or vice versa. For example, insulative layers 1003 and 1005 may have a thickness in the range of 15-30 µm while substrate layer 1001 has a thickness in the range of 0.1 to 0.15 mm. Such sensors may be manufactured in sheets wherein a single sheet includes a plurality of sensors. However, such a process generally requires singulation of the sensors prior to use. Where such singulation requires cutting through two or more conductive layers which are separated by insulative layers, shorting between the two conductive layers may occur, particularly if the insulative layers are thin. In order to avoid such shorting, fewer than all of the conductive layers may be cut through during the singulation process. For example, at least one of the conductive layers may be provided at least in part as an electrode, e.g., including a conductive trace, having a narrow width relative to one or more other conductive layers such that during the singulation process a first conductive layer separated from a second conductive layer only by a thin insulative layer, e.g., an insulative layer having a thickness in the range of 15-30 µm, is cut while a second conductive layer is not.

For example, with reference to FIGS. 10A and 10C, a sensor 1000 includes an at least generally planar insulative base substrate 1001. Positioned on the at least generally planar insulative base substrate 1001 is a first conductive layer 1002. A first relatively thin insulative layer 1003, e.g., an insulative layer having a thickness in the range of 15-30 µm, is positioned on the first conductive layer 1002 and second conductive layer 1004 is positioned on the relatively thin insulative layer 1003. Finally, a second relatively thin insulative layer 1005, e.g., an insulative layer having a thickness in the range of 15-30 µm, is positioned on the second conductive layer 1004.

As shown in FIG. 10B, first conductive layer 1002 may be an electrode having a narrow width relative to conductive layer 1004 as shown in the FIG. 10B cross-section taken at lines A-A. Alternatively, second conductive layer 1004 may be a conductive electrode having a narrow width relative to conductive layer 1002 as shown in the FIG. 1C cross-section taken at lines A-A. Singulation cut lines 1006 are shown in FIGS. 10B and 10C. The sensor may be singulated, for example, by cutting to either side of the relatively narrow conductive electrode, e.g., in regions 1007, as shown in FIGS. 10B and 10C. With reference to FIG. 10B, singulation by cutting along singulation cut lines 1006 results in cutting through conductive layer 1004 but not conductive layer 1002. With reference to FIG. 10C, singulation by cutting along singulation cut lines 1006 results in cutting through conductive layer 1002 but not conductive layer 1004.

An embodiment of a sensing region may be described as the area shown schematically in FIG. 5B as 508 and FIG. 9 as 908. As noted above the sensing region may be provided as a single sensing component as shown in FIG. 5B as 508, FIG. 7 as 702A and FIG. 8 as 802A, or provided as a plurality of sensing components as shown in FIG. 9 as 908. A plurality of sensing components or sensing "spots" is described in US Patent Application Publication No. 2012/0150005, incorporated by reference herein in its entirety.

The term "sensing region" is a broad term and may be described as the active chemical area of the biosensor. Those of ordinary skill in the art will readily recognize that the sensing region can take many forms. The sensing region can include just one component, or multiple components (e.g., such as sensing region 908 of FIG. 9). In the embodiment of FIG. 5B, for example, the sensing region is a generally planar structure, and can be characterized as a layer. Planar sensing regions can be smooth or can have minor surface (topological) variations. The sensing region can also be a non-planar structure. For example, the sensing region can have a cylindrical shape or a partially cylindrical shape, a hemispherical shape or other partially spherical shape, an irregular shape, or other rounded or curved shape.

The sensing region formulation, which can include a glucose-transducing agent, may include, for example, among other constituents, a redox mediator, such as, for example, a hydrogen peroxide or a transition metal complex, such as a ruthenium-containing complex or an osmium-containing complex, and an analyte-responsive enzyme, such as, for example, a glucose-responsive enzyme (e.g., glucose oxidase, glucose dehydrogenase, etc.) or lactate-responsive enzyme (e.g., lactate oxidase). In certain embodiments, the sensing region includes glucose oxidase. The sensing region may also include other optional components, such as, for example, a polymer and a bi-functional, short-chain, epoxide cross-linker, such as polyethylene glycol (PEG).

In certain instances, the analyte-responsive enzyme is distributed throughout the sensing region. For example, the analyte-responsive enzyme may be distributed uniformly throughout the sensing region, such that the concentration of the analyte-responsive enzyme is substantially the same throughout the sensing region. In some cases, the sensing region may have a homogeneous distribution of the analyte-responsive enzyme. In certain embodiments, the redox mediator is distributed throughout the sensing region. For example, the redox mediator may be distributed uniformly throughout the sensing region, such that the concentration of the redox mediator is substantially the same throughout the sensing region. In some cases, the sensing region may have a homogeneous distribution of the redox mediator. In certain embodiments, both the analyte-responsive enzyme and the redox mediator are distributed uniformly throughout the sensing region, as described above.

As noted above, analyte sensors may include an analyte-responsive enzyme to provide a sensing component or sensing region. Some analytes, such as oxygen, can be directly electrooxidized or electroreduced on a sensor, and more specifically at least on a working electrode of a sensor. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode. For these analytes, each working electrode includes a sensing region (see for example sensing region 508 of FIG. 5B) proximate to or on a surface of a working electrode. In many embodiments, a sensing region is formed near or on only a small portion of at least a working electrode.

The sensing region can include one or more components constructed to facilitate the electrochemical oxidation or reduction of the analyte. The sensing region may include, for example, a catalyst to catalyze a reaction of the analyte and produce a response at the working electrode, an electron transfer agent to transfer electrons between the analyte and the working electrode (or other component), or both.

A variety of different sensing region configurations may be used. The sensing region is often located in contact with or in proximity to an electrode, such as the working electrode. In certain embodiments, the sensing region is deposited on the conductive material of the working electrode. The sensing region may extend beyond the conductive material of the working electrode. In some cases, the sensing region may also extend over other electrodes, e.g., over the counter electrode and/or reference electrode (or if a counter/reference is provided).

A sensing region that is in direct contact with the working electrode may contain an electron transfer agent to transfer electrons directly or indirectly between the analyte and the working electrode, and/or a catalyst to facilitate a reaction of the analyte. For example, a glucose, lactate, or oxygen electrode may be formed having a sensing region which contains a catalyst, including glucose oxidase, glucose dehydrogenase, lactate oxidase, or laccase, respectively, and an electron transfer agent that facilitates the electrooxidation of the glucose, lactate, or oxygen, respectively.

In other embodiments, the sensing region is not deposited directly on the working electrode. Instead, the sensing region 508 (FIG. 5), for example, may be spaced apart from the working electrode, and separated from the working electrode, e.g., by a separation layer. A separation layer may include one or more membranes or films or a physical distance. In addition to separating the working electrode from the sensing region, the separation layer may also act as a mass transport limiting layer and/or an interferent eliminating layer and/or a biocompatible layer.

In certain embodiments which include more than one working electrode, one or more of the working electrodes may not have a corresponding sensing region, or may have a sensing region which does not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing regions by, for example, subtracting the signal.

In certain embodiments, the sensing region includes one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine, etc. Additional examples include those described in U.S. Pat. Nos. 6,736,957, 7,501,053 and 7,754,093, the disclosures of each of which are incorporated herein by reference in their entirety.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

Embodiments of polymeric electron transfer agents may contain a redox species covalently bound in a polymeric composition. An example of this type of mediator is poly (vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer including quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing region may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, including a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent, which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

In certain embodiments, the sensor operates at a low oxidizing potential, e.g., a potential of about +40 mV vs. Ag/AgCl. This sensing region uses, for example, an osmium (Os)-based mediator constructed for low potential operation. Accordingly, in certain embodiments the sensing element is a redox active component that includes (1) osmium-based mediator molecules that include (bidente) ligands, and (2) glucose oxidase enzyme molecules. These two constituents are combined together in the sensing region of the sensor.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating functions, etc.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over an enzyme-containing sensing region and allowing the solution to cure for about one to two days or other appropriate time period. The crosslinker-polymer solution may be applied to the sensing region by placing a droplet or droplets of the membrane solution on the sensor, by dipping the sensor into the membrane solution, by spraying the membrane solution on the sensor, and the like. Generally, the thickness of the membrane is controlled by the concentration of the membrane solution, by the number of droplets of the membrane solution applied, by the number of times the sensor is dipped in the membrane solution, by the volume of membrane solution sprayed on the sensor, or by any combination of these factors. A membrane applied in this manner may have any combination of the following functions: (1) mass transport limitation, e.g., reduction of the flux of analyte that can reach the sensing region, (2) biocompatibility enhancement, or (3) interferent reduction.

In some instances, the membrane may form one or more bonds with the sensing region. By bonds is meant any type of an interaction between atoms or molecules that allows chemical compounds to form associations with each other, such as, but not limited to, covalent bonds, ionic bonds, dipole-dipole interactions, hydrogen bonds, London dispersion forces, and the like. For example, in situ polymerization of the membrane can form crosslinks between the polymers of the membrane and the polymers in the sensing region. In certain embodiments, crosslinking of the membrane to the sensing region facilitates a reduction in the occurrence of delamination of the membrane from the sensing region.

In certain embodiments, the sensing system detects hydrogen peroxide to infer glucose levels. For example, a hydrogen peroxide-detecting sensor may be constructed in which a sensing region includes enzyme such as glucose oxides, glucose dehydrogenase, or the like, and is positioned proximate to the working electrode. The sensing region may be covered by one or more layers, e.g., a membrane that is selectively permeable to glucose. Once the glucose passes through the membrane, it is oxidized by the enzyme and reduced glucose oxidase can then be oxidized by reacting with molecular oxygen to produce hydrogen peroxide.

Certain embodiments include a hydrogen peroxide-detecting sensor constructed from a sensing region prepared by combining together, for example: (1) a redox mediator having a transition metal complex including an Os polypyridyl complex with oxidation potentials of about +200 mV vs. SCE, and (2) periodate oxidized horseradish peroxidase (HRP). Such a sensor functions in a reductive mode; the working electrode is controlled at a potential negative to that of the Os complex, resulting in mediated reduction of hydrogen peroxide through the HRP catalyst.

In another example, a potentiometric sensor can be constructed as follows. A glucose-sensing region is constructed by combining together (1) a redox mediator having a transition metal complex including Os polypyridyl complexes with oxidation potentials from about −200 mV to +200 mV vs. SCE, and (2) glucose oxidase. This sensor can then be used in a potentiometric mode, by exposing the sensor to a glucose containing solution, under conditions of zero current flow, and allowing the ratio of reduced/oxidized Os to reach an equilibrium value. The reduced/oxidized Os ratio varies in a reproducible way with the glucose concentration, and will cause the electrode's potential to vary in a similar way.

The substrate may be formed using a variety of non-conducting materials, including, for example, polymeric or plastic materials and ceramic materials. Suitable materials for a particular sensor may be determined, at least in part, based on the desired use of the sensor and properties of the materials.

In some embodiments, the substrate is flexible. For example, if the sensor is configured for implantation into a user, then the sensor may be made flexible (although rigid sensors may also be used for implantable sensors) to reduce pain to the user and damage to the tissue caused by the implantation of and/or the wearing of the sensor. A flexible substrate often increases the user's comfort and allows a wider range of activities. Suitable materials for a flexible substrate include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors are made using a relatively rigid substrate to, for example, provide structural support against bending or breaking. Examples of rigid materials that may be used as the substrate include poorly conducting ceramics, such as aluminum oxide and silicon dioxide. An implantable sensor having a rigid substrate may have a sharp point and/or a sharp edge to aid in implantation of a sensor without an additional insertion device.

It will be appreciated that for many sensors and sensor applications, both rigid and flexible sensors will operate adequately. The flexibility of the sensor may also be controlled and varied along a continuum by changing, for example, the composition and/or thickness of the substrate.

In addition to considerations regarding flexibility, it is often desirable that implantable sensors should have a substrate which is physiologically harmless, for example, a substrate approved by a regulatory agency or private institution for in vivo use.

The sensor may include optional features to facilitate insertion of an implantable sensor. For example, the sensor may be pointed at the tip to ease insertion. In addition, the sensor may include a barb which assists in anchoring the sensor within the tissue of the user during operation of the sensor. However, the barb is typically small enough so that little damage is caused to the subcutaneous tissue when the sensor is removed for replacement.

An implantable sensor may also, optionally, have an anticlotting agent disposed on a portion of the substrate which is implanted into a user. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents.

The anticlotting agent may be applied to at least a portion of that part of the sensor that is to be implanted. The anticlotting agent may be applied, for example, by bath, spraying, brushing, or dipping, etc. The anticlotting agent is allowed to dry on the sensor. The anticlotting agent may be immobilized on the surface of the sensor or it may be allowed to diffuse away from the sensor surface. The quantities of anticlotting agent disposed on the sensor may be below the amounts typically used for treatment of medical conditions involving blood clots and, therefore, have only a limited, localized effect.

Figure 11:
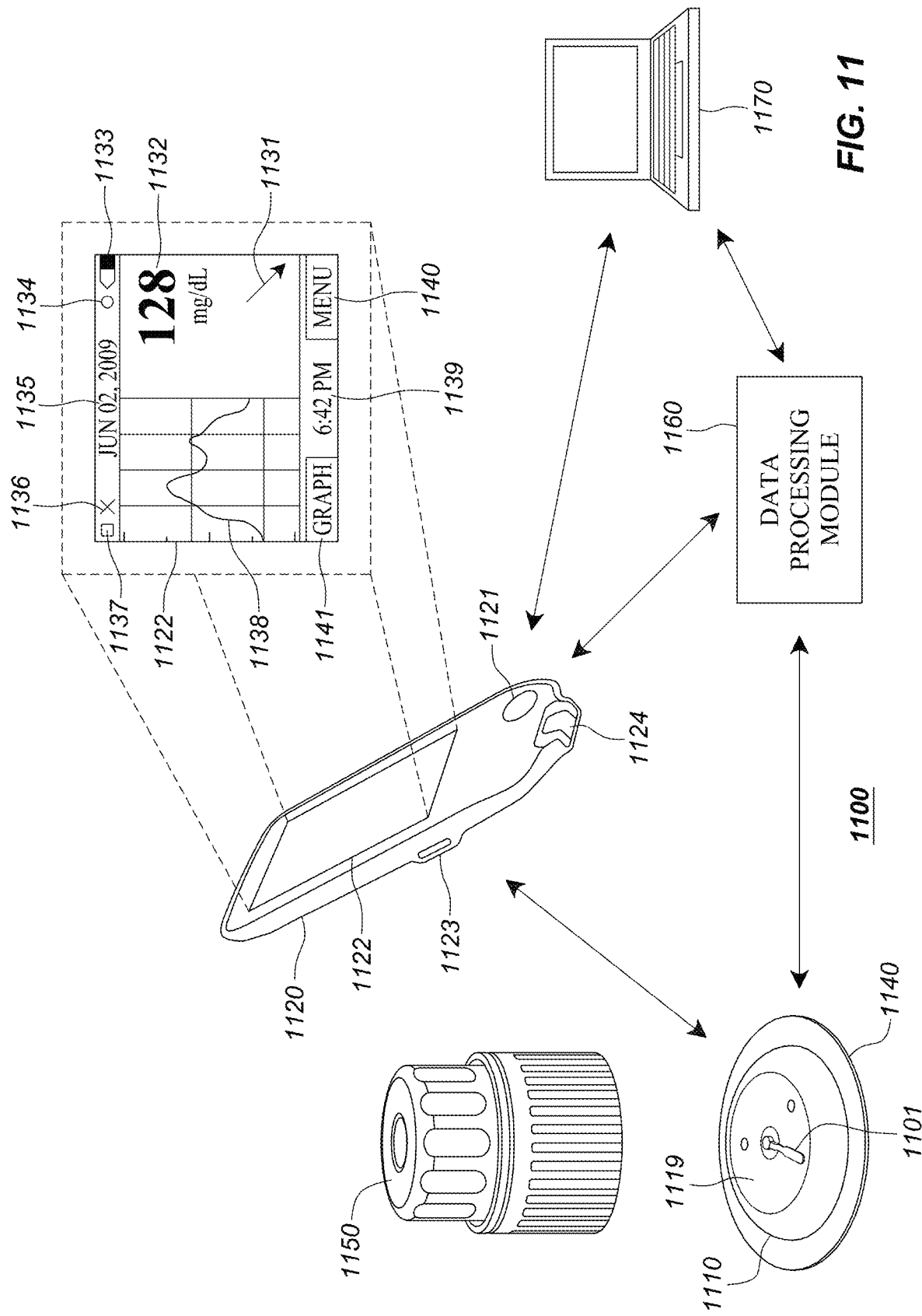
FIG. 11 is a conceptual view depicting an example embodiment of an analyte monitoring system.

FIG. 11 shows an example in vivo-based analyte monitoring system 1100 in accordance with certain embodiments of the present disclosure. As shown, analyte monitoring system 1100 includes on body electronics 1110 electrically coupled to in vivo analyte sensor 1101 (a proximal portion of which is shown in FIG. 11) and attached to adhesive layer 1140 for attachment on a skin surface on the body of a user. On body electronics 1110 includes on body housing 1119 that defines an interior compartment. Also shown in FIG. 11 is insertion device 1150 that, when operated, transcutaneously positions a portion of analyte sensor 1101 through a skin surface and in fluid contact with bodily fluid, and positions on body electronics 1110 and adhesive layer 1140 on a skin surface. In certain embodiments, on body electronics 1110, analyte sensor 1101 and adhesive layer 1140 are sealed within the housing of insertion device 1150 before use, and in certain embodiments, adhesive layer 1140 is also sealed within the housing or itself provides a terminal seal of the insertion device 1150.

Referring back to the FIG. 11, analyte monitoring system 1100 includes display device 1120 which includes a display 1122 to output information to the user, an input component 1121 such as a button, actuator, a touch sensitive switch, a capacitive switch, pressure sensitive switch, jog wheel or the like, to input data or command to display device 1120 or otherwise control the operation of display device 1120. It is noted that some embodiments may include display-less devices or devices without any user interface components. These devices may be functionalized to store data as a data logger and/or provide a conduit to transfer data from on body electronics and/or a display-less device to another device and/or location. Embodiments will be described herein as display devices for example purposes which are in no way intended to limit the embodiments of the present disclosure. It will be apparent that display-less devices may also be used in certain embodiments.

In certain embodiments, on body electronics 1110 may be configured to store some or all of the monitored analyte related data received from analyte sensor 1101 in a memory during the monitoring time period, and maintain it in memory until the usage period ends. In such embodiments, stored data is retrieved from on body electronics 1110 at the conclusion of the monitoring time period, for example, after removing analyte sensor 1101 from the user by detaching on body electronics 1110 from the skin surface where it was positioned during the monitoring time period. In such data logging configurations, real time monitored analyte level is not communicated to display device 1120 during the monitoring period or otherwise transmitted from on body electronics 1110, but rather, retrieved from on body electronics 1110 after the monitoring time period.

In certain embodiments, input component 1121 of display device 1120 may include a microphone and display device 1120 may include software configured to analyze audio input received from the microphone, such that functions and operation of the display device 1120 may be controlled by voice commands. In certain embodiments, an output component of display device 1120 includes a speaker for outputting information as audible signals. Similar voice responsive components such as a speaker, microphone and software routines to generate, process and store voice driven signals may be provided to on body electronics 1110.

In certain embodiments, display 1122 and input component 1121 may be integrated into a single component, for example a display that can detect the presence and location of a physical contact touch upon the display such as a touch screen user interface. In such embodiments, the user may control the operation of display device 1120 by utilizing a set of preprogrammed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Display device 1120 also includes data communication port 1123 for wired data communication with external devices such as remote terminal (personal computer) 1170, for example. Example embodiments of the data communication port 1123 include USB port, mini USB port, RS-232 port, Ethernet port, Firewire port, or other similar data communication ports configured to connect to the compatible data cables. Display device 1120 may also include an integrated in vitro glucose meter, including in vitro test strip port 1124 to receive an in vitro glucose test strip for performing in vitro blood glucose measurements.

Referring still to FIG. 11, display 1122 in certain embodiments is configured to display a variety of information—some or all of which may be displayed at the same or different time on display 1122. In certain embodiments, the displayed information is user-selectable so that a user can customize the information shown on a given display screen. Display 1122 may include but is not limited to graphical display 1138, for example, providing a graphical output of glucose values over a monitored time period (which may show important markers such as meals, exercise, sleep, heart rate, blood pressure, etc.), numerical display 1132, for example, providing monitored glucose values (acquired or received in response to the request for the information), and trend or directional arrow display 1131 that indicates a rate of analyte change and/or a rate of the rate of analyte change.

As further shown in FIG. 11, display 1122 may also include date display 1135 providing for example, date information for the user, time of day information display 1139 providing time of day information to the user, battery level indicator display 1133 which graphically shows the condition of the battery (rechargeable or disposable) of the display device 1120, sensor calibration status icon display 1134 for example, in monitoring systems that require periodic, routine or a predetermined number of user calibration events, notifying the user that the analyte sensor calibration is necessary, audio/vibratory settings icon display 1136 for displaying the status of the audio/vibratory output or alarm state, and wireless connectivity status icon display 1137 that provides indication of wireless communication connection with other devices such as on body electronics, data processing module 1160, and/or remote terminal 1170. As additionally shown in FIG. 11, display 1122 may further include simulated touch screen buttons 1140, 1141 for accessing menus, changing display graph output configurations or otherwise for controlling the operation of display device 1120.

Referring back to FIG. 11, in certain embodiments, display 1122 of display device 1120 may be additionally, or instead of visual display, configured to output alarms notifications such as alarm and/or alert notifications, glucose values etc., which may be audible, tactile, or any combination thereof. In one aspect, the display device 1120 may include other output components such as a speaker, vibratory output component and the like to provide audible and/or vibratory output indication to the user in addition to the visual output indication provided on display 1122.

After the positioning of on body electronics 1110 on the skin surface and analyte sensor 1101 in vivo to establish fluid contact with interstitial fluid (or other appropriate bodily fluid), on body electronics 1110 in certain embodiments is configured to wirelessly communicate analyte related data (such as, for example, data corresponding to monitored analyte level and/or monitored temperature data, and/or stored historical analyte related data) when on body electronics 1110 receives a command or request signal from display device 1120. In certain embodiments, on body electronics 1110 may be configured to at least periodically broadcast real time data associated with monitored analyte level which is received by display device 1120 when display device 1120 is within communication range of the data broadcast from on body electronics 1110, e.g., it does not need a command or request from a display device to send information.

For example, display device 1120 may be configured to transmit one or more commands to on body electronics 1110 to initiate data transfer, and in response, on body electronics 1110 may be configured to wirelessly transmit stored analyte related data collected during the monitoring time period to display device 1120. Display device 1120 may in turn be connected to a remote terminal 1170 such as a personal computer and functions as a data conduit to transfer the stored analyte level information from the on body electronics 1110 to remote terminal 1170. In certain embodiments, the received data from the on body electronics 1110 may be stored (permanently or temporarily) in one or more memory of the display device 1120. In certain other embodiments, display device 1120 is configured as a data conduit to pass the data received from on body electronics 1110 to remote terminal 1170 that is connected to display device 1120.

Referring still to FIG. 11, also shown in analyte monitoring system 1100 are data processing module 1160 and remote terminal 1170. Remote terminal 1170 may include a personal computer, a server terminal a laptop computer or other suitable data processing devices including software for data management and analysis and communication with the components in the analyte monitoring system 1100. For example, remote terminal 1170 may be connected to a local area network (LAN), a wide area network (WAN), or other data network for uni-directional or bi-directional data communication between remote terminal 1170 and display device 1120 and/or data processing module 1160.

Remote terminal 1170 in certain embodiments may include one or more computer terminals located at a physician's office or a hospital. For example, remote terminal 1170 may be located at a location other than the location of display device 1120. Remote terminal 1170 and display device 1120 could be in different rooms or different buildings. Remote terminal 1170 and display device 1120 could be at least about one mile apart, e.g., at least about 10 miles apart, e.g., at least about 1100 miles apart. For example, remote terminal 1170 could be in the same city as display device 1120, remote terminal 1170 could be in a different city than display device 1120, remote terminal 1170 could be in the same state as display device 1120, remote terminal 1170 could be in a different state than display device 1120, remote terminal 1170 could be in the same country as display device 1120, or remote terminal 1170 could be in a different country than display device 1120, for example.

In certain embodiments, a separate, optional data communication/processing device such as data processing module 1160 may be provided in analyte monitoring system 1100. Data processing module 1160 may include components to communicate using one or more wireless communication protocols such as, for example, but not limited to, infrared (IR) protocol, Bluetooth protocol, Zigbee protocol, and 802.11 wireless LAN protocol. Additional description of communication protocols including those based on Bluetooth protocol and/or Zigbee protocol can be found in U.S. Patent Publication No. 2006/0193375 incorporated herein by reference in its entirety for all purposes. Data processing module 1160 may further include communication ports, drivers or connectors to establish wired communication with one or more of display device 1120, on body electronics 1110, or remote terminal 1170 including, for example, but not limited to USB connector and/or USB port, Ethernet connector and/or port, FireWire connector and/or port, or RS-232 port and/or connector.

In certain embodiments, data processing module 1160 is programmed to transmit a polling or query signal to on body electronics 1110 at a predetermined time interval (e.g., once every minute, once every five minutes, or the like), and in response, receive the monitored analyte level information from on body electronics 1110. Data processing module 1160 stores in its memory the received analyte level information, and/or relays or retransmits the received information to another device such as display device 1120. More specifically in certain embodiments, data processing module 1160 may be configured as a data relay device to retransmit or pass through the received analyte level data from on body electronics 1110 to display device 1120 or a remote terminal (for example, over a data network such as a cellular or WiFi data network) or both.

In certain embodiments, on body electronics 1110 and data processing module 1160 may be positioned on the skin surface of the user within a predetermined distance of each other (for example, about 1-12 inches, or about 1-10 inches, or about 1-7 inches, or about 1-5 inches) such that periodic communication between on body electronics 1110 and data processing module 1160 is maintained. Alternatively, data processing module 1160 may be worn on a belt or clothing item of the user, such that the desired distance for communication between the on body electronics 1110 and data processing module 1160 for data communication is maintained. In a further aspect, the housing of data processing module 1160 may be configured to couple to or engage with on body electronics 1110 such that the two devices are combined or integrated as a single assembly and positioned on the skin surface. In further embodiments, data processing module 1160 is detachably engaged or connected to on body electronics 1110 providing additional modularity such that data processing module 1160 may be optionally removed or reattached as desired.

Referring again to FIG. 11, in certain embodiments, data processing module 1160 is programmed to transmit a command or signal to on body electronics 1110 at a predetermined time interval such as once every minute, or once every 5 minutes or once every 30 minutes or any other suitable or desired programmable time interval to request analyte related data from on body electronics 1110. When data processing module 1160 receives the requested analyte related data, it stores the received data. In this manner, analyte monitoring system 1100 may be configured to receive the continuously monitored analyte related information at the programmed or programmable time interval, which is stored and/or displayed to the user. The stored data in data processing module 1160 may be subsequently provided or transmitted to display device 1120, remote terminal 1170 or the like for subsequent data analysis such as identifying frequency of periods of glycemic level excursions over the monitored time period, or the frequency of the alarm event occurrence during the monitored time period, for example, to improve therapy related decisions. Using this information, the doctor, healthcare provider or the user may adjust or recommend modification to the diet, daily habits and routines such as exercise, and the like.

In another embodiment, data processing module 1160 transmits a command or signal to on body electronics 1110 to receive the analyte related data in response to a user activation of a switch provided on data processing module 1160 or a user initiated command received from display device 1120. In further embodiments, data processing module 1160 is configured to transmit a command or signal to on body electronics 1110 in response to receiving a user initiated command only after a predetermined time interval has elapsed. For example, in certain embodiments, if the user does not initiate communication within a programmed time period, such as, for example about 5 hours from last communication (or 10 hours from the last communication, or 24 hours from the last communication), the data processing module 1160 may be programmed to automatically transmit a request command or signal to on body electronics 1110. Alternatively, data processing module 1160 may be programmed to activate an alarm to notify the user that a predetermined time period of time has elapsed since the last communication between the data processing module 1160 and on body electronics 1110. In this manner, users or healthcare providers may program or configure data processing module 1160 to provide certain compliance with analyte monitoring regimen, so that frequent determination of analyte levels is maintained or performed by the user.

In certain embodiments, when a programmed or programmable alarm condition is detected (for example, a detected glucose level monitored by analyte sensor 1101 that is outside a predetermined acceptable range indicating a physiological condition which requires attention or intervention for medical treatment or analysis (for example, a hypoglycemic condition, a hyperglycemic condition, an impending hyperglycemic condition or an impending hypoglycemic condition), the one or more output indications may be generated by the control logic or processor of the on body electronics 1110 and output to the user on a user interface of on body electronics 1110 so that corrective action may be timely taken. In addition to or alternatively, if display device 1120 is within communication range, the output indications or alarm data may be communicated to display device 1120 whose processor, upon detection of the alarm data reception, controls the display 1122 to output one or more notification.

In certain embodiments, control logic or processors of on body electronics 1110 can execute software programs stored in memory to determine future or anticipated analyte levels based on information obtained from analyte sensor 1101, e.g., the current analyte level, the rate of change of the analyte level, the acceleration of the analyte level change, and/or analyte trend information determined based on stored monitored analyte data providing a historical trend or direction of analyte level fluctuation as function time during monitored time period. Predictive alarm parameters may be programmed or programmable in display device 1120, or the on body electronics 1110, or both, and output to the user in advance of anticipating the user's analyte level reaching the future level. This provides the user an opportunity to take timely corrective action.

Information, such as variation or fluctuation of the monitored analyte level as a function of time over the monitored time period providing analyte trend information, for example, may be determined by one or more control logic or processors of display device 1120, data processing module 1160, and/or remote terminal 1170, and/or on body electronics 1110. Such information may be displayed as, for example, a graph (such as a line graph) to indicate to the user the current and/or historical and/or and predicted future analyte levels as measured and predicted by the analyte monitoring system 1100. Such information may also be displayed as directional arrows (for example, see trend or directional arrow display 1131) or other icon(s), e.g., the position of which on the screen relative to a reference point indicated whether the analyte level is increasing or decreasing as well as the acceleration or deceleration of the increase or decrease in analyte level. This information may be utilized by the user to determine any necessary corrective actions to ensure the analyte level remains within an acceptable and/or clinically safe range. Other visual indicators, including colors, flashing, fading, etc., as well as audio indicators including a change in pitch, volume, or tone of an audio output and/or vibratory or other tactile indicators may also be incorporated into the display of trend data as means of notifying the user of the current level and/or direction and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, the system 1100 may include an algorithm stored on computer readable medium to determine the time it will take to reach a clinically significant level and will output notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring again back to FIG. 11, in certain embodiments, software algorithm(s) for execution by data processing module 1160 may be stored in an external memory device such as an SD card, microSD card, compact flash card, XD card, Memory Stick card, Memory Stick Duo card, or USB memory stick/device including executable programs stored in such devices for execution upon connection to the respective one or more of the on body electronics 1110, remote terminal 1170 or display device 1120. In a further aspect, software algorithms for execution by data processing module 1160 may be provided to a communication device such as a mobile telephone including, for example, WiFi or Internet enabled smart phones or personal digital assistants (PDAs) as a downloadable application for execution by the downloading communication device.

Examples of smart phones include Windows®, Android™, iPhone® operating system, Palm® WebOS™, Blackberry® operating system, or Symbian® operating system based mobile telephones with data network connectivity functionality for data communication over an internet connection and/or a local area network (LAN). PDAs as described above include, for example, portable electronic devices including one or more processors and data communication capability with a user interface (e.g., display/output unit and/or input unit, and configured for performing data processing, data upload/download over the internet, for example. In such embodiments, remote terminal 1170 may be configured to provide the executable application software to the one or more of the communication devices described above when communication between the remote terminal 1170 and the devices are established.

On Body Electronics

In certain embodiments, on body electronics (or sensor control device) 1110 (FIG. 11) includes at least a portion of the electronic components that operate the sensor and the display device. The electronic components of the on body electronics typically include a power supply for operating the on body electronics and the sensor, a sensor circuit for obtaining signals from and operating the sensor, a measurement circuit that converts sensor signals to a desired format, and a processing circuit (or processing circuitry) that, at minimum, obtains signals from the sensor circuit and/or measurement circuit and provides the signals to an optional on body electronics. In some embodiments, the processing circuit may also partially or completely evaluate the signals from the sensor and convey the resulting data to the optional on body electronics and/or activate an optional alarm system if the analyte level exceeds a threshold. The processing circuit often includes digital logic circuitry.

The on body electronics may optionally contain electronics for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the on body electronics.

Moreover, the on body electronics may also include digital and/or analog components utilizing semiconductor devices, including transistors. To operate these semiconductor devices, the on body electronics may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the measurement circuit. The measurement circuit converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit may then, optionally, evaluate the data and provide commands to operate the electronics.

Figure 12:
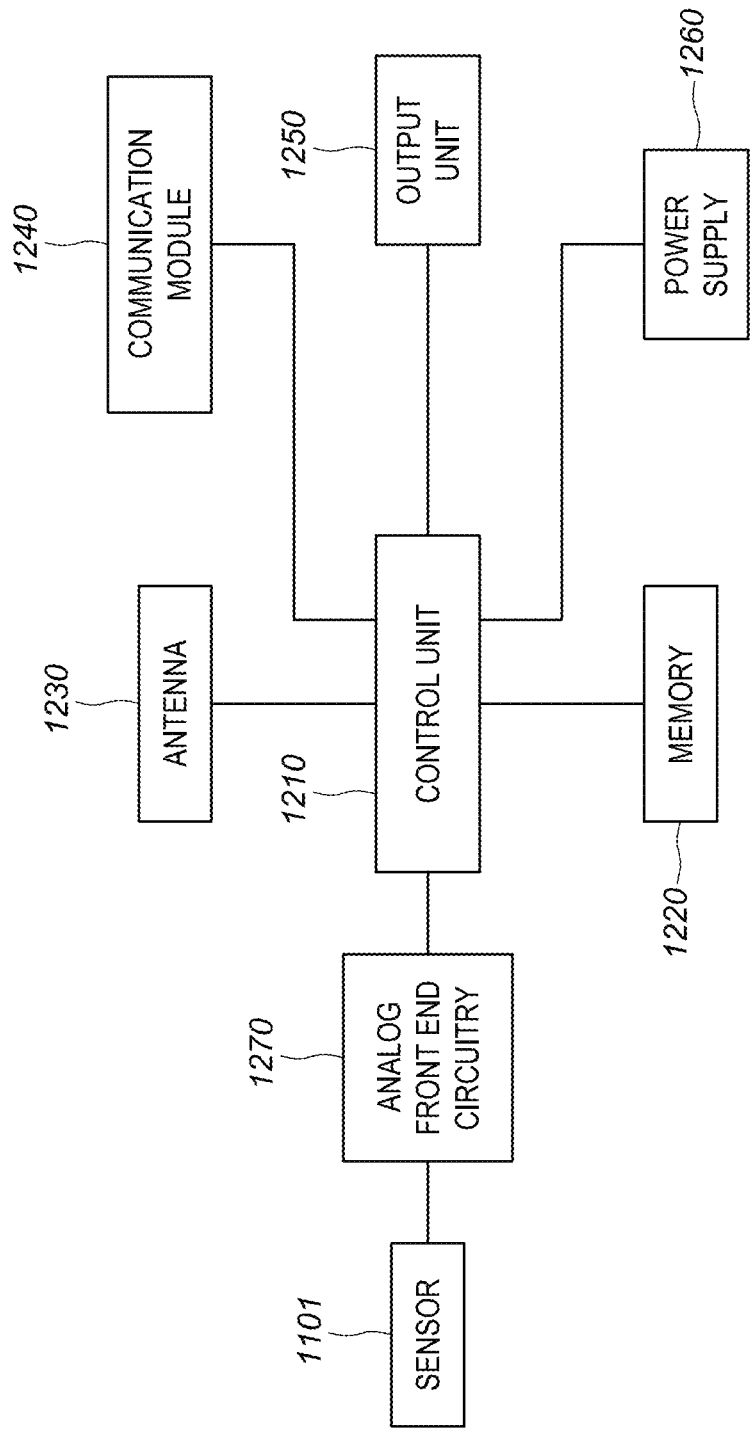
FIG. 12 is a block diagram depicting an example embodiment of on body electronics.

FIG. 12 is a block diagram of the on body electronics 1110 (FIG. 11) in certain embodiments. Referring to FIG. 12, on body electronics 1110 in certain embodiments includes a control unit 1210 (such as, for example but not limited to, one or more processors (or processing circuitry) and/or ASICs with processing circuitry), operatively coupled to analog front end circuitry 1270 to process signals such as raw current signals received from analyte sensor 1101. Also shown in FIG. 12 is memory 1220 operatively coupled to control unit 1210 for storing data and/or software routines for execution by control unit 1210. Memory 1220 in certain embodiments may include electrically erasable programmable read only memory (EEPROM), erasable programmable read only memory (EPROM), random access memory (RAM), read only memory (ROM), flash memory, or one or more combinations thereof.

In certain embodiments, control unit 1210 accesses data or software routines stored in the memory 1220 to update, store or replace stored data or information in the memory 1220, in addition to retrieving one or more stored software routines for execution. Also shown in FIG. 12 is power supply 1260 which, in certain embodiments, provides power to some or all of the components of on body electronics 1110. For example, in certain embodiments, power supply 1260 is configured to provide power to the components of on body electronics 1110 except for communication module 1240. In such embodiments, on body electronics 1110 is configured to operate analyte sensor 1101 to detect and monitor the analyte level at a predetermined or programmed (or programmable) time intervals, and generating and storing, for example, the signals or data corresponding to the detected analyte levels.

In certain embodiments, power supply 1260 in on body electronics 1110 may be toggled between its internal power source (e.g., a battery) and the RF power received from display device 1120. For example, in certain embodiments, on body electronics 1110 may include a diode or a switch that is provided in the internal power source connection path in on body electronics 1110 such that, when a predetermined level of RF power is detected by on body electronics 1110, the diode or switch is triggered to disable the internal power source connection (e.g., making an open circuit at the power source connection path), and the components of on body electronics is powered with the received RF power. The open circuit at the power source connection path prevents the internal power source from draining or dissipating as in the case when it is used to power on body electronics 1110.

When the RF power from display device 1120 falls below the predetermined level, the diode or switch is triggered to establish the connection between the internal power source and the other components of on body electronics 1110 to power the on body electronics 1110 with the internal power source. In this manner, in certain embodiments, toggling between the internal power source and the RF power from display device 1120 may be configured to prolong or extend the useful life of the internal power source.

The stored analyte related data, however, is not transmitted or otherwise communicated to another device such as display device 1120 (FIG. 11) until communication module 1240 is separately powered, for example, with the RF power from display device 1120 that is positioned within a predetermined distance from on body electronics 1110. In such embodiments, analyte level is sampled based on the predetermined or programmed time intervals as discussed above, and stored in memory 1220. When analyte level information is requested, for example, based on a request or transmit command received from another device such as display device 1120 (FIG. 11), using the RF power from the display device, communication module 1240 of on body electronics 1110 initiates data transfer to the display device 1120.

Referring back to FIG. 12, an optional output unit 1250 is provided to on body electronics 1110. In certain embodiments, output unit 1250 may include an LED indicator, for example, to alert the user of one or more predetermined conditions associated with the operation of the on body electronics 1110 and/or the determined analyte level. By way of nonlimiting example, the on body electronics 1110 may be programmed to assert a notification using an LED indicator, or other indicator on the on body electronics 1110 when signals (based on one sampled sensor data point, or multiple sensor data points) received from analyte sensor 1101 are indicated to be beyond a programmed acceptable range, potentially indicating a health risk condition such as hyperglycemia or hypoglycemia, or the onset or potential of such conditions. With such prompt or indication, the user may be timely informed of such potential condition, and using display device 1120, acquire the glucose level information from the on body electronics 1110 to confirm the presence of such conditions so that timely corrective actions may be taken.

Referring again to FIG. 12, antenna 1230 and communication module 1240 operatively coupled to the control unit 1210 may be configured to detect and process the RF power when on body electronics 1110 is positioned within predetermined proximity to the display device 1120 (FIG. 11) that is providing or radiating the RF power. Further, on body electronics 1110 may provide analyte level information and optionally analyte trend or historical information based on stored analyte level data, to display device 1120. In certain aspects, the trend information may include a plurality of analyte level information over a predetermined time period that are stored in the memory 1220 of the on body electronics 1110 and provided to the display device 1120 with the real time analyte level information. For example, the trend information may include a series of time spaced analyte level data for the time period since the last transmission of the analyte level information to the display device 1120. Alternatively, the trend information may include analyte level data for the prior 30 minutes or one hour that are stored in memory 1220 and retrieved under the control of the control unit 1210 for transmission to the display device 1120.

In certain embodiments, on body electronics 1110 is configured to store analyte level data in first and second FIFO buffers that are part of memory 1220. The first FIFO buffer stores 16 (or 10 or 20) of the most recent analyte level data spaced one minute apart. The second FIFO buffer stores the most recent 8 hours (or 10 hours or 3 hours) of analyte level data spaced 10 minutes (or 15 minutes or 20 minutes). The stored analyte level data are transmitted from on body electronics 1110 to display unit 1120 in response to a request received from display unit 1120. Display unit 1120 uses the analyte level data from the first FIFO buffer to estimate glucose rate-of-change and analyte level data from the second FIFO buffer to determine historical plots or trend information.

In certain embodiments, for configurations of the on body electronics that includes a power supply, the on body electronics may be configured to detect an RF control command (ping signal) from the display device 1120. More specifically, an On/Off Key (OOK) detector may be provided in the on body electronics which is turned on and powered by the power supply of the on body electronics to detect the RF control command or the ping signal from the display device 1120. Additional details of the OOK detector are provided in U.S. Patent Publication No. 2008/0278333, the disclosure of which is incorporated by reference in its entirety for all purposes. In certain aspects, when the RF control command is detected, on body electronics determines what response packet is necessary, and generates the response packet for transmission back to the display device 1120. In this embodiment, the analyte sensor 1101 continuously receives power from the power supply or the battery of the on body electronics and operates to monitor the analyte level continuously in use. However, the sampled signal from the analyte sensor 1101 may not be provided to the display device 1120 until the on body electronics receives the RF power (from the display device 1120) to initiate the transmission of the data to the display device 1120. In one embodiment, the power supply of the on body electronics may include a rechargeable battery which charges when the on body electronics receives the RF power (from the display device 1120, for example).

Referring back to FIG. 11, in certain embodiments, on body electronics 1110 and the display device 1120 may be configured to communicate using RFID (radio frequency identification) protocols. More particularly, in certain embodiments, the display device 1120 is configured to interrogate the on body electronics 1110 (associated with an RFID tag) over an RF communication link, and in response to the RF interrogation signal from the display device 1120, on body electronics 1110 provides an RF response signal including, for example, data associated with the sampled analyte level from the sensor 1101. Additional information regarding the operation of RFID communication can be found in U.S. Pat. No. 7,545,272, and in U.S. application Ser. Nos. 12/698,624, 12/699,653, 12/761,387, and U.S. Patent Publication No. 2009/0108992 the disclosures of all of which are incorporated herein by reference in their entireties and for all purposes.

For example, in one embodiment, the display device 1120 may include a backscatter RFID reader configured to provide an RF field such that when on body electronics 1110 is within the transmitted RF field of the RFID reader, on body electronics 1110 antenna is tuned and in turn provides a reflected or response signal (for example, a backscatter signal) to the display device 1120. The reflected or response signal may include sampled analyte level data from the analyte sensor 1101.

In certain embodiments, when display device 1120 is positioned in within a predetermined range of the on body electronics 1110 and receives the response signal from the on body electronics 1110, the display device 1120 is configured to output an indication (audible, visual or otherwise) to confirm the analyte level measurement acquisition. That is, during the course of the 5 to 10 days of wearing the on body electronics 1110, the user may at any time position the display device 1120 within a predetermined distance (for example, about 1-5 inches, or about 1-10 inches, or about 1-12 inches) from on body electronics 1110, and after waiting a few seconds of sample acquisition time period, an audible indication is output confirming the receipt of the real time analyte level information. The received analyte information may be output to the display 1122 (FIG. 11) of the display device 1120 for presentation to the user.

Display Devices

Figure 13:
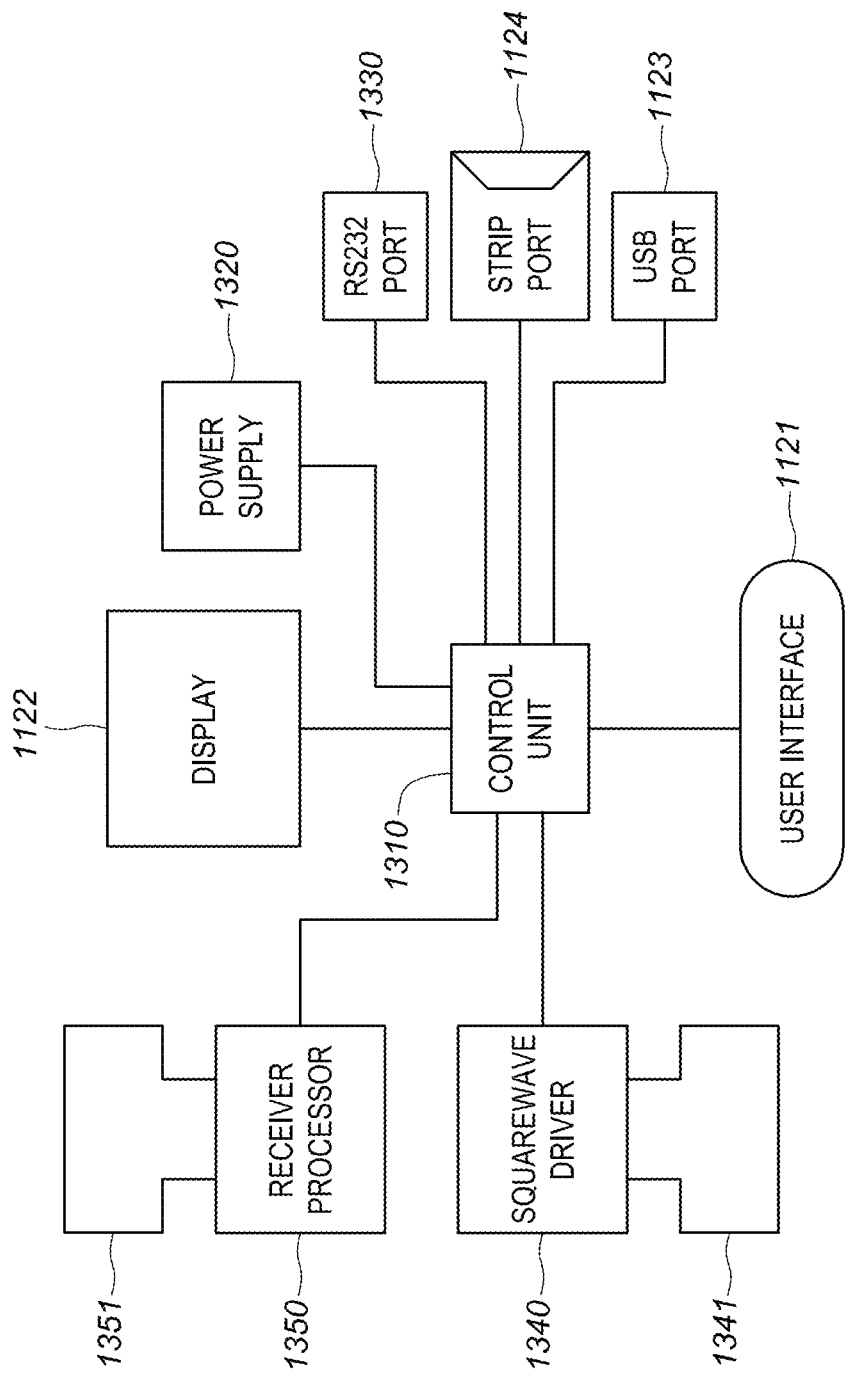
FIG. 13 is a block diagram depicting an example embodiment of a display device.

FIG. 13 is a block diagram of display device 1120 as shown in FIG. 11 in certain embodiments. Although the term display device is used, the device can be configured to read without displaying data, and can be provided without a display, such as can be the case with a relay or other device that relays a received signal according to the same or a different transmission protocol (e.g., NFC-to-Bluetooth or Bluetooth Low Energy). Referring to FIG. 13, display device 1120 (FIG. 11) includes control unit 1310, such as one or more processors (or processing circuitry) operatively coupled to a display 1122, and an input component (e.g., user interface) 1121. The display device 1120 may also include one or more data communication ports such as USB port (or connector) 1123 or RS-232 port 1330 (or any other wired communication ports) for data communication with a data processing module 1160 (FIG. 11), remote terminal 1170 (FIG. 11), or other devices such as a personal computer, a server, a mobile computing device, a mobile telephone, a pager, or other handheld data processing devices including mobile telephones such as internet connectivity enabled smart phones, with data communication and processing capabilities including data storage and output.

Referring back to FIG. 13, display device 1120 may include a strip port 1124 configured to receive in vitro test strips, the strip port 1124 coupled to the control unit 1310, and further, where the control unit 1310 includes programming to process the sample on the in vitro test strip which is received in the strip port 1124. Any suitable in vitro test strip may be employed, e.g., test strips that only require a very small amount (e.g., one microliter or less, e.g., about 0.5 microliter or less, e.g., about 0.1 microliter or less), of applied sample to the strip in order to obtain accurate glucose information. Display devices with integrated in vitro monitors and test strip ports may be configured to conduct in vitro analyte monitoring with no user calibration of the in vitro test strips (e.g., no human intervention calibration).

In certain embodiments, an integrated in vitro meter can accept and process a variety of different types of test strips (e.g., those that require user calibration and those that do not), some of which may use different technologies (those that operate using amperometric techniques and those that operate using coulometric techniques), etc. Detailed description of such test strips and devices for conducting in vitro analyte monitoring is provided in U.S. Pat. Nos. 6,377,894, 6,616,819, 7,749,740, 7,418,285; U.S. Patent Publication Nos. 2004/0118704, 2006/0096006, 2008/0066305, 2008/0267823, 2010/0094610, 2010/0094111, and 2010/0094112, and U.S. application Ser. No. 12/695,947, the disclosures of all of which are incorporated herein by reference in their entireties and for all purposes.

Glucose information obtained by the in vitro glucose testing device may be used for a variety of purposes. For example, the information may be used to calibrate analyte sensor 1101 (FIG. 11) if the sensor requires in vivo calibration, confirm results of analyte sensor 1101 to increase the confidence in the results from sensor 1101 indicating the monitored analyte level (e.g., in instances in which information obtained by sensor 1101 is employed in therapy related decisions), etc. In certain embodiments, analyte sensors do not require calibration by human intervention during its usage life. However, in certain embodiments, a system may be programmed to self-detect problems and take action, e.g., shut off and/or notify a user. For example, an analyte monitoring system may be configured to detect system malfunction, or potential degradation of sensor stability or potential adverse condition associated with the operation of the analyte sensor, the system may notify the user, using display device 1120 (FIG. 11) for example, to perform analyte sensor calibration or compare the results received from the analyte sensor corresponding to the monitored analyte level, to a reference value (such as a result from an in vitro blood glucose measurement).

In certain embodiments, when the potential adverse condition associated with the operation of the sensor, and/or potential sensor stability degradation condition is detected, the system may be configured to shut down (automatically without notification to the user, or after notifying the user) or disable the output or display of the monitored analyte level information received the on body electronics assembly. In certain embodiments, the analyte monitoring system may be shut down or disabled temporarily to provide an opportunity to the user to correct any detected adverse condition or sensor instability. In certain other embodiments, the analyte monitoring system may be permanently disabled when the adverse sensor operation condition or sensor instability is detected.

Referring still to FIG. 13, power supply 1320, such as one or more batteries, rechargeable or single use disposable, is also provided and operatively coupled to control unit 1310, and configured to provide the necessary power to display device 1120 (FIG. 11) for operation. In addition, display device 1120 may include an antenna 1351 such as a 433 MHz (or other equivalent) loop antenna, 13.56 MHz antenna, or a 2.45 GHz antenna, coupled to a receiver processor 1350 (which may include a 433 MHz, 13.56 MHz, or 2.45 GHz transceiver chip, for example) for wireless communication with the on body electronics 1110 (FIG. 11). Additionally, an inductive loop antenna 1341 is provided and coupled to a squarewave driver 1340 which is operatively coupled to control unit 1310.

In certain embodiments, data packets received from on body electronics and received in response to a request from display device, for example, include one or more of a current glucose level from the analyte sensor, a current estimated rate of glycemic change, and a glucose trend history based on automatic readings acquired and stored in memory of on skin electronics. For example, current glucose level may be output on display 1122 of display device 1120 as a numerical value, the current estimated rage of glycemic change may be output on display 1122 as a directional arrow 1131 (FIG. 11), and glucose trend history based on stored monitored values may be output on display 1122 as a graphical trace 1138 (FIG. 11). In certain embodiments, the processor (or processing circuitry) of display device 1120 may be programmed to output more or less information for display on display 1122, and further, the type and amount of information output on display 1122 may be programmed or programmable by the user.

Data Communication and Processing Routines

Figure 14:
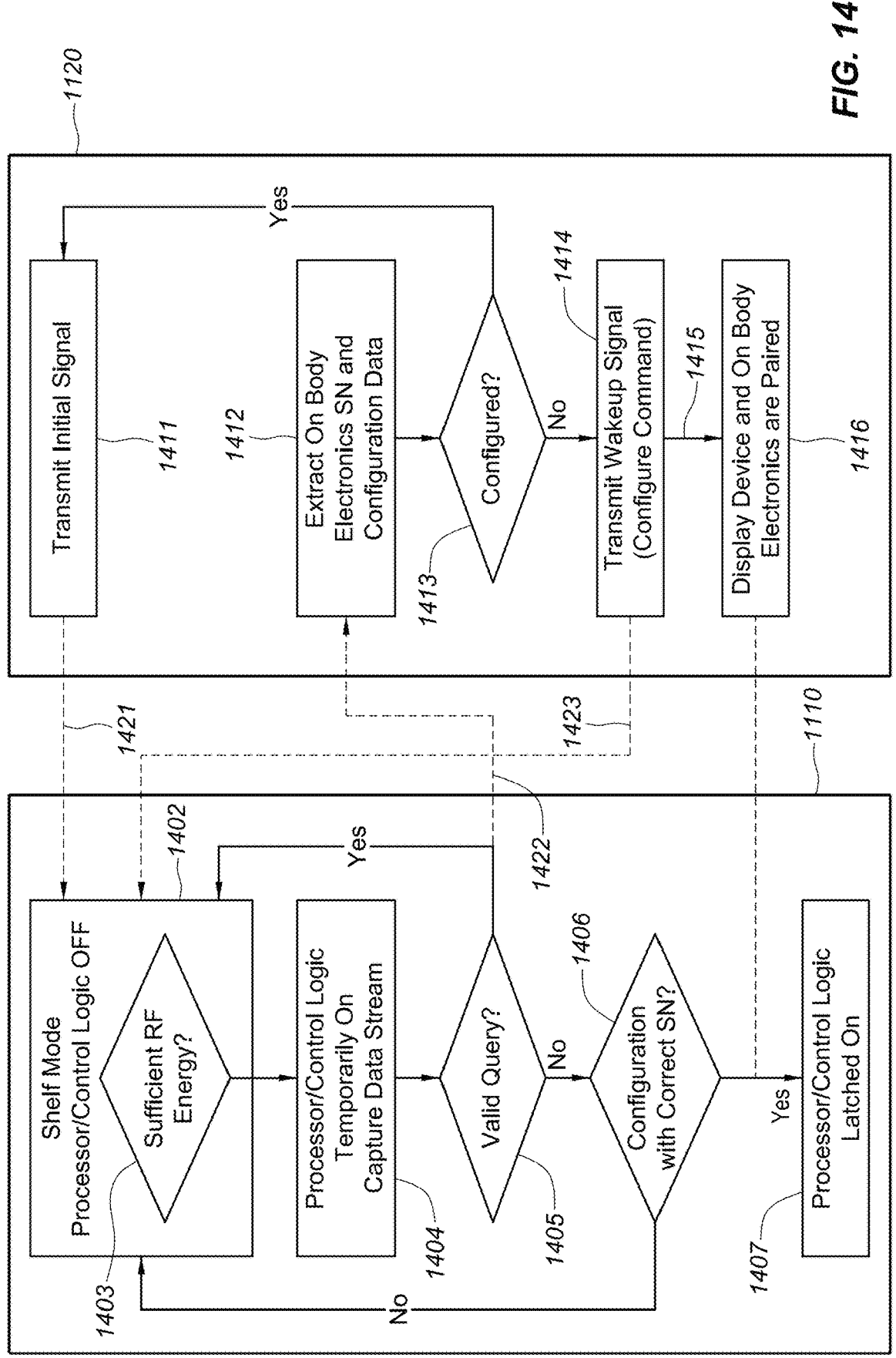
FIG. 14 is a flow diagram depicting an example embodiment of information exchange within and analyte monitoring system.

Referring now to FIG. 14 which illustrates data and/or commands exchange between on body electronics 1110 and display device 1120 during the initialization and pairing routine, display device 1120 provides and initial signal 1421 to on body electronics 1110. When the received initial signal 1421 includes RF energy exceeding a predetermined threshold level 1403, an envelope detector of on body electronics 1110 is triggered 1404, one or more oscillators of on body electronics 1110 turns on, and control logic or processors of on body electronics 1110 is temporarily latched on to retrieve and execute one or more software routines to extract the data stream from the envelope detector 1404. If the data stream from the envelope detector returns a valid query 1405, a reply signal 1422 is transmitted to display device 1120. The reply signal 1422 from on body electronics 1110 includes an identification code such as on body electronics 1110 serial number. Thereafter, the on body electronics 1110 returns to shelf mode in an inactive state.

On the other hand, if the data stream from the envelope detector does not return a valid query from display device 1120, on body electronics 1110 does not transmit a reply signal to display device 1120 nor is on body electronics 1110 serial number provided to display device 1120. Thereafter, on body electronics 1110 returns to shelf mode 1403, and remains in powered down state until it detects a subsequent initial signal 1421 from display device 1120.

When display device 1120 receives the data packet including identification information or serial number from on body electronics 1110, it extracts that information from the data packet 1412. With the extracted on body electronics 1110 serial number, display device 1120 determines whether on body electronics 1110 associated with the received serial number is configured. If on body electronics 1110 associated with the received serial number has already been configured, for example, by another display device, display device 1120 returns to the beginning of the routine to transmit another initial signal 1411 in an attempt to initialize another on body electronics that has not been configured yet. In this manner, in certain embodiments, display device 1120 is configured to pair with an on body electronics that has not already been paired with or configured by another display device.

Referring back to FIG. 14, if on body electronics 1110 associated with the extracted serial number has not been configured 1413, display device 1120 is configured to transmit a wake up signal to on body electronics 1110 which includes a configure command. In certain embodiments, wake up command from display device 1120 includes a serial number of on body electronics 1110 so that only the on body electronics with the same serial number included in the wake up command detects and exits the inactive shelf mode and enters the active mode. More specifically, when the wake up command including the serial number is received by on body electronics 1110, control logic or one or more processors (or processing circuitry) of on body electronics 1110 executes routines 1403, 1404, and 1405 to temporarily exit the shelf mode, when the RF energy received with the wakeup signal (including the configure command) exceeds the threshold level, and determines that it is not a valid query (as that determination was previously made and its serial number transmitted to display device 1120). Thereafter, on body electronics 1110 determines whether the received serial number (which was received with the wake up command) matches its own stored serial number 1406. If the two serial numbers do not match, routine returns to the beginning where on body electronics 1110 is again placed in inactive shelf mode 1402. On the other hand, if on body electronics 1110 determines that the received serial number matches its stored serial number 1406, control logic or one or more processors of on body electronics 1110 permanently latches on 1407, and oscillators are turned on to activate on body electronics 1110. Further, referring back to FIG. 14, when on body electronics 1110 determines that the received serial number matches its own serial number 1406, display device 1120 and on body electronics 1110 are successfully paired 1416.

In this manner, using a wireless signal to turn on and initialize on body electronics 1110, the shelf life of on body electronics 1110 may be prolonged since very little current is drawn or dissipated from on body electronics 1110 power supply during the time period that on body electronics 1110 is in inactive, shelf mode prior to operation. In certain embodiments, during the inactive shelf mode, on body electronics 1110 has minimal operation, if any, that require extremely low current. The RF envelope detector of on body electronics 1110 may operate in two modes—a desensitized mode where it is responsive to received signals of less than about 1 inch, and normal operating mode with normal signal sensitivity such that it is responsive to receives signals at a distance of about 3-12 inches.

During the initial pairing between display device 1120 and on body electronics 1110, in certain embodiments, display device 1120 sends its identification information such as, for example, 4 bytes of display device ID which may include its serial number. On body electronics 1110 stores the received display device ID in one or more storage unit or memory component and subsequently includes the stored display device ID data in response packets or data provided to the display device 1120. In this manner, display device 1120 can discriminate detected data packets from on body electronics 1110 to determine that the received or detected data packets originated from the paired or correct on body electronics 1110. The pairing routine based on the display device ID in certain embodiments avoids potential collision between multiple devices, especially in the cases where on body electronics 1110 does not selectively provide the analyte related data to a particular display device, but rather, provide to any display device within range and/or broadcast the data packet to any display device in communication range.

In certain embodiments, the payload size from display device 1120 to on body electronics 1110 is 12 bytes, which includes 4 bytes of display device ID, 4 bytes of on body device ID, one byte of command data, one byte of spare data space, and two bytes for CRC (cyclic redundancy check) for error detection.

After pairing is complete, when display device 1120 queries on body electronics 1110 for real time monitored analyte information and/or logged or stored analyte data, in certain embodiments, the responsive data packet transmitted to display device 1120 includes a total of 418 bytes that includes 34 bytes of status information, time information and calibration data, 96 bytes of the most recent 16 one-minute glucose data points, and 288 bytes of the most recent 15 minute interval glucose data over the 12 hour period. Depending upon the size or capacity of the memory or storage unit of on body electronics 1110, data stored and subsequently provided to the display device 1120 may have a different time resolution and/or span a longer or shorter time period. For example, with a larger data buffer, glucose related data provided to the display device 1120 may include glucose data over a 24 hour time period at 15 minute sampling intervals, 10 minute sampling intervals, 5 minute sampling intervals, or one minute sampling interval. Further, the determined variation in the monitored analyte level illustrating historical trend of the monitored analyte level may be processed and/or determined by the on body electronics 1110, or alternatively or in addition to, the stored data may be provided to the display device 1120 which may then determine the trend information of the monitored analyte level based on the received data packets.

The size of the data packets provided to display device 1120 from on body electronics 1110 may also vary depending upon the communication protocol and/or the underlying data transmission frequency—whether using a 433 MHz, a 13.56 MHz, or 2.45 GHz in addition to other parameters such as, for example, the presence of data processing devices such as a processor or processing circuitry (e.g., central processing unit CPU) in on body electronics 1110, in addition to the ASIC state machine, size of the data buffer and/or memory, and the like.

In certain embodiments, upon successful activation of on body electronics 1110 and pairing with display device 1120, control unit of display device 1120 may be programmed to generate and output one or more visual, audible and/or haptic notifications to output to the user on display 1122, or on the user interface of display device 1120. In certain embodiments, only one display device can pair with one on body electronics at one time. Alternatively, in certain embodiments, one display device may be configured to pair with multiple on body electronics at the same time.

Once paired, display 1122 of display device 1120, for example, outputs, under the control of the processor of display device 1120, the remaining operational life of the analyte sensor 1101 in user. Furthermore, as the end of sensor life approaches, display device may be configured to output notifications to alert the user of the approaching end of sensor life. The schedule for such notification may be programmed or programmable by the user and executed by the processor of the display device.

Referring back to FIG. 11, in certain embodiments, analyte monitoring system 1100 may store the historical analyte data along with a date and/or time stamp and/or and contemporaneous temperature measurement, in memory, such as a memory configured as a data logger as described above. In certain embodiments, analyte data is stored at the frequency of about once per minute, or about once every ten minutes, or about once an hour, etc. Data logger embodiments may store historical analyte data for a predetermined period of time, e.g., a duration specified by a physician, for example, e.g., about 1 day to about 1 month or more, e.g., about 3 days or more, e.g., about 5 days or more, e.g., about 7 days or more, e.g., about 2 weeks or more, e.g., about 1 month or more.

Other durations of time may be suitable, depending on the clinical significance of the data being observed. The analyte monitoring system 1100 may display the analyte readings to the subject during the monitoring period. In some embodiments, no data is displayed to the subject. Optionally, the data logger can transmit the historical analyte data to a receiving device disposed adjacent, e.g., in close proximity to the data logger. For example, a receiving device may be configured to communicate with the data logger using a transmission protocol operative at low power over distances of a fraction of an inch to about several feet. For example, and without limitation, such close proximity protocols include Certified Wireless USB™ TransferJet™, Bluetooth® (IEEE 802.15.1), WiFi™ (IEEE 802.11), ZigBee® (IEEE 802.15.4-2006), Wibree™, or the like.

The analyte data parameters may be computed by a processor or processing circuitry executing a program stored in a memory. In certain embodiments, the processor executing the program stored in the memory is provided in data processing module 1160 (FIG. 11). In certain embodiments, the processor executing the program stored in the memory is provided in display device 1120. An example technique for analyzing data is the applied ambulatory glucose profile (AGP) analysis technique. Additional detailed descriptions are provided in U.S. Pat. Nos. 5,264,104; 5,262,305; 5,320, 715; 5,593,852; 6,175,752; 6,650,471; 6,746, 582, 6,284, 478, 7,299,082, and in U.S. patent application Ser. Nos. 10/745,878; 11/060,365, the disclosures of all of which are incorporated herein by reference in their entireties for all purposes.

As described above, in certain aspects of the present disclosure, discrete glucose measurement data may be acquired on-demand or upon request from the display device, where the glucose measurement is obtained from an in vivo glucose sensor transcutaneously positioned under the skin layer of a user, and further having a portion of the sensor maintained in fluid contact with the bodily fluid under the skin layer. Accordingly, in aspects of the present disclosure, the user of the analyte monitoring system may conveniently determine real time glucose information at any time, using the RFID communication protocol as described above.

In one aspect, the integrated assembly including the on body electronics and the insertion device may be sterilized and packaged as one single device and provided to the user. Furthermore, during manufacturing, the insertion device assembly may be terminal packaged providing cost savings and avoiding the use of, for example, costly thermoformed tray or foil seal. In addition, the insertion device may include an end cap that is rotatably coupled to the insertion device body, and which provides a safe and sterile environment (and avoid the use of desiccants for the sensor) for the sensor provided within the insertion device along with the integrated assembly. Also, the insertion device sealed with the end cap may be configured to retain the sensor within the housing from significant movement during shipping such that the sensor position relative to the integrated assembly and the insertion device is maintained from manufacturing, assembly and shipping, until the device is ready for use by the user.

Drug Delivery Systems

The on body device and/or display device can also include or be integrated with a drug (e.g., insulin, etc.) delivery device into a system such that they, e.g., share a common housing. In other embodiments the on body device, display device, and drug delivery device can each be separate and discrete devices, e.g., they each have their own housing. The drug delivery device can provide a drug to counteract the high or low level of the analyte in response to a signal from a sensor of the on body device, or the system may monitor the drug concentration to ensure that the drug remains within a desired therapeutic range. Examples of such drug delivery devices can include medication pumps having a cannula that remains in the body to allow infusion over a multi-hour or multi-day period (e.g., wearable pumps for the delivery of basal and bolus insulin). When combined with a medication pump, the on body device or display device can include a reservoir to store the drug, a pump connectable to transfer tubing, and an infusion cannula. The pump can force the drug from the reservoir, through the tubing and into the diabetic's body by way of the cannula inserted therein. Other examples of drug delivery devices that can be included with (or integrated with) a display device include portable injection devices that pierce the skin only for each delivery and are subsequently removed (e.g., insulin pens). A display device, when combined with a portable injection device, can include an injection needle, a reservoir for carrying the drug, an interface for controlling the amount of drug to be delivered, and an actuator to cause injection to occur. The device can be used repeatedly until the drug is exhausted, at which point the combined device can be discarded, or the reservoir can be replaced with a new one, at which point the combined device can be reused repeatedly. The needle can be replaced after each injection.

An on body device combined with a drug delivery device, or a display device combined with a drug delivery device, can both function as part of a closed-loop system (e.g., an artificial pancreas system requiring no user intervention to operate) or semi-closed loop system (e.g., an insulin loop system requiring seldom user intervention to operate, such as to confirm changes in dose). For example, the diabetic's analyte level can be monitored in a repeated automatic fashion by the on body device, which can then communicate that monitored analyte level to the display device, and the appropriate drug dosage to control the diabetic's analyte level can be automatically determined and subsequently delivered to the diabetic's body (e.g., by the display device integrated with the drug delivery device, or by communication of the dosage from the display device to a discrete drug delivery device). Software instructions for controlling the pump and the amount of insulin delivered can be stored in the memory of the display device and executed by the display device's processing circuitry. These instructions can also cause calculation of drug delivery amounts and durations (e.g., a bolus infusion and/or a basal infusion profile) based on the analyte level measurements obtained directly or indirectly from the on body device. In some embodiments, the on body device can determine the drug dosage and communicate that to the display device.

Example Embodiments of In Vitro Analyte Monitoring Systems

In vitro analyte monitoring systems often utilize an in vitro analyte sensor in the form of a test strip or strip that has a region adapted for contact with a sample of a bodily fluid (e.g., blood) that has been removed from a living body, typically by lancing the skin with a sharp such that one or several drops of blood exit the skin. Such in vitro devices can be referred to as strip-based in vitro devices. In vitro analyte sensors can be configured to sense the same analytes described earlier with respect to in vivo analyte sensors. Many embodiments of in vitro sensors can be formed on a substrate, e.g., a substantially planar substrate. In certain embodiments, the in vitro sensor includes a working electrode. A working ink may be disposed on at least a portion of the working electrode. The in vitro sensor may also include at least one counter electrode (or counter/reference electrode) and/or at least one reference electrode or at least one reference/counter electrode.

Figure 15A:
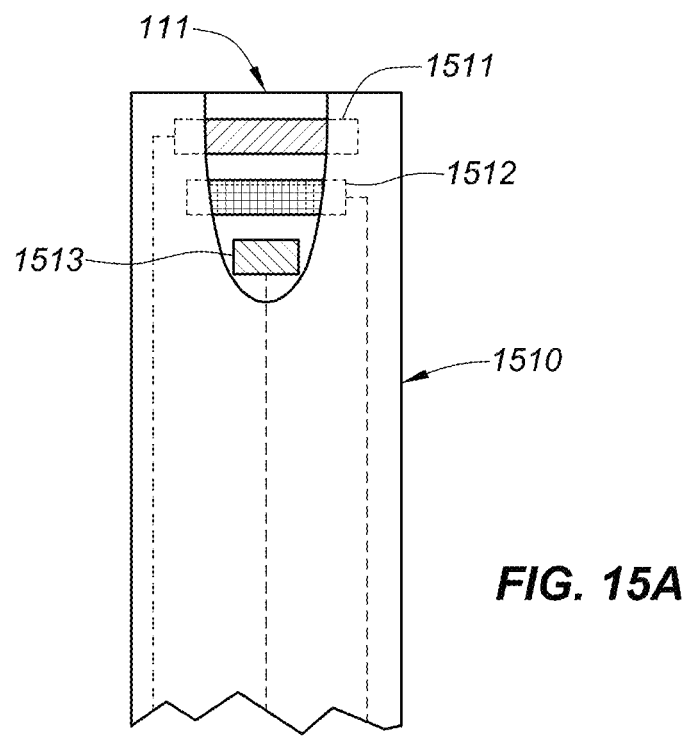
FIGS. 15A, 15B, and 16 are top down views depicting example embodiments of in vitro analyte sensors.

In certain embodiments, the in vitro sensor may include a first, second and a third electrode as illustrated in FIGS. 15A and 15B, 16, and 17. For example, as shown in the in vitro sensor 1510 of FIG. 15A, the first electrode 1511 may be closest to the sample application site 111, followed by the second electrode 1512, and third electrode 1513. The in vitro sensor in FIG. 15A is depicted as having a first substrate 1530 onto which the electrodes are disposed and further having an insulative layer 1531, with a cut-out for the sample chamber 1532, disposed on the electrodes, the cut-out exposes the electrodes in the sample chamber while covering other portions of the electrodes. Accordingly, within the sample chamber, the electrodes are disposed such that a sample applied at the tip of the sensor at application site 111, contacts the first electrode 1511 first, then the second electrode 1512, and then the third electrode 1513. The conductive trace portions of the electrodes which connect the electrodes to a meter are covered by the insulative layer. These in vitro sensors may have an additional layer, such as a second substrate disposed over the insulative layer. The cut out in the insulative layer and the first and second substrates defines the sample chamber. In certain embodiments, the first electrode 1511 may be a counter electrode or a reference/counter electrode, the second electrode 1512 may be a working electrode, and third electrode 1513 may be a trigger electrode that indicates that sample volume sufficient for accurate analyte measurement is present in the sample chamber.

In other embodiments, at least two of the electrodes may be in a facing configuration. For example, the first electrode may be on a first substrate of the in vitro sensor while the second and/or the third electrode may be on a second substrate of the sensor, where the arrangement of the electrode with regard to the sample application site may be as described above.

Figure 15B:
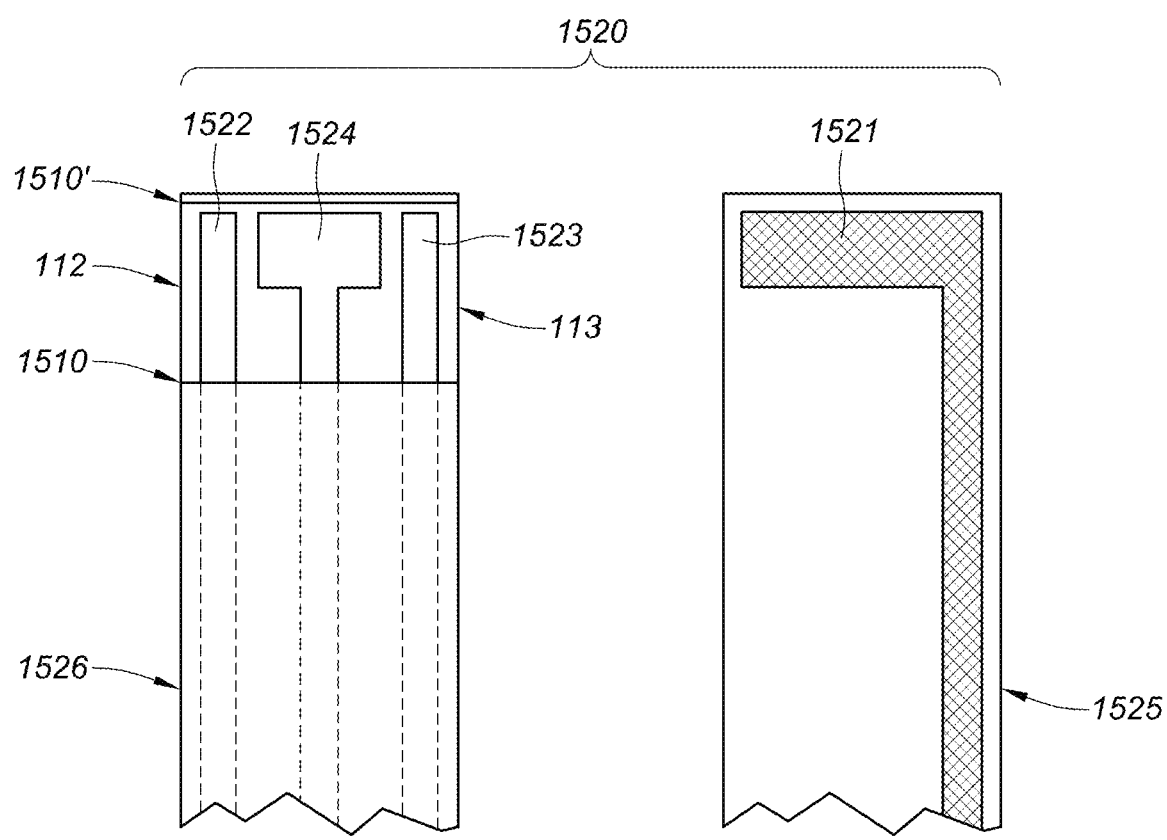

In other embodiments, the in vitro sensor may be as shown in FIG. 15B. In FIG. 15B, the sensor 1520 includes a first electrode 1521 on a first substrate 1525; two second electrodes 1522 and 1523, for detecting sufficient filling of the sample chamber, and third electrode 1524 on a second substrate 1526. In the assembled sensor, the first electrode 1521 is a facing orientation to electrodes 1522, 1523, and 1524. In the sensor of FIG. 15B, the sample may be filled from either side entrance 112 or 113. A spacer layer 1510 and 1510' in combination with the two substrates 1525 and 1526 define the sample chamber. The sensor in FIG. 15B includes two side entrances 112 and 113 either of which can be used to fill the sensor with a sample. In these embodiments, the sample may contact the first (1521) and second (1522) electrodes simultaneously and before the sample contacts the third electrode 1524, when the sample enters at entrance 112. In other embodiments, the sample enters at entrance 113 and contacts electrodes 1521 and 1523 simultaneously before contacting electrode 1522. In certain embodiments, the second electrodes act as trigger electrodes which indicate that sample volume sufficient for accurate analyte measurement is present in the sample chamber. In certain embodiments, the third electrode 1524 may be a working electrode and first electrode 1521 may be a counter electrode or a reference/counter electrode.

Figure 16:
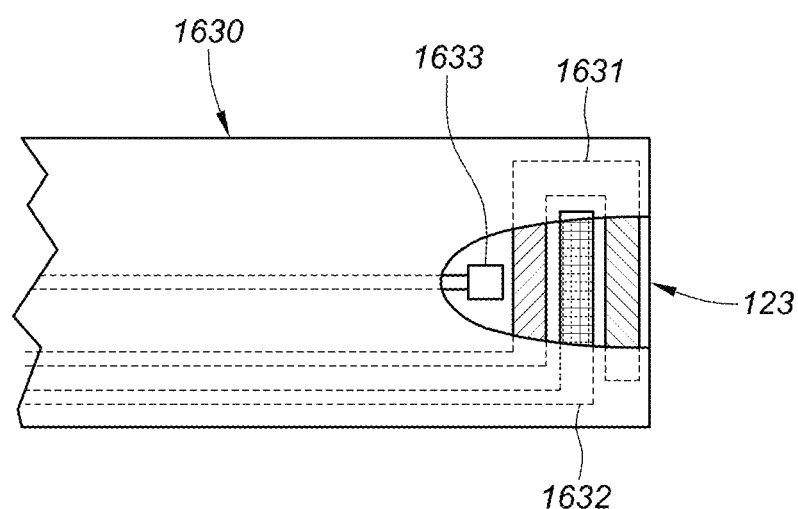

In another embodiment, the in vitro sensor may be as shown in FIG. 16. In this embodiment, the all electrodes are disposed on a single surface of the same substrate 1630. These coplanar electrodes include a counter electrode or a counter/reference electrode 1631 disposed in wrap-around configuration with reference to the working electrode 1632. A trigger electrode 1633 is disposed downstream to electrodes 1631 and 1632 such that a sample applied to the application site 123 contacts the trigger electrode 1633 after contacting electrodes 1631 and 1632.

Figure 17:
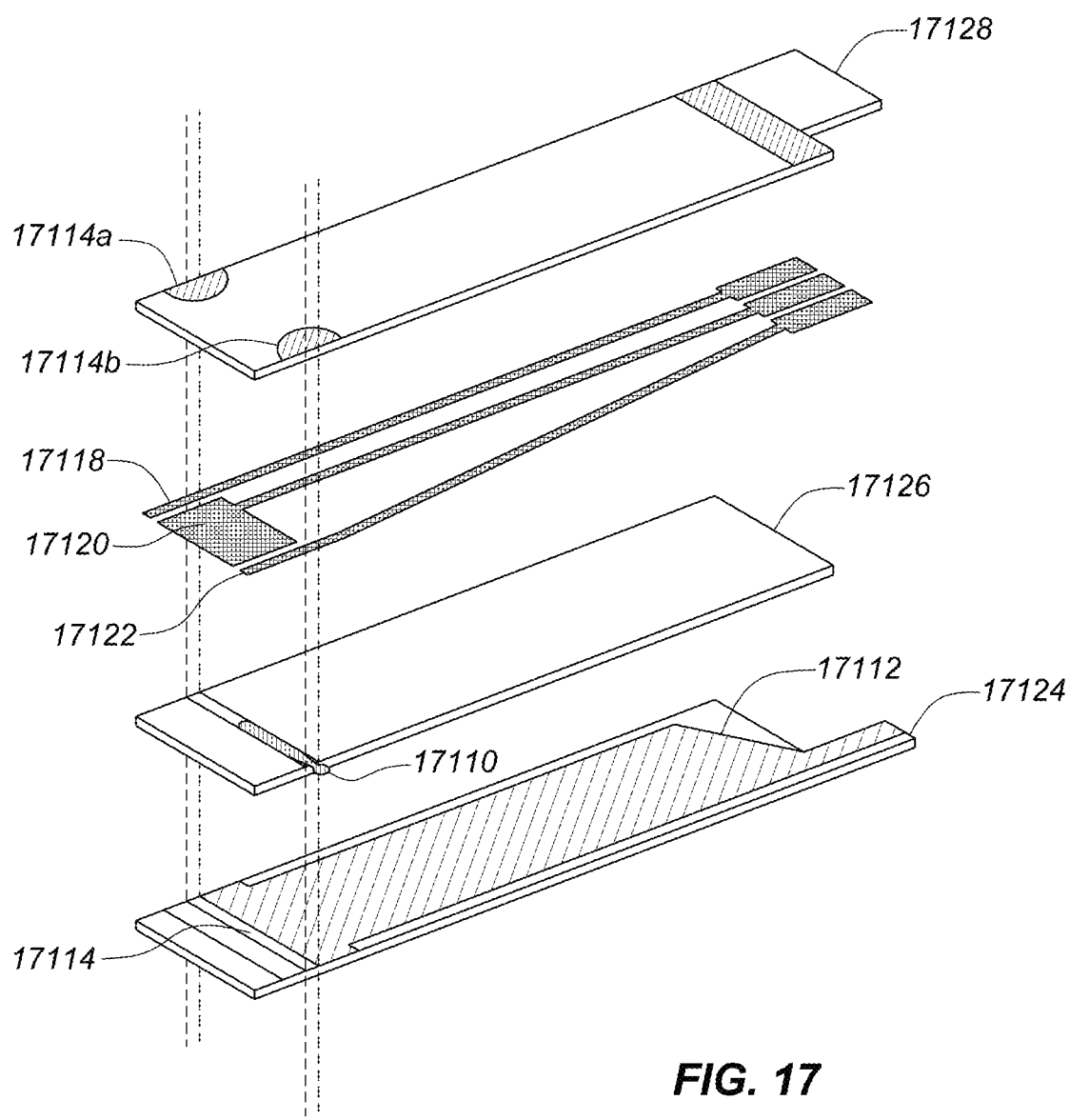
FIG. 17 is an exploded view depicting an example embodiment of an in vitro analyte sensor.

An embodiment of an in vitro analyte sensor with electrodes in a facing configuration is illustrated in FIG. 17 which shows an exploded view of such a sensor. The in vitro sensor includes a working electrode 17112 disposed on substrate 17124. Electrodes 17118, 17120, and 17122 are disposed on second substrate 17128. Spacer layer 17126 (e.g., an adhesive) separates working electrode 17112 from electrodes 17118, 17120, and 17122. 17118 and 17122 are trigger electrodes and 17120 may be a silver/silver chloride combined counter/reference electrode. Substrates 17128, 17124, in combination with spacer 17126 define the sample chamber 17114. Sample chamber 17114 includes two entrances on side edges of the sensor, the entrances are marked by reference numerals 17114a and 17114b. 17110 depicts a sample as it is filled into the sample chamber 17114. Sample chamber 17114 includes the working electrode 17112. The trigger electrode closest to the side where the sample has been applied indicates when the sample has started filling the sample chamber and the trigger electrode at the opposite side of the sample chamber indicates when the sample chamber has been filled by the sample.

The terms "working electrode", "counter electrode", "reference electrode" and "counter/reference electrode" are used herein to refer to a portion or portions of a conductive trace which are configured to function as a working electrode, counter electrode, reference electrode, or a counter/reference electrode, respectively. In other words, a working electrode is that portion of a conductive trace which functions as a working electrode as described herein, e.g., that portion of a conductive trace which is exposed to an environment containing the analyte or analytes to be measured and not covered by an insulative layer (such as a spacer layer, a tape, or a cover), and which, in some cases, has been modified with one or more sensing layers as described herein. Similarly, a reference electrode is that portion of a conductive trace which functions as a reference electrode as described herein, e.g., that portion of a conductive trace which is exposed to an environment containing the analyte or analytes to be measured and not covered by an insulative layer, and which, in some cases, includes a secondary conductive layer, e.g., a Ag/AgCl layer. A counter electrode is that portion of a conductive trace which is configured to function as a counter electrode as described herein, e.g., that portion of a conductive trace which is exposed to an environment containing the analyte or analytes to be measured and not covered by an insulative layer. As noted above, in some embodiments, a portion of a conductive trace may function as either or both of a counter electrode and a reference electrode.

In certain embodiments, a working ink comprising an analyte responsive enzyme may be disposed in the sample chamber of the in vitro sensor. In certain embodiments, a sample chamber is defined by a first substrate, a second substrate, and a spacer layer disposed between the first and second substrates. The spacer layer may be shorter than the first substrate and a second substrate or may include a cut-out that defines a space between the first substrate and the second substrate. The sample chamber includes at least a portion of the working electrode and the counter or the counter/reference electrode. In certain embodiments, the working ink may be disposed on the working electrode (e.g., in a sensor with a facing electrode configuration) or may be disposed on both the working electrode and the counter or the counter/reference electrode (e.g., in a sensor with a coplanar electrode configuration). The portion of the working electrode that is exposed in the sample chamber, e.g., is not covered with the spacer layer, defines a working region that is available for measuring an analyte related signal from a sample present in the sample chamber. In certain embodiments, the working region is a working pad covered with the working ink. In certain embodiments, the working ink in addition to containing an analyte responsive enzyme may also include a redox mediator. The area of the working pad may be dependent on the area of the working electrode as well as the area of the working electrode not covered by the spacer layer that holds the first and second substrates in a spaced apart manner. The thickness of the working pad may be a thickness suitable for measurement of the analyte and may be controlled during the manufacturing process.

In certain embodiments, the electrodes are connected to contact pads via a trace. The contact pads facilitate connection of the electrodes to a meter or another device that detects the electrochemical signal generated by the interaction of the analyte in the sample and the analyte specific enzyme. In general, at least a portion of the electrodes and contact pads are not covered by the spacer layer or another insulating layer when the trace is covered by the spacer layer or another insulating layer in the assembled sensor. In certain embodiments, the trace may be made from the same material as the electrodes and contact pads. The resistance of the trace is dependent upon the trace area as well as the trace material.

The in vitro sensors can be configured for top-filling, tip-filling, corner-filling and/or side-filling. In some embodiments, the in vitro sensors include one or more optional fill assist structures, e.g., one or more notches, cut-outs, indentations, and/or protrusions, which facilitate the collection of the fluid sample. For example, the in vitro sensor can be configured such that the proximal end of the in vitro sensor is narrower than the distal end of the sensor. In one such embodiment, the analyte sensor includes a tapered tip at the proximal end of the in vitro sensor, e.g., the end of the in vitro sensor that is opposite from the end that engages with a meter.

The in vitro analyte sensors can be configured to include one or more protrusions which facilitate filling of the sensors. The one or more protrusions may extend from the first substrate or the second substrate or both. In some embodiments, the in vitro analyte sensors include one or more spacers positioned with respect to protrusions such that they provide structural support for the protrusions. Additional fill assist structures are described in U.S. Patent Publication No. 2008/0267823, and U.S. patent application Ser. No. 11/461,725, filed Aug. 1, 2006, the disclosures of both of which are incorporated by reference herein in their entireties and for all purposes.

Figure 18A:
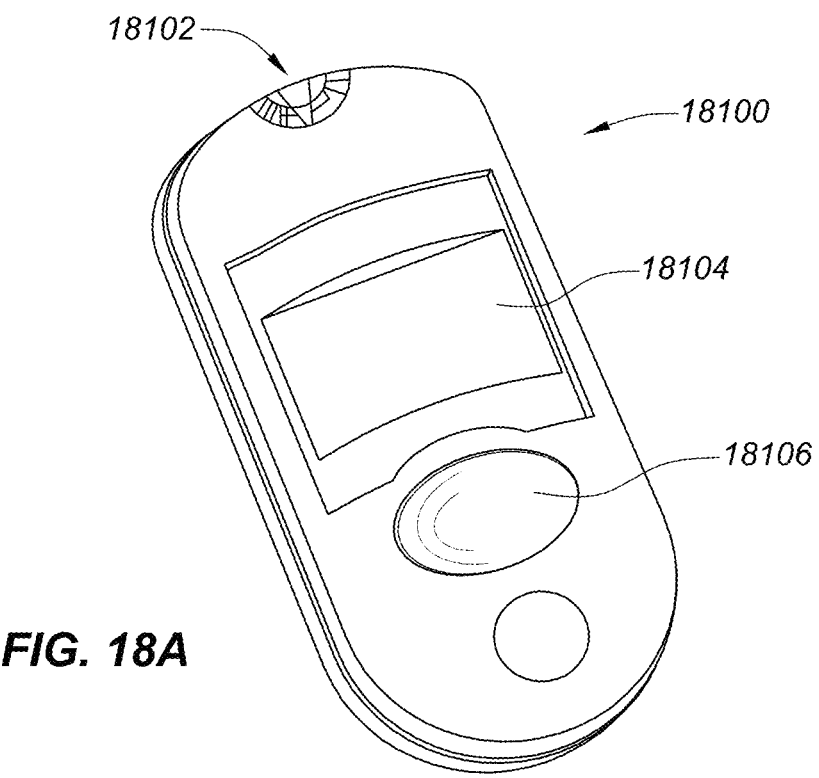
FIG. 18A is a perspective view depicting an example embodiment of an in vitro analyte meter.
Figure 18B:
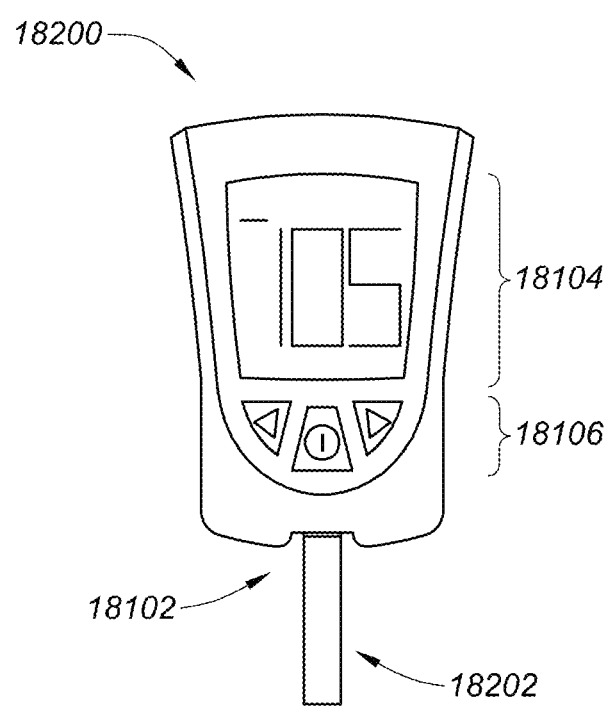
FIG. 18B is a frontal view depicting an example embodiment of an in vitro analyte meter.

The configuration and operation of in vitro meters is well known in the art. FIG. 18A is a perspective view depicting an example embodiment of an in vitro analyte meter 18100. In this embodiment, the meter 18100 includes a test strip slot or port 18102, a display 18104 and one or more operational buttons 18106. Although not shown in FIG. 18A, the meter 18100 can also include component circuitry for receiving signals that depend on the analyte level of a fluid applied to a strip that is inserted into the slot 18102, and component circuitry for determining the analyte level based on the received signals. This component circuitry can include processing circuitry communicatively coupled with non-transitory memory. The non-transitory memory can include one or more software instructions that, when executed by the processing circuitry, cause the processing circuitry to calculate the analyte level from the signals received from the test strip, and because the processing circuitry to cause the display of the analyte level to the user. FIG. 18B is a frontal view depicting an analyte meter 18200 with display 18104 and operational buttons 18106, and also having a glucose test strip 18202 inserted into a slot 18102 for testing a body fluid sample (e.g., blood) applied to the strip 18202.

Example Embodiments of Calibration

Biochemical sensors can be described by one or more sensing characteristics. A common sensing characteristic is referred to as the biochemical sensor's sensitivity, which is a measure of the sensor's responsiveness to the concentration of the chemical or composition it is designed to detect. For electrochemical sensors, this response can be in the form of an electrical current (amperometric) or electrical charge (coulometric). For other types of sensors, the response can be in a different form, such as a photonic intensity (e.g., optical light). The sensitivity of a biochemical analyte sensor can vary depending on a number of factors, including whether the sensor is in an in vitro state or an in vivo state.

Figure 19A:
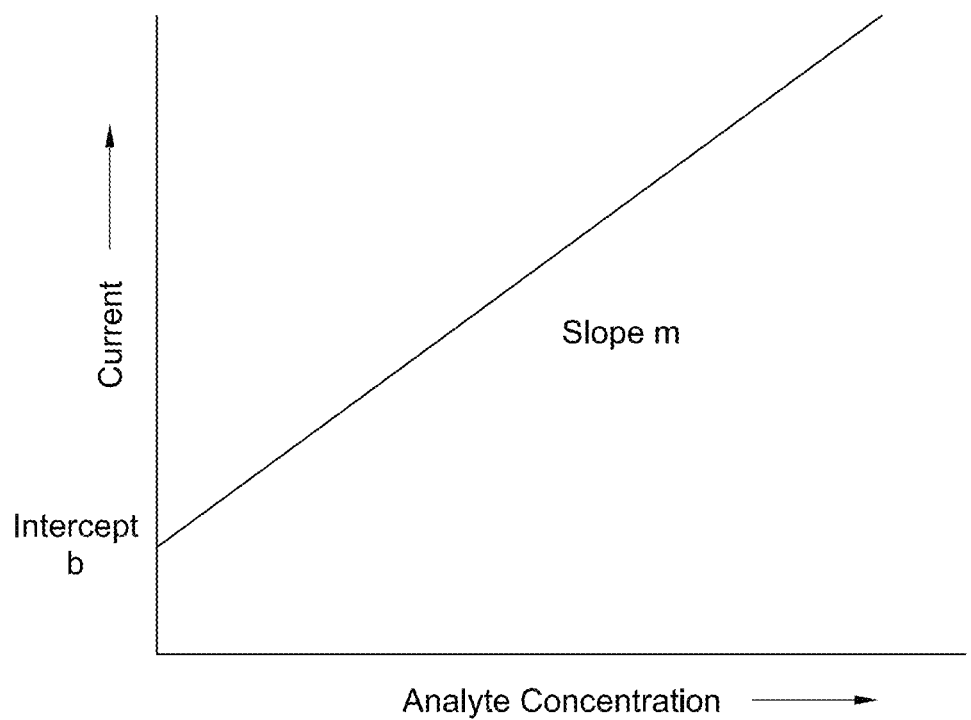
FIG. 19A is a graph depicting an example of an in vitro sensitivity of an analyte sensor.

FIG. 19A is a graph depicting the in vitro sensitivity of an amperometric analyte sensor. The in vitro sensitivity can be obtained by in vitro testing the sensor at various analyte concentrations and then performing a regression (e.g., linear or non-linear) or other curve fitting on the resulting data. In this example, the analyte sensor's sensitivity is linear, or substantially linear, and can be modeled according to the equation $y=mx+b$, where y is the sensor's electrical output current, x is the analyte level (or concentration), m is the slope of the sensitivity and b is the intercept of the sensitivity, where the intercept generally corresponds to a background signal (e.g., noise). For sensors with a linear or substantially linear response, the analyte level that corresponds to a given current can be determined from the slope and intercept of the sensitivity. Sensors with a non-linear sensitivity require additional information to determine the analyte level resulting from the sensor's output current, and those of ordinary skill in the art are familiar with manners by which to model non-linear sensitivities. In certain embodiments of in vivo sensors, the in vitro sensitivity may be the same as the in vivo sensitivity, but in other embodiments a transfer (or conversion) function is used to translate the in vitro sensitivity into the in vivo sensitivity that is applicable to the sensor's intended in vivo use.

Figure 19B:
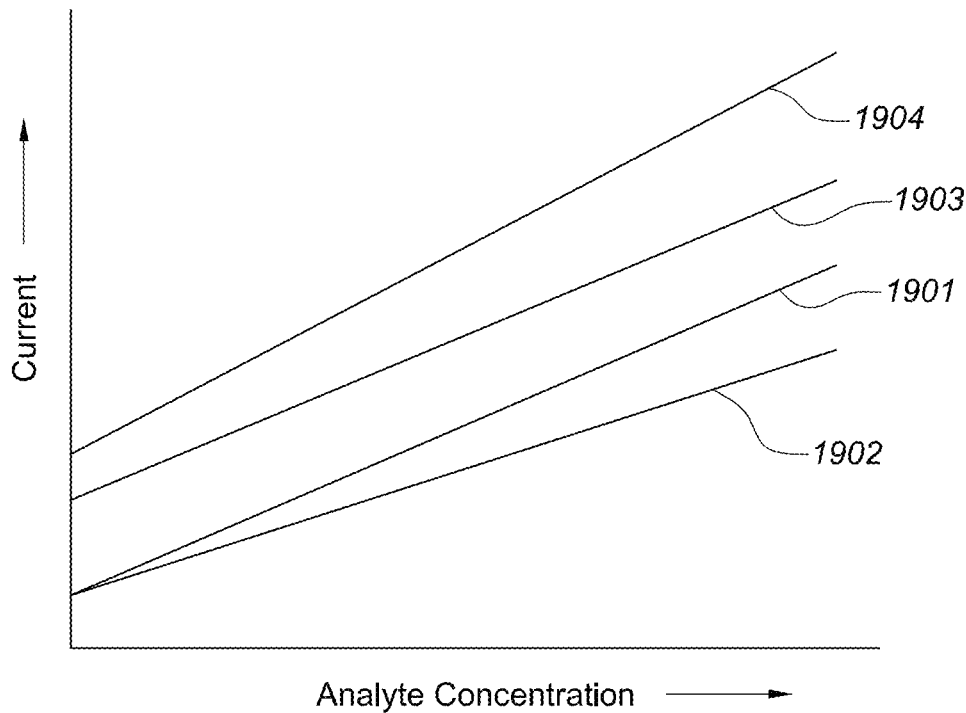
FIG. 19B is a graph depicting examples of different sensitivities for analyte sensors.

Biochemical sensors of the same design undergoing the same manufacturing process can have different in vitro sensitivities (as well as in vivo sensitivities, if applicable) due to variations in that manufacturing process and the materials used for fabrication. FIG. 19B depicts examples of different sensitivities 1901-1904 for different analyte sensors of the same mechanical and electrochemical design. The sensitivities 1901-1904 in this example are linear for ease of illustration, but in other examples can be non-linear. Here, a first sensitivity 1901 has the same intercept as a second sensitivity 1902, but a greater slope. A third sensitivity 1903 has generally the same slope as that of sensitivity 1902, but a greater intercept. A fourth sensitivity 1904 has a still greater slope and intercept that those of sensitivities 1901-1903.

In order to compensate for these variations, the sensor can be calibrated. Calibration is a technique for improving or maintaining accuracy by adjusting a sensor's measured output to reduce the differences with the sensor's expected output. One or more parameters that describe the sensor's sensing characteristics, like its sensitivity, are established for use in the calibration adjustment. However in vitro testing of the sensor can destroy, degrade, contaminate, or otherwise render the sensor not suitable for distribution from the possession of the manufacturer to the possession of users (e.g., for clinical testing, commercial use, etc.), and thus in vitro testing each sensor prior to distribution is not a practical option.

Examples of In Vivo Calibration

After using an in vivo sensor to obtain a raw measurement signal from the user's body, the on body electronics can apply analog signal conditioning to the raw signal and convert the signal into a digital form of the conditioned raw signal. For example, the digital raw data can be in counts converted by an A/D converter from the raw analog signal (for example, voltage or amps). In some embodiments, this conditioned raw digital data can be encoded for transmission to another device, e.g., a display device as described herein, which then algorithmically processes that digital raw data into a processed result representative of the user's analyte level (e.g., a result readily made suitable for display to the user). This algorithmic processing utilizes the calibration information for the sensor to arrive at the processed result, and can utilize other one or more other variables depending upon the implementation. Algorithmic processes for using calibration information to convert raw digital data into the processed result are within the skill of those in the art. This algorithmically processed result can then be digitally formatted or graphically processed for digital display to the user. In other embodiments, the on body electronics itself can algorithmically process the digital raw data into the processed result that is representative of the user's measured analyte level, and then encode and wirelessly communicate that data to a display device, which in turn can format or graphically process the received data for digital display to the user. In some such embodiments, the on body electronics can further graphically process the processed result of the data such that it is ready for display, and then display that data on a display of on body electronics or transmit the data to a display device. In some embodiments, the processed analyte data result (prior to graphic processing) is used by the system (e.g., incorporated into a diabetes monitoring regime) without processing for display to the user. In some embodiments, the on body electronics and/or the display device transmit the digital raw data to another computer system for algorithmic processing and display.

Certain embodiments of in vivo analyte monitoring systems require calibration to occur after implantation of the sensor into the user or patient, either by user interaction or by the system itself in an automated fashion. For example, when user interaction is required, the user performs an in vitro measurement (e.g., a blood glucose (BG) measurement using a finger stick and an in vitro test strip) and enters this into the system, while the analyte sensor is implanted. The system then compares the in vitro measurement with the in vivo signal and, using the differential, determines an estimate of the sensor's in vivo sensitivity. The in vivo sensitivity can then be used in an algorithmic process to transform the data collected with the sensor to a value that indicates the user's analyte level. This and other processes that require user action to perform calibration are referred to as "user calibration." Systems may require user calibration due to instability of the sensor's sensitivity, such that the sensitivity drifts or changes over time. Thus, multiple user calibrations (e.g., according to a periodic (e.g., daily) schedule or on an as-needed basis) may be required to maintain accuracy. While the embodiments described herein can incorporate a degree of user calibration for a particular implementation, generally this is not preferred as it requires the user to perform a painful or otherwise burdensome BG measurement, and can introduce user error.

Some embodiments of in vivo analyte monitoring systems have been proposed that regularly adjust the calibration parameters through the use of automated measurements of characteristics of the sensor made by the system itself (e.g., processing circuitry executing software). One such system repeatedly measures the sensor's impedance and uses this to update the sensitivity, and is described in US Publ. No. 2012/0265037, which is incorporated by reference herein in its entirety for all purposes. The repeated adjustment of the sensor's sensitivity based on a variable measured by the system (and not the user) is referred to generally as "system" (or automated) calibration, and can be performed with user calibration, such as an early BG measurement, or without user calibration. Like the case with repeated user calibrations, repeated system calibrations are typically necessitated by drift in the sensor's sensitivity over time. Thus, while the embodiments described herein can be used with a degree of automated system calibration, preferably the sensor's sensitivity is relatively stable over time such that post-implantation calibration is not required.

Some embodiments of in vivo analyte monitoring systems operate with a sensor that is factory calibrated. Factory calibration refers to the determination or estimation of the one or more calibration parameters prior to distribution to the user or healthcare professional (HCP). The calibration parameter can be determined by the sensor manufacturer (or the manufacturer of the other components of the sensor control device if the two entities are different). Many in vivo sensor manufacturing processes fabricate the sensors in groups or batches referred to as production lots, manufacturing stage lots, or simply lots. A single lot can include thousands of sensors.

Production lots are often individually numbered or coded to provide traceability throughout the manufacturing process. In some examples of factory calibration, one or a subset of sensors from each individual lot is tested and one or more nominal calibration parameters are determined and applied to the remaining, untested sensors in that particular lot that are designated for distribution into the field (e.g., for commercial use, clinical testing, etc.). Thus, each and every sensor distributed from that lot is assigned the same nominal calibration parameter. This can be referred to as "lot-level" calibration and, depending on the outcome of the lot testing, the sensors of a first lot may have a calibration parameter that is different than the sensors of a second lot.

One or more calibration parameters can be stored in the memory of the corresponding sensor control devices, such that when a user initiates operation of the sensor control device, the requisite calibration parameters are readily available. Embodiments of factory calibrated sensors with relatively unstable sensitivities can be used with one or more user calibration steps and/or one or more system calibration steps.

Factory calibrated sensors with stable or substantially stable sensitivities can be operated without user calibration and without system calibration. For example, in all of the embodiments described herein, the in vivo sensors can be calibrated by the manufacturer and then provided to the user, who can then use such sensors for the duration of their lifespan to accurately monitor the user's in vivo analyte levels, and no step of user calibration nor step of system calibration is performed during that lifespan. Such systems and methods determine clinically accurate analyte concentrations at least over the predetermined sensing period of analyte sensor systems without obtaining one or more independent analyte measurements (e.g., without using an in vitro test strip or other reference device) for calibration of a generated analyte related signal from the analyte sensor during the usage life of the sensor, e.g., post-manufacture. In other words, once the analyte sensors are positioned in the body of the user, control logic or microprocessors in the electronics, or the microprocessors in the display device include one or more algorithms or programming to accurately convert or correlate signals related to the sensed analyte (e.g., in nanoamps (nA), counts, or other appropriate units) to a corresponding analyte level (e.g., converted to an analyte level in milligrams per deciliter (mg/dL) or other appropriate units) without a reference value provided to the system, rendering sensor calibration "invisible" to the user such that the system does not require any human intervention for analyte sensor calibration.

Examples of In Vitro Calibration

Like in vivo analyte monitoring systems, in vitro analyte monitoring systems can also benefit from calibration. In vitro strips are typically used only once, and any calibration information associated with that in vitro sensor is determined by the manufacturer and not by the user. In some examples, the calibration parameter or code can be printed on the packaging containing the group of in vitro sensors. Each time the user uses one of the in vitro sensors, the user enters the calibration parameter into the meter so that the meter can appropriately adjust the result. The algorithmic processing performed by the in vitro systems is similar to that described with respect to the in vivo systems, where a raw measurement signal can undergo analog conditioning and conversion into a digital form of the conditioned raw signal, and then algorithmically processed into a processed result representative of the user's analyte level (e.g., a result readily made suitable for display to the user). This algorithmic processing utilizes the calibration information for the in vitro sensor to arrive at the processed result, and can utilize other one or more other variables depending upon the implementation. As with factory-calibrated in vivo sensors, the calibration code is determined for a production lot of in vitro sensors (or multiple production lots) and each in vitro sensor within the production lot is assigned the same calibration code.

Example Embodiments Relating to Individualized Calibration For Medical Devices

Many medical device manufacturing processes fabricate the medical devices in production lots. In vivo analyte sensors and in vitro analyte sensors (e.g., test strips) are just a few examples of medical devices manufacturable by lot. The example embodiments described herein allow an individualized calibration parameter to be independently determined, or estimated, for each and every medical device within a lot. Thus, instead of lot-level calibration, the embodiments allow for individual "device-level" calibration (e.g., "sensor-level" calibration). The terms "individualized calibration information" and "individualized calibration parameter" as used herein represent calibration information or a calibration parameter that has been determined using (or is otherwise based on or represents) at least one characteristic, measurement, or aspect that is specific to an individual medical device within a group (e.g., a production lot) and that can vary across the medical devices of the group. While "individualized calibration information" and an "individualized calibration parameter" may also be determined using a characteristic, measurement, or aspect that is not specific to an individual medical device but rather shared by the medical devices within the group, those terms remain distinguishable from both lot-level calibration information and a lot-level calibration parameter. The individualized calibration parameter can be determined for a particular medical device without in vitro testing that particular medical device, as that testing can render the device unsuitable for distribution to third party users as described above.

Figure 20A:
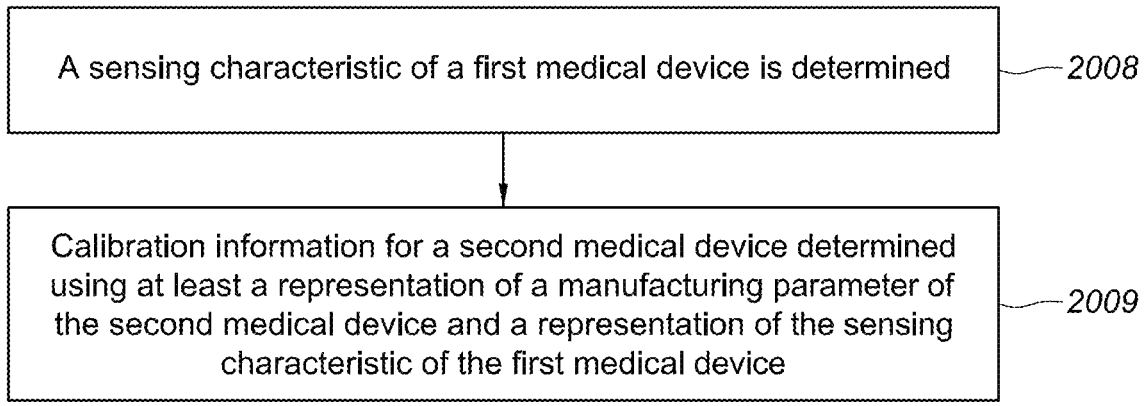
FIGS. 20A-20C are flow diagrams depicting example embodiments of methods for calibrating a medical device capable of sensing a biomedical attribute.

FIG. 20A is a flow diagram depicting an example embodiment of a method 2000 for individually calibrating a medical device capable of sensing a biomedical attribute. At 2008, a sensing characteristic of a first medical device is determined. For an analyte sensor, this sensing characteristic can be a sensitivity to the analyte for example. The sensing characteristic can be determined with in vitro (or in vivo) testing, such that the testing renders the first medical device unsuitable for distribution. At 2009, calibration information for a second medical device can be determined using at least a representation of a manufacturing parameter of the second medical device and a representation of the sensing characteristic of the first medical device. The representation of the manufacturing parameter can be the value of the manufacturing parameter as measured, a representative value that is calculated from the manufacturing parameter (e.g., a relative difference of the manufacturing parameter from a reference (nominal value or central tendency of the manufacturing parameter)), a representative aspect of the manufacturing parameter, or otherwise. The representation of the sensing characteristic, as will be described further below, can be the value of the sensing characteristic itself, a representative value that is calculated from the sensing characteristic (e.g., a relative difference of the sensing characteristic from a reference (nominal value or central tendency of the sensing characteristic)), a representative aspect of the sensing characteristic, or otherwise. The first and second medical devices are preferably of the same structural and chemical configuration and design.

In many cases the manufacturing parameter is specific to the second medical device. For example, the second device's manufacturing parameter can be measured directly or indirectly from the second device during or after manufacturing. Examples of manufacturing parameters are described in greater detail herein. The manufacturing parameter of the second device can be used with the sensing characteristic of the first device to determine, estimate, calculate, or extrapolate calibration information for the second device. In this manner, calibration information specific to the second device can be determined using characteristics of the second device that are obtained in a non-degrading, non-destructive or non-contaminatory manner, while also utilizing an actual sensing characteristic measured from the first medical device.

Figure 20B:
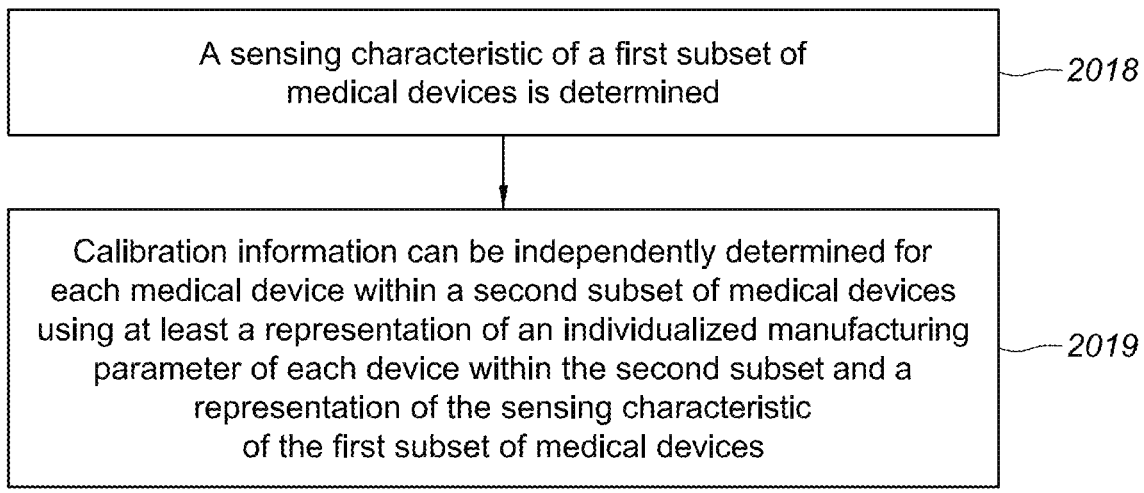

The method of FIG. 20A was described with respect to two individual medical devices (a first and a second), but this subject matter can be extended to larger scales. FIG. 20B is a flow diagram depicting another example embodiment of a method 2010 for individually calibrating a multitude of medical devices (e.g., in vivo or in vitro analyte sensors) capable sensing a biochemical attribute. At 2018, a sensing characteristic of a first subset of medical devices is determined. This first subset can be referred to herein as a sample subset, or a baseline subset, and the sensing characteristic taken from the first subset can be referred to herein as a sample sensing characteristic or baseline sensing characteristic. For analyte sensors, this sensing characteristic can be a sensitivity to the analyte for example. The sensing characteristic can be determined with in vitro (or in vivo if applicable) testing of the first subset of medical devices, such that the testing renders the first subset of medical devices unsuitable for distribution. Examples of testing will be described in more detail herein.

At 2019, calibration information can be independently determined for each medical device within a second subset of medical devices using at least a representation of an individualized manufacturing parameter of each device within the second subset and a representation of the sensing characteristic of the first subset of medical devices. Put differently, for example, if the second subset includes 100 individual medical devices, then 100 independent determinations of calibration information can be made (e.g., by processing circuitry executing software instructions). These 100 independent determinations can be performed as 100 discrete mathematical steps, or in one mathematical step such as by using number arrays. The second subset of medical devices corresponds to the subset intended for distribution to users such as patients and/or HCPs, and can be referred to herein as the distribution subset.

The medical devices within the baseline subset that are subject to in vitro testing are different from the medical devices within the distribution subset. In some embodiments, the baseline and distribution subsets are portions of a larger multitude of medical devices that have undergone one or more manufacturing steps together as a common group or batch. For example, the larger multitude can be a production lot that undergoes all or almost all manufacturing steps together. The baseline subset of medical devices can be taken from the production lot and used to derive the baseline sensing characteristic that is then used in part to determine the individualized calibration information for each sensor within the distribution subset. The baseline subset and distribution subset together do not have to account for every medical device within the production lot as certain medical devices within the lot can be removed (e.g., for failing an in-line inspection) or utilized for other purposes (e.g., quality control).

It is desirable to take the baseline subset and distribution subset from the same lot as this will inherently account for many manufacturing variations, particularly those that occur uniformly across the lot but may vary between lots. However, for manufacturing processes where significant variations are more limited within and between lots, then the medical devices within the baseline subset and the distribution subset are not taken from the same lot, although care should be taken so as not to significantly lessen the applicability of the baseline test results to the distribution subset. For example, in some embodiments, the medical devices within the baseline subset can be taken from two or more different production lots and the distribution subset can be taken from a production lot that is the same as the production lot of one or more medical devices within the baseline subset (e.g., the baseline subset represents a cross-section of many production lots to which the baseline sensing characteristic is then applied). In other embodiments, the baseline subset of medical devices can be taken from one production lot and the distribution subset of medical devices can be taken from a second, different production lot. In still other embodiments, the baseline subset can be taken from two or more different production lots and the distribution subset can be taken from a production lot from which no sensor is included within the baseline subset. In the embodiments just described, the notion of whether baseline and distribution subsets come from the same or different production lots is viewed with respect to whether the devices were processed together during one or more manufacturing stages.

Generally, the more medical devices within the baseline subset, the more accurate the resulting in vitro sensing characteristic will be. However, because the in vitro testing is often destructive etc., the medical devices within the baseline subset will generally not be available for distribution. Thus, the quantity of devices in the baseline subset can be determined by balancing the ability to obtain accurate and representative results against the decrease to production yields (and cost resulting therefrom). The quantity of devices in the baseline subset can also be related to the quantity of devices within the production lot (or an average production lot). For example only, the baseline subset can be approximately 0.01-10% (e.g., 0.01%, 0.1%, 0.5%, 1.0%, 5%, or 10%) of the medical devices within a production lot. By way of another example, the number of medical devices within the baseline subset can be approximately 0.01-10% (e.g., 0.01%, 0.1%, 1.0%, 5%, or 10%) of the number of medical devices within the distribution subset. Percentages outside of these ranges are also within the scope of this disclosure.

Figure 20C:
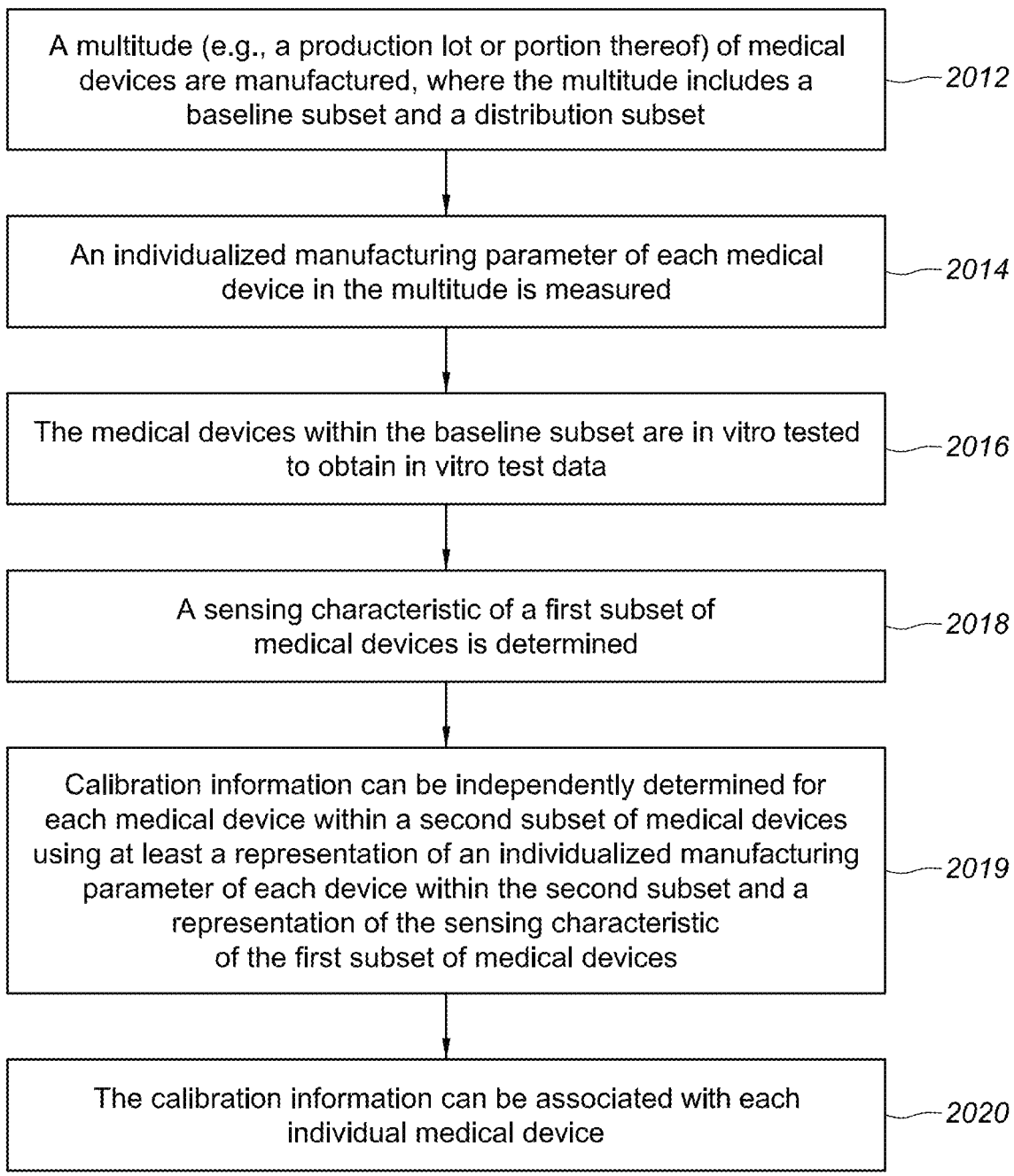

FIG. 20C is a flow diagram depicting another example embodiment of method 2010 (FIG. 20B) with additional steps that can be included by discretion. At 2012, a multitude (e.g., a production lot or portion thereof) of medical devices are at least partially manufactured, where the multitude includes a baseline subset and a distribution subset. At 2014, an individualized manufacturing parameter of each medical device in the multitude is measured. In some embodiments, the individualized manufacturing parameter is only measured for those medical devices in the distribution subset. The measuring step can be performed while the multitude of medical devices are being manufactured in step 2012, such as with in-line testing or monitoring occurring during or after each stage of manufacturing. The measurements can be performed after manufacturing of the medical device is complete, such as for those manufacturing parameters that are measurable at that stage. If the medical device is subsequently assembled with other components into a larger device, then measurements can be made after that assembly, if those manufacturing parameters remain measurable. At 2016, the medical devices within the baseline subset are in vitro tested to obtain in vitro test data. In vitro testing can be performed after manufacturing of the sensors has reached a stage that permits accurate in vitro testing (e.g., after application and postprocessing of the membrane but prior to assembly of the sensor with the electrical components associated therewith). As with the embodiment if FIG. 20B, at 2018, a sensing characteristic of the baseline subset of medical devices is determined and then at 2019, calibration information can be independently determined for each medical device within the distribution subset using at least a representation of an individualized manufacturing parameter of each medical device within the distribution subset and a representation of the sensing characteristic of the baseline subset of medical devices.

At 2020, the calibration information can be associated with each individual medical device. Various techniques for doing this are described in greater detail herein. For example, for in vivo devices, this can be achieved by storing the individualized calibration information within non-transitory memory of electronics assigned to the individual in vivo device, or by storing the individualized calibration information in non-transitory memory associated with a server such that the calibration information can be communicated to a device in the field (e.g., a reader device) that is operating with the individual in vivo sensor. For in vitro devices, this can be accomplished by recording the calibration information on a medium located on or with each individual in vitro device. In certain examples where the in vitro devices are strips, the strips can be packaged together with other strips having the same individually determined calibration information, which can be printed on the packaging.

Examples of Manufacturing Parameters

The term manufacturing parameter is a broad one intended to encompass any aspect of a medical device measurable (directly or indirectly) during or after the manufacturing process, or any descriptor of the manner in which a particular medical device (or group of medical devices) was manufactured. The manufacturing parameter is preferably specific to one individual medical device such that it can vary between medical devices in the same group or lot, in which case it is referred to herein as an individualized manufacturing parameter. This is in contrast to a manufacturing parameter that is not specific to one individual medical device, which is referred to herein as a "group" manufacturing parameter or "lot" manufacturing parameter. Examples of which can include an environmental parameter present while a batch of medical devices are concurrently processed (such as in a common chamber), or an identification of equipment that is used to manufacture a production lot.

The medical devices are preferably traceable throughout the manufacturing process such that the identity of the medical device during each manufacturing stage can be tracked. An individualized manufacturing parameter can be stored as data in a manner that associates it with the respective individual medical device from which it was obtained. When a manufacturing parameter is obtained for a particular medical device, that newly obtained manufacturing parameter can be stored with any and all other manufacturing parameters measured for that same medical device. Each individual medical device can therefore have one or more manufacturing parameters associated with it, for example, in a data or log file.

Examples of manufacturing parameters can include size or dimensional measurements of an individual medical device. The dimensional measurement can be any dimension in three-dimensional space. The size measurement can be one-dimensional, such as a length, width, height, thickness, radius, diameter, chord, or otherwise. The size measurement can represent a two-dimensional (2D) space, such as an area of a planar surface or a magnitude of a periphery of a planar surface, an arc, or otherwise. The size measurement can represent a three-dimensional (3D) space, such as an area of a nonplanar surface (e.g., cylindrical, hemispherical, irregular or portions thereof), a volume, or otherwise. Dimensional measurements can be obtainable directly or indirectly. For example, 2D and 3D measurements can be obtained by measuring various single dimensions and then calculating or estimating the 2D or 3D size. In some examples, dimensions such as height or thickness of a particular structure may be difficult to measure directly, but can be estimated by measuring other comparable structures (e.g., artwork) that can act as a surrogate. Size measurements can be obtained using inspection equipment (e.g., optical sensors) or the like.

In the context of in vivo analyte sensors, all the aforementioned sizes can be measured from any component thereof, such as any and all electrodes, a sensing region, a membrane, a contact, an insulating member, a substrate, an electrical trace, and so forth. In many embodiments, as will be described herein, the size or dimensional characteristics of the sensing region and/or the membrane of an in vivo analyte sensor can be particularly important in determining accurate calibration information for the sensor, although the embodiments described herein are not limited to only these examples. By way of non-limiting example, the size of the sensing region can be representative of at least one of the following: a width of the sensing region, a length of the sensing region, a thickness of the sensing region, a peripheral length of the sensing region, an area of the sensing region, or a volume of the sensing region. By way of non-limiting example, the size of the membrane can be representative of at least one of the following: a width of the membrane, a length of the membrane, a thickness of the membrane, a peripheral length of the membrane, an area of the membrane, or a volume of the membrane.

In the context of in vitro analyte sensors such as strips, all the aforementioned sizes can be measured from any component thereof, such as any and all electrodes, a working pad, a working ink, an insulating member, a substrate, a spacer, a trace, a cutout, and so forth. In some embodiments, the size (e.g., length, width, area, thickness or height, perimeter, volume, etc.) of the working pad can be particularly important in determining accurate calibration information, although the embodiments described herein are not limited to such.

Examples of manufacturing parameters can include chemical compositions or concentrations of any portion or component of the medical device. The chemical composition or concentration can be that of any of the structures described herein or otherwise known in the art. In the context of in vivo analyte sensors, the chemical composition can be that of any and all electrodes, a sensing region and components thereof, a membrane, a contact, a substrate, an insulating layer, an electrical trace, and so forth. In the context of in vitro sensors such as strips, the chemical composition can be that of any and all electrodes, a working pad, a working ink, an insulating member, a substrate, a spacer, an electrical trace, and so forth. Numerous chemical aspects of medical devices are described herein and these will not be repeated other than to note that the manufacturing parameter can relate to the composition and/or concentration of each chemical aspect described. In addition, the chemical composition or concentration can be representative of an impurity level within the medical device. Examples of manufacturing parameters can also include material characteristics, such as porosity, surface roughness or smoothness, density, frangibility, conduit width, conduit length, and the like.

Examples of manufacturing parameters can include electrical characteristics such as resistance, impedance, capacitance, leakage, and so forth. In the context of in vivo analyte sensors, the electrical characteristics can be measured from any component thereof, such as any and all electrodes, conductive members (such as wires, interconnects, traces, or contacts), insulating members (e.g., resistance, impedance, leakage), the sensing region, the membrane, a substrate, and so forth. In the context of in vitro sensors such as strips, the electrical characteristics can be measured from any component thereof, such as any and all electrodes, conductive members (such as wires, interconnects, traces, or contacts), insulating members, substrates, the working pad, the working ink, a spacer, and so forth. In some embodiments, the trace resistances can be particularly important in determining accurate calibration information, although the embodiments described herein are not limited to such.

Examples of manufacturing parameters that can be either individualized parameters (e.g., such as with single unit processing where an individual medical device is acted upon alone by the manufacturing equipment of a particular stage) or that are not individualized (e.g., such as with batch processing), can include environmental conditions. One example can be temperatures or amounts of temperature variation exhibited during a particular manufacturing stage, such as an anneal. Another example can be ambient pressures or amounts of pressure variation exhibited during a particular manufacturing stage, such as a vapor deposition. The amount of time a particular medical device (or batch or production lot) spends in a particular stage of manufacturing, or between stages of manufacturing if such is relevant, can also qualify as a manufacturing parameter Manufacturing parameters can be qualitative as well. The identity of a particular piece of equipment used on the medical device during manufacturing can be a qualitative manufacturing parameter, as can the order in which medical devices are processed. For example, the position of a particular medical device (or batch of medical devices) within a sequence of medical devices (or batches of medical devices) being acted upon by a particular piece of equipment can be a qualitative manufacturing parameter. In some embodiments, in vitro strips can be fabricated from a printed card that is subsequently separated into individual test strips, and the position of the strip in each row can be particularly important in determining accurate calibration information, although the embodiments described herein are not limited to such. Likewise, the fact that a medical device is subjected to reprocessing at any stage during manufacturing, e.g., for being out of specification, can be a qualitative manufacturing parameter.

Referring back to measurements of a sensing region area of an example sensor, FIG. 21A is a top down view depicting an example embodiment of the surface of a substrate 2102 having a sensing region that includes three sensing elements 2103-1, 2103-2, and 2103-3 with diameters indicated, and the area of the sensing region can be the sum of the area of each of the three sensing elements. FIGS. 21B-C are cross-sectional views taken along line 21BC-21BC, where electrodes and other components are omitted for simplicity. In FIG. 21B, each of the three sensing elements 2103 has a planar surface. In FIG. 21C, each of the three sensing elements 2103 as a domed or rounded surface the area of which can be approximated as the area of a two-dimensional circle or calculated as a three-dimensional structure. FIG. 22A is a top down view depicting an example embodiment of the surface of a substrate 2202 having a sensing region that includes one sensing layer 2203, the area of which can be determined as the product of the length 2204 and width 2205. FIGS. 22B-C are cross-sectional views taken along line 22BC-22BC, where electrodes and other components are omitted for simplicity. In FIG. 22B, sensing layer 2203 is disposed above substrate 2202 while in FIG. 22C, sensing layer 2203 is inset or disposed within a well created within substrate 2202. FIG. 23A is a perspective view depicting an example embodiment of a section of a cylindrical or substantially cylindrical in vivo sensor 2301 having a sensing region 2303 located between insulative (or non-sensing) portions 2302. FIG. 23B is a cross-sectional view taken along line 23B-23B of FIG. 23A and depicts sensing region 2303 surrounding a core region 2305, which can be conductive material. In this embodiment the area of sensing region 2303 can be calculated as the area of a cylinder with a length 2304 and diameter 2306.

Figure 24:
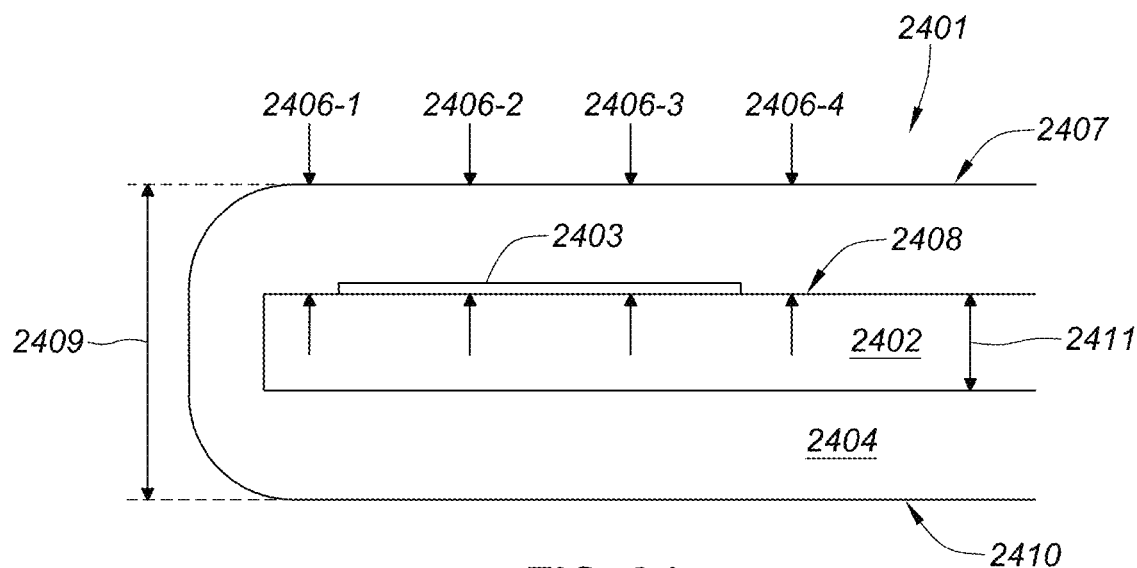
FIG. 24 is a cross-sectional view depicting an example embodiment of an in vivo sensor.
Figure 25A:
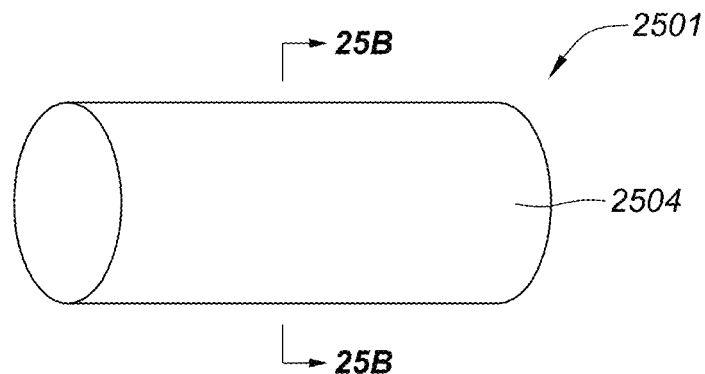
FIG. 25A is a perspective view depicting an example embodiment of an analyte sensor.
Figure 25B:
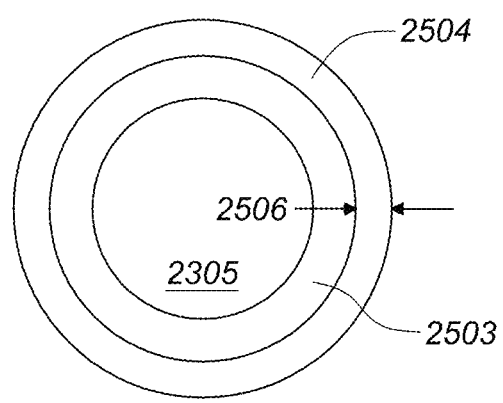
FIG. 25B is a cross-sectional view depicting an example embodiment of an analyte sensor taken along line 25B-25B of FIG. 25A.

Referring back to measurements of membrane thickness, FIG. 24 is a cross-sectional view depicting an example embodiment of an in vivo sensor 2401 having a substrate 2402, a sensing region 2403, and a membrane 2404 that encompasses the terminal end of substrate 2402 and sensing region 2403. The thickness of membrane 2404 can be determined by taking one or more measurements 2406 between the outer surface 2407 of membrane 2404 and surface 2408 of substrate 2402. Examples of various measurement locations are depicted by arrows 2406-1 through 2406-4, which can be aligned or coincide with sensing region 2403 (locations 2406-2 and 2406-3) or outside of sensing region 2403 (locations 2406-1 and 2406-4). If multiple measurements of membrane thickness are taken, then the value used as the individualized manufacturing parameter can be a central tendency (e.g., median, mean) of those measurements. In some cases it may be difficult to measure membrane thickness directly, in which case it can be inferred by measuring the total thickness or diameter 2409 of the membrane 2404 between surfaces 2407 and 2410 (if measured multiple times in a central tendency can be taken) and a known, nominal, or estimated thickness 2411 of substrate 2402 (or substrate 2402 and sensing region 2403) can be subtracted from the total thickness 2409, and then halved) or otherwise divided as appropriate) to estimate the thickness of membrane 2404 in the region between surfaces 2407 and 2408 (or between surface 2407 and the upper surface of sensing region 2403). FIG. 25A is a perspective view of an example embodiment of a sensor 2501 similar to that of FIG. 23A but showing an outer membrane 2504. FIG. 25B is a cross-sectional view taken along line 25B-25B of FIG. 25A that shows core region 2305 with sensing region 2303 located thereon and membrane 2504 located on sensing region 2503. A thickness of membrane 2504 as indicated by 2506.

Examples of Sensing Characteristics Derived from Testing

As described, one or more medical devices within the baseline subset can be tested to empirically determine a sensing characteristic for that baseline subset. The testing is, in many embodiments, capable of producing data that verifiably represents the ability of the medical device to sense the biochemical attribute. In many in vivo analyte sensor and in vitro analyte sensor (e.g., test strip) embodiments, the sensing characteristic can be the sensitivity of the analyte sensor to the presence of the analyte. Often this testing will be performed in vitro and will result in the collection of in vitro test data. The sensing characteristic derived or otherwise resulting from the in vitro test data for the baseline subset can be referred to as an in vitro sensing characteristic (e.g., in vitro sensitivity).

Figure 26A:
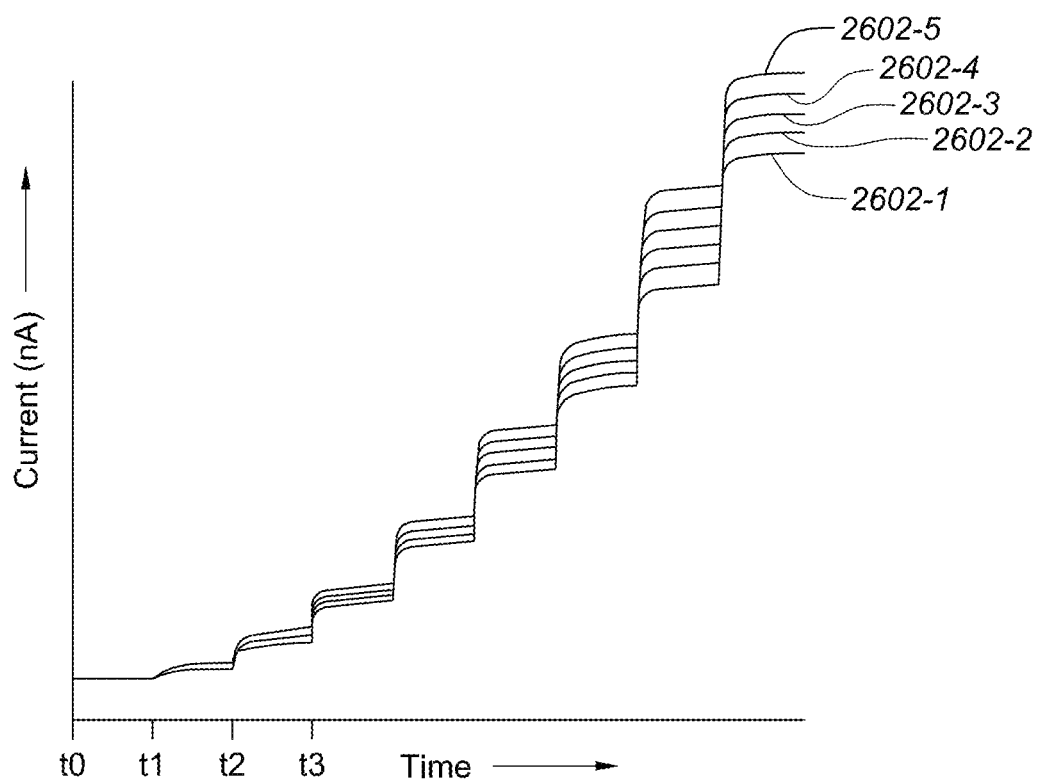
FIG. 26A is an example plot of in vitro test data.

FIG. 26A is an example plot of in vitro test data obtained by in vitro testing amperometric in vivo glucose sensors constituting a baseline subset. In this example, the baseline subset includes five sensors and the in vitro test data sets corresponding to each of those five sensors are labeled 2602-1 through 2602-5. The baseline subset may include quantities other than five, without departing from the scope of the present subject matter. The in vitro test data sets were obtained by applying various glucose solutions to each analyte sensor and monitoring the electrical current produced as a result, which can be on the order of nanoamps, picoamps, or otherwise depending on the sensor design. From time t0 to time t1 no solution is applied to the sensors (or a solution having no glucose concentration is applied). At time t1 a first glucose solution having a first relatively low concentration (e.g., one millimole per liter (mmol/L)) is applied to the in vivo sensor and the resulting response is recorded. At time t2 a second glucose solution having a relatively higher concentration than the first solution is applied to the in vivo sensor and the resulting response is again recorded. The process can proceed iteratively at t3 and thereafter with ever increasing concentrations of glucose solution to obtain empirical data representing the sensitivity of the in vivo glucose sensor across a wide range of glucose concentrations. As can be seen, these embodiments of the glucose sensors react differently to the presence of the glucose solution and these differences become more pronounced as the concentration of the glucose solution increases. Note that the x-axis indicates time and not glucose concentration, so while the in vitro test data may appear to be slightly nonlinear, the resulting sensitivity derived from the in vitro test data can still be linear.

Figure 26B:
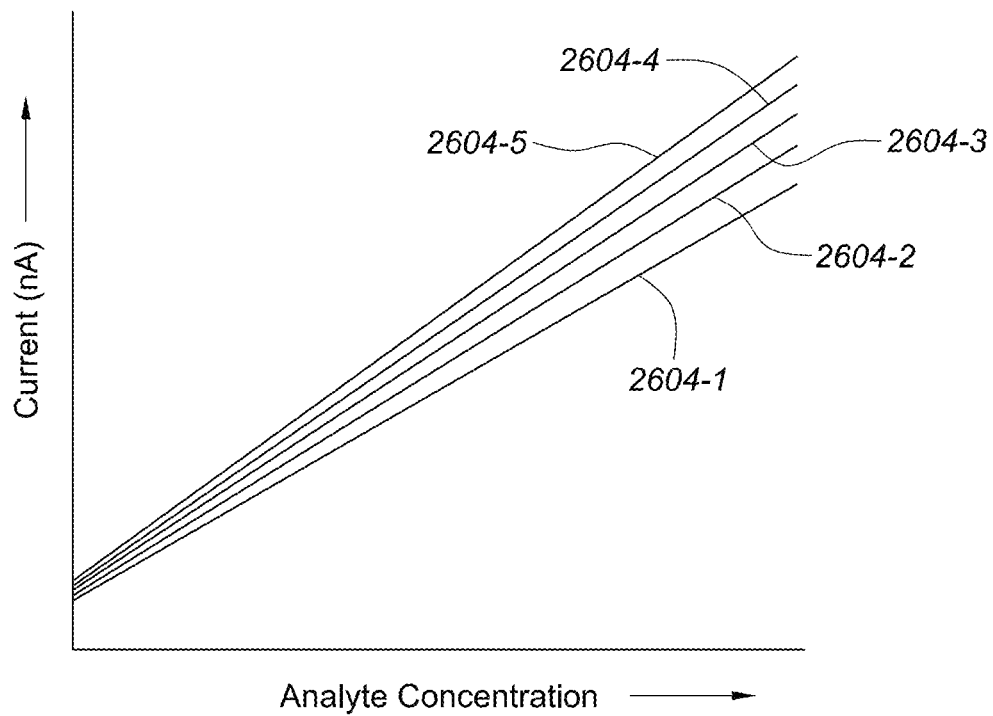
FIG. 26B is an example plot of sensitivities corresponding to the in vitro test data of FIG. 26A.

FIG. 26B is an example plot of sensitivities 2604-1 through 2604-5 corresponding to the in vitro test data sets 2602-1 through 2602-5 of FIG. 26A. Sensitivities 2604-1 through 2604-5 can be determined by performing a regression (e.g., linear or non-linear) independently on each respective in vitro test data set 2602-1 through 2602-5. In some embodiments, such as for nonlinear sensitivities, the in vitro data set can be portioned to separate response zones, with each zone being modeled with a linear sensitivity to approximate the nonlinear curve, such that the resulting calibration information will differ depending on the degree of response (e.g., current) being measured.

In the example of FIG. 26B, the various sensitivities 2604 are each linear or substantially linear. The in vitro sensitivity (or other sensing characteristic) of the baseline subset can be determined in any desired fashion. In some embodiments, the baseline in vitro sensitivity can be a central tendency of sensitivities 2604-1 through 2604-5, such as a mean or median of sensitivities 2604-1 through 2604-5. The median in this example would be sensitivity 2604-3. In some embodiments, the baseline in vitro sensitivity can be a central tendency (e.g., mean or median) of one aspect or characteristic of sensitivities 2604-1 through 2604-5, such as the central tendency of the slopes of sensitivities 2604-1 through 2604-5 or the central tendency of the intercepts of sensitivities 2604-1 through 2604-5. Other aspects of the sensitivities can also be used as the in vitro sensitivity for the baseline subset. In some embodiments, instead of deriving individual sensitivities 2604-1 through 2604-5 from each of the in vitro test data sets 2602-1 through 2602-5, a single regression can be performed for the entirety of the in vitro test data from the baseline subset and this single regression, or an aspect thereof, can be used as the baseline in vitro sensitivity. In all of these embodiments, the in vitro test data sets or the in vitro sensing characteristics determined therefrom (such as those shown in FIG. 26B) can be filtered to remove one or more values (e.g., values below a minimum threshold, above a maximum threshold, within a threshold, atypical values, etc.) prior to determining the baseline in vitro sensitivity.

Additional Example Embodiments Relating to Individualized Factory Calibration

Figure 27C:
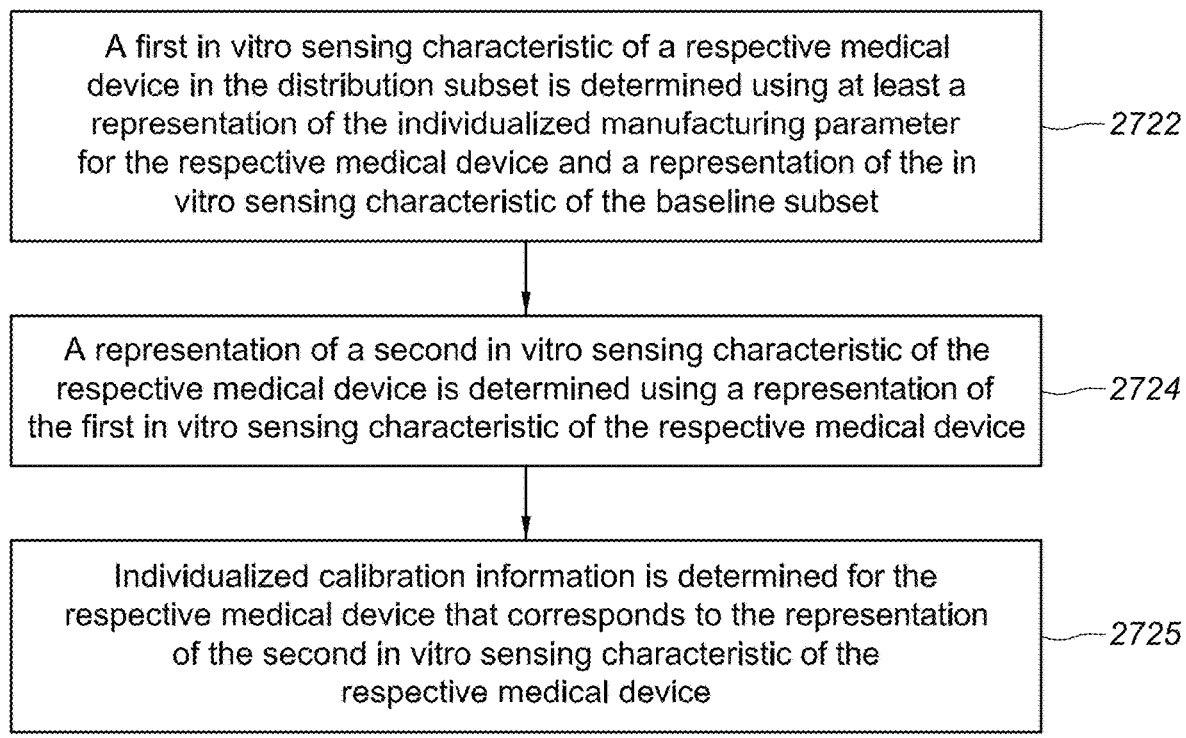

Turning back to example embodiments for individualized calibration, FIGS. 27A, 27B, and 27C are flow diagrams depicting example embodiments of methods 2700, 2710, and 2720, respectively, of determining individualized calibration information, such as could be performed in step 2009 of the embodiment of FIG. 20A, or step 2019 of the embodiments of FIGS. 20B and 20C. In many embodiments, methods 2700, 2710, and 2720 are performed independently for each medical device in the distribution subset. The methods refer to a "respective" medical device, which, in this and the other embodiments described herein, is one particular medical device in the subset (e.g., distribution or baseline) that changes each time the method is performed. Here, the "respective" medical device is a first medical device of the distribution subset the first time method 2700 is performed, the respective medical device then becomes the second medical device the second time method 2700 is performed, and so forth until method 2700 has been performed independently on all medical devices in the distribution subset. The same applies to methods 2710 and 2720. Methods 2700, 2710, and 2720 are described with respect to a representation of an individualized manufacturing parameter but can also be applied with a non-individualized (e.g., environmental) manufacturing parameter. Likewise, methods 2700, 2710, and 2720 are described with respect to a representation of an in vitro sensing characteristic but can also be applied with other sensing characteristics (or representations thereof).

Turning now to FIG. 27A, at 2702, an in vitro sensing characteristic (or a representation thereof) of a respective medical device in the distribution subset is determined using at least a representation of the individualized manufacturing parameter for the respective medical device and a representation of the in vitro sensing characteristic of the baseline subset. At 2705, individualized calibration information is determined for the respective medical device that corresponds to the representation of the in vitro sensing characteristic of the respective medical device. This individualized calibration information can be determined directly from the in vitro sensing characteristic of 2702, or the in vitro sensing characteristic can be modified or converted to another value, in one or more steps, and the resulting modified or converted value can then be used to determine the individualized calibration information.

FIG. 27B depicts method 2710, which can have particular applicability to an in vivo medical device. Here, at 2712 an in vitro sensing characteristic (or a representation thereof) of a respective medical device in the distribution subset is determined using at least a representation of the individualized manufacturing parameter for the respective medical device and a representation of the in vitro sensing characteristic of the baseline subset. This can be performed by applying a model to at least the representation of the individualized manufacturing parameter and the representation of the baseline in vitro sensing characteristic into a model or equation, such that the in vitro sensing characteristic for the respective medical device (or a representation thereof) is produced by the model. At 2714, a representation of an in vivo sensing characteristic of the respective medical device can be determined using at least a representation of the in vitro sensing characteristic of the respective medical device. At 2715, individualized calibration information is determined for the respective medical device that corresponds to the representation of the in vivo sensing characteristic of the respective medical device.

FIG. 27C depicts method 2720, which can have particular applicability to an in vitro medical device where the in vitro sensing characteristic is modified prior to determining individualized calibration information. Here, at 2722 a first in vitro sensing characteristic (or a representation thereof) of a respective medical device in the distribution subset is determined using at least a representation of the individualized manufacturing parameter for the respective medical device and a representation of the in vitro sensing characteristic of the baseline subset. As with the prior example, this can be performed by inputting at least the representation of the individualized manufacturing parameter and the representation of the baseline in vitro sensing characteristic into a model or equation that outputs the first in vitro sensing characteristic for the respective medical device (or a representation thereof). At 2724, a second in vitro sensing characteristic (or a representation thereof) of the respective medical device can be determined using at least a representation of the first in vitro sensing characteristic of the respective medical device. At 2725, individualized calibration information is determined for the respective medical device that corresponds to the representation of the second in vitro sensing characteristic of the respective medical device. An example application for method 2720 is with an in vitro test strip, where the first in vitro sensing characteristic corresponds to test results obtained by in vitro testing with a glucose solution, which can then be modified (such as with a transfer function described in more detail herein) to the second in vitro sensing characteristic, which corresponds to the sensing characteristic in the presence of the sampled bodily fluid (e.g., blood).

For embodiments where the manufacturing parameter is a quantitative value or measurement, the representation of the manufacturing parameter (or individualized manufacturing parameter) can be an actual measured value of the manufacturing parameter, a relative indication of the measured manufacturing parameter, or other information calculated or derived from the actual measured value. In certain example embodiments, it may be desirable to use the relative difference of a quantitatively measured manufacturing parameter from a central tendency (e.g., mean, median, etc.) of the quantitatively measured manufacturing parameter for a larger group (e.g., the entire lot or the entire distribution subset, etc.). The manufacturing parameter can be an area of a sensing region of the medical device for example. Instead of using the actual measurement of the area of the sensing region (or the measured length and width of the sensing region) to determine the calibration information, it may be desirable to use the relative difference of the measured sensing area from a central tendency of the sensing area for the larger group. For a quantitative manufacturing parameter (MP) that varies between individual medical devices, a relative representation of that manufacturing parameter (RMP) can be determined according to (1) immediately below:

$$RMP = 100 * \left( \frac{(MP \text{ of Individual Medical Device} - \text{Central Tendency of } MP \text{ of Group})}{\text{Central Tendency of } MP \text{ of Group}} \right)$$

As already noted, other manufacturing parameters for various devices, such as membrane thickness, working pad area, working ink resistance, etc., can be used with or instead of the sensing area. Similarly, the representation of the baseline in vitro sensing characteristic can be the actual in vitro sensing characteristic determined for the baseline subset, a relative indication of the degree of variation of that in vitro sensing characteristic from another sensing characteristic (e.g., such as a benchmark), or otherwise. Likewise, the representation of the in vivo sensing characteristic can be an estimated in vivo sensing characteristic, a relative indication of the degree of variation of the in vivo sensing characteristic from another sensing characteristic (e.g., a benchmark), or otherwise.

Steps 2702, 2712, and 2722 of methods 2700, 2710, and 2720, respectively, can be performed by inputting at least the representation of the individualized manufacturing parameter and the representation of the baseline in vitro sensing characteristic into a model (or equation) that outputs a representation of the in vitro sensing characteristic for the individual medical device. Many different models (or equations) can be used, including but not limited to a linear regression model; a multiple variable regression model, a random forest model, a non-linear model, a Bayesian regression model, a neural network, a machine learning model, a non-random decision tree, or a discriminant analysis model, to name a few. Examples of models incorporating or determined by multiple variable regression analysis are described below, while examples of these other models are further discussed in the appendix section.

Many example embodiments described herein determine the sensing characteristic for the individual medical device by utilizing a manufacturing parameter of that individual medical device centered around the empirically determined baseline sensing characteristic. In some embodiments, the individualized calibration information is determined directly from the individualized manufacturing parameters without reference to the baseline sensing characteristic. However, incorporation of the empirically determined baseline sensing characteristic into a model, particularly when the representation of the manufacturing parameter is a relative difference from the group at large, can minimize the effects of group-to-group (e.g., lot-to-lot) variations. The following (2, 3) are examples of a multiple variable regression-based model that can be used with embodiments described herein:

$$SC_{MD} = SC_B + \alpha + (\beta RMP_A) \tag{2}$$

$$SC_{MD} = SC_B + (1 + 0.1(\alpha + (\beta RMP_A))) \tag{3}$$

where $SC_{MD}$ is the modeled or calculated in vitro sensing characteristic for the individual medical device, $SC_B$ is the in vitro characteristic for the baseline subset, $\alpha$ is an optional adjustment factor (zero or non-zero), $RMP_A$ is the representation of the manufacturing parameter, and $\beta$ is a coefficient for $RMP_A$. $\beta$ and $\alpha$ can be constants (positive or negative) that are empirically determined, e.g., by comparison of estimated in vitro sensing characteristics for medical devices with those that are empirically observed for the same medical devices. In these examples (2, 3) and the other examples of models (4)-(7) below, RMP is a quantitative measurement, as opposed to a qualitative descriptor, like the identity of manufacturing equipment, or an indication of whether a device was reprocessed. In the above, eq. (3) takes the form of a more relative correction than eq. (2). A constant value other than 0.1 can be used in eq. (3), and in eqs. (5) and (7) below.

In some embodiments, higher order exponential terms can be included within the model to account for nonlinearities in the manufacturing parameter data. The following (4, 5) are examples of a model with a higher order term that can be used with all of the embodiments described herein, where $\delta$ can be another empirically determined coefficient for the $RMP_A$ squared term:

$$SC_{MD} = SC_B + \alpha + (\beta RMP_A) + (\delta RMP_A^2) \tag{4}$$

$$SC_{MD} = SC_B + (1 + 0.1(\alpha + (\beta RMP_A) + (\delta RMP_A^2))) \tag{5}$$

In some embodiments, the model can make use of multiple different manufacturing parameters, with or without higher order terms. The following (6, 7) are two examples of models utilizing two different manufacturing parameters that can be used with all of the embodiments described herein:

$$SC_{MD} = SC_B + \alpha + (\beta RMP_A) + (\delta RMP_A^2) + (\gamma RMP_B) + (\varepsilon RMP_B^2) + (\rho RMP_A \, RMP_B) \tag{6}$$

$$SC_{MD} = SC_B + (1 + 0.01(\alpha + (\beta RMP_A) + (\delta RMP_A^2) + (\gamma RMP_B) + (\varepsilon RMP_B^2) + (\rho RMP_A \, RMP_B))) \tag{7}$$

where $RMP_A$ is a first manufacturing parameter, $RMP_B$ is a second manufacturing parameter, $\gamma$ is a coefficient for $RMP_B$, $\varepsilon$ is a coefficient for the $RMP_B$ exponential, and $\rho$ is a coefficient for the product of $RMP_A$ and $RMP_B$. Each of these coefficients can also be empirically determined, can be constants, and can be positive or negative. These coefficients can be determined and then applied across all production lots. In other embodiments, these coefficients can be determined on a lot-by-lot basis such that the coefficients are constant for all devices in a lot (or other group) but may differ for all devices in a different lot (or group). The coefficients can also be determined on an individual basis. The higher order product of $RMP_A$ and $RMP_B$ can assist in capturing interactions between those manufacturing parameters. For example, the effect of a relatively lower value of $RMP_A$ (as compared to a nominal value of $RMP_A$) may be greater when $RMP_B$ has a relatively higher value (as compared to a nominal value of $RMP_B$). Those of ordinary skill in the art can expand and implement these models with three or more different manufacturing parameters. Any and all of the coefficients described in (2)-(7) can be weighted, e.g., to account for a confidence level.

Referring back to FIG. 27B, at 2714 the in vivo sensing characteristic of the respective medical device is determined using the representation of the in vitro sensing characteristic (e.g., in vitro $SC_{MD}$) of the respective medical device, and referring back to FIG. 27C, at 2724 the second in vitro sensing characteristic of the respective medical device is determined using the representation of the first in vitro sensing characteristic (e.g., in vitro $SC_{MD}$) of the respective medical device. These and similar determinations described herein can be made by applying the representation of the in vitro sensing characteristic of 2714 (or the first in vitro sensing characteristic of 2724) to a transfer function. Transfer functions for use in converting an in vitro sensing characteristic to an in vivo sensing characteristic, and for converting between in vitro sensing characteristics are within the skill of those in the art. The transfer function can be determined analytically. For example, a transfer function for converting from an in vitro sensing characteristic to an in vivo sensing characteristic can take into account factors that differ between in vitro and in vivo states like absolute glucose concentration, temperature, oxygen, and interfering substances, to name a few. In addition to these, a transfer function for converting between in vitro sensing characteristics, such as one for an analyte test solution and one for a bodily fluid, can also take into account hematocrit percentage, for example. The transfer function can also be determined empirically, for example, by performing clinical studies and comparing the in vivo response to the in vitro data, or by comparing in vitro responses to different substances. If the relationship is in the form of an offset, then the transfer function can be accomplished by adding or subtracting a constant value. More complex transfer functions can involve multiplication by a constant value, multiplication by a variable value (e.g., where the variable is dependent on the magnitude of the in vitro sensing characteristic), or others.

In all of the embodiments herein, a representation of the sensing characteristic (e.g., $SC_{MD}$, $SC_B$, etc.) can be the sensing characteristic itself, (e.g., the sensitivity itself (e.g., a slope and an intercept)), an aspect of the sensing characteristic, such as just the slope of the sensitivity or just the intercept of the sensitivity, a relative variation of the sensing characteristic from a reference value (e.g., nominal value, mean, average, etc.), a relative variation of the aspect of the sensing characteristic (e.g., relative slope, relative intercept, etc.) from the reference value (e.g., nominal value, mean, average, etc.), or others. Referring back to methods 2700, 2710, and 2720, individualized calibration information is determined from the in vitro sensing characteristic of the individual medical device (step 2705 of method 2700), from the in vivo sensing characteristic of the individual medical device (step 2715 of method 2710), or from a second in vitro sensing characteristic (step 2725 of method 2720). The individualized calibration information can capture the sensing characteristic in the form of a factor or code that can be recorded or stored in a manner such that it is accessible to the processing circuitry that processes the raw or conditioned data collected by the individual medical device. Many different techniques exist for making calibration information accessible to the appropriate processing circuitry and the technique that is implemented is generally dependent on the type of medical device and the needs of the implementation. Several embodiments of devices and techniques for recording and making individualized calibration information accessible to the processing circuitry are described in greater detail below.

Figure 27D:
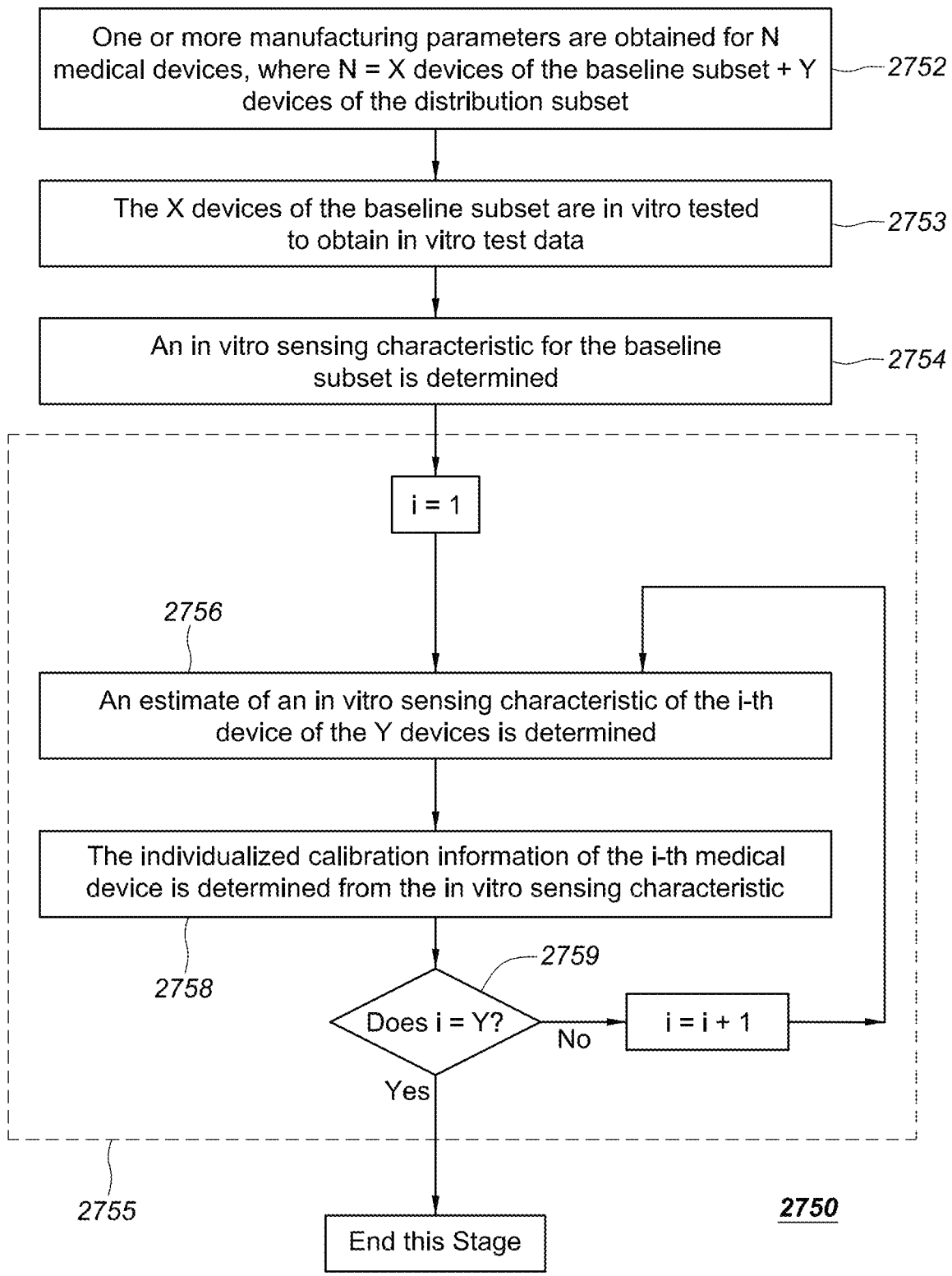

FIG. 27D is a flow diagram depicting another example embodiment of a method 2750 for determining individualized calibration information for an individual medical device. Method 2750 combines many of the aspects of embodiments discussed previously. At 2752, one or more manufacturing parameters are obtained for N medical devices, where N=X devices of the baseline subset+Y devices of the distribution subset. In some embodiments, the one or more manufacturing parameters are obtained only for the Y devices of the distribution subset. The manufacturing parameters can be individualized manufacturing parameters or non-individualized manufacturing parameters (e.g., environmental factors, equipment identification, etc.), although if only non-individualized manufacturing parameters are measured than the resulting calibration information will also not be individualized. The manufacturing parameters can be obtained at various different stages of the manufacturing process. By way of illustration, in one example embodiment where the medical devices are in vivo analyte sensors, at least two different individualized manufacturing parameters are measured: a size of the sensing region after fabrication of the sensing region, and a size of the membrane after application of the membrane. If N=1000, then after fabrication of the sensing region for the N sensors and measurement thereof, 1000 different measurements of sensing region sizes will have been obtained. After placement (e.g., deposition) of the membrane on the N sensors and measurement thereof, 1000 different measurements of membrane sizes will have been obtained, or 2000 measurements in total. Depending upon the quantity and types of measurement equipment, the 1000 different sensing region measurements can be obtained in serial fashion, in concurrent fashion, or a combination thereof, and the same applies to the measurements of membrane size or any other manufacturing parameter.

At 2753, the X devices of the baseline subset are in vitro tested to obtain in vitro test data. The in vitro testing can be performed in a manner similar to that described with respect to FIG. 26A such that the data is an empirical representation of the in vitro sensing characteristic of each of the X devices. Each of the X devices can be tested individually to produce an individual in vitro test data set. Where X is greater than one, depending on the number and type of in vitro test equipment, the in vitro testing of the X devices can occur in serial fashion, in concurrent fashion, or a combination thereof. If each of the X devices is individually tested, then performance of step 2753 will result in X individual in vitro test data sets. By way of illustration only, X can be a relatively small fraction of N, such as 5, 10, or 20 medical devices when N=1000, with Y being much larger, 995, 990, or 980, respectively. Other values of N, X, and Y are within the scope of this disclosure.

At 2754, an in vitro sensing characteristic for the baseline subset is determined. In some example embodiments, this can be accomplished by first converting the X individual in vitro test data sets into X in vitro sensing characteristics (one for each of the X devices), and then determining a single in vitro sensing characteristic for the entire baseline subset (e.g., $SC_B$) from the X in vitro sensing characteristics. For example, the baseline in vitro sensing characteristic can be a central tendency (e.g., mean or median) of the X in vitro sensing characteristics. In another embodiment, the baseline in vitro sensing characteristic can be determined by performing a regression analysis on the X individual in vitro test data sets. Again, the in vitro sensing characteristic can be the sensitivity or an aspect thereof (e.g., slope or intercept).

At 2755, the individualized calibration information for the Y medical devices of the distribution subset is determined. In this embodiment, the individualized calibration information for each particular medical device within the distribution subset is determined in a manner similar to that described with respect to method 2700 of FIG. 27A.

With i=1, at 2756 an estimate of the in vitro sensing characteristic (e.g., $SC_{MD}$) of the i-th device of the Y devices is determined. This estimate can be accomplished, for example, using a model such as those described herein. Then, at 2758 the individualized calibration information of the i-th medical device is determined from the in vitro sensing characteristic. At 2759, a determination is made whether i=Y. If not, then i is incremented by one (e.g., i=i+1) and method 2750 proceeds back to step 2756. The process repeats itself until i=Y, in which case Y independent determinations of individualized calibration information will have been made, one for each of the Y medical devices.

Figure 27E:
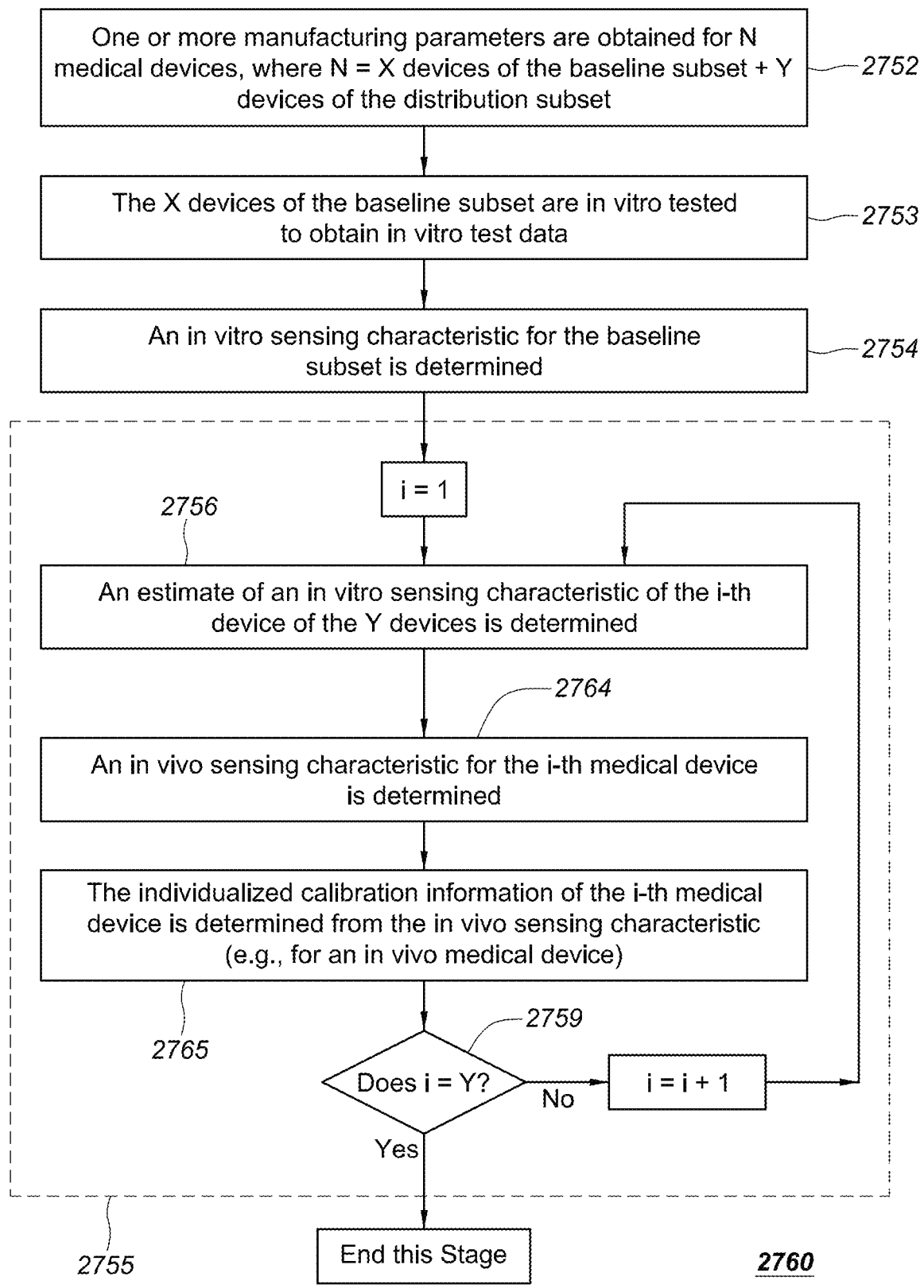

FIG. 27E is a flow diagram depicting another example embodiment of a method 2760 for determining individualized calibration information for an individual medical device. Method 2760 combines many of the aspects of embodiments discussed previously and steps 2752-2756 are similar to the embodiment of FIG. 27D. At 2755, the individualized calibration information for the Y medical devices of the distribution subset is determined. In this embodiment, the individualized calibration information for each particular medical device within the distribution subset is determined in a manner similar to that described with respect to method 2710 of FIG. 27B and is particularly applicable to in vivo devices.

At 2756, with i=1, an estimate of the in vitro sensing characteristic (e.g., $SC_{MD}$) of the i-th device of the Y devices is determined. Again, this estimate can be accomplished using a model such as those described herein. In the example embodiment where the medical devices are in vivo analyte sensors and the manufacturing parameters are a size of the sensing region and a size of the membrane, $SC_{MD}$ can be determined according to eqs. (6) or (7), where $RMP_A$ is a size (e.g., area) of the sensing region and $RMP_B$ is a size (e.g., thickness) of the membrane. Then, at 2764 the in vivo sensing characteristic for the i-th medical device is determined. This can be accomplished, for example, by use of a transfer function. Then, at 2765 the individualized calibration information of the i-th medical device is determined from the in vivo sensing characteristic. At 2759, a determination is made whether i=Y. If not, then i is incremented by one (e.g., i=i+1) and method 2760 proceeds back to step 2756. The process repeats itself until i=Y, in which case Y independent determinations of individualized calibration information will have been made, one for each of the Y medical devices.

Figure 27F:
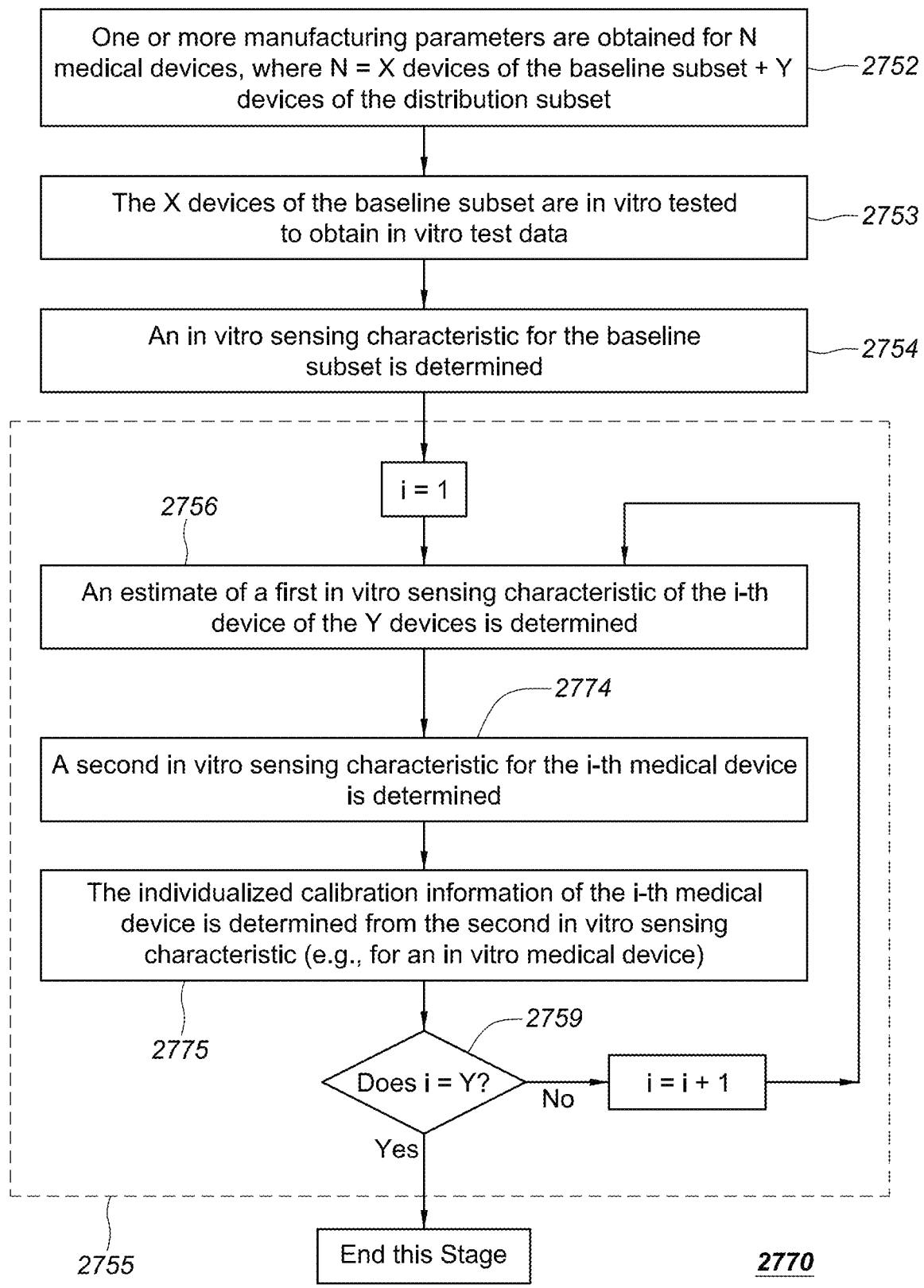

FIG. 27F is a flow diagram depicting another example embodiment of a method 2770 for determining individualized calibration information for an individual medical device. Method 2770 also combines many of the aspects of embodiments discussed previously and steps 2752-2756 are similar to the embodiment of FIG. 27D. At 2755, the individualized calibration information for the Y medical devices of the distribution subset is determined. In this embodiment, the individualized calibration information for each particular medical device within the distribution subset is determined in a manner similar to that described with respect to method 2720 of FIG. 27C and is particularly applicable to in vitro devices.

At 2756, with i=1, a first estimate of an in vitro sensing characteristic (e.g., $SC_{MD}$) of the i-th device of the Y devices is determined. Again, this estimate can be accomplished using a model such as those described herein. Then, at 2774 a second in vitro sensing characteristic for the i-th medical device is determined. This can be accomplished, for example, by use of a transfer function. Then, at 2775 the individualized calibration information of the i-th medical device can be determined from the second in vitro sensing characteristic. At 2759, a determination is made whether i=Y. If not, then i is incremented by one (e.g., i=i+1) and method 2760 proceeds back to step 2756. The process repeats itself until i=Y, in which case Y independent determinations of individualized calibration information will have been made, one for each of the Y medical devices.

In the example embodiments of FIGS. 27D-27F, the substeps within 2755 are performed once, in sequence, for one individual medical device before performing those substeps again for the next individual medical device. In other embodiments, each substep can be performed Y times before proceeding to the next substep. For example, with respect to FIG. 27F, step 2756 can be performed Y times for all of the Y medical devices before steps 2774 or 2775 are performed. For example, step 2756 can be performed Y times, then step 2774 can be performed Y times, then step 2775 can be performed Y times. In many embodiments, the substeps of 2755 (e.g., 2756, 2774, and 2775) will be performed by processing circuitry executing software instructions, and those of ordinary skill in the art will recognize the many different ways these steps can be implemented by those instructions without departing from the scope of the subject matter described herein.

Figure 28A:
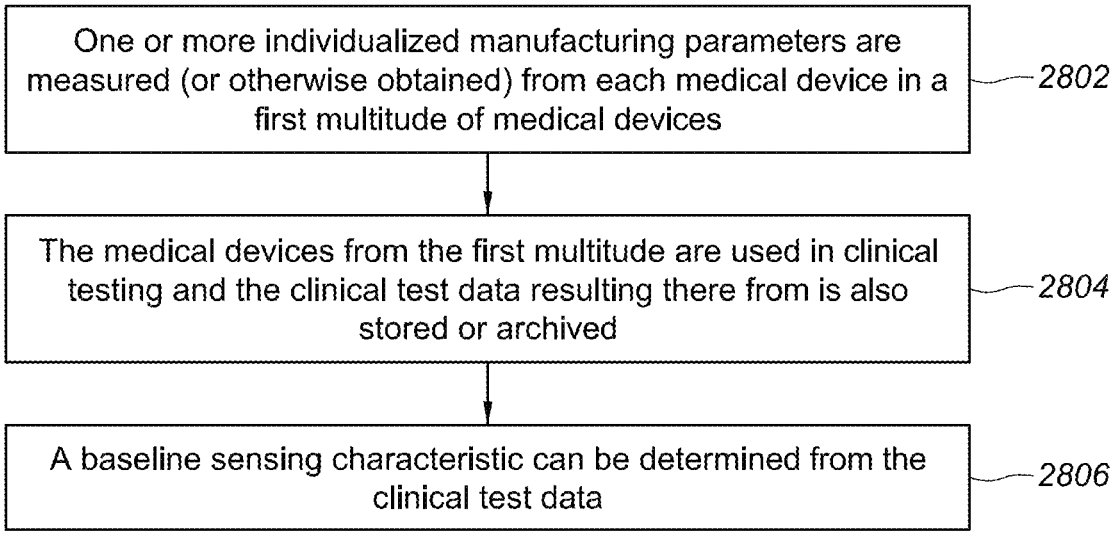
FIGS. 28A-28B are flow diagrams depicting additional example embodiments of methods related to determining individualized calibration information.
Figure 28B:
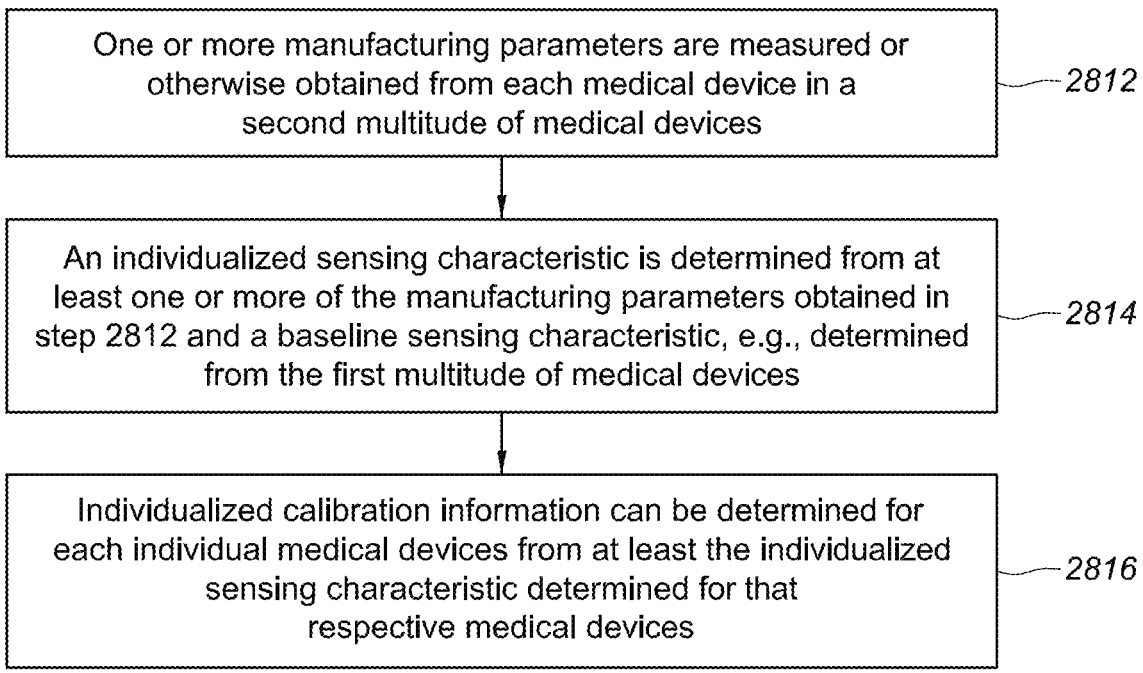

FIGS. 28A and 28B are flow diagrams depicting additional example embodiments of methods relating to the determination of individualized calibration information. These methods utilize direct analysis of clinical data to determine or derive a baseline sensing characteristic for all or a majority of the medical devices produced by the manufacturing process, which in turn minimizes, or eliminates altogether, the need for regular in vitro testing of baseline subsets from each production lot (or various lots).

FIG. 28A depicts a method 2800 for determining a baseline sensing characteristic from clinical data. At 2802, one or more individualized manufacturing parameters are measured (or otherwise obtained) from each medical device in a first multitude of medical devices. The resulting manufacturing parameter data is stored or archived for later use. Then, at 2804, the medical devices from the first multitude are used in clinical testing and the clinical test data resulting there from is also stored or archived. At 2806, a baseline sensing characteristic can be determined from the clinical test data. As with the other embodiments described herein, the baseline sensing characteristic can be for in vivo or in vitro states of the medical device, and can be, for example, a sensitivity or an aspect of the sensitivity of the medical device.

For example, the clinical testing is preferably performed on a sizable population of participants to obtain a robust data set. Traceability between each participant and the specific medical device or devices used by that participant is preferably maintained. In this manner, the medical device used by each participant can be tracked and the manufacturing parameters measured from that medical device can be correlated to the resulting clinical data produced by that medical device and otherwise collected in the clinical test. Then statistical and/or other analyses can be performed to determine the baseline sensing characteristic from that clinical data. In some examples, the baseline sensing characteristic can be a central tendency of the clinical data such as a mean or a median. The baseline sensing characteristic is preferably representative of the medical devices produced by the manufacturing process as a whole. The manner and degree to which the measured manufacturing parameters impact the sensing characteristic can be ascertained by reference and analysis to the archived manufacturing parameters and clinical test data.

FIG. 28B depicts a method 2810 for determining individualized sensing characteristics from at least a baseline sensing characteristic (or a representation thereof), such as that determined in method 2800. At 2812, one or more manufacturing parameters are measured or otherwise obtained from each medical device in a second multitude of medical devices. At 2814, an individualized sensing characteristic is determined from at least one or more of the manufacturing parameters obtained in step 2812 and the baseline sensing characteristic, e.g., determined from the first multitude of medical devices. This can be performed, for example, with a model such as those models described herein, and with those manufacturing parameters identified as substantially impacting the baseline sensing characteristic. Then, at 2816, individualized calibration information can be determined for each individual medical device from at least the individualized sensing characteristic determined for that respective medical devices. This individualized calibration information can then be associated with the respective medical device as described elsewhere herein.

The second multitude of medical devices can be a portion of a production lot or the entirety of a production lot, and in some embodiments can be multiple production lots. Furthermore, in many embodiments the production lots can be manufactured and released for distribution to users without regular in vitro testing or other testing of a baseline subset from the production line that renders those devices in the baseline subset unsuitable for distribution to users. Or, if such testing is not eliminated entirely, the amount of testing required for each production lot or across multiple production lots can be significantly reduced as compared to techniques where a baseline sensing characteristic is not determined directly from clinical data. In both cases because such testing is reduced or eliminated, a corresponding increase in production yield is obtained. The embodiments described with respect to FIGS. 28A and 28B can be implemented with any of the in vivo or in vitro medical devices described herein.

Figure 29A:
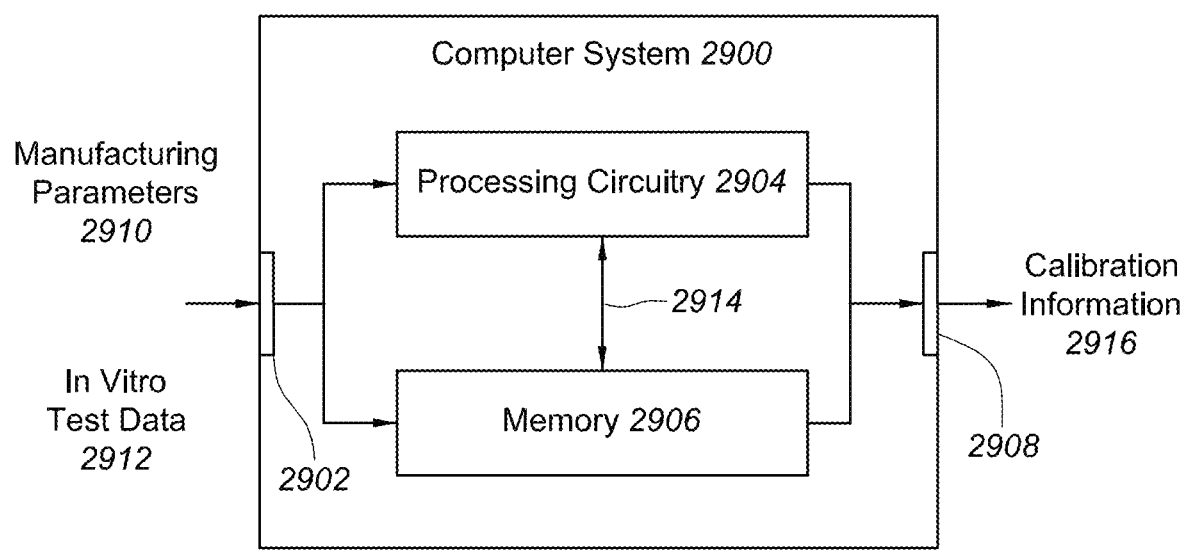
FIG. 29A is a block diagram depicting an example embodiment of a computer system that can be used to implement the calibration embodiments described herein.

FIG. 29A is a block diagram depicting an example embodiment of a computer system 2900 that can be used to implement the calibration embodiments described herein. Computer system 2900 is shown here as a single system but can also be implemented in distributed fashion. System 2900 can include an input port 2902, processing circuitry 2904, non-transitory memory 2906, and an output port 2908. Input port 2902 can be communicatively coupled with processing circuitry 2904 and memory 2906. Examples of data that can be supplied to input port 2902 include: the representations of manufacturing parameters 2910 collected during or after the medical device manufacturing process, the in vitro test data 2912 collected during in vitro testing of the baseline subset of medical devices. Other examples that are not shown can include data identifying the individual medical devices, data logs tracing the flow of each medical device through the manufacturing process and the medical device's current location, identification of the production lot to which each medical device belongs, data identifying electronics to be used with the medical devices, assignments of particular medical devices to associated electronics, and data logs tracing the flow of each electronics unit through the manufacturing process and the unit's current location, to name a few. This input data can be stored within memory 2906 and read by processing circuitry 2904 by way of internal bus 2914. Memory 2906 can also store software instructions that, when executed by processing circuitry 2904, cause processing circuitry 2904 to perform various steps, including all or a portion of the steps of making determinations, estimations, calculations, use of models, use of transfer functions, causing the storage of data, receiving data, and causing the output of data described herein. For example, processing circuitry 2904 can perform any and all of steps 2008 and 2009 of FIG. 20A; 2018 and 2019 of FIG. 20B; 2018, 2019 and 2020 of FIG. 20C; 2702 and 2705 of FIG. 27A; 2712, 2714, and 2715 of FIG. 27B; 2722, 2724, and 2725 of FIG. 27C; 2753, 2754, 2755, 2756, 2758 and 2759 of FIG. 27D; 2753, 2754, 2755, 2756, 2764, 2765 and 2759 of FIG. 27E; 2753, 2754, 2755, 2756, 2774, 2775 and 2759 of FIG. 27F; 2806 of FIG. 28A; and 2814 and 2816 of FIG. 28B.

Processing circuitry 2904 can determine the calibration information from the appropriate sensing characteristic in a number of ways. In some embodiments, one of a number of predetermined codes are identified that most closely approximate or match the sensing characteristic, such that the relatively large number of potential sensing characteristic values can be reduced to a more limited number of options without sacrificing significant performance. The predetermined code can be in the form of the sensing characteristic set itself, for example, if a slope of five is to be indicated, then the number five can be used as the calibration information. In other embodiments, the predetermined code is an alphanumeric value or string that does not indicate the calibration information itself, but rather is set by system 2900 such that it can be used by the device (e.g., reader device, meter, sensor control device, etc.) to look up the corresponding calibration information, for example by reference to a translation matrix. In some embodiments, an in vivo sensor and the on body electronics having that in vivo sensor's calibration information stored in memory thereof can be provided in separate packaging, in which case both the packaging for the in vivo sensor and the packaging for the on body electronics can have the calibration information or some other code printed thereon so that, in case the two are separated, the user can identify which sensor goes with which on body electronics.

Processing circuitry 2904 can also cause the output of determined calibration information (e.g., calibration codes) 2914 from output port 2908. Processing circuitry 2904 can be implemented as a single discrete processor device or in distributed fashion as processing circuitry shared amongst multiple devices. Likewise, memory 2906 can be implemented as a single discrete memory or multiple memories, or as a single database or multiple databases, or combinations thereof. Memory 2906 can be located on the same chip or device as other functional circuitry, including processing circuitry 2904. Memory 2906 can be partially within computer system 2900 or distributed at other locations (such as separate databases) accessible by the manufacturer's network.

The individual medical devices can be traceable through the manufacturing process, such that the correlation of the manufacturing parameter with the individual medical device from which it was collected is maintained. In some embodiments, each individual medical device can be uniquely identifiable by an identifier physically associated with it. In certain examples of in vitro strips, the strips are manufactured on a printed card or substrate and then subsequently separated into the individual strips, and one identifier can be associated with that card or substrate. Each strip can then be uniquely traced by the identifier of the card and data indicating the relative position of the strip on that card.

The identifier can be in the form of a barcode, printed QR code, optical character recognizable (OCR) text such as an alphanumeric string, a resistive code (such as described in U.S. Publ. No. 2014/0200917, which is incorporated by reference herein in its entirety and for all purposes), a radio frequency (RF) readable device (e.g., an RFID element or a Near Field Communication (NFC) element), or the like. The identifier (or a second identifier) can also identify the production lot with which the medical device is associated. Each time the medical device is subjected to a particular manufacturing stage and/or each time manufacturing parameter data is obtained, the identifier is read and a log can be created (or an existing log retrieved and appended) with an indication of the current date and time, the identification of the manufacturing stage, the identity of manufacturing equipment used to process the medical device, the length of time medical device spends in the manufacturing stage, and/or any manufacturing parameters that are obtained in relation to the processing of that medical device in that particular manufacturing stage.

Figure 29B:
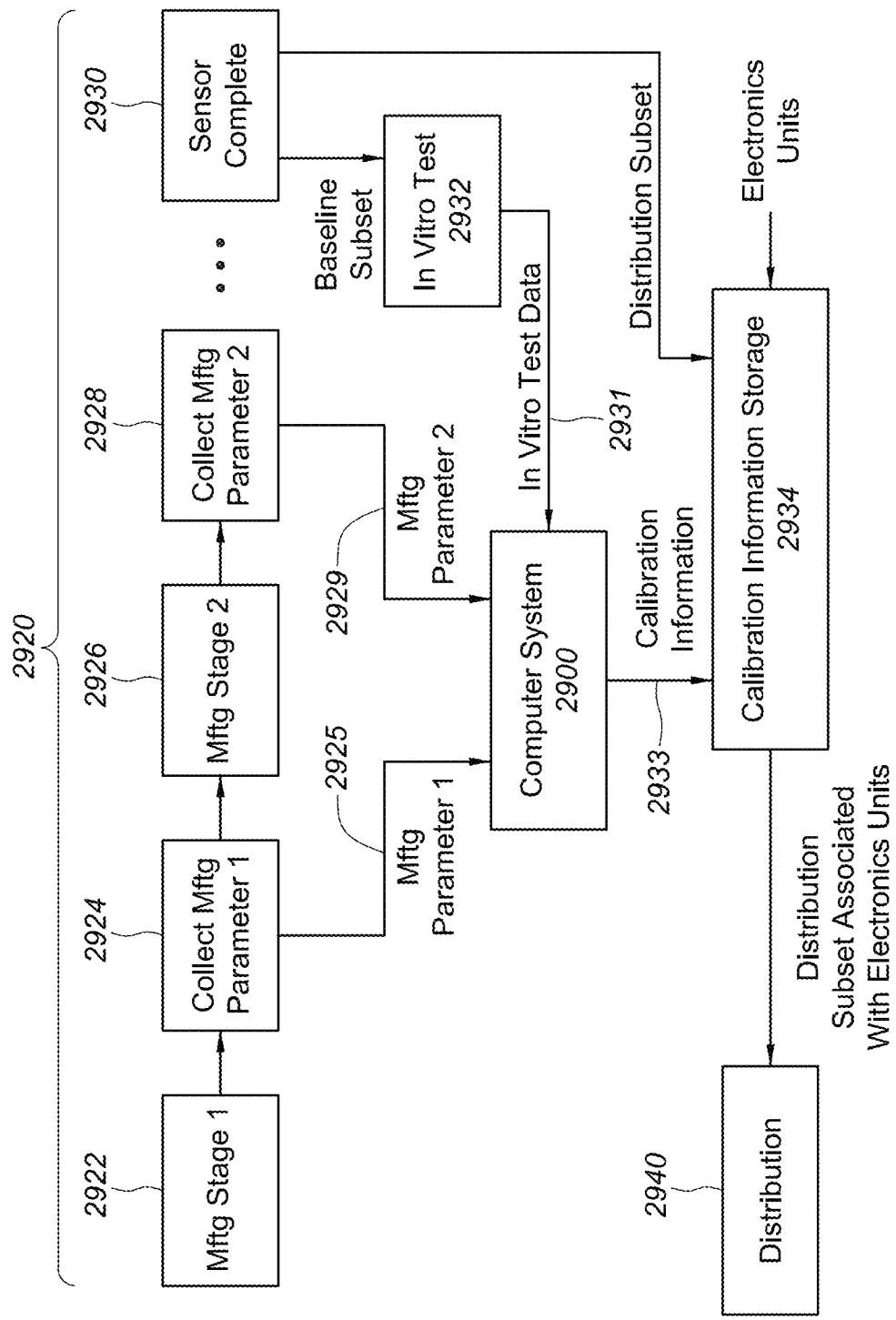
FIGS. 29B-29D are block diagrams depicting conceptual process and information flows with respect to the manufacturing of biochemical sensors.
Figure 29C:
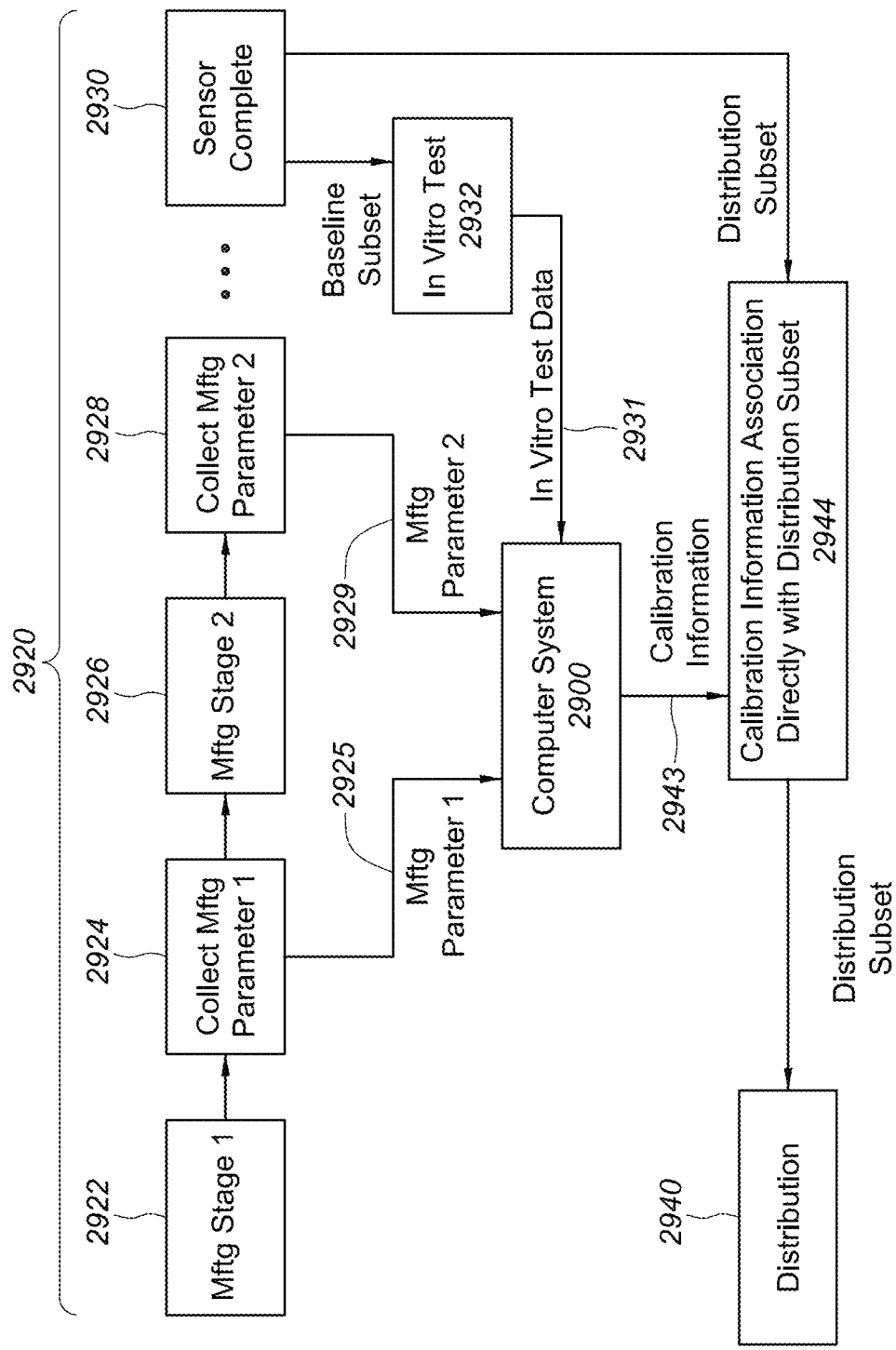
Figure 29D:
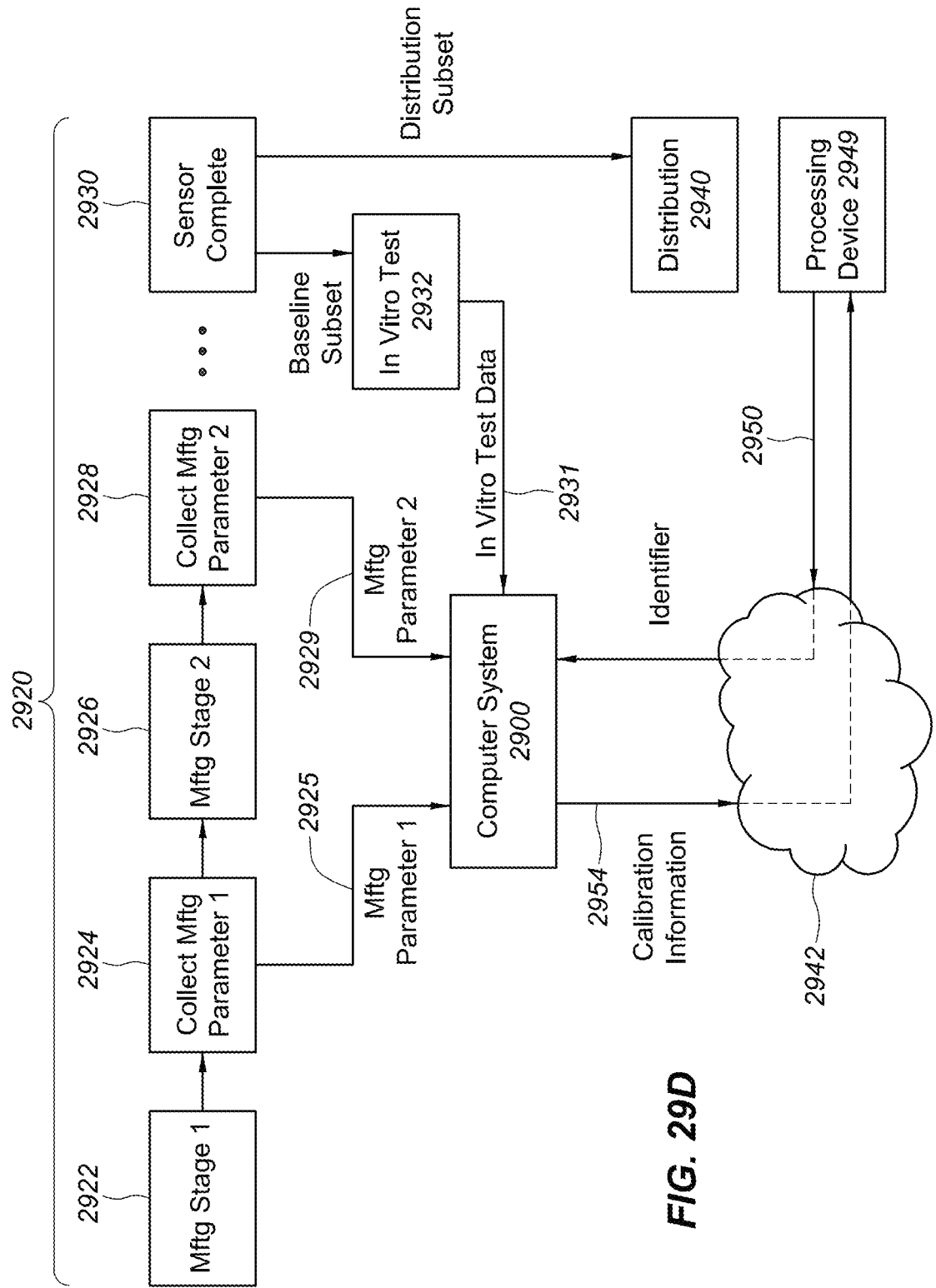

FIGS. 29B-29D are block diagrams depicting conceptual process and information flows with respect to the manufacturing of biochemical sensors. Although not limited to such, FIG. 29B is particularly suited for in vivo sensors. Referring first to FIG. 29B, section 2920 generally depicts stages of manufacturing and collection of manufacturing parameter data. A group of medical devices (e.g., a production lot) is processed through a first manufacturing stage at 2922 and manufacturing parameters for the medical devices within the group are than measured or otherwise obtained at 2924. Depending on the type of manufacturing parameter being collected, step 2924 can occur concurrently with manufacturing stage 2922 or afterwards. The group of medical devices then proceeds to a second manufacturing stage 2926, and again manufacturing parameter data can be collected at 2928 either concurrently or after conclusion of stage 2926. This process can continue through all manufacturing stages until, at 2930, construction of the medical devices is complete, or completed to the point where in vitro test data can be obtained. As manufacturing parameter data is collected, e.g., at 2924 or 2928, that manufacturing parameter data can be output to computer system 2900 for storage, as shown by information paths 2925 and 2929, respectively. The test or monitoring equipment that obtains the manufacturing data can be communicatively coupled or linked to computer system 2900 over a data network of the manufacturer.

In vitro testing of the baseline subset of medical devices is performed at 2932 and the resulting in vitro test data can be output via information path 2931 to computer system 2900. Again the equipment that records the results of the in vitro testing can be communicatively coupled with computer system 2900 over the data network. In alternative embodiments (e.g., those described with respect to FIGS. 28A-28B) where in vitro testing is not performed (or only minimally performed and not relied upon in determining individualized calibration information), the in vitro testing at 2932 or the communication of in vitro test data over path 2931 can be omitted in FIGS. 29B-D. In addition, the baseline subset may be eliminated altogether and the distribution subset can be the entirety of the production lot.

Computer system 2900 can then take the manufacturing parameter data and in vitro test data and determine the individualized calibration information for each medical device in the distribution subset. Computer system 2900 can assign each medical device in the distribution subset to a particular electronics unit (e.g., 1110). Alternatively, this assignment task can be performed in another manner, manually or automatically by manufacturing equipment, at another location within the manufacturing assembly line. The identity of the electronics unit assigned to each medical device can be communicated to computer system 2900.

In some embodiments, the individualized calibration information is stored in the non-transitory memory of the electronics unit (e.g., the memory of on body electronics 1110) to which the individual medical device is assigned. The individualized calibration information can be provided by computer system 2900 to the device responsible for writing the data within the non-transitory memory of the electronics unit as indicated by 2933. That data can then be written to the electronics unit at 2934 (e.g., a point of release stage), such as by wirelessly transmitting to the electronics unit or inputting the data over a wired access port, such as a universal serial bus (USB) port if available, or an internal data port, such as a serial boundary scan port. The individual medical device can then be packaged with the associated electronics unit to physically maintain the assigned relationship (this step can also be performed prior to writing the data to the electronics unit). The final assembly can then be distributed to users at stage 2940.

The devices can be distributed to the users in the form of a kit or package that can include one or more sensors. For example, in vivo devices can be distributed (e.g., sold) to users in a common packaging that includes multiple (two, three, four, five, six, seven, eight, nine, ten, eleven, twelve, or more) in vivo sensors and their associated electronics units (e.g., sensor control devices). Each electronics unit can have a non-transitory memory on which the individualized calibration information is stored that is based on at least a measured individualized manufacturing parameter of the associated in vivo sensor and is specific to that associated in vivo sensor. In some embodiments, the in vivo sensor can be packaged separately from the associated electronics unit, which can also be packaged, with both packaged within the common packaging. In these embodiments some user assembly may be performed prior to or concurrent with use.

FIG. 29C depicts a flow where the individualized calibration information is output from system 2900 at 2943 and associated directly with the medical device itself at 2944, and is particularly applicable to medical devices such as in vitro test strips that do not have an electronics unit already associated therewith. There are many approaches that can be employed. In some embodiments, prior to leaving the manufacturing process, the individualized calibration information can be determined and printed directly on the medical device, such as in the form of a printed alphanumeric code, printed 2D barcode or 3D QR code, or a data matrix code. A resistive code (such as described in the incorporated U.S. Publ. No. 2014/0200917) can be placed on the medical device and read by circuitry on the meter. In other embodiments, the individualized calibration information can be associated with the medical device by attaching an RF tag (e.g., RFID or NFC) that has the calibration information stored therein. In addition, ROM calibrators could be used, such as individual ones programmed to correspond to individual sensors.

As already described, in some embodiments in vitro strips can be segregated and grouped according to their individualized calibration codes, and then groups having the same calibration code can be packaged and sold as one unit. In these embodiments, the individualized calibration information can be associated directly with each individual strip or associated with the packaging for the group of strips, e.g., using any of the printed, RF, or ROM calibrator approaches described.

In order to program the code in the meter or other processing device, printed alphanumeric codes could be entered by the user, selected from a list of options provided to the user, or read by OCR by a camera on the meter or in the strip port (so that they can be read automatically upon strip insertion). Similar camera-based or bar-code based approaches could be employed for QR codes or printed barcodes or data matrix codes. If RF tags (e.g., RFID or NFC) are used, then the meter or processing device would include an RF tag reader, which could potentially be included in the strip port for automatic reading upon strip insertion. One such approach is described in U.S. Pat. No. 8,115,635, which is incorporated by reference herein in its entirety for all purposes. In other examples, ROM calibrators can be used. In some examples, a computing device, such as a mobile phone, can obtain the calibration information using one of the aforementioned techniques (e.g., optical scan, NFC or RFID communication, etc.) and a meter can include Bluetooth communication circuitry and establish a Bluetooth link with the computing device. The obtained calibration information can be transferred from the computing device to the meter over the Bluetooth link. In another example, the computing device such as a mobile phone can obtain the calibration information from a server (via the cloud, as described with respect to FIG. 29D below) if the computing device has the identifier for the in vitro medical device (which can also be obtained by one of the aforementioned techniques) and communicates it to the server, and then after receiving the calibration information the computing device can transfer it to the meter over the Bluetooth link.

FIG. 29D depicts an example embodiment where the calibration information can be provided to a processing device 2949 in the field that is being used to process biochemical data collected by the individual medical device after its distribution. For example, a reader device, a meter, or other processing device can obtain the identifier of the individual medical device. If that individual medical device has an associated electronics unit, then the identifier can be requesting from or otherwise provided by the electronics unit (e.g., 1110). Otherwise, the identifier can be obtained directly from the medical device, such as by a user manually reading the identifier from the medical device or its packaging and inputting it into the processing device 2949, or the processing device 2949 can read the identifier from the medical device or the packaging in one of the manners already described. At 2950, the processing device 2949 can transmit the identifier to computer system 2900 (or a trusted server) over the Internet or a cloud network 2942. Computer system 2900 can read the identifier, select the appropriate individualized calibration information, and output, at 2954, that calibration information back to the processing device 2949, which can then algorithmically process the data collected by the medical device and render it to the user via a display (or output to another device).

Improvements Related to Calibration

Studies have confirmed that the calibration embodiments described herein result in tangible improvements in the accuracy of biochemical sensing measurements made by the medical devices. This represents an improvement in the operation of the calibrated medical devices themselves, and further results in an improvement in the operation of the monitoring systems and monitoring devices incorporating these medical devices, as well as an improvement in the operation of the computing devices that process or otherwise utilize the improved accuracy data produced by the calibrated medical devices. Improvements through lessening variations between medical devices were also confirmed, as were improvements to the manufacturing yield of the medical devices. These and other improvements constitute grounds upon which the present subject matter is patent eligible, such as under 35 U.S.C. section 101 in the United States and similar requirements in other jurisdictions.

For example, studies of in vivo analyte sensors were conducted that explored relationships between the in vivo glucose sensitivities of those sensors obtained through clinical studies, and various manufacturing parameters collected during manufacturing of those same sensors. Subjects in the clinical studies were asked to take an in vivo measurement with an implanted in vivo sensor immediately after performing a blood glucose (BG) reference test using a finger stick and test strip. The relative bias between the BG reference test and the subsequent in vivo sensor reading was modeled against the various manufacturing parameters for that in vivo sensor. Correlation (traceability) between the clinical data and the manufacturing data was maintained using lot reports, unique identifiers for the in vivo sensor, and unique identifiers for the in vivo systems incorporating that sensor.

Figure 30A:
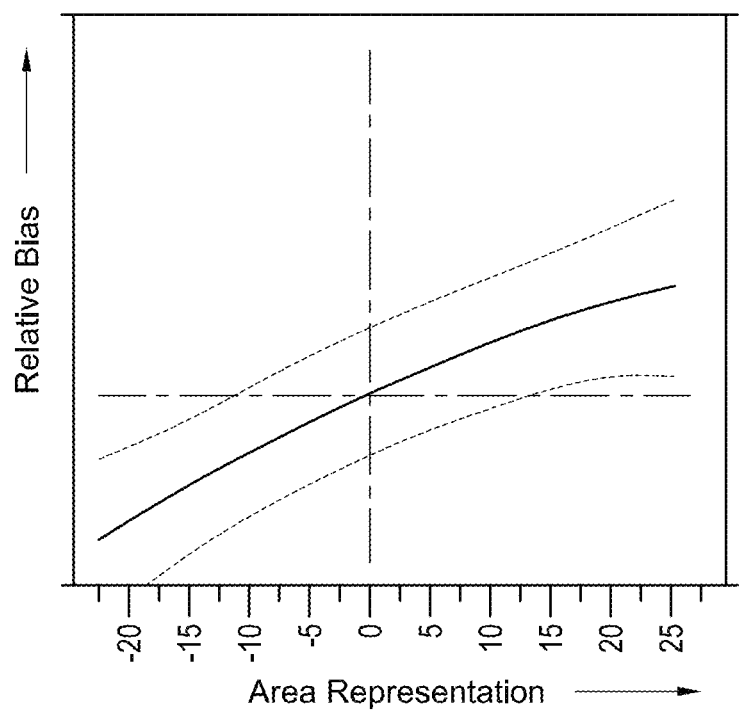
FIGS. 30A-30B are plots depicting example data sets demonstrating statistically significant associations between in vivo sensitivity and certain manufacturing parameters.
Figure 30B:
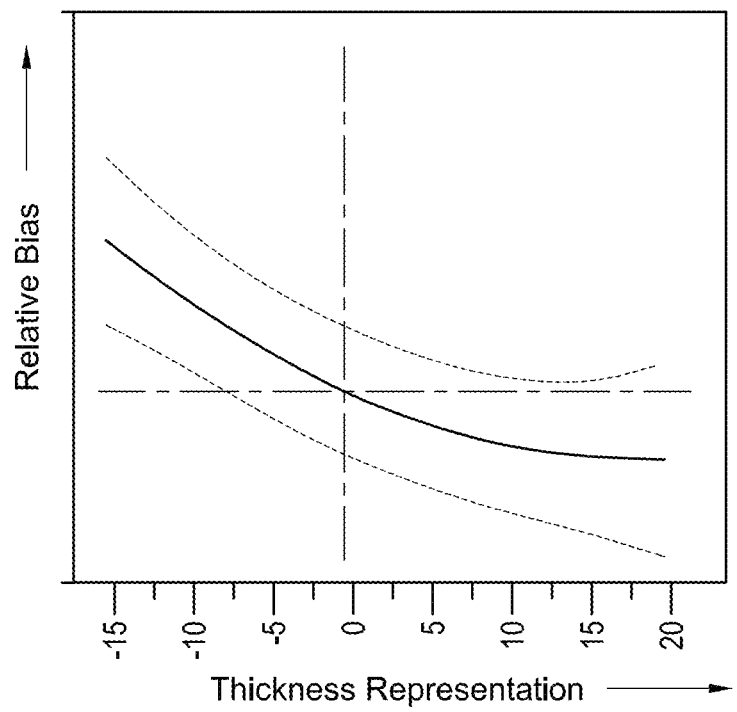

Various statistically significant associations were identified. FIGS. 30A-30B are plots depicting example data sets demonstrating statistically significant associations between in vivo results and manufacturing parameters. FIG. 30A depicts, on the y-axis, a relative bias between in vivo readings and corresponding in vitro blood glucose (BG) measurements plotted against, on the x-axis, a representation of the area of the sensing region (e.g., $mm^2$) for each of the sensors studied. More particularly, the x-axis indicates the relative difference in area between each individual sensor and a central tendency of the production lot from which it came. FIG. 30A indicates a positive correlation between sensing area and in vivo sensitivity, such that a relatively larger sensing area correlates to a relatively higher in vivo sensitivity, while a relatively lower sensing area correlates to a relatively lower in vivo sensitivity.

FIG. 30B depicts, on the y-axis, the relative bias between in vivo readings and corresponding in vitro blood glucose (BG) measurements plotted against, on the x-axis, a representation of the thickness of the membrane (e.g., μm) for each of the sensors studied. In this example, the total lateral thickness of the sensor is measured at multiple locations at and near the sensing region and an average value is determined. A representative value for the sensor thickness beneath the membrane (e.g., a nominal substrate thickness) is then subtracted from the average value to provide the average membrane thickness for each particular sensor, which was then used as the representation of the thickness of the membrane. FIG. 30B indicates a negative correlation between membrane thickness and in vivo sensitivity, such that a relatively larger membrane thickness correlates to a relatively lower in vivo sensitivity, while a relatively lower membrane thickness correlates to a relatively higher in vivo sensitivity.

Individualized calibration information was determined (sensitivity slopes in this example) for the sensors used in the clinical studies using both sensing area and membrane thickness as the manufacturing parameters. The clinical studies were reanalyzed using each sensor's individualized calibration information rather than a lot level calibration code. The reanalysis showed that the difference in mean absolute relative difference (MARD) by lot improved using the individualized calibration information. The reanalysis also showed that the total standard deviation of relative difference between sensors also improved using the individualized calibration information. In addition, the mean relative difference (MRD), or precision performance, also improved.

Figure 31A:
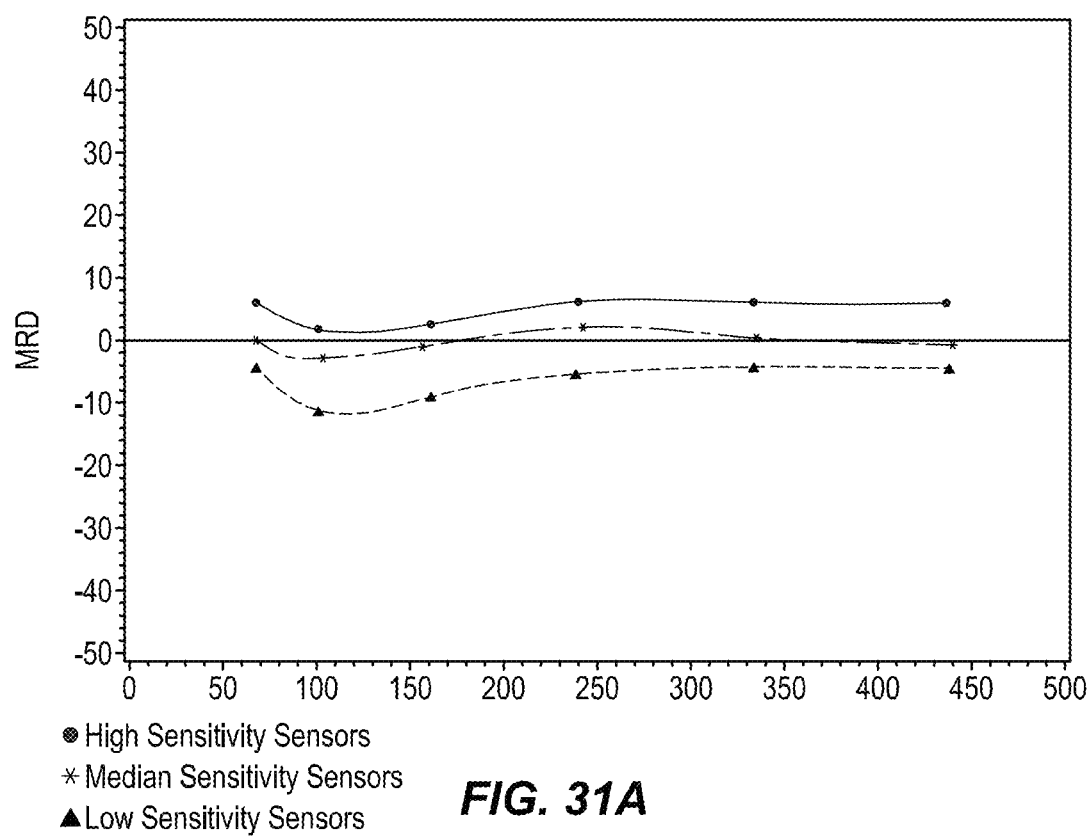
FIGS. 31A-31B are plots depicting sample data sets used in evaluating certain example embodiments.
Figure 31B:
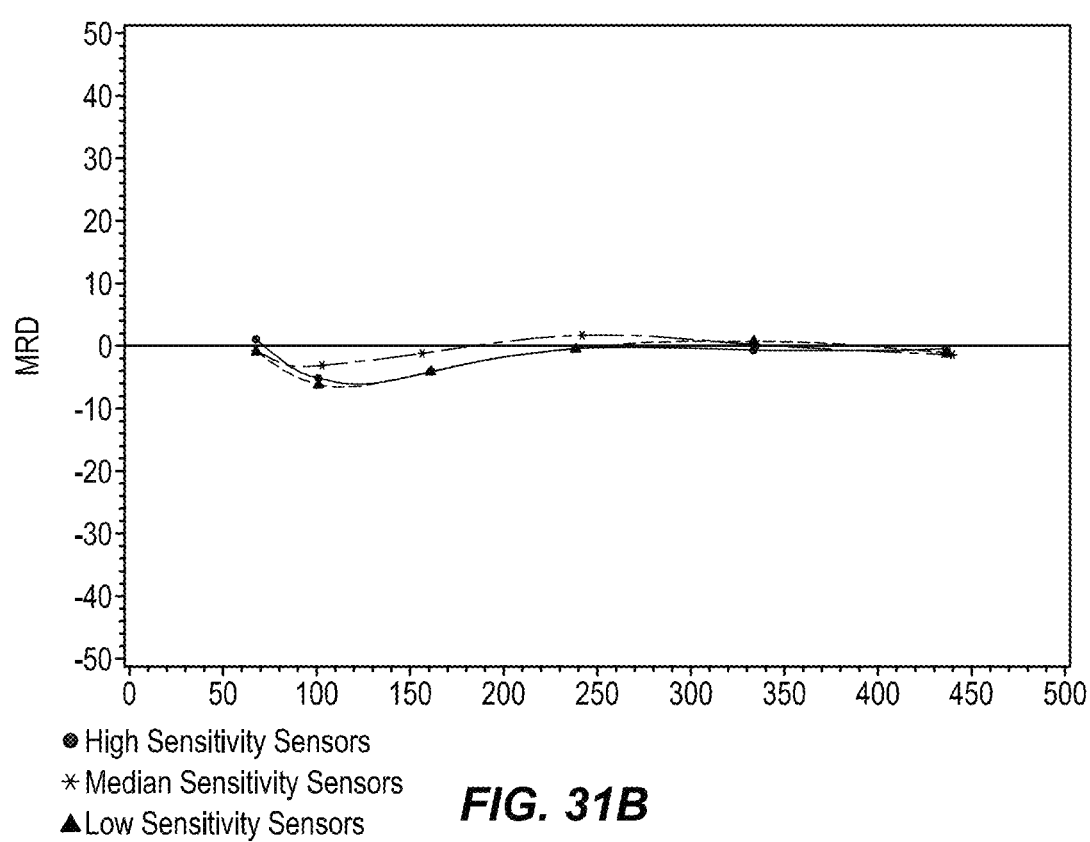

An additional study was conducted using sensors from a single lot that were divided into three groups: a first group where the individualized calibration information represents a relatively high predicted in vivo sensitivity, a second group where the individualized calibration information represents relatively low predicted in vivo sensitivity, and third group where the individualized calibration information represents a median or moderate predicted in vivo sensitivity between the first and second groups. In this study the sensors from the three groups were used by subjects and the accuracy of the resulting data was analyzed and compared to data from sensors that were factory calibrated on a lot-level basis. FIGS. 31A-31B are plots depicting sample data sets used in the study, with MRD on the y axis and glucose level (mg/dL) on the X axis. FIG. 31A depicts the MRD for each of the three groups when the lot-level calibration information was used and FIG. 31B depicts the MRD for each of the three groups when the individualized, sensor-level calibration information was used. As can be seen here, use of the individualized calibration information minimized the performance variation across the production lot and also resulted in an improvement in MARD.

Use of the individualized calibration information resulted in an improvement in production yield. Use of the individualized calibration information was found to improve between sensor variation (e.g., sensor-to-sensor variation) within a production lot by substantially lowering it and thus permitting more medical devices to pass tests for sensitivity precision. Utilizing the embodiments of individualized calibration information, an improvement in precision performance of greater than 20% has been obtained.

Still other statistically significant associations are possible and can depend upon the specifics of the design of the medical device and the associated manufacturing process. Some embodiments of medical devices within the scope of the present disclosure may have a sensing region different from that described herein, and may have membrane different from that described herein, or may lack a membrane altogether. Because the present subject matter is not limited to any one design or manufacturing process, it is likely and indeed expected that other statistically significant associations will exist for different designs and processes. Those of ordinary skill in the art will readily recognize that the present subject matter is not limited to determining individualized calibration information using only a size of the sensing region and or size of the membrane.

In addition, the models used in the example embodiments herein can be continually refined to capture variability not explained by the model. When in vivo or in vitro sensors are in vitro tested and have their predicted in vitro sensing characteristic (e.g., $SC_{MD}$) determined, a residual sensing characteristic can be calculated. In some embodiments this residual sensing characteristic ($SC_R$) can be determined according to (5):

$$SC_R = (\text{Actual } In \text{ Vitro } SC - SC_{MD}) + Lot \text{ Level } In \text{ Vitro } SC$$

Here, the lot-level in vitro sensing characteristic (SC) can be a central tendency and can be for the baseline subset, e.g., the baseline sensing characteristic $SC_B$. As described before, the evaluated sensing characteristic can be the sensitivity or an aspect thereof (e.g., slope or intercept). The residual sensing characteristic looks at the differences between the observed and predicted sensing characteristics from the model and shows the level of variability not explained by manufacturing parameters within the model. These differences can be evaluated as variability around the lot level in vitro sensing characteristic and thus indicates a measure of how much variation is unexplained by the model.

While many embodiments have been described with respect to sensors for biochemical attributes, the embodiments can also be applicable to sensors for other physiological attributes as well. Also, while many embodiments have been described with respect to determining or utilizing calibration information, the embodiments can also be applicable to determine or utilize other types of information that characterizes the medical device.

Example Embodiments of Modifying a Surface of a Sensor Substrate

Embodiments are also set forth herein that relate to modifying a surface of a sensor substrate to assist in positioning of a sensing element (or portion thereof) on the sensor surface. While not limited to such, these embodiments can be particularly useful when applying a liquid to the sensor surface to form the sensing element. Electromagnetic radiation and/or mechanical force can be applied to a surface to modify the surface in a particular area or location. That modified area can affect how the liquid disperses or gathers on the surface. When used in the fabrication of a sensor, this technique can permit more accurate and precise sizing (e.g., area and/or depth) and positioning of sensing elements produced during manufacturing. It also reduces the variability in size and location of each sensing element as compared to one or more other sensing elements on the same sensor and/or sensing elements of other sensors. This, in turn, can lead to reduced variation in sensitivities between sensors, and thus more accurate, precise, and consistent analyte measurements for users.

FIGS. 32A-32F are schematic diagrams depicting various example embodiments of a portion of a sensor substrate 3202 at various stages during manufacture of a sensing element. Substrate 3202 can be, for example, on insertion tip 530 of the embodiment of sensor 500 described with respect to FIG. 5A, or can be part of any of the other embodiments of in vivo and in vitro sensors described herein (e.g., the embodiments described with respect to FIGS. 4, 5B, 6-10C, 15A-17, and 21A-25B).

Figure 32A:
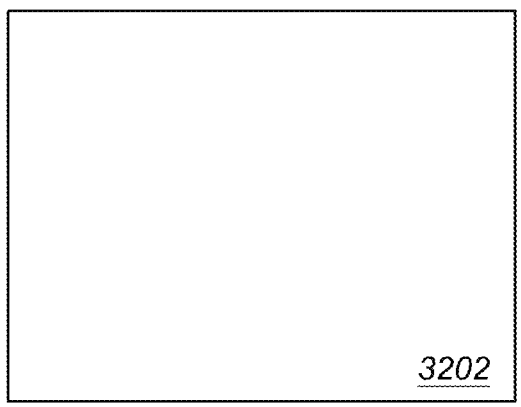
FIGS. 32A-32F are schematic views depicting example embodiments of a sensor substrate at various stages of manufacturing.

A liquid or liquid agent is applied to the substrate to form the sensing element. This liquid agent can have an electrochemical characteristic that detects or assists in detection of the analyte (e.g., glucose) and can be referred to as an electrochemical agent. The electrochemical agent can be a solution, such as water-based or otherwise. Embodiments of the surface modification technique can be used with other agents as well, such as agents that form a sensor membrane, treating agents, adjuvants, secondary electrochemical agents, fixing agents (e.g., a crosslinker), or others. FIG. 32A depicts substrate 3202 prior to modification. Substrate 3202 can be any portion of a sensor upon which placement of a sensing element is desired, e.g., a base, a coating or layer on a base, an electrode, and the like.

Figure 32B:
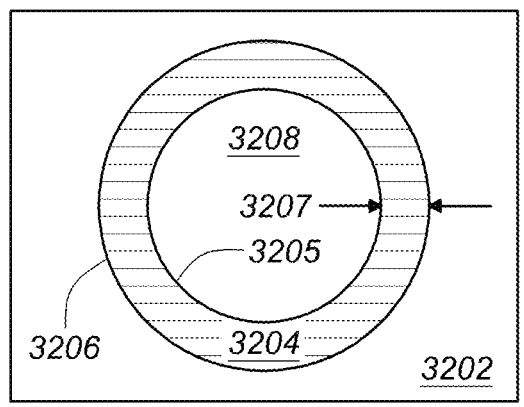

FIG. 32B depicts substrate 3202 after modification of area 3204 by the application of electromagnetic radiation. Application of the electromagnetic radiation may result in a change to the visible appearance of substrate 3202, although not always. In this example, area 3204 has a ring-like shape formed by inner and outer boundaries 3205 and 3206, which in this embodiment are concentric circles, separated by a distance 3207. Other shapes can also be used (as described further below). Inner boundary 3205 defines an unmodified interior 3208 of area 3204, which is the target area for placement of the sensing element. The area of substrate 3202 beyond outer boundary 3206 is also unmodified.

Application of the electromagnetic radiation modifies a surface characteristic of the substrate in area 3204 as compared to the adjacent areas that were not exposed to the electromagnetic radiation. The surface characteristic can affect the mobility of the liquid in various ways. For example, the modified surface characteristic can be such that the liquid is attracted to the modified area even when the liquid is not in direct contact with the modified area (e.g., a liquid on the surface but not in contact with the modified area can move towards the modified area). Such a modified surface characteristic can also cause or increase attraction between the liquid and the modified area when in direct contact as compared to an unmodified area (e.g., a philic characteristic that facilitates spreading of the liquid across the modified area). Although the modified and unmodified surface characteristics are such that the liquid moves towards the modified area, the liquid may proceed only to the boundary of the modified area and not move over the modified area itself (see, e.g., FIG. 32D). If the magnitude of the surface characteristic is increased, such as by application of a relatively higher power (an example of one of various factors that can control the characteristic), then in such embodiments the liquid can move towards and over the modified area (see, e.g., FIG. 32E).

Figure 32C:
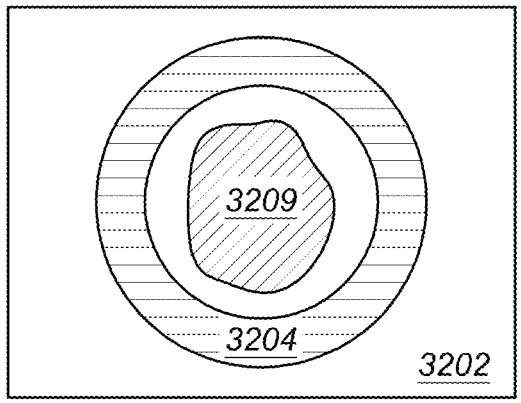
Figure 32D:
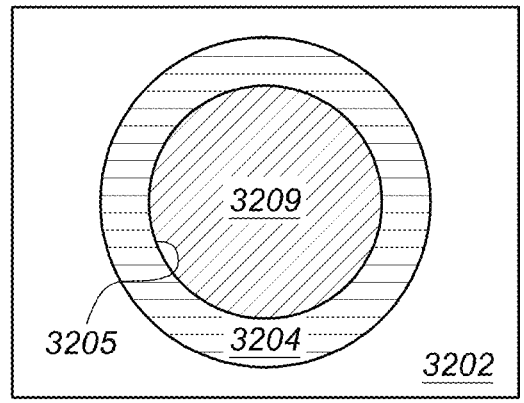
Figure 32E:
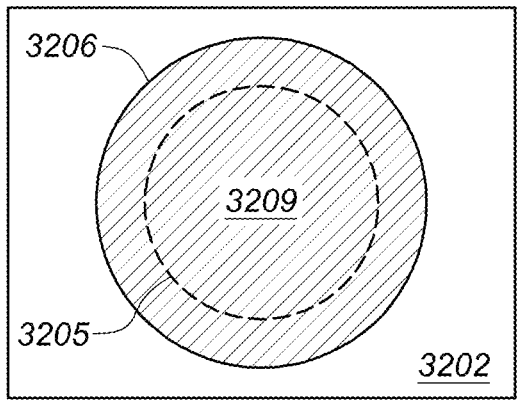
Figure 32F:
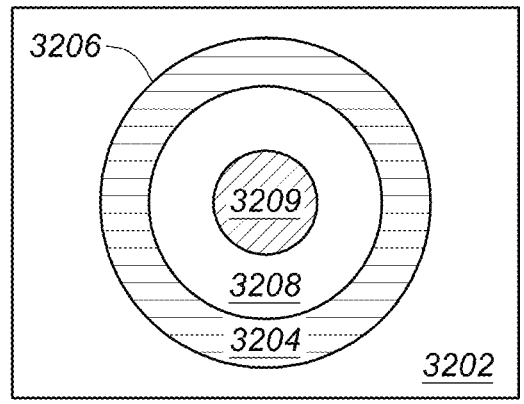

In other examples, the modified surface characteristic can be such that the liquid is repelled by the modified area even when the liquid is not in direct contact with the modified area (e.g., a liquid placed in a location not in contact with the modified area can move away from the modified area; see, e.g., FIG. 32F). Such a characteristic can also cause or increase repulsion (or decrease attraction) between the liquid and the modified area when in direct contact as compared to an unmodified area (e.g., a phobic characteristic that causes beading of the liquid or impedes spreading across the modified area). Further, a combination of these techniques can be used. For example, multiple modified areas can be created with opposing characteristics to cause the liquid to move from a first modified area to a second modified area (that also acts as a target area).

FIG. 32C depicts substrate 3202 at a moment immediately after application of the liquid 3209. Here, liquid 3209 has been applied to an area in the interior of area 3204 that is smaller than that defined by inner boundary 3205. The shape of the applied liquid at this time can be irregular and off-center. FIG. 32D depicts substrate 3202 after liquid 3209 has dispersed on the surface of substrate 3202. In this embodiment, the modification to area 3204 attracts liquid 3209 and causes liquid 3209 to disperse or spread out across the entire unmodified interior 3208 up to inner boundary 3205, where the dispersion ceases. The border of the dispersed liquid 3209 generally aligns with inner boundary 3205. Liquid 3209 can then dry and form a relatively uniform sensing element across interior region 3208 for the sensor.

FIG. 32E depicts another example embodiment of substrate 3202 after application of liquid 3209 as shown in FIG. 32C. In this embodiment, the modification to area 3204 attracts liquid 3209 and causes liquid 3209 to spread out across the entire interior 3208 of area 3204 (as depicted in FIG. 32D) but also past inner boundary 3205 to outer boundary 3206, where the dispersion ceases. The border of the dispersed liquid 3209 generally aligns with outer boundary 3206. Liquid 3209 can then dry and form a relatively uniform sensing element across both interior region 3208 and modified area 3204.

FIG. 32F depicts another example embodiment of substrate 3202 after application of liquid 3209 as shown in FIG. 32C. In this embodiment, the modification to area 3204 repels liquid 3209 and causes liquid 3209 to move to the center of interior 3208, where it forms a bead or accumulation. In this embodiment, the target area is the area on which liquid 3209 is present, which is in proximity to modified area 3204 but neither on nor immediately adjacent to (i.e., bordering) modified area 3204. Liquid 3209 can then dry and form a sensing element in this center area.

Figure 33A:
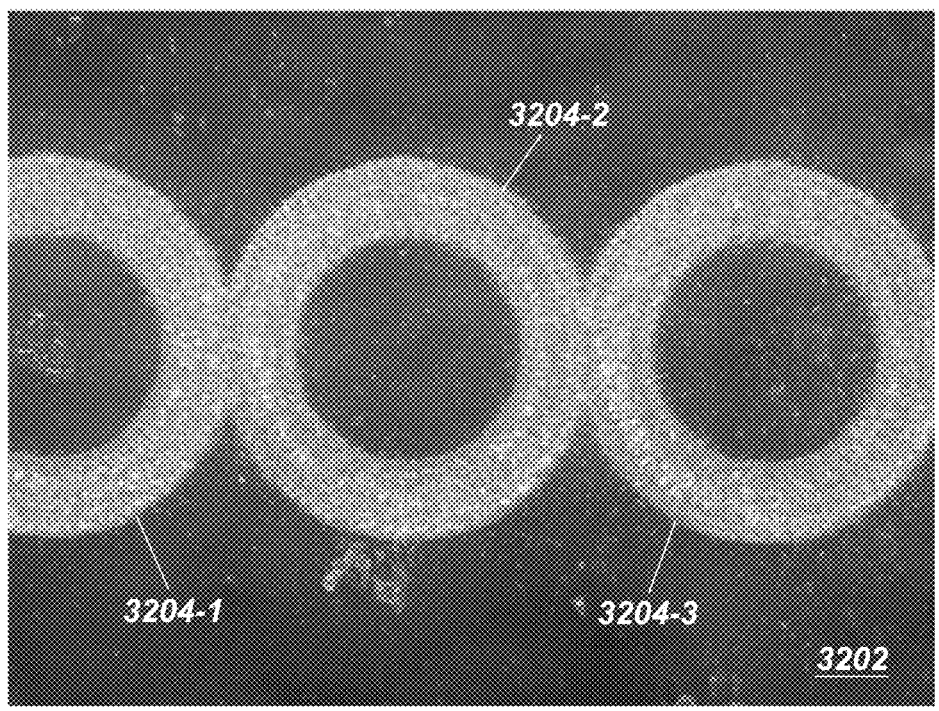
FIGS. 33A-B are top down photographs depicting example embodiments of sensor substrates.
Figure 33B:
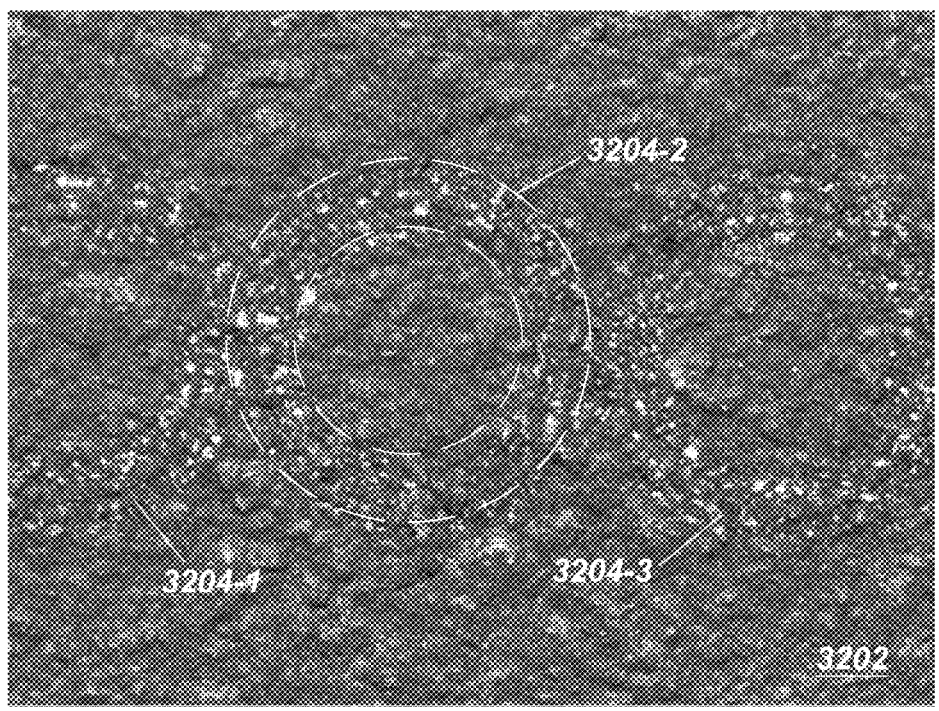

The types of electromagnetic radiation used for surface modification can vary, as can the surface compositions themselves. FIGS. 33A and 33B are photographs depicting example embodiments of substrates 3202 having a series of ring-like surface modifications 3204-1, 3204-2, and 3204-3 formed by the application of laser radiation. Various frequencies of laser radiation can be used to accomplish the surface modification, such as ultraviolet, visible, and infrared. FIG. 33A is a photograph of the laser modification to a bare polyethylene terephthalate (PET) substrate 3202. FIG. 33B is a photograph of the laser modification to a carbon printed PET substrate 3202, where the outline of the middle area 3204-2 has been annotated for ease of visibility. Substrates such as ultraviolet (UV) curable dielectrics (and others) can also be used.

In the samples depicted in both FIGS. 33A-B, the surface modification to one ring-shaped region 3204 was performed by directing the laser at the substrate in five adjacent circles of progressively increasing diameter. Each adjacent circle was created by pulsing the laser at discrete spots arranged in a circular pattern, although the adjacent circles (or the entire ring-shaped region itself) can be created by continuous non-pulsed application of the laser, with or without adjacent circles. Applied power, wavelength, and duration of application of the laser can generally be used to modify the surface characteristic (e.g., whether it attracts or repels and by how much). In pulsed embodiments, the size of a pulsed spot and the spacing between pulsed spots can also be used to modify the surface characteristic. The size of a spot can be controlled by focal length of the lens, the laser wavelength, the distance from lens to the working surface, and the laser pulse energy. Similar techniques can be used to create the other shapes of region 3204 described herein. These regions 3204 can also be generated in other manners using laser or non-laser sources.

Figure 34A:
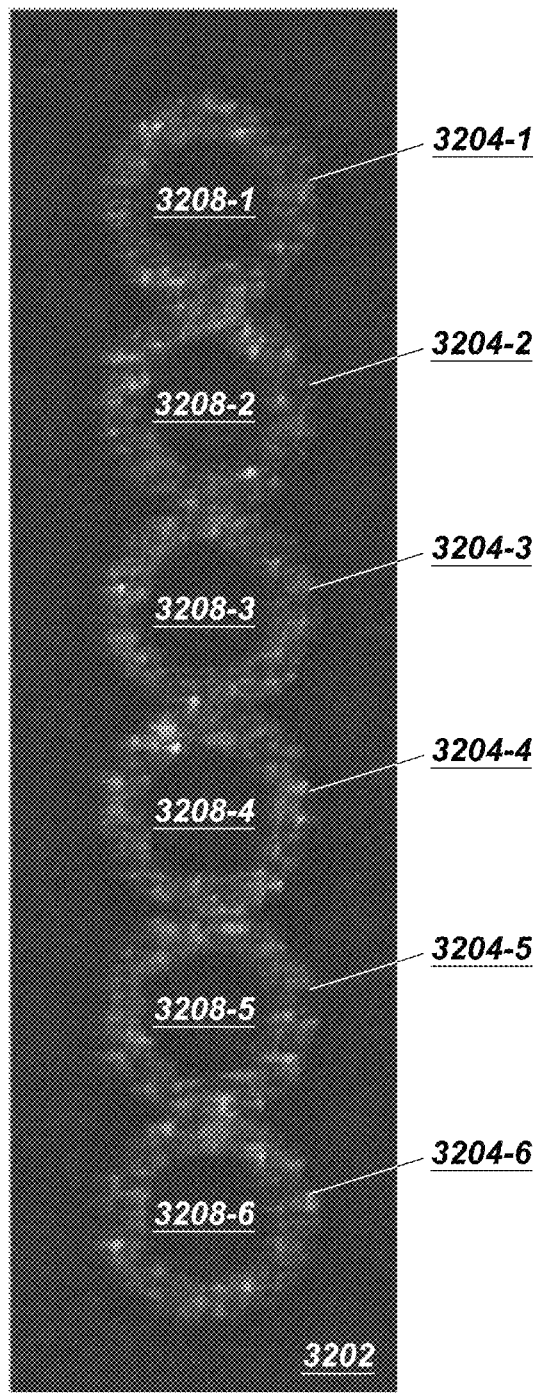
FIGS. 34A-34B are top down photographs depicting example embodiments of sensing elements formed on sensor substrates.
Figure 34B:
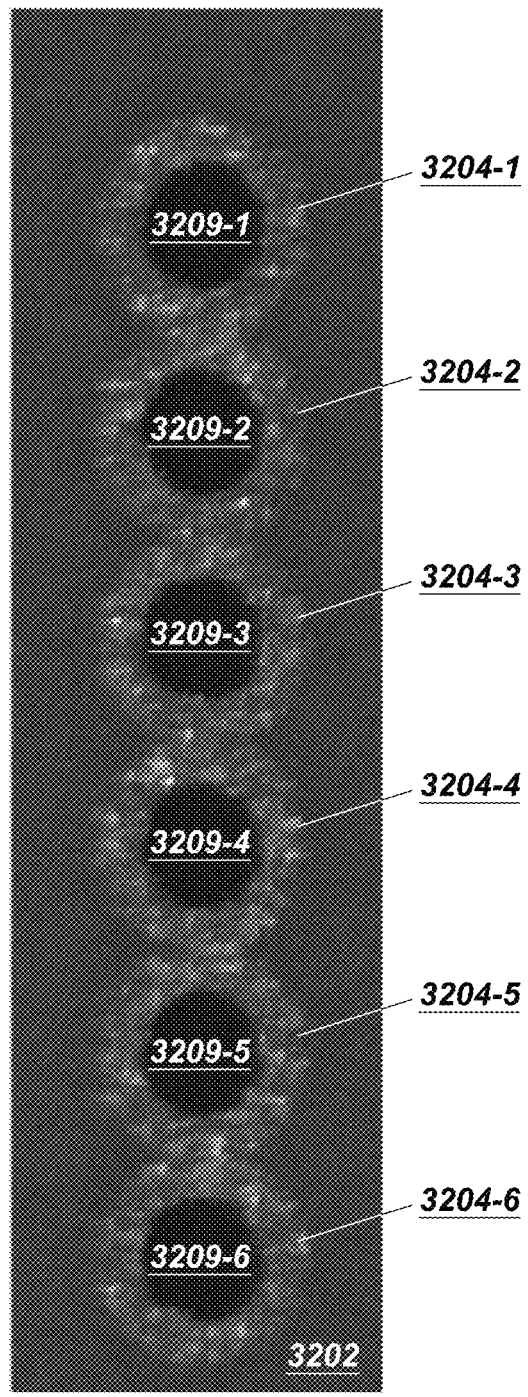

FIGS. 34A and 34B are photographs depicting an example embodiment of a carbon printed PET substrate 3202 with a series of six modified areas 3204-1 through 3204-6. FIG. 34A shows substrate 3202 prior to dispensing an electrochemical agent, where unmodified interior regions 3208-1 through 3208-6 are bare. FIG. 34B shows substrate 3202 after dispense of individual drops of the electrochemical agent into interior regions 3208 by a piezoelectric nozzle. Here, the interior regions are now covered by the electrochemical agent to form sensing elements 3209-1 through 3209-6. As can be seen in FIG. 34B, the border of elements 3209 closely aligns with the interior boundary of modified areas 3204, and each element 3209 has the same or similar size and shape. Although the embodiments described herein are not limited to such, the modified surface characteristics for the embodiment of FIGS. 34A-34B were generated at approximately 50-60 milliwatts (mW), measured in a position near-equivalent to the surface itself, with an approximately 340-350 nanometer (nm) wavelength laser. Different wavelength lasers (having wavelengths greater or less than 340-350 nm) and different powers (greater or less than 50-60 mW) can also be used to achieve the surface characteristics described herein. Different wavelengths will typically require different powers to achieve the same effect.

Although the embodiments described herein are not limited to such, each element 3209 in FIG. 34B is generally circular with a nominal diameter of 170 microns and each element 3209 is nominally 250 microns apart (center to center). As mentioned, modified area 3204 can have other sizes and shapes. FIG. 35A is a schematic view of an example embodiment where modified area 3204 is shaped as a solid circle. In this embodiment, area 3204 can be modified so as to attract the liquid such that the target area for the sensing element is area 3204. Instead of a solid circle, other shapes can also be used, such as a solid ellipse, a solid polygon (e.g., triangle, square, rectangle, trapezoid, pentagon, hexagon, etc.) with rounded or sharp corners, or a combination thereof (e.g., a D-shape). Similarly, ring-shaped area 3204 need not be formed from concentric circles, and can instead be formed by ellipses, polygons (e.g., triangle, square, rectangle, trapezoid, pentagon, hexagon, etc.) with rounded or sharp corners, or a combination thereof (e.g., a D-shape), where the inner and outer boundaries are concentric or eccentric. By way of example, FIG. 35B depicts an embodiment where ring-shaped region 3204 is formed by concentric ellipses, and FIG. 35C depicts an embodiment where ring-shaped region 3204 is formed by concentric squares. Whether in the form of a ring or solid shape, the modified area 3204 can be configured such that it is or is part of the target area (the area in which the liquid agent comes to rest) or the modified area 3204 can be configured such that an adjacent area or non-adjacent area in close proximity (see, e.g., FIG. 32F) is the target area. In addition, if multiple sensing elements are present on a substrate, then those elements can be arranged in any desired pattern or grid (e.g., with one or more rows and/or one or more columns). FIG. 35D depicts an example embodiment where the sensing elements are solid circles arranged in an X-shaped grid.

FIG. 36A is a flow diagram depicting an example embodiment of a method 3600 of manufacturing a sensor by modifying a surface with electromagnetic radiation. At 3602, the method includes modifying an area of a surface of a sensor substrate with electromagnetic radiation to create a modified area. Then, at 3604, the method includes applying a liquid to the surface of the sensor substrate such that the liquid comes to rest in a target area on the surface, where the target area is determined at least in part by the location of the modified area. Steps 3602 and 3604 can be repeated as necessary to form one single sensing element, or can be repeated to form multiple sensing elements at different locations on the substrate.

The magnitude of the modified surface characteristic can be time dependent, such that the characteristic degrades after modification. Thus, it can be beneficial to perform liquid application step 3604 relatively quickly after modification step 3602 during the time when the modified surface characteristic remains adequately present. While not limited to such, step 3604 should be performed within twenty-four hours of step 3602. In many embodiments step 3604 is performed within several hours of step 3602, and in some embodiments step 3604 is performed within one hour or less of step 3602, preferably within ten or fifteen minutes.

If desired, the application of liquid in step 3604 can occur in one or more iterations. For example, the liquid can be applied as a sequence of two or more drops where the drops are applied to form one sensing element before proceeding to a next sensing element (on the same or different substrate). In examples where multiple sensing elements are present on one substrate, then a first drop of the liquid can be applied to each sensing element (sometimes referred to as a pass) and then a second drop can be applied to each sensing element (e.g., a second pass) and the passes can be repeated until the desired number of drops are applied to each sensing element on the substrate. Alternatively, each pass can include the application of multiple drops to each sensing element, and multiple such passes can be used. In some embodiments, the multiple drops (either in one pass or in sequential passes) can be applied to different locations to form one sensing element. Such an approach can be useful for: sensing elements that are relatively large as compared to the volume of the drop; sensing elements that have a longitudinal axis (e.g., as in an embodiment similar to FIG. 32B where the sensing element is formed in the interior of the elliptical ring, and drops are placed at different locations along the long axis of the elliptical ring (between left and right in the figure)); sensing elements in a ring-shape where drops are placed in a ring-shaped pattern along the surface of the ring-shape; or others.

FIG. 36B is a flow diagram depicting another example embodiment of method 3600 where the electromagnetic radiation is laser radiation. Method 3600 utilizes a laser marking system that may, in some embodiments, include a user interface, alignment optics, control hardware and software, a power source, and the laser. At 3612, a size of the modified area can be entered into the laser marking system. This may be performed for each marking, or may be performed once for a production run of many sensors. At 3614, the laser marking system can focus (and/or align at the proper location) on a substrate of a sensor. At 3616, the laser marking system can radiate a laser to create a modified area on the substrate. This may involve multiple activations of the laser marking system (e.g., when using laser pulses, or when creating multiple sensing elements where each is created with the continuous application of the laser, etc.), where each activation also includes a step of focusing 3614. The resulting modified area can have a modified surface characteristic as compared to one or more adjacent areas, and this modified characteristic may act to attract or repel an electrochemical agent as desired. Modification of the surface characteristic between those that cause relative attraction to those that cause relative repulsion can be accomplished, in some embodiments, by adjustment of modulation of the laser power and focus height. At 3618, if two or more modified areas are to be created on a single substrate, then either the substrate or the laser can be moved and step 3616 (and optionally step 3614) can be repeated to create the next modified area. At 3620, the substrate can be moved to an electrochemical dispersion system, and the electrochemical agent can be deposited (e.g., in the form of one or more drops dispensed from a nozzle) to a target area defined by each modified area. As described this can occur within a few hours or less of the modification step(s). The liquid can then be dried and transferred to the next manufacturing stage (e.g., application of a membrane, etc.).

Figure 37A:
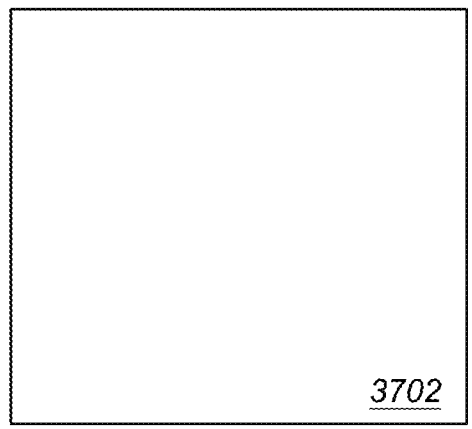
FIGS. 37A-37B are schematic views depicting an example embodiment of a sensor substrate at various stages of manufacturing.
Figure 37B:
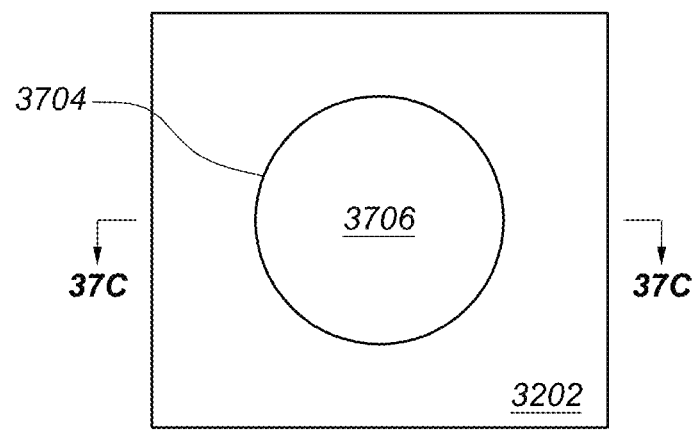

Another technique for modifying a surface of a sensor substrate is to apply mechanical force to the substrate to create a well, indentation, impression for placement of a sensing element. FIGS. 37A and 37B are top down views of an example embodiment of a substrate 3702 before and after creation of a well 3704. Substrate 3702 can be, for example, on insertion tip 530 of the embodiment of sensor 500 described with respect to FIG. 5A, or can be part of any of the other embodiments of in vivo and in vitro sensors described herein (e.g., the embodiments described with respect to FIGS. 4, 5B, 6-10C, 15A-17, and 21A-25).

Figure 37C:
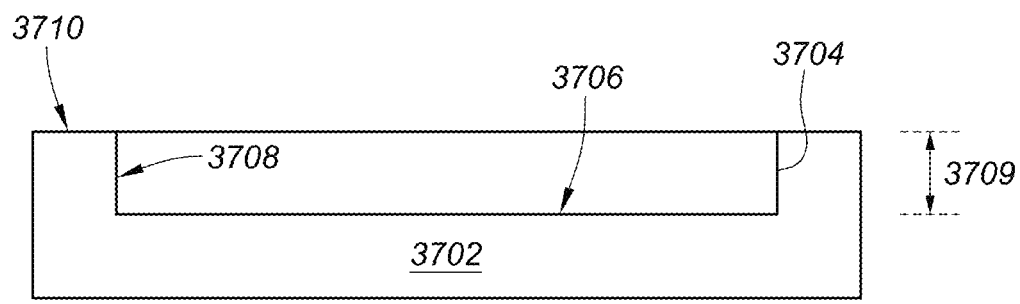
FIG. 37C is a cross-section taken along line 37C-37C of FIG. 37B.

In FIG. 37B, well 3704 has a round, more specifically circular, top down profile. FIG. 37C is a cross-section of substrate 3702 taken across line 37C-37C of FIG. 37B, and shows that, in this embodiment, well 3704 includes a flat bottom surface 3706 with a sidewall 3708 that is perpendicular to bottom surface 3706. Well 3704 has a depth 3709 measured between bottom surface 3706 and surface 3710 of substrate 3702 adjacent to well 3704. In this configuration, well 3704 has a generally cylindrical interior space, where the height of the cylinder is height 3709.

Figure 37D:
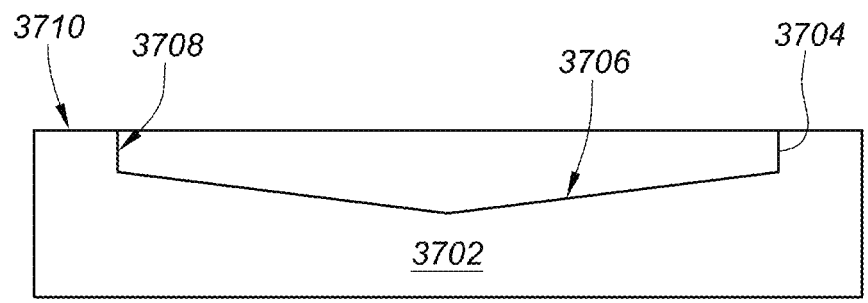
FIGS. 37D-F are cross-sections of additional example embodiments of a sensor substrate.
Figure 37E:
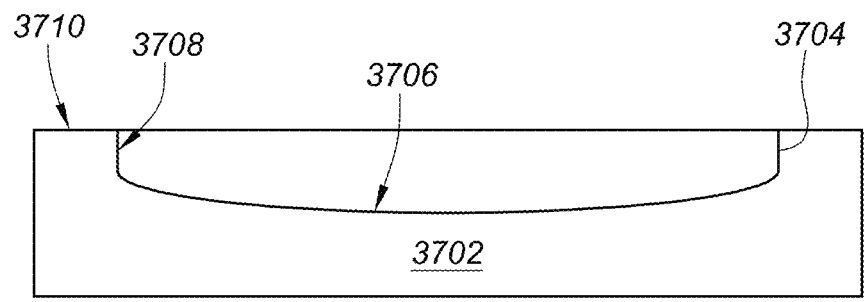
Figure 37F:
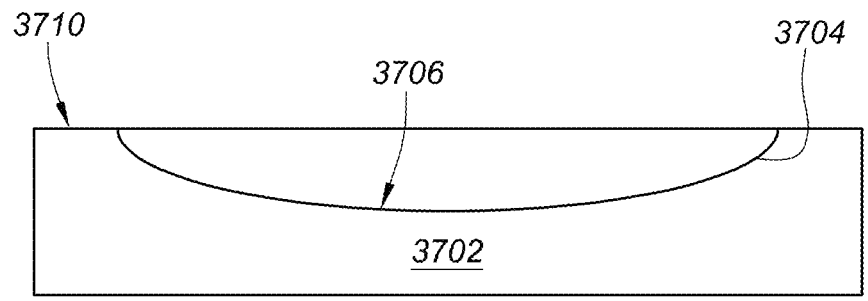

While the top-down profile of well 3704 is circular, other top down profile shapes can be used for well 3704 including, but not limited to: an ellipse, a polygon (e.g., triangle, square, rectangle, trapezoid, pentagon, hexagon, etc.) with rounded or sharp corners, or a combination thereof (e.g., a D-shape). Further, for each of the top-down profile shapes, different side profile shapes can be implemented. In FIG. 37C, well 3704 has a generally rectangular side profile, but in other embodiments the side profile can be a partial circle (e.g., a semi-circle), a partial ellipse, other polygonal or partially polygonal shapes (e.g., square, trapezoid, five-sided shape, etc.) with square or rounded corners, and combinations thereof (e.g., D-shaped). FIG. 37D-37F are cross-sectional views of other embodiments of wells 3704 having circular top-down profiles such as that depicted in FIG. 37B, but with: a five-sided shape (e.g., partial hexagon) (FIG. 37D), a D-shape (FIG. 37E), and a partial elliptical shape where surface 3706 is both a bottom and side surface (FIG. 37F).

Figure 37G:
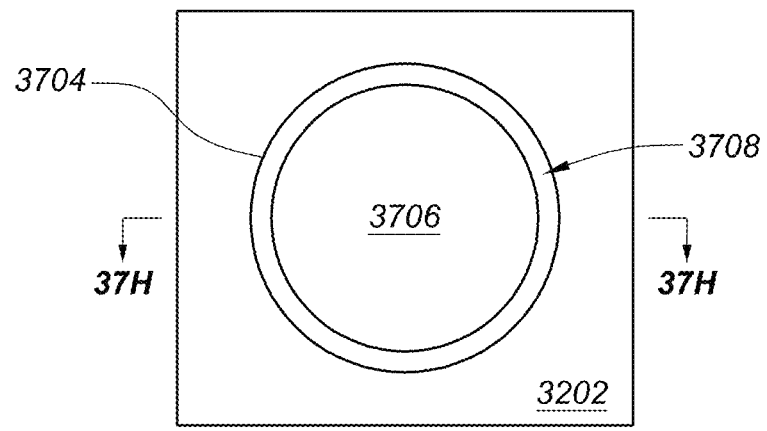
FIG. 37G is a top down schematic view of an example embodiment of a sensor substrate.
Figure 37H:
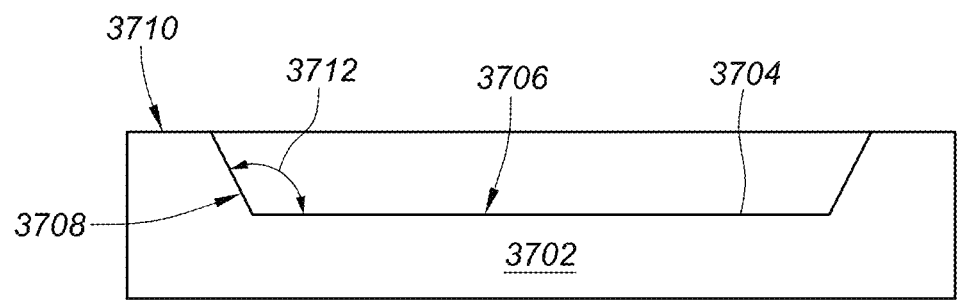
FIG. 37H is a cross-section taken along line 37H-37H of FIG. 37G.

FIG. 37G is a top down view of another example embodiment of a well 3704 and FIG. 37H is a cross-section taken along line 37H-37H of FIG. 3G. Here, angle 3712 between bottom 3706 and sidewall 3708 is approximately 120 degrees although any obtuse angle less than 180 degrees can be used. The presence of the sloped sidewall 3708 gives well 3704 a top down profile appearance of two concentric circles.

Figure 38A:
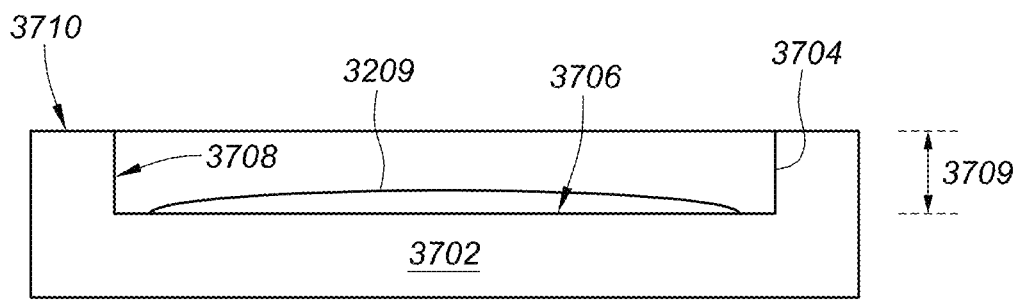
FIGS. 38A-38D are cross-sections of example embodiments of a sensor substrate with electrochemical agents deposited thereon.
Figure 38B:
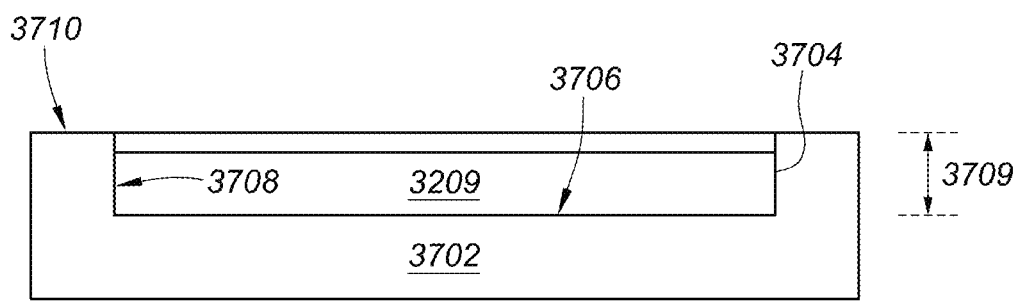
Figure 38C:
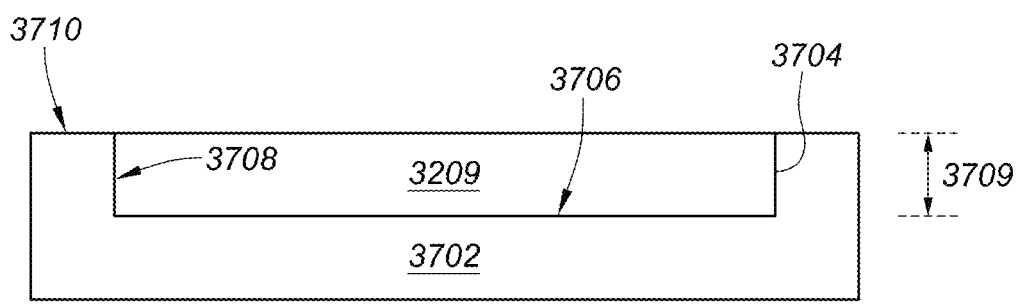
Figure 38D:
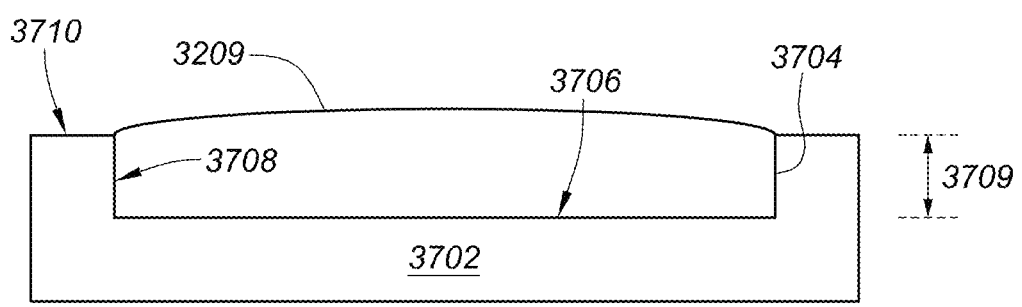

For any of these shapes and configurations, well 3704 can be filled with a liquid (e.g., electrochemical agent) that can be dried and used as a sensing element. FIGS. 38A-38D are cross-sections depicting the example embodiment of FIG. 37C with different fill levels. In the embodiment of FIG. 38A, well 3704 is under-filled, and sensing element 3209 only partially covers bottom surface 3706. In the embodiment of FIG. 38B, well 3704 is under-filled, and sensing element 3209 covers the entire bottom surface 3706, but fills only part of the depth 3709 of well 3704 (e.g., sensing element 3209 has a height that is less than depth 3709). Element 3209 is in contact with, or substantially in contact with, sidewall 3708. In other embodiments, element 3209 can reside mainly on one side of bottom surface 3706 (without covering the entire bottom surface 3706) and also be in contact, or substantially in contact, with sidewall 3708 on that one side of well 3704. In the embodiment of FIG. 38C, sensing element 3209 covers the entire bottom surface 3706, fills the entire depth 3709 of well 3704, and is flush with substrate surface 3710 (e.g., sensing element 3209 has a height that is equal to depth 3709). In the embodiment of FIG. 38D, well 3704 is over-filled, and sensing element 3209 fills the entire depth 3709 of well 3704 and extends to a height greater than substrate surface 3710 (e.g., sensing element 3209 has a height that is greater than depth 3709).

Figure 39A:
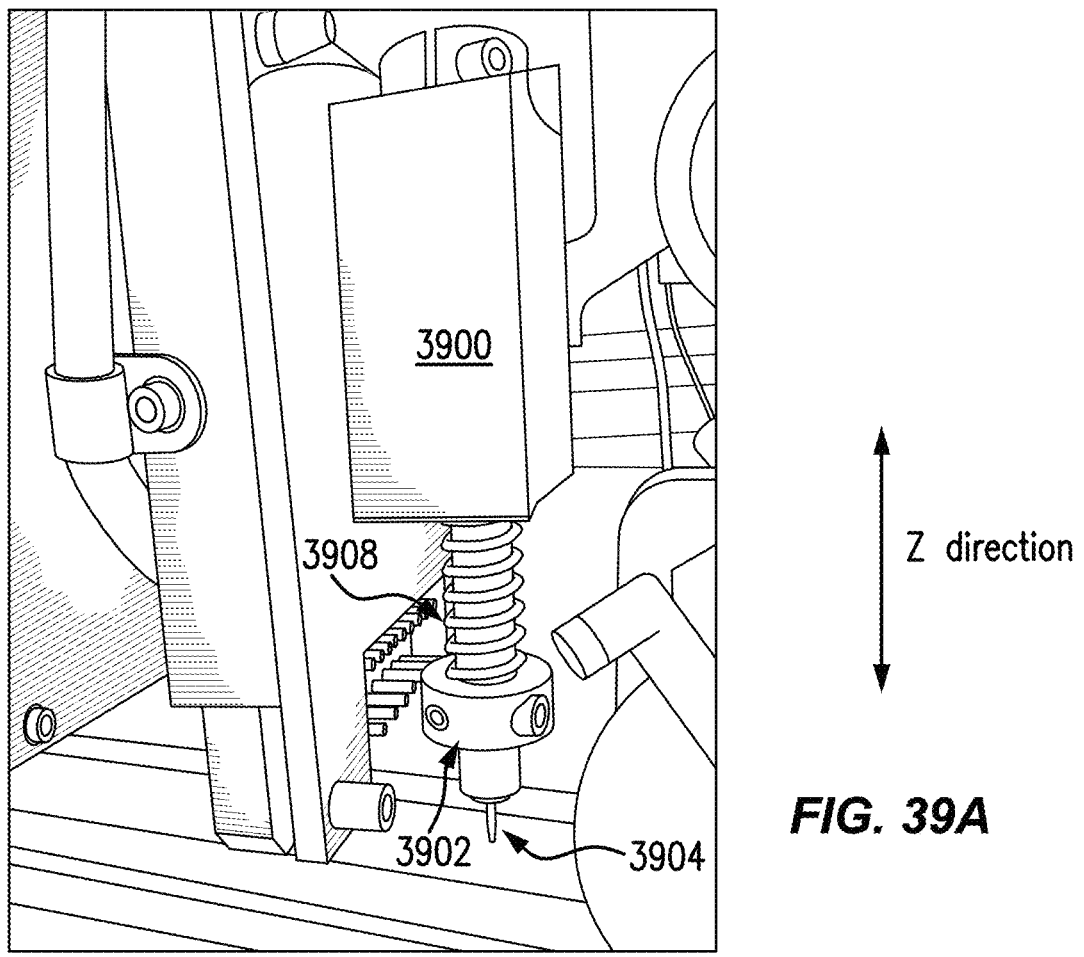
FIGS. 39A-39B are photographs depicting an example embodiment of a tamping instrument.
Figure 39B:
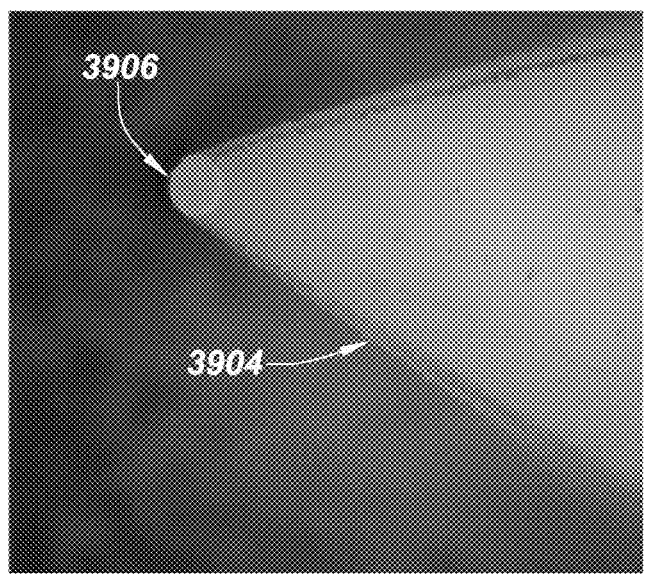

The size and shape of the well corresponds to the size and shape of the portion of the tool that forces into the substrate, e.g., a cylindrical tool will create a reverse or negative impression and produce a cylindrical well of the same size. FIG. 39A is a photograph of an example embodiment of a tool 3900 for creating wells. This tool can be referred to as a tamping instrument. Tool 3900 includes a shaft 3902 movable up and down in the Z direction. Shaft 3902 has an end portion 3904 that is shown in greater detail in the photograph of FIG. 39B. End portion 3904 tapers to a tip 3906 with a generally flat bottom surface. End portion 3904 and tip 3906 will create a well similar to that described with respect to FIGS. 37G-37H, where the slope of the taper determines the slope of sidewall 3708. Force applied to shaft 3902 will cause shaft 3902 to move downwards into a substrate (not shown) to create the well. While various types of sources can be used to apply the force, in this embodiment a coil spring 3908 is compressed and applies force against the large cylinder of shaft 3902 (see arrow in FIG. 39A). Tool 3900 can also include a user interface, alignment optics, control hardware and software, and a power source.

The well depth depends on the size of tip 3906, the spring constant, the degree of compression of spring 3908, and how far tip 3906 is from the substrate prior to releasing the compressed spring 3908. If a tapered tip 3906 is used, then the well diameter is dependent upon these factors as well. In other embodiments, pneumatic force, electrically generated force, and others force generating devices can be used.

Figure 40A:
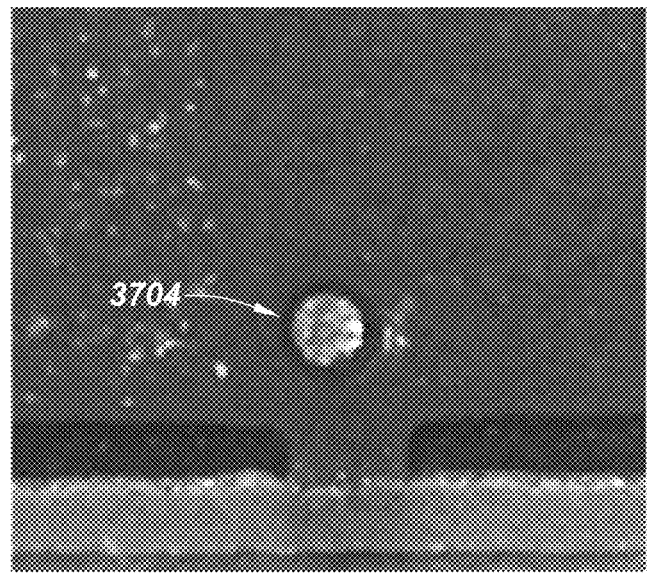
FIGS. 40A-40B are photographs depicting example embodiments of sensor substrates having a well therein.
Figure 40B:
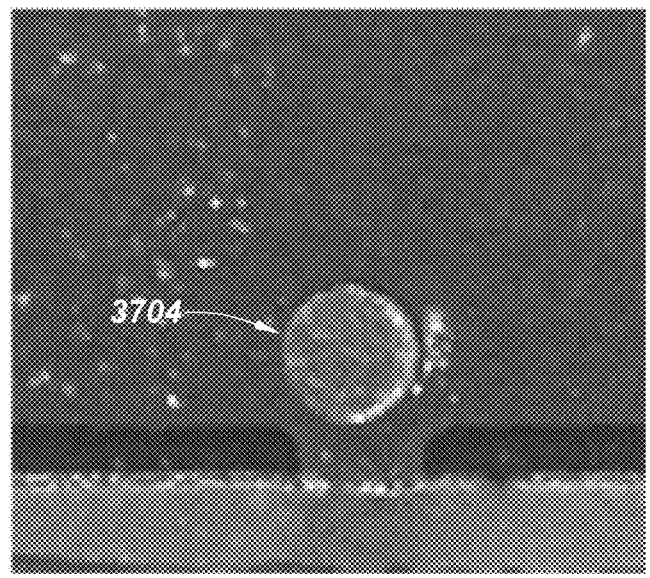

FIGS. 40A and 40B are top down photographs depicting example embodiments of wells 3704 produced with tool 3900. The photographs are at comparable magnification and illustrate two examples of different size wells that can be produced by varying the aforementioned factors. In FIG. 40A, well 3704 has a diameter of approximately 152 microns, and in FIG. 40B well 3704 has a diameter of approximately 267 microns. In general, this technique can be used to create wells of any desired size, depending on the dimensions of the tamping instrument and the number of consistent sized tamping iterations the instrument will be used for (e.g., factoring in wear).

Figure 41A:
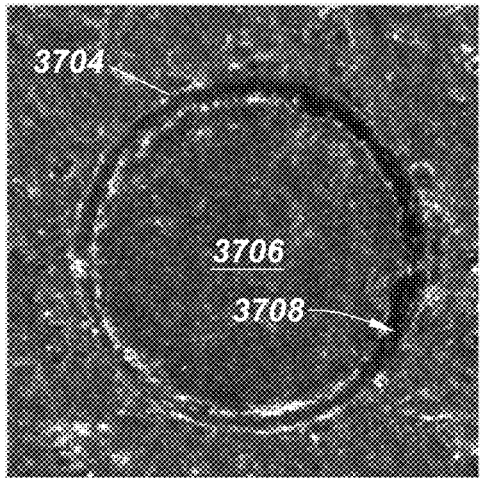
FIGS. 41A and 41B are top down photographs depicting an example embodiment of a well in a sensor substrate before and after agent dispersion.
Figure 41B:
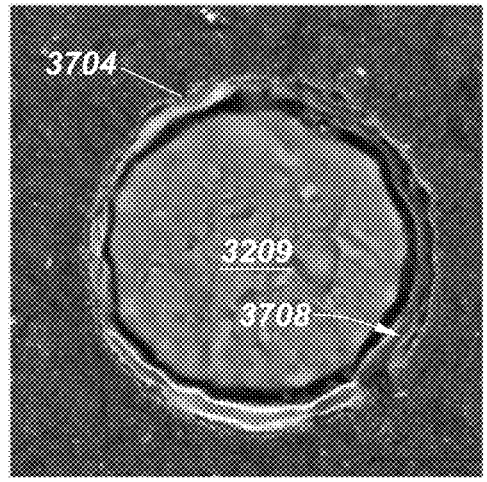
Figure 42A:
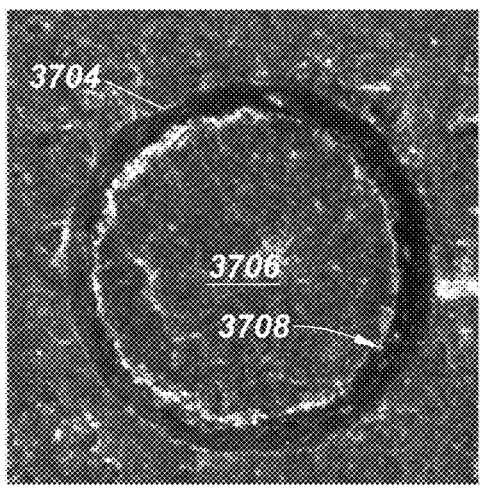
FIGS. 42A and 42B are top down photographs depicting an example embodiment of a well in a sensor substrate before and after agent dispersion.
Figure 42B:
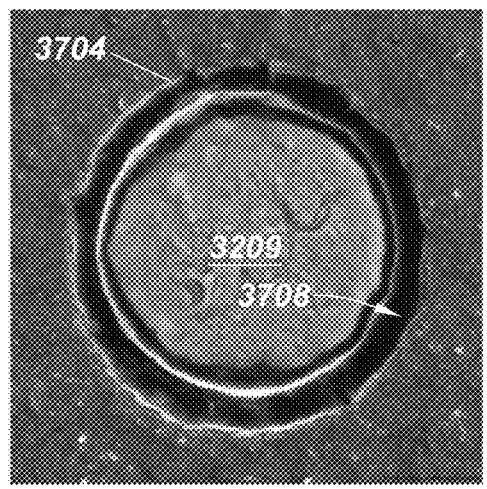

FIG. 41A is a top down photograph depicting an example embodiment of a well 3704 formed with tool 3900 to a depth of approximately five microns prior to application of the electrochemical agent. FIG. 41B is a top down photograph depicting the example embodiment of FIG. 41A after dispensing the electrochemical agent 3209 over bottom surface 3706 and partially filling well 3704. FIGS. 42A and 42B are top down photographs depicting an example embodiment of a well 3704 formed with tool 3900 to a depth of approximately fifteen microns prior to dispense and after partial filling with agent 3209, respectively. As can be seen in FIGS. 41B and 42B, the shape of agent 3209 closely approximates the circular profiles of the wells 3704.

Figure 43:
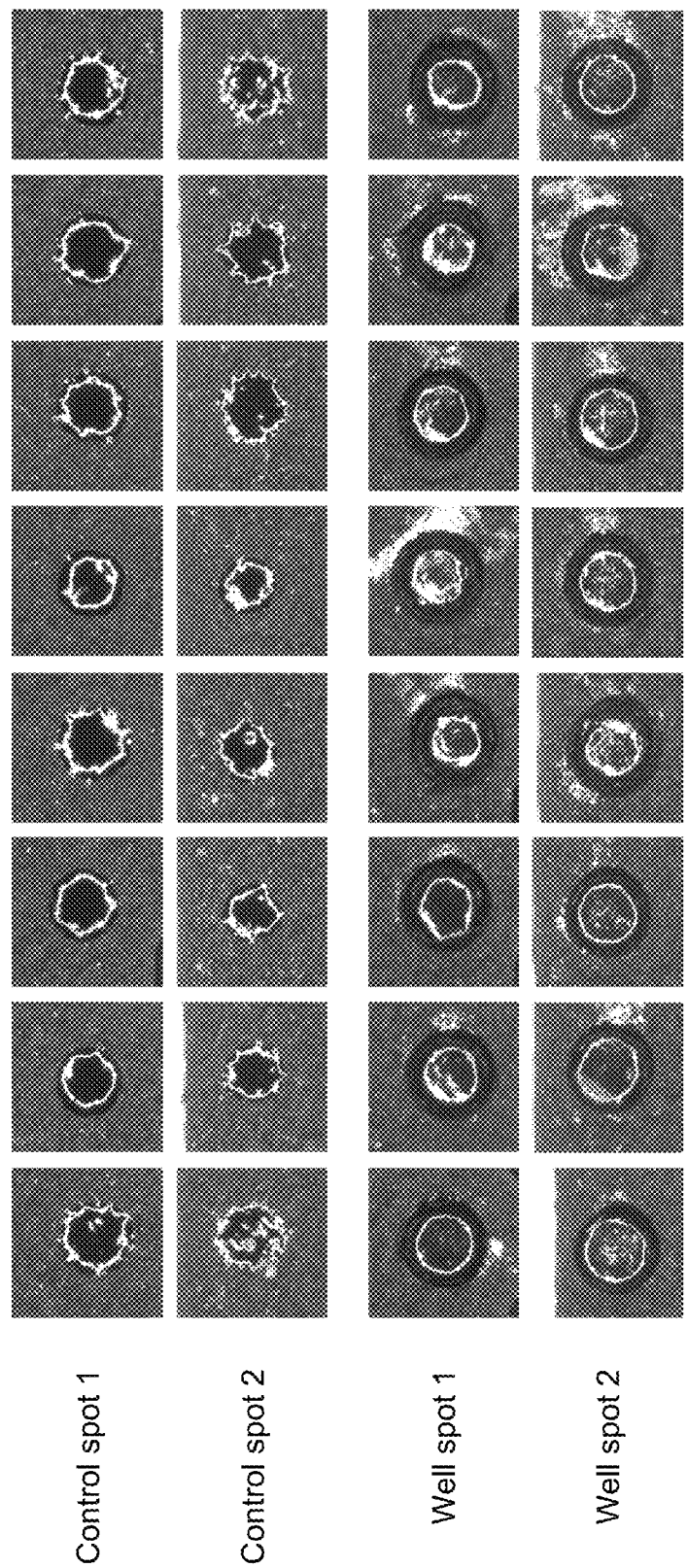
FIG. 43 is a series of top down photographs depicting various examples of agent dispersion on sensor substrates with and without wells.

It has been found that the use of wells is effective in improving accuracy of the size of sensing elements and in improving accuracy of their placement. A significant decrease in the coefficient of variability across sensing elements on the same and different sensor substrates was observed. FIG. 43 is a series of photographs showing these improvements. A number of substrates were used, and on each substrate the liquid agent was dispensed in two locations (spot 1 and spot 2) separated by a distance. In the "control" cases no well was created and the liquid was dispensed directly on the unmodified substrate surface. In the "well" cases two wells were created (one at spot 1 and one at spot 2) and the liquid agent was dispensed therein. As can be seen by the photographs, the dispensed agent in the "well" cases have more uniform borders and less variation in size than those in the "control cases."

Figure 44A:
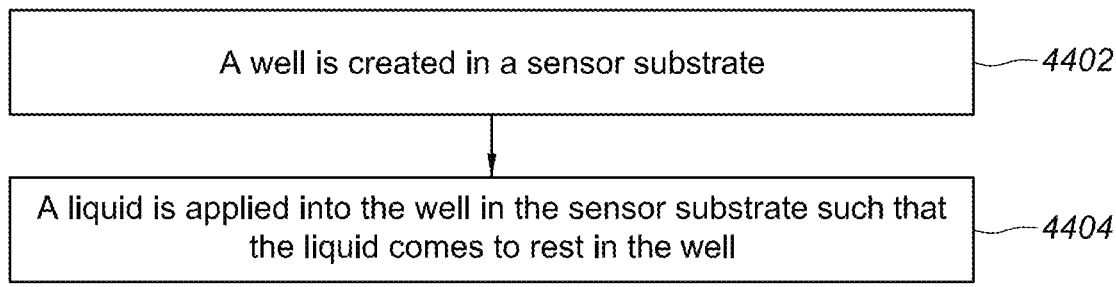
FIGS. 44A-44B are flow diagrams depicting example embodiments of methods of manufacturing one or more sensing elements.

FIG. 44A is a flow diagram depicting an example embodiment of a method 4400 of manufacturing a sensor by creating a well for a sensing element. At 3602, a well is created in a sensor substrate. Then, at 3604, a liquid is applied into the well in the sensor substrate such that the liquid comes to rest in the well.

Figure 44B:
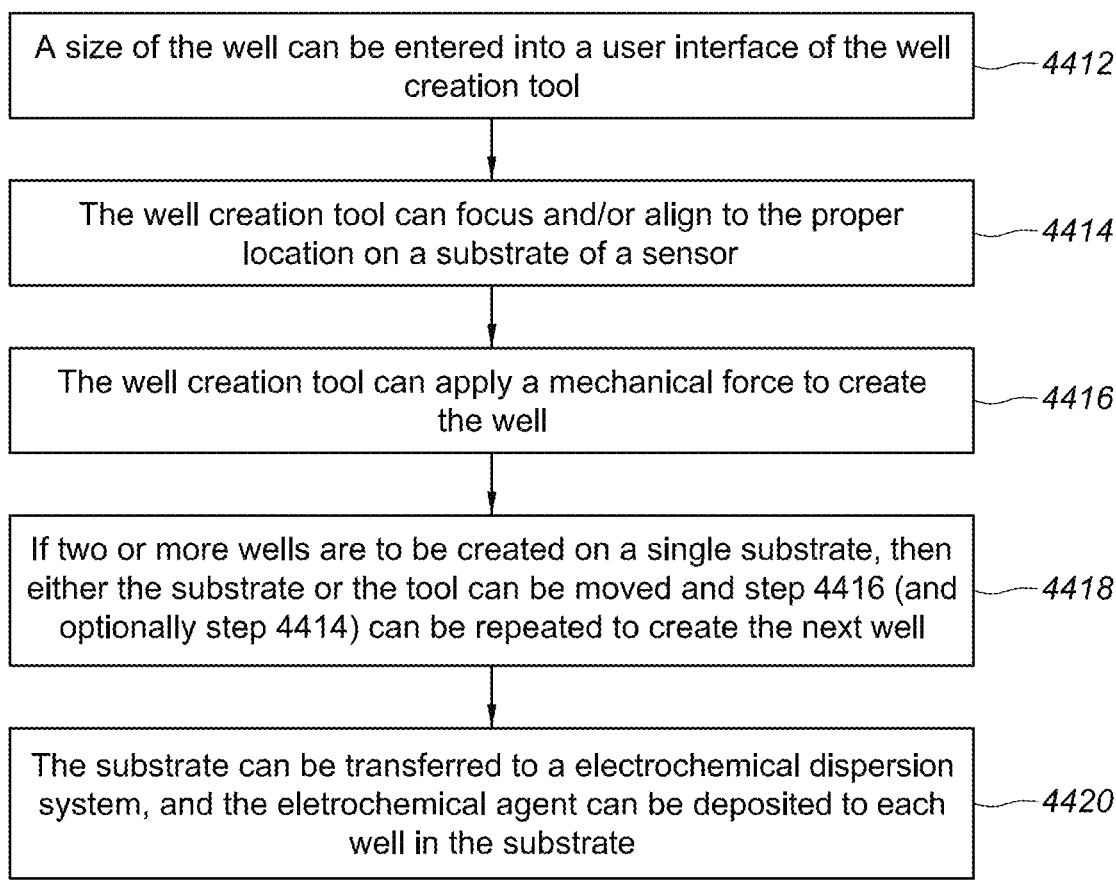

FIG. 44B is a flow diagram depicting another example embodiment of method 4400. At 4412, a size of the well can be entered into a user interface of the well creation tool (e.g., tool 3900). This may be performed for each marking, or may be performed once for a production run of many sensors. At 4414, the well creation tool can focus and/or align to the proper location on a substrate of a sensor. At 4416, the well creation tool can apply a mechanical force to create the well. This may involve one or more downward strikes, where each downward strike can include a step of alignment 4414. At 4418, if two or more wells are to be created on a single substrate, then either the substrate or the tool can be moved and step 4416 (and optionally step 4414) can be repeated to create the next well. At 4420, the substrate can be moved to an electrochemical dispersion system, and the electrochemical agent can be deposited (e.g., in the form of one or more drops dispensed from a nozzle) to each well in the substrate. The liquid can then be dried and transferred to the next manufacturing stage (e.g., application of a membrane, etc.).

While the creation of wells has been described primarily by the application of mechanical force, in other embodiments the wells can be created in other ways, such as with photolithography, laser or electrical etching or ablation, and others.

In some example embodiments, the sensor substrate can be modified with both a well and with a radiation treated surface. For example, referring back to FIGS. 37B-H, any of the bottom surfaces 3706, sidewall surfaces 3708, top substrate surfaces 3710, and/or combinations thereof can be modified with radiation to alter the liquid mobility characteristic, e.g., to either increase or decrease the mobility as compared to unmodified adjacent surfaces. For example, a ring-shaped modified area (e.g., 3204 of FIG. 32B) can be created around bottom surface 3706, where the ring-shaped area is just sidewall surface 3708, or is just top surface 3710 bordering the perimeter of well 3704, or both. In another example, a ring-shaped modified area can be placed around the perimeter of bottom surface 3706 (or a portion thereof).

In yet another example, the entirety of bottom surface 3706 can be modified to attract the agent.

Furthermore, all of the embodiments of surface modification (e.g., with radiation and/or the creation of wells) can be combined all of the calibration embodiments described herein. Such combinations can further enhance those improvements related to calibration already discussed herein. For example, the description of manufacturing parameters herein can also apply to the size or dimension of the modified area, the target area, the well, and/or a sensing element (in liquid or dried form) applied to the modified area, target area, and/or well. To the extent multiple sensing elements are applied to a single substrate, the manufacturing parameter can be representative of any or all such sensing elements (e.g., a total area). By way of non-limiting example, a measured manufacturing parameter can be the area of interior space 3208 of ring-shaped area 3204 of FIG. 32B, the area of ring-shaped area 3204 (FIG. 32B), the diameter or circumference of inner or outer boundaries 3205 and 3206 (FIG. 32B), the diameter, circumference or area of bottom surface 3706 of well 3704 (FIGS. 37B-37H), the measured or estimated volume of sensing element 3209 within well 3704, and others. Those of ordinary skill in the art, upon reading this description, will readily recognize the many different manufacturing parameters that can be measured in relation to modified areas, target areas, wells, and sensing elements. In some cases, the reduction in variation resulting from use of modified areas and wells can decrease the significance of the size of the sensing region as a manufacturing parameter for individualized calibration, allowing the calibration to utilize other measurements like membrane thickness and exclude the size of the sensing region.

The embodiments described herein are restated and expanded upon in the following paragraphs without explicit reference to the figures. In many example embodiments, a method for calibrating individual medical devices is provided that includes: at least partially manufacturing a multitude of medical devices, the multitude including a first subset and a second subset, where each of the medical devices in the multitude are adapted to sense a biochemical attribute; measuring an individualized manufacturing parameter of each medical device in the multitude; determining, with processing circuitry, an in vitro sensing characteristic of the first subset from data obtained by in vitro testing the first subset; and determining, with processing circuitry, individualized calibration information for each medical device in the second subset using at least a representation of the individualized manufacturing parameter for each medical device and a representation of the in vitro sensing characteristic of the first subset of medical devices, where the medical devices in the first subset are different from the medical devices in the second subset.

In some embodiments, each of the medical devices in the multitude is an analyte sensor and the biochemical attribute is a level of an analyte. Further, each analyte sensor in the multitude can be adapted to sense the analyte level in vivo, and the in vitro sensing characteristic can be an in vitro sensitivity to the analyte.

In some embodiments, each of the analyte sensors in the multitude includes a sensing region, optionally where the individualized manufacturing parameter is a size of the sensing region. In certain embodiments, the size of the sensing region is representative of at least one of the following: a width of the sensing region, a length of the sensing region, a thickness of the sensing region, a peripheral length of the sensing region, an area of the sensing region, or a volume of the sensing region. In certain embodiments, the representation of the individualized manufacturing parameter for a respective analyte sensor in the second subset is a deviation of the size of the sensing region of the respective analyte sensor from a central tendency of a size of the sensing region for the multitude of analyte sensors.

In some embodiments, each of the analyte sensors in the multitude includes a membrane for the sensing region, optionally where the individualized manufacturing parameter is a size of the membrane. In certain embodiments, the size of the membrane is representative of at least one of the following: a width of the membrane, a length of the membrane, a thickness of the membrane, a peripheral length of the membrane, an area of the membrane, or a volume of the membrane. In certain embodiments, the representation of the individualized manufacturing parameter for a respective analyte sensor in the second subset is a deviation of the size of the membrane of the respective analyte sensor from a central tendency of a size of the membrane for the multitude of analyte sensors.

In some embodiments, each of the analyte sensors in the multitude includes a sensing region and a membrane for the sensing region, optionally where measuring an individualized manufacturing parameter of each analyte sensor in the multitude includes measuring a size of the sensing region and a size of the membrane of each analyte sensor. In certain embodiments, the individualized calibration information for each analyte sensor in the second subset is determined using: a representation of the size of the sensing region of a respective analyte sensor in the second subset; a representation of the size of the membrane of the respective analyte sensor in the second subset; and a representation of the in vitro sensitivity of the first subset. In certain embodiments, the representation of the in vitro sensitivity can include a slope of a central tendency of in vitro sensitivity of the first subset, an intercept of a central tendency of in vitro sensitivity of the first subset, or both a slope and an intercept of a central tendency of in vitro sensitivity of the first subset.

In some embodiments, determining individualized calibration information for each analyte sensor in the second subset includes performing (a)-(c) independently for each analyte sensor in the second subset using processing circuitry: (a) determining an in vitro sensitivity of a respective analyte sensor in the second subset using at least the representation of the individualized manufacturing parameter for the respective analyte sensor and the representation of the in vitro sensitivity of the first subset; (b) determining an in vivo sensitivity of the respective analyte sensor using a representation of the in vitro sensitivity of the respective analyte sensor; and (c) determining individualized calibration information for the respective analyte sensor that corresponds to the in vivo sensitivity of the respective analyte sensor. In certain embodiments, determining the in vitro sensitivity of the respective analyte sensor in the second subset includes modeling a correlation between the representation of the individualized manufacturing parameter for the respective analyte sensor and the representation of the in vitro sensitivity of the first subset, where modeling the correlation utilizes one of the following models: a linear regression model; a multiple variable regression model; a random forest model; a non-linear model; a Bayesian regression model; a neural network; a machine learning model; a non-random decision tree; or a discriminant analysis model. In certain embodiments, modeling the correlation utilizes a model at least partially represented by: $SC_{MD}=SC_B+\alpha+(\beta RMP_A)$ or $SC_{MD}=SC_B+(1+0.1(\alpha+(\beta RMP_A)))$, where $SC_{MD}$ is the in vitro sensitivity of the respective analyte sensor, $SC_B$ is the representation of the in vitro sensitivity of the first subset, $\alpha$ is a zero or non-zero adjustment factor, $RMP_A$ is the representation of the individualized manufacturing parameter for the respective analyte sensor, and $\beta$ is a coefficient for $RMP_A$. In certain embodiments, modeling the correlation utilizes a model at least partially represented by: $SC_{MD}=SC_B+\alpha+(\beta RMP_A)+(\delta\ RMP_A^2)$ or $SC_{MD}=SC_B+(1+0.1(\alpha+(\beta RMP_A)+(\delta\ RMP_A^2)))$, where $SC_{MD}$ is the in vitro sensitivity of the respective analyte sensor, $SC_B$ is the representation of the in vitro sensitivity of the first subset, $\alpha$ is a zero or non-zero adjustment factor, $RMP_A$ is the representation of the individualized manufacturing parameter for the respective analyte sensor, and $\beta$ is a coefficient for $RMP_A$, and $\delta$ is a coefficient for $RMP_A$ squared.

In some embodiments, the individualized manufacturing parameter is a first individualized manufacturing parameter, and determining individualized calibration information for each analyte sensor in the second subset includes performing (a)-(c) independently for each analyte sensor in the second subset using processing circuitry: (a) determining an in vitro sensitivity of a respective analyte sensor in the second subset using at least: the representation of the first individualized manufacturing parameter for the respective analyte sensor, a representation of a second individualized manufacturing parameter for the respective analyte sensor, and the representation of the in vitro sensitivity of the first subset; (b) determining an in vivo sensitivity of the respective analyte sensor using a representation of the in vitro sensitivity of the respective analyte sensor; and (c) determining individualized calibration information for the respective analyte sensor that corresponds to the in vivo sensitivity of the respective analyte sensor. In certain embodiments, the representation of the first individualized manufacturing parameter for the respective analyte sensor, the representation of a second individualized manufacturing parameter for the respective analyte sensor, and the representation of the in vitro sensitivity of the first subset are input into a model to determine the in vitro sensitivity of the respective analyte sensor. In certain embodiments, the model is at least partially represented by: $SC_{MD}=SC_B+\alpha+(\beta RMP_A)+(\delta RMP_A^2)+(\gamma RMP_B)+(\varepsilon RMP_B^2)+(\rho RMP_A\ RMP_B)$ or $SC_{MD}=SC_B+(1+0.01\ (\alpha+(\beta RMP_A)+(\delta\ RMP_A^2)+(\gamma RMP_B)+(\varepsilon RMP_B^2)+(\rho RMP_A\ RMP_B)))$, where $SC_{MD}$ is the in vitro sensitivity of the respective analyte sensor, $SC_B$ is the representation of the in vitro sensitivity of the first subset, $\alpha$ is a zero or non-zero adjustment factor, $RMP_A$ is the representation of the first individualized manufacturing parameter for the respective analyte sensor, $\beta$ is a coefficient for $RMP_A$, $\delta$ is a coefficient for $RMP_A$ squared, $RMP_B$ is the second individualized manufacturing parameter, $\gamma$ is a coefficient for $RMP_B$, $\varepsilon$ is a coefficient for $RMP_B$ squared, and $\rho$ is a coefficient for the product of $RMP_A$ and $RMP_B$.

In some embodiments, each analyte sensor of the multitude includes a sensing region and a membrane for the sensing region, where measuring an individualized manufacturing parameter of each analyte sensor in the multitude includes measuring a size of the sensing region and a size of the membrane of each analyte sensor in the multitude, and where determining the in vitro sensitivity of the respective analyte sensor in the second subset includes inputting a representation of the size of the sensing region, a representation of the size of the membrane, and a representation of the in vitro sensitivity into a model.

In some embodiments, the in vivo sensitivity of the respective analyte sensor is determined by applying a representation of the in vitro sensitivity of the respective analyte sensor to a transfer function. In some embodiments, determining individualized calibration information for the respective analyte sensor includes identifying, from a multitude of predetermined calibration codes, a calibration code that most closely represents the in vivo sensitivity of the respective analyte sensor.

In some embodiments, each analyte sensor in the second subset is associated with a different sensor electronics assembly of a multitude of sensor electronics assemblies, and each sensor electronics assembly of the multitude of sensor electronics assemblies includes a non-transitory memory. In certain embodiments, the non-transitory memory of each sensor electronics assembly has individualized calibration information for the associated analyte sensor stored thereon. In certain embodiments, each sensor electronics assembly in the multitude of sensor electronics assemblies includes processing circuitry communicatively coupled with the non-transitory memory. In some embodiments, each non-transitory memory includes instructions that, when executed by the processing circuitry communicatively coupled thereto, causes that processing circuitry to determine an analyte level from raw analyte data measured by the associated analyte sensor and from the individualized calibration information for that associated analyte sensor. In other embodiments, each non-transitory memory includes instructions that, when executed by the processing circuitry communicatively coupled thereto, causes that processing circuitry to cause transmission of the individualized calibration information for the associated analyte sensor to a wirelessly connected reader device.

In some embodiments, determining individualized calibration information for each analyte sensor in the second subset includes performing (a) and (b) independently for each analyte sensor in the second subset using processing circuitry: (a) determining an in vitro sensitivity of a respective analyte sensor in the second subset using at least the representation of the individualized manufacturing parameter for the respective analyte sensor and the representation of the in vitro sensitivity of the first subset; and (b) determining individualized calibration information for the respective analyte sensor that corresponds to the in vitro sensitivity of the respective analyte sensor.

In some embodiments, determining individualized calibration information for each analyte sensor in the second subset includes performing (a) and (b) independently for each analyte sensor in the second subset using processing circuitry: (a) determining a first in vitro sensitivity of a respective analyte sensor in the second subset using at least the representation of the individualized manufacturing parameter for the respective analyte sensor and the representation of the in vitro sensitivity of the first subset; (b) determining a second in vitro sensitivity of the respective analyte sensor in the second subset using at least a representation of the first in vitro sensitivity of the respective analyte sensor; and (c) determining individualized calibration information for the respective analyte sensor that corresponds to the in vitro sensitivity of the respective analyte sensor. In certain embodiments, the first in vitro sensitivity corresponds to the presence of the analyte in an analyte test solution, and the second in vitro sensitivity corresponds to the presence of the analyte in a bodily fluid.

In some embodiments, each medical device in the multitude is an in vitro analyte sensor, optionally a test strip. In certain embodiments, each in vitro analyte sensor includes a working pad and the individualized manufacturing parameter is a size of the working pad. In certain embodiments, the individualized manufacturing parameter is an area of the working pad, while in other embodiments the individualized manufacturing parameter is a thickness of the working pad. In certain embodiments, each in vitro analyte sensor includes at least one electrical trace and the individualized manufacturing parameter is a resistance of the trace.

In some embodiments, the individualized manufacturing parameter of each medical device in the multitude is measured during or after a stage of manufacturing of the multitude of medical devices.

In some embodiments, the method further includes assigning the individualized calibration information to each medical device in the second subset.

In many embodiments, the biochemical attribute is a level of glucose.

In some embodiments, the first and second subsets are taken from a same production lot. In some embodiments, the multitude of medical devices is a production lot of the medical devices.

In some embodiments, the plurality of medical devices is a plurality of analyte sensors each including a sensor substrate, and at least partially manufacturing the plurality of analyte sensors includes: modifying an area of a surface of each sensor substrate with electromagnetic radiation to create a modified area; and applying a liquid agent to the surface of each sensor substrate such that the liquid agent comes to rest in a target area on the surface, where the target area is determined at least in part by the location of the modified area. The modified area can border the target area, and the modified area can repel or attract the liquid agent. In some embodiments, at least partially manufacturing the plurality of analyte sensors can further include: focusing a laser on the surface of each sensor substrate; and activating the laser to modify the area of the surface of each sensor substrate with electromagnetic radiation to create the modified area. In some embodiments, at least partially manufacturing the plurality of analyte sensors can further include: transferring each sensor substrate to a liquid agent dispense system having a nozzle; and applying the liquid agent from the nozzle to the surface of each sensor substrate such that the liquid agent comes to rest in the target area on the surface.

In some embodiments, the plurality of medical devices is a plurality of analyte sensors each including a sensor substrate, and at least partially manufacturing the plurality of analyte sensors includes: creating a well in each sensor substrate; and applying a liquid agent into the well in each sensor substrate such that the liquid agent comes to rest in the well. The liquid agent can cover at least a portion of the bottom and substantially contact the sidewall. The method can further include: aligning a tip of a tool with an alignment feature on a surface of the sensor substrate; and forcing the tip of the tool into the substrate to create the well in the substrate. The method can further include: transferring the substrate to a liquid agent dispense system having a nozzle, where applying the liquid agent into the well in the sensor substrate such that the liquid agent comes to rest in the well includes dispensing a drop of the liquid agent from the nozzle into the well.

In many embodiments, a method for calibrating individual medical devices is provided, where the method includes: measuring an individualized manufacturing parameter of each medical device in a multitude of medical devices; and determining, with processing circuitry, individualized calibration information for each medical device in the multitude using at least a representation of the individualized manufacturing parameter for each medical device and a representation of a baseline sensing characteristic.

In some embodiments, each of the medical devices in the multitude is an analyte sensor adapted to sense an analyte.

In some embodiments, the multitude of medical devices is a second multitude, and the method further includes determining the baseline sensing characteristic from clinical test data of a first multitude of medical devices.

In some embodiments, the multitude of medical devices is a second multitude, and the method further includes: measuring an individualized manufacturing parameter of each medical device in a first multitude of medical devices; performing clinical testing with the first multitude of medical devices to obtain clinical test data; and determining the baseline sensing characteristic from the clinical test data. In certain embodiments, each medical device in the first multitude is an in vivo analyte sensor, and the clinical testing is in vivo testing. In certain embodiments, each medical device in the first multitude is an in vitro analyte sensor, and the clinical testing is in vitro testing. In certain embodiments, the second multitude is a production lot of medical devices. In certain embodiments, the first and second pluralities of medical devices are from different production lots.

In some embodiments, determining individualized calibration information for each sensor in the multitude includes performing (a) and (b) independently for each sensor in the multitude using processing circuitry: (a) determining a representation of an individualized sensing characteristic of a respective analyte sensor in the multitude using at least the representation of the individualized manufacturing parameter for the respective sensor and the representation of the baseline sensing characteristic; and (b) determining individualized calibration information for the respective analyte sensor that corresponds to the individualized sensing characteristic of the respective analyte sensor. In certain embodiments, determining the representation of the individualized sensing characteristic of the respective analyte sensor includes modeling a correlation between the representation of the individualized manufacturing parameter for the respective analyte sensor and the representation of the baseline sensing characteristic. In certain embodiments, modeling the correlation utilizes at least one of the following: a linear regression model; a multiple variable regression model; a random forest model; a non-linear model; a Bayesian regression model; a neural network; a machine learning model; a non-random decision tree; or a discriminant analysis model. In certain embodiments, modeling the correlation utilizes a model at least partially represented by: $SC_{MD}=SC_B+\alpha+(\beta RMP_A)$ or $SC_{MD}=SC_B+(1+0.1(\alpha+(\beta RMP_A)))$, where $SC_{MD}$ is the representation of the individualized sensing characteristic of the respective analyte sensor, $SC_B$ is the representation of the baseline sensing characteristic, $\alpha$ is a zero or non-zero adjustment factor, $RMP_A$ is the representation of the individualized manufacturing parameter for the respective analyte sensor, and $\beta$ is a coefficient for $RMP_A$. In certain embodiments, modeling the correlation utilizes a model at least partially represented by: $SC_{MD}=SC_B+\alpha+(\beta RMP_A)+(\delta\ RMP_A^2)$ or $SC_{MD}=SC_B+(1+0.1(\alpha+(\beta RMP_A)+(\delta\ RMP_A^2)))$, where $SC_{MD}$ is the representation of the individualized sensing characteristic of the respective analyte sensor, $SC_B$ is the representation of the baseline sensing characteristic, $\alpha$ is a zero or non-zero adjustment factor, $RMP_A$ is the representation of the individualized manufacturing parameter for the respective analyte sensor, $\beta$ is a coefficient for $RMP_A$, and $\delta$ is a coefficient for $RMP_A$ squared.

In some embodiments, the individualized manufacturing parameter is a first individualized manufacturing parameter, and the method further includes measuring a second individualized manufacturing parameter of each medical device in the multitude of medical devices. In certain embodiments, determining individualized calibration information for each analyte sensor in the multitude includes performing (a)-(b) independently for each analyte sensor in the multitude using processing circuitry: (a) determining an individualized sensing characteristic of a respective analyte sensor in the multitude using at least: the representation of the first individualized manufacturing parameter for the respective analyte sensor, a representation of the second individualized manufacturing parameter for the respective analyte sensor, and the representation of the baseline sensing characteristic; and (b) determining individualized calibration information for the respective analyte sensor that corresponds to the individualized sensing characteristic of the respective analyte sensor. In certain embodiments, the method further includes modeling a correlation between the representation of the first individualized manufacturing parameter for the respective analyte sensor, the representation of a second individualized manufacturing parameter for the respective analyte sensor, and the representation of the baseline sensing characteristic to determine the individualized sensing characteristic of the respective analyte sensor. In certain embodiments, modeling the correlation utilizes a model at least partially represented by: $SC_{MD}=SC_B+\alpha+(\beta RMP_A)+(\delta RMP_A^2)+(\gamma RMP_B)+(\varepsilon RMP_B^2)+(\rho RMP_A\ RMP_B)$ or $SC_{MD}=SC_B+(1+0.01\ (\alpha+(\beta RMP_A)+(\delta RMP_A^2)+(\gamma RMP_B)+(\varepsilon RMP_B^2)+(\rho RMP_A\ RMP_B)))$, where $SC_{MD}$ is a representation of the individualized sensing characteristic of the respective analyte sensor, $SC_B$ is the representation of the baseline sensing characteristic, $\alpha$ is a zero or non-zero adjustment factor, $RMP_A$ is the representation of the first individualized manufacturing parameter for the respective analyte sensor, $\beta$ is a coefficient for $RMP_A$, $\delta$ is a coefficient for $RMP_A$ squared, $RMP_B$ is the second individualized manufacturing parameter, $\gamma$ is a coefficient for $RMP_B$, $\varepsilon$ is a coefficient for $RMP_B$ squared, and $\rho$ is a coefficient for the product of $RMP_A$ and $RMP_B$.

In some embodiments, the individualized manufacturing parameter is a size of a sensing region of each medical device or a size of a membrane of each medical device. In some embodiments, the multitude of medical devices is a production lot of the medical devices.

In some embodiments, the individualized manufacturing parameter is a size of a sensing region of each medical device, the sensing region including a sensing element, where the sensing element is in a well of a sensor substrate and/or the sensing element is on or adjacent to a modified area of the sensor substrate having a liquid mobility characteristic different than an adjacent area of the sensor substrate.

In many embodiments, a method for calibrating individual analyte sensors is provided, where the method includes: at least partially manufacturing a multitude of analyte sensors, the multitude including a first subset and a second subset, where each of the analyte sensors in the multitude are adapted for in vivo sensing of an analyte level; measuring an individualized manufacturing parameter of each analyte sensor in the multitude; determining, with processing circuitry, an in vitro sensitivity of the first subset from data obtained by in vitro testing the first subset; and performing (a)-(c) for each analyte sensor in the second subset using processing circuitry: (a) determining an in vitro sensitivity of a respective analyte sensor in the second subset using at least the representation of the individualized manufacturing parameter for the respective analyte sensor and the representation of the in vitro sensitivity of the first subset;

(b) determining an in vivo sensitivity of the respective analyte sensor using a representation of the in vitro sensitivity of the respective analyte sensor; and (c) determining individualized calibration information for the respective analyte sensor that corresponds to the in vivo sensitivity of the respective analyte sensor.

In some embodiments, each analyte sensor in the multitude includes a sensing region and the individualized manufacturing parameter is a size of the sensing region. In certain embodiments, the representation of the individualized manufacturing parameter for the respective analyte sensor is a deviation of the size of the sensing region of the respective analyte sensor from a central tendency of a size of the sensing region for the multitude of analyte sensors.

In some embodiments, the sensing region includes a sensing element, the sensing element being in a well of a sensor substrate and/or the sensing element being on or adjacent to a modified area of the sensor substrate having a liquid mobility characteristic different than an adjacent area of the sensor substrate.

In some embodiments, each of the analyte sensors in the multitude includes a membrane for the sensing region and the individualized manufacturing parameter is a size of the membrane. In certain embodiments, the representation of the individualized manufacturing parameter for the respective analyte sensor is a deviation of the size of the membrane of the respective analyte sensor from a central tendency of a size of the membrane for the multitude of analyte sensors.

In some embodiments, each of the analyte sensors in the multitude includes a sensing region and a membrane for the sensing region, where measuring an individualized manufacturing parameter of each analyte sensor in the multitude includes measuring a size of the sensing region and a size of the membrane of each analyte sensor. In certain embodiments, the in vitro sensitivity of the respective analyte sensor is determined using: a representation of the size of the sensing region of the respective analyte sensor; a representation of the size of the membrane of the respective analyte sensor; and a representation of the in vitro sensitivity of the first subset. In certain embodiments, the representation of the in vitro sensitivity includes a slope of a central tendency of in vitro sensitivity of the first subset, or an intercept of a central tendency of in vitro sensitivity of the first subset, or a slope and an intercept of a central tendency of in vitro sensitivity of the first subset. In certain embodiments, the in vitro sensitivity of the respective analyte sensor in the second subset is determined by modeling a correlation between a representation of the size of the sensing region of the respective analyte sensor, a representation of the size of the membrane of the respective analyte sensor, and a representation of the in vitro sensitivity of the first subset. In certain embodiments, modeling the correlation utilizes at least one of the following: a linear regression model; a multiple variable regression model; a random forest model; a non-linear model; a Bayesian regression model; a neural network; a machine learning model; a non-random decision tree; or a discriminant analysis model.

In some embodiments, the in vivo sensitivity of the respective analyte sensor is determined by applying a representation of the in vitro sensitivity of the respective analyte sensor to a transfer function.

In some embodiments, determining individualized calibration information for the respective analyte sensor includes identifying, from a multitude of predetermined calibration codes, a calibration code that most closely represents the in vivo sensitivity of the respective analyte sensor.

In some embodiments, each analyte sensor in the second subset is associated with a different sensor electronics assembly of a multitude of sensor electronics assemblies, each sensor electronics assembly of the multitude of sensor electronics assemblies including a non-transitory memory. In certain embodiments, the non-transitory memory of each sensor electronics assembly has individualized calibration information for the associated analyte sensor stored thereon. In certain embodiments, each sensor electronics assembly in the multitude of sensor electronics assemblies includes processing circuitry communicatively coupled with the non-transitory memory. In certain embodiments, each non-transitory memory includes instructions that, when executed by the processing circuitry communicatively coupled thereto, causes that processing circuitry to determine an analyte level from raw analyte data measured by the associated analyte sensor and from the individualized calibration information for that associated analyte sensor. In certain embodiments, each non-transitory memory includes instructions that, when executed by the processing circuitry communicatively coupled thereto, causes that processing circuitry to cause transmission of the individualized calibration information for the associated analyte sensor to a wirelessly connected reader device.

In some embodiments, the analyte level is a glucose level.

In some embodiments, the first and second subsets are taken from a same production lot. In some embodiments, the multitude of in vivo analyte sensors is a production lot of the analyte sensors.

In some embodiments, the in vitro testing includes applying an analyte solution to each of the analyte sensors in the first subset. In some embodiments, the in vitro testing degrades or contaminates each analyte sensor in the first subset.

In many embodiments, a method for calibrating individual medical devices is provided, where the method includes: at least partially manufacturing a first medical device and a second medical device, where the first and second medical devices are adapted to sense a biochemical attribute; measuring a manufacturing parameter of the second medical device; determining, with processing circuitry, an in vitro sensing characteristic of the first medical device from data obtained by in vitro testing the first medical device; and determining, with processing circuitry, calibration information for the second medical device using at least a representation of the manufacturing parameter of the second medical device and a representation of the in vitro sensing characteristic of the first medical device.

In some embodiments, measuring the manufacturing parameter of the second medical device is performed by a manufacturer.

In some embodiments, the first medical device is a first analyte sensor, the second medical device is a second analyte sensor, and the biochemical attribute is an analyte level. In certain embodiments, the first and second analyte sensors are adapted to sense the analyte level in vivo. In certain embodiments, the second analyte sensor includes a sensing region and a membrane for the sensing region and in certain embodiments, the manufacturing parameter is a size of the sensing region or a size of the membrane. In certain embodiments, measuring the manufacturing parameter of the second analyte sensor includes measuring a size of the sensing region and a size of the membrane of the second analyte sensor, and the calibration information for the second analyte sensor is determined using a representation of the size of the sensing region, a representation of the size of the membrane, and a representation of the in vitro sensing characteristic of the first analyte sensor.

In some embodiments, the sensing region includes a sensing element, the sensing element being in a well of a sensor substrate and/or the sensing element being on or adjacent to a modified area of the sensor substrate having a liquid mobility characteristic different than an adjacent area of the sensor substrate.

In some embodiments, the in vitro sensing characteristic is a slope of a sensitivity of the first analyte sensor to the analyte level. In certain embodiments, the in vitro sensing characteristic is the sensitivity of the first analyte sensor to the analyte level.

In some embodiments, determining calibration information for the second analyte sensor includes: determining, with processing circuitry, an in vitro sensing characteristic of the second analyte sensor using at least the representation of the manufacturing parameter of the second analyte sensor and the representation of the in vitro sensing characteristic of the first analyte sensor; determining, with processing circuitry, an in vivo sensing characteristic of the second analyte sensor using a representation of the in vitro sensing characteristic of the second analyte sensor; and determining, with processing circuitry, calibration information for the second analyte sensor that corresponds to the in vivo sensing characteristic of the second analyte sensor. In certain embodiments, the method further includes determining the in vitro sensing characteristic of the second analyte sensor with a model, where the representation of the manufacturing parameter of the second analyte sensor and the representation of the in vitro sensing characteristic of the first analyte sensor are inputs to the model. In certain embodiments, the model is one of the following: a linear regression model; a multiple variable regression model; a random forest model; a non-linear model; a Bayesian regression model; a neural network; a machine learning model; a non-random decision tree; or a discriminant analysis model.

In certain embodiments, the second analyte sensor includes a sensing region and the manufacturing parameter is a size of the sensing region. In certain embodiments, the second analyte sensor includes a membrane and the manufacturing parameter is a size of the membrane. In certain embodiments, the second analyte sensor includes a sensing region and a membrane for the sensing region, where measuring the manufacturing parameter of the second analyte sensor includes measuring a size of the sensing region and a size of the membrane of the second analyte sensor, and where a representation of the size of the sensing region, a representation of the size of the membrane, and a representation of the in vitro sensing characteristic are inputs to the model.

In certain embodiments, the in vivo sensing characteristic of the second analyte sensor is determined by applying a representation of the in vitro sensing characteristic of the second analyte sensor to a transfer function.

In certain embodiments, determining calibration information for the second analyte sensor that corresponds to the in vivo sensing characteristic of the second analyte sensor includes identifying, from a multitude of predetermined calibration codes, a calibration code that most closely represents the in vivo sensing characteristic of the second analyte sensor.

In some embodiments, the method further includes storing the calibration information for the second analyte sensor in a non-transitory memory of sensor electronics assigned to the second analyte sensor. In certain embodiments, the sensor electronics include processing circuitry and the non-transitory memory includes instructions that, when executed by the processing circuitry, cause the processing circuitry to determine an analyte level from a raw analyte measurement made by the second analyte sensor and the calibration information for the second analyte sensor. In certain embodiments, the sensor electronics include processing circuitry and the non-transitory memory includes instructions that, when executed by the processing circuitry, cause the processing circuitry to cause transmission of the calibration information for the second analyte sensor to a wirelessly connected reader device.

In some embodiments, the method further includes storing the calibration information for the second analyte sensor in a non-transitory memory of a server. In certain embodiments, the method further includes: receiving a request, at the server, for the calibration information for the second analyte sensor from a requesting device; and downloading the calibration information from the server to the requesting device.

In some embodiments, the method includes: at least partially manufacturing a third medical device capable of sensing a biochemical attribute; measuring a manufacturing parameter of the third medical device; and determining, with processing circuitry, calibration information for the third medical device using a representation of the manufacturing parameter of the third medical device and the representation of the in vitro sensing characteristic of the first medical device.

In some embodiments, the second medical device is not in vitro tested.

In many embodiments, a method for calibrating individual medical devices adapted to sense a biochemical attribute is provided, where the method includes: determining, with processing circuitry, a sensing characteristic of a first medical device; and determining, with processing circuitry, calibration information for a second medical device using at least a representation of a manufacturing parameter of the second medical device and a representation of the sensing characteristic of the first medical device.

In some embodiments, the method further includes at least partially manufacturing the first medical device and the second medical device and measuring the manufacturing parameter of the second medical device.

In some embodiments, the sensing characteristic is an in vitro sensing characteristic determined from data obtained by in vitro testing the first medical device.

In some embodiments, the first medical device is a first analyte sensor, the second medical device is a second analyte sensor, and the biochemical attribute is an analyte level. In certain embodiments, the first and second analyte sensors are adapted to sense the analyte level in vivo.

In some embodiments, the second medical device includes a sensing region. In certain embodiments, the manufacturing parameter is a size of the sensing region.

In some embodiments, the second medical device includes a membrane. In certain embodiments, the manufacturing parameter is a size of the membrane.

In some embodiments, the first and second medical devices are in vitro analyte sensors. In certain embodiments, each in vitro analyte sensor is a test strip. In certain embodiments, each in vitro analyte sensor includes a working pad and the manufacturing parameter is a size of the working pad, an area of the working pad, or a thickness of the working pad. In certain embodiments, each in vitro analyte sensor includes an electrical trace and the manufacturing parameter is a resistance of the electrical trace.

In some embodiments, the manufacturing parameter is a qualitative value.

In some embodiments, the sensing region includes a sensing element, the sensing element being in a well of a sensor substrate and/or the sensing element being on or adjacent to a modified area of the sensor substrate having a liquid mobility characteristic different than an adjacent area of the sensor substrate.

In many embodiments, a computer system for calibrating individual medical devices adapted to sense a biochemical attribute is provided, where the computer system includes: processing circuitry and non-transitory memory communicatively coupled with the processing circuitry, where the non-transitory memory has a multitude of instructions stored thereon that, when executed by the processing circuitry, cause the processing circuitry to: determine a sensing characteristic of a first medical device; and determine calibration information for a second medical device using at least a representation of a manufacturing parameter of the second medical device and a representation of the sensing characteristic of the first medical device.

In some embodiments, the sensing characteristic is an in vitro sensing characteristic, where the multitude of instructions, when executed by the processing circuitry, cause the processing circuitry to determine the in vitro sensing characteristic from in vitro test data of the first medical device.

In some embodiments, the first medical device is a first analyte sensor, the second medical device is a second analyte sensor, and the biochemical attribute is an analyte level. In certain embodiments, the first and second analyte sensors are adapted to sense the analyte level in vivo. In certain embodiments, the manufacturing parameter is a size of a sensing region of the second analyte sensor. In certain embodiments, the manufacturing parameter is a size of a membrane of the second analyte sensor.

In some embodiments, the sensing region includes a sensing element, the sensing element being in a well of a sensor substrate and/or the sensing element being on or adjacent to a modified area of the sensor substrate having a liquid mobility characteristic different than an adjacent area of the sensor substrate.

In some embodiments, the first medical device is a first in vitro analyte sensor and the second medical device is a second in vitro analyte sensor. In certain embodiments, each in vitro analyte sensor is a strip. In certain embodiments, each in vitro analyte sensor includes a working pad and the manufacturing parameter is a size of the working pad, an area of the working pad, or a thickness of the working pad. In certain embodiments, each in vitro analyte sensor includes an electrical trace and the manufacturing parameter is a resistance of the electrical trace.

In some embodiments, the manufacturing parameter is a qualitative value. In some embodiments, the manufacturing parameter is an individualized manufacturing parameter that is quantitative.

In many embodiments, a computer system for calibrating individual medical devices adapted to sense a biochemical attribute is provided, where the computer system includes: processing circuitry and non-transitory memory communicatively coupled with the processing circuitry, where the non-transitory memory has a multitude of instructions stored thereon that, when executed by the processing circuitry, cause the processing circuitry to: determine an in vitro sensing characteristic of a first subset of a multitude of medical devices from in vitro test data of the first subset; and determine individualized calibration information for each medical device in a second subset of the multitude of medical devices using at least a representation of an individualized manufacturing parameter for each medical device in the second subset and a representation of the in vitro sensing characteristic of the first subset, where the medical devices in the first subset are different from the medical devices in the second subset.

In some embodiments, each of the medical devices in the multitude is an analyte sensor and the biochemical attribute is a level of an analyte. In certain embodiments, each analyte sensor in the multitude is adapted to sense the analyte level in vivo, and the in vitro sensing characteristic is in vitro sensitivity to the analyte.

In some embodiments, the individualized manufacturing parameter is a size of a sensing region of each analyte sensor in the second subset. In certain embodiments, the size of the sensing region is representative of at least one of the following: a width of the sensing region, a length of the sensing region, a thickness of the sensing region, a peripheral length of the sensing region, an area of the sensing region, or a volume of the sensing region.

In some embodiments, the representation of the individualized manufacturing parameter for a respective analyte sensor in the second subset is a deviation of the size of a sensing region of the respective analyte sensor from a central tendency of a size of a sensing region for the multitude of analyte sensors.

In some embodiments, the sensing region includes a sensing element, the sensing element being in a well of a sensor substrate and/or the sensing element being on or adjacent to a modified area of the sensor substrate having a liquid mobility characteristic different than an adjacent area of the sensor substrate.

In some embodiments, the individualized manufacturing parameter is a size of a membrane of each analyte sensor in the second subset. In certain embodiments, the size of the membrane is representative of at least one of the following: a width of the membrane, a length of the membrane, a thickness of the membrane, a peripheral length of the membrane, an area of the membrane, or a volume of the membrane. In certain embodiments, the representation of the individualized manufacturing parameter for a respective analyte sensor in the second subset is a deviation of the size of the membrane of the respective analyte sensor from a central tendency of a size of the membrane for the multitude of analyte sensors.

In some embodiments, the multitude of instructions, when executed by the processing circuitry, cause the processing circuitry to determine the individualized calibration information for each analyte sensor in the second subset using: a representation of a size of a sensing region of a respective analyte sensor in the second subset; a representation of a size of a membrane of the respective analyte sensor in the second subset; and the representation of the in vitro sensitivity of the first subset. In certain embodiments, the representation of the in vitro sensitivity includes a slope of a central tendency of in vitro sensitivity of the first subset, or an intercept of a central tendency of in vitro sensitivity of the first subset, or a slope and an intercept of a central tendency of in vitro sensitivity of the first subset.

In some embodiments, the multitude of instructions, when executed by the processing circuitry, cause the processing circuitry to determine individualized calibration information for each analyte sensor in the second subset by performance of (a)-(c) independently for each analyte sensor in the second subset: (a) determine an in vitro sensitivity of a respective analyte sensor in the second subset with at least the representation of the individualized manufacturing parameter for the respective analyte sensor and the representation of the in vitro sensitivity of the first subset; (b) determine an in vivo sensitivity of the respective analyte sensor with a representation of the in vitro sensitivity of the respective analyte sensor; and (c) determine individualized calibration information for the respective analyte sensor that corresponds to the in vivo sensitivity of the respective analyte sensor. In certain embodiments, the multitude of instructions, when executed by the processing circuitry, cause the processing circuitry to determine the in vitro sensitivity of the respective analyte sensor in the second subset by modeling a correlation between the representation of the individualized manufacturing parameter for the respective analyte sensor and the representation of the in vitro sensitivity of the first subset with a model. In certain embodiments, the model is one of the following: a linear regression model; a multiple variable regression model; a random forest model; a non-linear model; a Bayesian regression model; a neural network; a machine learning model; a non-random decision tree; or a discriminant analysis model. In certain embodiments, the model is at least partially represented by: $SC_{MD}=SC_B+\alpha+(\beta RMP_A)$ or $SC_{MD}=SC_B+(1+0.1(\alpha+(\beta RMP_A)))$, where $SC_{MD}$ is the in vitro sensitivity of the respective analyte sensor, $SC_B$ is the representation of the in vitro sensitivity of the first subset, $\alpha$ is a zero or non-zero adjustment factor, $RMP_A$ is the representation of the individualized manufacturing parameter for the respective analyte sensor, and $\beta$ is a coefficient for $RMP_A$. In certain embodiments, the model is at least partially represented by: $SC_{MD}=SC_B+\alpha+(\beta RMP_A)+(\delta RMP_A^2)$ or $SC_{MD}=SC_B+(1+0.1(\alpha+(\beta RMP_A)+(\delta RMP_A^2)))$, where $SC_{MD}$ is the in vitro sensitivity of the respective analyte sensor, $SC_B$ is the representation of the in vitro sensitivity of the first subset, $\alpha$ is a zero or non-zero adjustment factor, $RMP_A$ is the representation of the individualized manufacturing parameter for the respective analyte sensor, and $\beta$ is a coefficient for $RMP_A$, and $\delta$ is a coefficient for $RMP_A$ squared.

In some embodiments, the individualized manufacturing parameter is a first individualized manufacturing parameter, and the multitude of instructions, when executed by the processing circuitry, cause the processing circuitry to determine individualized calibration information for each analyte sensor in the second subset by performance of (a)-(c) independently for each analyte sensor in the second subset: (a) determine an in vitro sensitivity of a respective analyte sensor in the second subset using at least: the representation of the first individualized manufacturing parameter for the respective analyte sensor, a representation of a second individualized manufacturing parameter for the respective analyte sensor, and the representation of the in vitro sensitivity of the first subset; (b) determine an in vivo sensitivity of the respective analyte sensor using a representation of the in vitro sensitivity of the respective analyte sensor; and (c) determine individualized calibration information for the respective analyte sensor that corresponds to the in vivo sensitivity of the respective analyte sensor. In certain embodiments, the representation of the first individualized manufacturing parameter for the respective analyte sensor, the representation of a second individualized manufacturing parameter for the respective analyte sensor, and the representation of the in vitro sensitivity of the first subset are input into a model to determine the in vitro sensitivity of the respective analyte sensor. In certain embodiments, the model is at least partially represented by: $SC_{MD}=SC_B+\alpha+(\beta RMP_A)+(\delta RMP_A^2)+(\gamma RMP_B)+(\varepsilon RMP_B^2)+(\rho RMP_A RMP_B)$ or $SC_{MD}=SC_B+(1+0.01\ (\alpha+(\beta RMP_A)+(\delta RMP_A^2)+(\gamma RMP_B)+(\varepsilon RMP_B^2)+(\rho RMP_A RMP_B)))$, where $SC_{MD}$ is the in vitro sensitivity of the respective analyte sensor, $SC_B$ is the representation of the in vitro sensitivity of the first subset, $\alpha$ is a zero or non-zero adjustment factor, $RMP_A$ is the representation of the first individualized manufacturing parameter for the respective analyte sensor, $\beta$ is a coefficient for $RMP_A$, $\delta$ is a coefficient for $RMP_A$ squared, $RMP_B$ is the second individualized manufacturing parameter, $\gamma$ is a coefficient for $RMP_B$, $\varepsilon$ is a coefficient for $RMP_B$ squared, and $\rho$ is a coefficient for the product of $RMP_A$ and $RMP_B$.

In some embodiments, each analyte sensor of the multitude includes a sensing region and the individualized manufacturing parameter is a size of the sensing region.

In some embodiments, each analyte sensor of the multitude includes a membrane and the individualized manufacturing parameter is a size of the membrane.

In some embodiments, each analyte sensor of the multitude includes a sensing region and a membrane for the sensing region, where the multitude of instructions, when executed by the processing circuitry, cause the processing circuitry to determine the in vitro sensitivity of the respective analyte sensor in the second subset by input of a representation of a size of the sensing region of the respective analyte sensor, a representation of a size of the membrane of the respective analyte sensor, and a representation of the in vitro sensitivity into a model.

In some embodiments, the multitude of instructions, when executed by the processing circuitry, cause the processing circuitry to determine the in vivo sensitivity of the respective analyte sensor by application of a representation of the in vitro sensitivity of the respective analyte sensor to a transfer function.

In some embodiments, the multitude of instructions, when executed by the processing circuitry, cause the processing circuitry to determine individualized calibration information for the respective analyte sensor by identification of, from a multitude of predetermined calibration codes, a calibration code that most closely represents the in vivo sensitivity of the respective analyte sensor.

In some embodiments, each analyte sensor in the second subset is associated with a different sensor electronics assembly of a multitude of sensor electronics assemblies, and each sensor electronics assembly of the multitude of sensor electronics assemblies includes a non-transitory memory, and the multitude of instructions, when executed by the processing circuitry, cause the processing circuitry to output corresponding individualized calibration information for storage in each non-transitory memory.

In some embodiments, the multitude of instructions, when executed by the processing circuitry, cause the processing circuitry to determine individualized calibration information for each analyte sensor in the second subset by performance of (a) and (b) independently for each analyte sensor in the second subset: (a) determine an in vitro sensitivity of a respective analyte sensor in the second subset with at least the representation of the individualized manufacturing parameter for the respective analyte sensor and the representation of the in vitro sensitivity of the first subset; and (b) determine individualized calibration information for the respective analyte sensor that corresponds to the in vitro sensitivity of the respective analyte sensor.

In some embodiments, each medical device in the multitude is an in vitro analyte sensor. In certain embodiments, each in vitro analyte sensor is a test strip. In certain embodiments, each in vitro analyte sensor includes a working pad and the manufacturing parameter is a size of the working pad, an area of the working pad, or a thickness of the working pad. In certain embodiments, each in vitro analyte sensor includes an electrical trace and the manufacturing parameter is a resistance of the electrical trace.

In some embodiments, the biochemical attribute is a level of glucose.

In some embodiments, the first and second subsets are from a same production lot. In some embodiments, the multitude of medical devices is a production lot of the medical devices.

In many embodiments, an analyte monitoring system is provided that includes: a sensor control device including: an in vivo analyte sensor and electronics communicatively coupled with the in vivo analyte sensor, the electronics including non-transitory memory, where individualized calibration information is stored in the memory, and where the individualized calibration information is based on a measured manufacturing parameter of the in vivo analyte sensor and is specific to the in vivo analyte sensor.

In some embodiments, the electronics further include wireless communication circuitry and processing circuitry, and the non-transitory memory has a multitude of instructions stored thereon that, when executed by the processing circuitry, cause the processing circuitry to: determine an analyte level from raw data measured by the in vivo analyte sensor and from the individualized calibration information; and output the determined analyte level to the wireless communication circuitry for transmission.

In some embodiments, the electronics further include wireless communication circuitry and processing circuitry, and the non-transitory memory includes a multitude of instructions stored thereon that, when executed by the processing circuitry, cause the processing circuitry to: output the individualized calibration information to the wireless communication circuitry for transmission; and output raw analyte data collected by the in vivo analyte sensor to the wireless communication circuitry for transmission.

In some embodiments, the sensor control device has a lifespan and is usable for the lifespan without user calibration.

In some embodiments, the sensor control device has a lifespan and is usable for the lifespan without user calibration and without system calibration.

In some embodiments, the system further includes: a reader device including processing circuitry, wireless communication circuitry, and non-transitory memory including a multitude of instructions that, when executed by the processing circuitry, cause the processing circuitry to determine an analyte level from raw data measured by the in vivo analyte sensor and from the individualized calibration information, the raw analyte data and individualized communication information being received from the sensor control device.

In some embodiments, the measured manufacturing parameter is a size of a sensing region of the in vivo analyte sensor, and the sensing region includes a sensing element, the sensing element being in a well of a sensor substrate and/or the sensing element being on or adjacent to a modified area of the sensor substrate having a liquid mobility characteristic different than an adjacent area of the sensor substrate.

In many embodiments, a method of analyte monitoring is provided where the method includes: processing raw analyte data, collected with an analyte sensor, with individualized calibration information to determine an analyte level of a user, where the individualized calibration information is based on a measured manufacturing parameter of the analyte sensor and is specific to the analyte sensor.

In some embodiments, the analyte sensor is an in vivo analyte sensor that is a component of a sensor control device that further includes processing circuitry, where the processing circuitry of the sensor control device processes the raw analyte data with individualized calibration information to determine the analyte level of the user.

In some embodiments, the method further includes collecting raw analyte data from a user with the in vivo analyte sensor prior to processing the raw analyte data.

In some embodiments, the method further includes: wirelessly communicating the individualized calibration information to a reader device and wirelessly communicating the collected raw analyte data to a reader device. In certain embodiments, the reader device includes processing circuitry, where the processing circuitry of the reader device processes the raw analyte data with individualized calibration information to determine the analyte level of the user.

In some embodiments, the in vivo analyte sensor has a lifespan, and the method further includes using the in vivo analyte sensor for the lifespan without performing user calibration.

In some embodiments, the in vivo analyte sensor has a lifespan, and the method further includes using the in vivo analyte sensor for the lifespan without performing user calibration and without performing system calibration.

In some embodiments, the analyte sensor is an in vitro analyte sensor. In certain embodiments, the in vitro analyte sensor is a strip-based in vitro analyte sensor.

In some embodiments, the measured manufacturing parameter is a size of a sensing region of the analyte sensor, and the sensing region includes a sensing element, the sensing element being in a well of a sensor substrate and/or the sensing element being on or adjacent to a modified area of the sensor substrate having a liquid mobility characteristic different than an adjacent area of the sensor substrate.

In many embodiments, a kit is provided that includes: a first in vivo analyte sensor of a first sensor control device; first electronics of the first sensor control device, the first electronics including a first non-transitory memory on which is stored first individualized calibration information that is based on a measured manufacturing parameter of the first in vivo analyte sensor and is specific to the first in vivo analyte sensor; a second in vivo analyte sensor of a second sensor control device; and second electronics of the second sensor control device, the second electronics including a second non-transitory memory on which is stored second individualized calibration information that is based on a measured manufacturing parameter of the second in vivo analyte sensor and is specific to the second in vivo analyte sensor, where the first in vivo analyte sensor, the first electronics, the second in vivo analyte sensor, and the second electronics are coupled with each other by a common packaging.

In some embodiments, the first and second in vivo analyte sensors are from the same in vivo sensor manufacturing lot.

In some embodiments, the kit further includes: a third in vivo analyte sensor of a third sensor control device; and third electronics of the third sensor control device, the third electronics including a third non-transitory memory on which is stored third individualized calibration information that is based on a measured manufacturing parameter of the third in vivo analyte sensor and is specific to the third in vivo analyte sensor, where the first in vivo analyte sensor, the first electronics, the second in vivo analyte sensor, the second electronics, the third in vivo sensor, and the third electronics are coupled with each other by a common packaging.

In some embodiments, the first, second, and third in vivo analyte sensors are from the same in vivo sensor manufacturing lot.

In some embodiments, the measured manufacturing parameter is a size of a sensing region of the first in vivo analyte sensor, and the sensing region includes a sensing element, the sensing element being in a well of a sensor substrate and/or the sensing element being on or adjacent to a modified area of the sensor substrate having a liquid mobility characteristic different than an adjacent area of the sensor substrate.

In many embodiments, a method of analyte monitoring is provided where the method includes: collecting a sample of body fluid from a living body on an in vitro strip, the in vitro strip including an in vitro analyte sensor; inserting the in vitro strip into a meter; and determining an analyte level in the sample of body fluid using individualized calibration information and a signal received from the in vitro analyte sensor, where the individualized calibration information is based on a measured manufacturing parameter of the in vitro analyte sensor and is specific to the in vitro analyte sensor.

In some embodiments, the method further includes manually typing the individualized calibration information into the meter.

In some embodiments, the method further includes automatically inputting the individualized calibration information into the meter.

In some embodiments, the method further includes automatically inputting the individualized calibration information into the meter by using an optical scanner and at least one of the following: a barcode, a data matrix code, a two-dimensional code, or a three-dimensional code.

In some embodiments, the method further includes automatically inputting the individualized calibration information into the meter by using at least one of the following: an RF tag, a resistive coded trace, a ROM calibrator, or Bluetooth circuitry.

In some embodiments, the method further includes: obtaining the calibration information by a second electronic device; and sending the calibration information to the meter over a Bluetooth connection. In certain embodiments, the second electronic device is a mobile phone. In certain embodiments, the calibration information is obtained by use of an optical scanner or Near Field Communication (NFC) circuitry of the phone.

In some embodiments, the measured manufacturing parameter is a size of a sensing region of the in vitro analyte sensor, and the sensing region includes a sensing element, the sensing element being in a well of a sensor substrate and/or the sensing element being on or adjacent to a modified area of the sensor substrate having a liquid mobility characteristic different than an adjacent area of the sensor substrate.

In many embodiments, a method for individualized medical device calibration is provided, where the method includes determining, with processing circuitry, individualized calibration information for a medical device using at least a representation of a manufacturing parameter of the medical device.

In some embodiments, the medical device is a first medical device, and the method further includes determining, with processing circuitry, the individualized calibration information for the first medical device using at least the representation of the manufacturing parameter for the first medical device and a representation of a sensing characteristic of a second medical device.

In certain embodiments, the method further includes determining, with processing circuitry, the representation of the sensing characteristic of the second medical device.

In certain embodiments, the method further includes performing an in vitro test on the second medical device and determining, with processing circuitry, the representation of the sensing characteristic of the second medical device from in vitro test data collected from the in vitro test.

In certain embodiments, the method further includes obtaining the manufacturing parameter from the first medical device. In certain embodiments, the manufacturing parameter is obtained during or after a manufacturing stage for the first medical device.

In certain embodiments, the first and second medical devices are in vivo sensors. In certain embodiments, the first and second medical devices are in vitro sensors. In certain embodiments, the first and second medical devices are in vitro test strips. In certain embodiments, the first and second medical devices are adapted to sense a biochemical attribute.

In certain embodiments, the representation of the manufacturing parameter is a representation of an individualized manufacturing parameter.

In some embodiments, the manufacturing parameter is a size of a sensing region of the medical device, and the sensing region includes a sensing element, the sensing element being in a well of a sensor substrate and/or the sensing element being on or adjacent to a modified area of the sensor substrate having a liquid mobility characteristic different than an adjacent area of the sensor substrate.

In many embodiments, a method of manufacturing is provided, the method including: modifying an area of a surface of a sensor substrate with electromagnetic radiation to create a modified area; and applying a liquid agent to the surface of the sensor substrate such that the liquid agent comes to rest in a target area on the surface, where the target area is determined at least in part by the location of the modified area. The modified area can border the target area.

In some embodiments, the modified area has a ring-like shape. The target area can be within an interior of the ring-like shape. In some embodiments, the ring-like shape can have an interior border that defines an interior of the ring-like shape, and the target area can be the interior of the ring-like shape. The ring-line shape can be a region between two concentric circles.

In some embodiments, the target area is round or polygonal. In some embodiments, the target area is not adjacent to the modified area. In some embodiments, the modified area and the target area are the same.

In some embodiments, the modified area attracts the liquid agent. In other embodiments, the modified area repels the liquid agent.

In some embodiments, the electromagnetic radiation is laser radiation in the ultraviolet or visible spectrum. The laser radiation can be pulsed to create the modified area.

In some embodiments, the modified area of the sensor substrate includes carbon.

In some embodiments, the method further includes: focusing a laser on the surface of the sensor substrate; and activating the laser to modify the area of the surface of the sensor substrate with laser radiation to create the modified area.

In some embodiments, the electromagnetic radiation is laser radiation, and the method further includes: entering a size for the modified area into a laser marking system; and focusing the laser marking system on the substrate prior to modifying the area of the surface of the sensor substrate with laser radiation. The modified area can be a first modified area, and the method can further include: moving either the substrate or a portion of the laser marking system; and modifying a second area of the surface of the sensor substrate with laser radiation to create a second modified area. In some embodiments, the method includes transferring the substrate to a liquid agent dispense system having a nozzle; and applying the liquid agent from the nozzle to the surface of the sensor substrate such that the liquid agent comes to rest in the target area on the surface.

In some embodiments, the liquid agent is an electrochemical agent.

In some embodiments, the method further includes drying the liquid agent to form a sensing element in the target area.

In some embodiments, the modified area is at least one of: a bottom of a well in the substrate, a sidewall of a well in the substrate, or an area surrounding a well in the substrate.

In many embodiments, a method of manufacturing is provided, the method including: creating a well in a sensor substrate; and applying a liquid agent into the well in the sensor substrate such that the liquid agent comes to rest in the well.

In some embodiments, the well includes a bottom and a sidewall. The liquid agent can be applied to the bottom of the well.

In some embodiments, the liquid agent is an electrochemical agent. The method can further include drying the liquid agent to form a sensing element in the well. In some embodiments, the well includes a bottom and a sidewall, and the sensing element covers a majority of the bottom. In some embodiments, the well includes a bottom and a sidewall, and the sensing element covers the entire bottom.

In some embodiments, the well includes a bottom surface that is round, circular, or polygonal.

In some embodiments, the method further includes: aligning a tip of a tool with an alignment feature on a surface of the sensor substrate; and forcing the tip of the tool into the substrate to create the well in the substrate. In some embodiments, the well is a first well, and the method further includes: moving either the substrate or the tip of the tool; and forcing the tip of the tool into the substrate to create a second well in the substrate. In some embodiments, the method further includes: transferring the substrate to a liquid agent dispense system having a nozzle, where applying the liquid agent into the well in the sensor substrate such that the liquid agent comes to rest in the well includes dispensing a drop of the liquid agent from the nozzle into the well.

In some embodiments, a bottom surface of the well has been modified with electromagnetic radiation and has a liquid mobility characteristic that is different from an adjacent surface of the substrate.

In some embodiments, a sidewall surface of the well has been modified with electromagnetic radiation and has a liquid mobility characteristic that is different from an adjacent surface of the substrate.

In some embodiments, a surface of the substrate surrounding the well has been modified with electromagnetic radiation and has a liquid mobility characteristic that is different from an adjacent surface of the substrate.

In many embodiments, an analyte monitoring system is provided, the analyte monitoring system including: an in vivo analyte sensor including a substrate and at least one sensing element on the substrate, the at least one sensing element including an electrochemical agent, where the sensing element is on, adjacent to, or in proximity to a modified area on a surface of the substrate, the modified area having a liquid mobility characteristic that is different from an area of the surface of the substrate adjacent to the modified area.

In some embodiments, the modified area has a ring-like shape. The sensing element can be within an interior of the ring-like shape. The ring-like shape can have an interior border that defines an interior of the ring-like shape, and the sensing element covers the interior of the ring-like shape. The ring-line shape can be a region between two concentric circles.

In some embodiments, the modified area is round, such as circular or elliptical.

In some embodiments, the sensing element is on the modified area.

In some embodiments, the sensing element is adjacent to the modified area.

In some embodiments, the liquid mobility characteristic is such that the electrochemical agent in liquid form is relatively more attracted to the modified area than the area of the surface of the substrate adjacent to the modified area.

In some embodiments, the liquid mobility characteristic is such that the electrochemical agent in liquid form is relatively more attracted to the area of the surface of the substrate adjacent to the modified area than to the modified area.

In some embodiments, the modified area is at least one of a bottom of a well in the substrate, a sidewall of a well in the substrate, or an area surrounding a well in the substrate.

In some embodiments, the system further includes: electronics communicatively coupled with the in vivo analyte sensor, the electronics including non-transitory memory, where individualized calibration information is stored in the memory, where the individualized calibration information is based on a measured manufacturing parameter of the in vivo analyte sensor and is specific to the in vivo analyte sensor.

In some embodiments, the measured manufacturing parameter is representative, at least in part, of a size of the sensing element.

In some embodiments, the in vivo analyte sensor includes a membrane, and the measured manufacturing parameter is representative, at least in part, of a size of the membrane.

In many embodiments, an analyte monitoring system is provided, the system including: an in vivo analyte sensor having a substrate and at least one sensing element on the substrate, the at least one sensing element including an electrochemical agent, where the sensing element is in a well in a surface of the substrate.

In some embodiments, the well includes a bottom surface. The sensing element can cover only a portion of the bottom surface of the well, or the sensing element can cover the entire bottom surface of the well.

In some embodiments, the sensing element has a height that is less than a depth of the well. In some embodiments, the sensing element has a height that is equal to a depth of the well. In some embodiments, the sensing element has a height that is greater than a depth of the well.

In some embodiments, the well includes a bottom surface that is round or polygonal.

In some embodiments, a bottom surface of the well has a liquid mobility characteristic that is different from an adjacent surface of the substrate.

In some embodiments, the well incudes a bottom surface and a sidewall surface. In some embodiments, the bottom surface of the well has a liquid mobility characteristic that is different from an adjacent surface of the substrate. In some embodiments, the sidewall surface of the well has a liquid mobility characteristic that is different from an adjacent surface of the substrate. In some embodiments, a surface of the substrate surrounding the well has a liquid mobility characteristic that is different from an adjacent surface of the substrate.

In some embodiments, the system further includes electronics communicatively coupled with the in vivo analyte sensor, the electronics including non-transitory memory, where individualized calibration information is stored in the memory, where the individualized calibration information is based on a measured manufacturing parameter of the in vivo analyte sensor and is specific to the in vivo analyte sensor. In some embodiments, the measured manufacturing parameter is representative, at least in part, of a size of the sensing element. In some embodiments, the in vivo analyte sensor includes a membrane, and the measured manufacturing parameter is representative, at least in part, of a size of the membrane.

APPENDIX: EXAMPLES OF MODELS

The following is a general description of various models that can be used with the calibration embodiments described herein. Those of ordinary skill in the art will recognize the many different ways these and other models can be implemented in light of the disclosure presented in this appendix and elsewhere throughout this description.

Random forest models are an ensemble learning method which can construct a multitude of decision trees as samples of the full data and outputting the class which is the mean prediction of the individual trees. Each tree can be created by partitioning the space into smaller regions where interactions are more manageable, which can then be partitioned again, e.g., recursive partitioning. The following is an example of a general random forest algorithm:

1) Start with the single node. Calculate for each partition leaf c, $S=\Sigma_{c \in leaves(T)} \Sigma_{i \in C}(y_i - m_c)^2$ where $$m_c = \frac{1}{n_c} \sum_{i \in C} y_c$$

2) Search over all binary splits of all variables to see which will reduce S as much as possible. If the largest decrease is less than a threshold $\delta$ or the node contains less than q points then stop. Otherwise create the two new nodes
3) In each new node go back to step 1.

Non-linear regressions are a form of regression analysis modelled by a function which is a nonlinear combination of the model parameters and depends on one of more independent variables. $Y=f(X, \beta)$, where X is a vector of p predictors and $\beta$ is a vector of k parameters. The following is an example of a general nonlinear regression:

$$y_i = \frac{\beta_0 + \beta_1 x_1}{1 + \beta_2 e^{\beta_3 x_3}}$$

Bayesian regression models are another example. In Bayesian statistics, the posterior distribution is conditional probability of an unknown treated as a random variable—$p(\beta|X)$. It is proportional to the likelihood function which is the probability of the evidence given the parameters. $p(X|\beta)$ multiplied by a prior belief that the probability distribution function is $p(\beta)$. An example of a Bayesian linear regression follows:

$$E[y|\beta]=A\theta$$

Where $\beta$ is a vector of p parameters, A is a known n×p matrix and C is the variance-covariance dispersion matrix. Then where N is the normal distribution $$y \sim N(A\beta, C)$$

Where A and C are known:

$$\beta \sim N(\mu, C2)$$

Where $\mu$ and C are also known.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

In all of the embodiments described herein, electronic devices capable of processing data or information can include processing circuitry communicatively coupled with non-transitory memory, where the non-transitory memory can store one or more computer program or software instructions that, when executed by the processing circuitry, cause the processing circuitry to take actions. For every embodiment of a method disclosed herein, systems and devices capable of performing those methods, or portions thereof, with processing circuitry and non-transitory memory having one or more instructions stored thereon that, when executed by the processing circuitry, cause that processing circuitry to execute one or more steps of the method (or cause the execution of one or more steps of the method, such as transmission or display of information), are within the scope of the present disclosure.

Computer program or software instructions for carrying out operations in accordance with the described subject matter may be written in any combination of one or more programming languages, including an object oriented programming language such as Java, JavaScript, Smalltalk, C++, C #, Transact-SQL, XML, PHP or the like and conventional procedural programming languages, such as the "C" programming language or similar programming languages. The program instructions may execute entirely on the computing device, partly on the computing device, as a stand-alone software package, partly on a local computing device and partly on a remote computing device or entirely on a remote computing device or server. In the latter scenario, the remote computing device may be connected to the local computing device through any type of network, including a local area network (LAN) or a wide area network (WAN), or the connection may be made to an external computer (for example, through the Internet using an Internet Service Provider).

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method for manufacturing an in vivo glucose sensor system, comprising:
   providing a plurality of in vivo glucose sensors, each in vivo glucose sensor of the plurality of in vivo glucose sensors comprising a respective unique identifier for uniquely identifying each respective in vivo glucose sensor of the plurality of in vivo glucose sensors during each of a plurality of stages of manufacturing, wherein each unique identifier is one of a barcode, a printed QR code, an optical character recognizable text, a resistive code, and a radio frequency readable device, wherein each in vivo glucose sensor is configured to generate electrical signals indicative of levels of glucose in an interstitial fluid, and each glucose sensor includes:
      a proximal portion configured to be positioned above a skin surface of a user, and
      a distal portion configured to be inserted through the skin surface and in contact with the interstitial fluid;
   subjecting a first in vivo glucose sensor of the plurality of in vivo glucose sensors to a first manufacturing stage, wherein the first manufacturing stage includes:
      electronically reading the respective unique identifier to uniquely identify the first in vivo glucose sensor;
      measuring a first individualized manufacturing parameter associated with the first in vivo glucose sensor; and
      storing, in a log, the first individualized manufacturing parameter associated with the first in vivo glucose sensor, an indication of a first date corresponding to the first manufacturing stage, and an indication of a first time corresponding to the first manufacturing stage;
   subjecting the first in vivo glucose sensor of the plurality of in vivo glucose sensors to a second manufacturing stage, wherein the second manufacturing stage includes:
      electronically reading the respective unique identifier to uniquely identify the first in vivo glucose sensor;
      measuring a second individualized manufacturing parameter associated with the first in vivo glucose sensor; and
      storing, in the log, the second individualized manufacturing parameter associated with the first in vivo glucose sensor, an indication of a second date corresponding to the second manufacturing stage, and an indication of a second time corresponding to the second manufacturing stage;
   obtaining, by at least one processor, individualized calibration information associated with the first in vivo glucose sensor, wherein the individualized calibration information is based at least in part on at least one of the first individualized manufacturing parameter associated with the respective in vivo glucose sensor and the second individualized manufacturing parameter associated with the respective in vivo glucose sensor;
   assigning the first in vivo glucose sensor to a first electronics unit, the first electronics unit having a non-transitory memory;
   fixedly connecting the first in vivo glucose sensor with the first electronics unit to form a first integrated in vivo glucose sensor system;
   transmitting to the first electronics unit the individualized calibration information associated with the first in vivo glucose sensor for storage in the non-transitory memory of the first electronics unit; and
   packaging the first integrated in vivo glucose sensor system;
   wherein the first integrated in vivo glucose sensor system has a predetermined monitoring time period and is usable for the predetermined monitoring time period without an in vitro blood glucose measurement calibration using a finger stick and an in vitro glucose test strip.

2. The method of claim 1, wherein transmitting occurs prior to packaging.

3. The method of claim 1, where transmitting the individualized calibration information associated with the first in vivo glucose sensor comprises wirelessly transmitting the individualized calibration information associated with the first in vivo glucose sensor.

4. The method of claim 3, wherein packaging occurs prior to transmitting.

5. The method of claim 1, further comprising subjecting each additional in vivo glucose sensor of the plurality of in vivo glucose sensors to the first manufacturing stage.

6. The method of claim 5, wherein the first manufacturing stage comprises, for each of the additional in vivo glucose sensors:
   electronically reading the respective unique identifier to uniquely identify the respective in vivo glucose sensor;
   measuring a first respective individualized manufacturing parameter associated with the respective in vivo glucose sensor; and
   storing, in the log, the first respective individualized manufacturing parameter associated with the respective in vivo glucose sensor, an indication of a first respective date corresponding to the first manufacturing stage, and an indication of a first respective time corresponding to the first manufacturing stage.

7. The method of claim 6, further comprising subjecting each of the additional in vivo glucose sensors of the plurality of in vivo glucose sensors to the second manufacturing stage.

8. The method of claim 7, wherein the second manufacturing stage comprises, for each of the additional in vivo glucose sensors:
   electronically reading the respective unique identifier to uniquely identify the respective in vivo glucose sensor;

measuring a second respective individualized manufacturing parameter associated with the respective in vivo glucose sensor; and storing, in the log, the second respective individualized manufacturing parameter associated with the respective in vivo glucose sensor, an indication of a second respective date corresponding to the second manufacturing stage, and an indication of a second respective time corresponding to the second manufacturing stage.

9. The method of claim 8, further comprising, for each of the additional in vivo glucose sensors:

obtaining, by the at least one processor, individualized calibration information associated with the respective in vivo glucose sensor, wherein the individualized calibration information is based at least in part on at least one of the first respective individualized manufacturing parameter associated with the respective in vivo glucose sensor and the second respective individualized manufacturing parameter associated with the respective in vivo glucose sensor;

assigning the respective in vivo glucose sensor to a respective electronics unit, the respective electronics unit having a non-transitory memory;

fixedly connecting the respective in vivo glucose sensor with the respective electronics unit to form a respective integrated in vivo glucose sensor system; and packaging the respective integrated in vivo glucose sensor system.

10. The method of claim 9, further comprising, for each of the additional in vivo glucose sensors, transmitting to the respective electronics unit the individualized calibration information associated with the respective in vivo glucose sensor for storage in the non-transitory memory of the respective electronics unit.

11. The method of claim 10, wherein transmitting occurs prior to packaging.

12. The method of claim 10, where transmitting the individualized calibration information associated with the respective in vivo glucose sensor comprises wirelessly transmitting the individualized calibration information associated with the respective in vivo glucose sensor.

13. The method of claim 12, wherein packaging occurs prior to transmitting.

14. The method of claim 1, further comprising subjecting a baseline subset of the plurality of in vivo glucose sensors to in vitro testing to provide in vitro test data.

15. The method of claim 14, wherein the individualized calibration information is further based at least in part on the in vitro test data.

16. The method of claim 1, wherein the unique identifier is a radio frequency readable device.

17. The method of claim 1, wherein the unique identifier is a printed QR code.

18. The method of claim 1, wherein the unique identifier is a barcode.

19. The method of claim 1, wherein the unique identifier is an optical character recognizable (OCR) text.

20. The method of claim 1, wherein the unique identifier is a resistive code.

21. The method of claim 1, wherein the first individualized manufacturing parameter obtained at the first manufacturing stage comprises a quantitative manufacturing parameter.

22. The method of claim 1, wherein the first individualized manufacturing parameter obtained at the first manufacturing stage comprises an individualized qualitative manufacturing parameter.

23. The method of claim 1, wherein the first manufacturing stage further includes storing the first manufacturing stage in the log.

24. The method of claim 1, wherein the first individualized manufacturing parameter obtained at the first manufacturing stage comprises a length of time the first in vivo glucose sensor spent at the first manufacturing stage.

25. The method of claim 1, wherein the first individualized manufacturing parameter obtained at the first manufacturing stage comprises a size or dimensional measurement associated with the first in vivo glucose sensor.

26. The method of claim 1, wherein the first individualized manufacturing parameter obtained at the first manufacturing stage comprises a chemical composition or chemical concentration associated with the first in vivo glucose sensor.

27. The method of claim 1, wherein the first individualized manufacturing parameter obtained at the first manufacturing stage comprises an electrical characteristic associated with the first in vivo glucose sensor.

28. The method of claim 1, wherein the first individualized manufacturing parameter obtained at the first manufacturing stage comprises an environmental condition.

29. The method of claim 1, wherein each of the plurality of in vivo glucose sensors comprises a sensing region comprising a sensing element, the sensing element being on a modified area of a sensor substrate having a liquid mobility characteristic different than an adjacent area of the sensor substrate.

* * * * *